US011014183B2

(12) United States Patent
Becker et al.

(10) Patent No.: US 11,014,183 B2
(45) Date of Patent: May 25, 2021

(54) SYSTEM AND METHOD OF MARKING A WELDING WORKPIECE

(71) Applicant: ILLINOIS TOOL WORKS INC., Glenview, IL (US)

(72) Inventors: William Joshua Becker, Manitowoc, WI (US); Kyle Andrew Pfiefer, Appleton, WI (US)

(73) Assignee: Illinois Tool Works Inc., Glenview, IL (US)

( * ) Notice: Subject to any disclaimer, the term of this patent is extended or adjusted under 35 U.S.C. 154(b) by 635 days.

(21) Appl. No.: 14/808,842

(22) Filed: Jul. 24, 2015

(65) Prior Publication Data

US 2016/0039034 A1 Feb. 11, 2016

Related U.S. Application Data

(60) Provisional application No. 62/034,642, filed on Aug. 7, 2014.

(51) Int. Cl.
*B23K 9/095* (2006.01)
*A61F 9/06* (2006.01)
(Continued)

(52) U.S. Cl.
CPC .............. *B23K 9/0956* (2013.01); *A61F 9/06* (2013.01); *B23K 9/095* (2013.01); *B23K 9/0953* (2013.01);
(Continued)

(58) Field of Classification Search
CPC ....... B41F 17/00; B23K 9/0956; B23K 9/095; B23K 9/32; B23K 9/0953; B41J 3/413;
(Continued)

(56) References Cited

U.S. PATENT DOCUMENTS 1,340,270 A 5/1920 Emil
2,045,800 A 6/1936 Walther
(Continued)

FOREIGN PATENT DOCUMENTS

CA 2311685 12/2001
CA 2517874 12/2001
(Continued)

OTHER PUBLICATIONS

Aiteanu Dorin (hereinafter Aiteanu) "Virtual and Augmented Reality Supervisor for a New Welding Helmet" Nov. 15, 2005, pp. 1-150 (Year: 2005).*
(Continued)

*Primary Examiner* — Dramos Kalapodas
(74) *Attorney, Agent, or Firm* — McAndrews, Held & Malloy, Ltd.

(57) ABSTRACT

An embodiment of a system includes a marking tool configured to apply one or more markers on a first surface of a workpiece for a live welding session. The one or more markers have known geometric properties that may facilitate determination of the first surface and a weld joint. An embodiment of a method includes applying a first set of one or more markers to a first surface of a workpiece, detecting the applied first set of one or more markers with a camera, and determining, via processing circuitry coupled to the camera, at least one of the first surface of the workpiece and a weld joint based at least in part on the detected first set of one or more markers.

22 Claims, 55 Drawing Sheets

(51) Int. Cl.
  *B25H 7/04* (2006.01)
  *B41J 3/413* (2006.01)
  *B23K 9/16* (2006.01)
  *B23K 9/32* (2006.01)
  *G09B 19/24* (2006.01)

(52) U.S. Cl.
  CPC ............... *B23K 9/16* (2013.01); *B23K 9/32* (2013.01); *B23K 9/322* (2013.01); *B25H 7/04* (2013.01); *B41J 3/413* (2013.01); *G09B 19/24* (2013.01)

(58) Field of Classification Search
  CPC .......... G09B 19/24; G09B 9/00; G09B 19/00; G09B 5/02; G05B 2219/45135; A61F 9/06
  See application file for complete search history.

(56) References Cited

U.S. PATENT DOCUMENTS

| | | |
|---|---|---|
| 2,045,801 A | 6/1936 | Richter |
| 2,045,802 A | 6/1936 | Walther |
| 2,333,192 A | 10/1942 | Moberg |
| 2,351,910 A | 6/1944 | Blankenbuehler |
| 3,391,691 A | 7/1968 | Young |
| 3,679,865 A | 7/1972 | Jesnitzer |
| 3,867,769 A | 2/1975 | Schow |
| 4,028,522 A | 6/1977 | Chihoski |
| 4,041,615 A | 8/1977 | Whitehill |
| 4,044,377 A | 8/1977 | Bowerman |
| 4,124,944 A | 11/1978 | Blair |
| 4,132,014 A | 1/1979 | Schow |
| 4,144,766 A | 3/1979 | Wehrmeister |
| 4,224,501 A | 9/1980 | Lindbom |
| 4,253,648 A | 3/1981 | Meeks |
| 4,294,440 A | 10/1981 | Severt |
| 4,375,026 A | 2/1983 | Kearney |
| 4,375,165 A | 3/1983 | deSterke |
| 4,389,561 A | 6/1983 | Weman |
| 4,396,945 A | 8/1983 | DiMatteo |
| 4,412,121 A | 10/1983 | Kremers |
| 4,452,589 A | 6/1984 | Denison |
| 4,459,114 A | 7/1984 | Barwick |
| 4,471,207 A | 9/1984 | Hawkes |
| 4,484,059 A | 11/1984 | Lillquist |
| 4,518,361 A | 5/1985 | Conway |
| 4,541,055 A | 9/1985 | Wolfe |
| 4,555,614 A | 11/1985 | Morris |
| 4,557,191 A * | 12/1985 | Speicher ............... B25J 9/04 101/35 |
| 4,577,499 A | 3/1986 | Silke |
| 4,590,356 A | 5/1986 | Povlick |
| 4,591,689 A | 5/1986 | Brown |
| 4,594,497 A | 6/1986 | Takahashi |
| 4,595,186 A | 6/1986 | Reed |
| 4,595,368 A | 6/1986 | Cole |
| 4,595,820 A | 6/1986 | Richardson |
| 4,609,806 A | 9/1986 | Grabkowski |
| 4,628,176 A | 12/1986 | Kojima |
| 4,638,146 A | 1/1987 | Koyama |
| 4,641,292 A | 2/1987 | Tunnell |
| 4,677,277 A | 6/1987 | Cook |
| 4,680,014 A | 7/1987 | Paton |
| 4,689,021 A | 8/1987 | Vasiliev |
| 4,716,273 A | 12/1987 | Paton |
| 4,721,947 A | 1/1988 | Brown |
| 4,728,768 A | 3/1988 | Cueman |
| 4,739,404 A | 4/1988 | Richardson |
| 4,767,109 A | 8/1988 | Raketich |
| 4,820,901 A | 4/1989 | Peviani |
| 4,829,365 A | 5/1989 | Eichenlaub |
| 4,830,261 A | 5/1989 | Mello |
| 4,867,685 A | 9/1989 | Brush |
| 4,868,649 A | 9/1989 | Gaudin |
| 4,877,940 A | 10/1989 | Bangs |
| 4,881,678 A | 11/1989 | Gaudin |
| 4,920,249 A | 4/1990 | McLaughlin |
| 4,931,018 A | 6/1990 | Herbst |
| 4,937,427 A | 6/1990 | McVicker |
| 4,943,702 A | 7/1990 | Richardson |
| 4,954,690 A | 9/1990 | Kensrue |
| 4,992,881 A | 2/1991 | Tomasek |
| 4,993,159 A * | 2/1991 | Hull ............... B25H 7/045 101/328 |
| 4,996,409 A | 2/1991 | Paton |
| 5,061,841 A | 10/1991 | Richardson |
| 5,103,376 A | 4/1992 | Blonder |
| 5,185,561 A | 2/1993 | Good |
| 5,208,436 A | 5/1993 | Blankenship |
| 5,211,564 A | 8/1993 | Martinez |
| 5,231,928 A | 8/1993 | Phillips |
| 5,243,265 A | 9/1993 | Matsuura |
| 5,281,921 A | 1/1994 | Novak |
| 5,283,418 A | 2/1994 | Bellows |
| 5,302,799 A | 4/1994 | Kennedy |
| 5,304,774 A | 4/1994 | Durheim |
| 5,306,893 A | 4/1994 | Morris |
| 5,320,538 A | 6/1994 | Baum |
| 5,343,011 A | 8/1994 | Fujii |
| 5,380,978 A | 1/1995 | Pryor |
| 5,397,872 A | 3/1995 | Baker |
| 5,404,181 A | 4/1995 | Hung |
| 5,426,732 A | 6/1995 | Boies |
| 5,430,643 A | 7/1995 | Seraji |
| 5,448,405 A | 9/1995 | Clausen |
| 5,464,957 A | 11/1995 | Kidwell |
| 5,508,757 A | 4/1996 | Chen |
| 5,514,846 A | 5/1996 | Cecil |
| 5,517,420 A | 5/1996 | Kinsman |
| 5,521,843 A | 5/1996 | Hashima |
| 5,533,146 A | 7/1996 | Iwai |
| 5,543,863 A | 8/1996 | Lin |
| 5,546,476 A | 8/1996 | Mitaka |
| 5,571,431 A | 11/1996 | Lantieri |
| 5,592,241 A | 1/1997 | Kita |
| 5,617,335 A | 4/1997 | Hashima |
| 5,626,672 A * | 5/1997 | Rossetti ............... B05C 17/0207 118/258 |
| 5,659,479 A | 8/1997 | Duley |
| 5,668,612 A | 9/1997 | Hung |
| 5,674,415 A | 10/1997 | Leong |
| 5,675,229 A | 10/1997 | Thorne |
| 5,681,490 A | 10/1997 | Chang |
| 5,708,253 A | 1/1998 | Bloch |
| 5,709,219 A | 1/1998 | Chen |
| 5,747,042 A | 5/1998 | Choquet |
| 5,823,785 A | 10/1998 | Matherne, Jr. |
| 5,832,139 A | 11/1998 | Batterman |
| 5,845,053 A | 12/1998 | Watanabe |
| 5,856,844 A | 1/1999 | Batterman |
| 5,930,093 A | 7/1999 | Morrissett |
| 5,959,425 A * | 9/1999 | Bieman ............... G05B 19/4207 318/568.13 |
| 5,961,859 A | 10/1999 | Chou |
| 5,973,677 A | 10/1999 | Gibbons |
| 5,999,909 A | 12/1999 | Rakshit |
| 6,003,052 A | 12/1999 | Yamagata |
| 6,018,729 A | 1/2000 | Zacharia |
| 6,019,359 A | 2/2000 | Fly |
| 6,024,273 A | 2/2000 | Ludewig |
| 6,033,226 A | 3/2000 | Bullen |
| 6,039,494 A | 3/2000 | Pearce |
| 6,046,431 A * | 4/2000 | Beattie ............... B23K 9/1274 219/124.34 |
| 6,046,754 A | 4/2000 | Stanek |
| 6,049,059 A | 4/2000 | Kim |
| 6,051,805 A | 4/2000 | Vaidya |
| 6,101,455 A | 8/2000 | Davis |
| 6,107,601 A | 8/2000 | Shimogama |
| 6,115,025 A | 9/2000 | Buxton |
| 6,130,407 A | 10/2000 | Villafuerte |
| 6,136,946 A | 10/2000 | Yao |
| 6,153,848 A | 11/2000 | Nagae |

(56) References Cited

U.S. PATENT DOCUMENTS

| | | |
|---|---|---|
| 6,155,475 A | 12/2000 | Ekelof |
| 6,163,946 A | 12/2000 | Pryor |
| 6,226,395 B1 | 5/2001 | Gilliland |
| 6,236,017 B1 | 5/2001 | Smartt |
| 6,242,711 B1 | 6/2001 | Cooper |
| 6,271,500 B1 | 8/2001 | Hirayama |
| 6,288,359 B1 | 9/2001 | Koch |
| 6,290,740 B1 | 9/2001 | Schaefer |
| 6,301,763 B1 | 10/2001 | Pryor |
| 6,315,186 B1 | 11/2001 | Friedl |
| 6,329,635 B1 | 12/2001 | Leong |
| 6,337,458 B1 | 1/2002 | Lepeltier |
| 6,371,765 B1 | 4/2002 | Wall |
| 6,417,894 B1 | 7/2002 | Goff |
| 6,441,342 B1 | 8/2002 | Hsu |
| 6,445,964 B1 | 9/2002 | White |
| 6,469,752 B1 | 10/2002 | Ishikawa |
| 6,476,354 B1 | 11/2002 | Jank |
| 6,479,793 B1 | 11/2002 | Wittmann |
| 6,506,997 B2 | 1/2003 | Matsuyama |
| 6,516,300 B1 | 2/2003 | Rakshit |
| 6,572,379 B1 | 6/2003 | Sears |
| 6,583,386 B1 | 6/2003 | Ivkovich |
| 6,596,972 B1 | 7/2003 | Di Novo |
| 6,614,002 B2 | 9/2003 | Weber |
| 6,621,049 B2 | 9/2003 | Suzuki |
| 6,622,906 B1 | 9/2003 | Kushibe |
| 6,647,288 B2 | 11/2003 | Madill |
| 6,670,574 B1 | 12/2003 | Bates |
| 6,697,761 B2 | 2/2004 | Akatsuka |
| 6,703,585 B2 | 3/2004 | Suzuki |
| 6,710,298 B2 | 3/2004 | Eriksson |
| 6,728,582 B1 | 4/2004 | Wallack |
| 6,734,393 B1 | 5/2004 | Friedl |
| 6,744,011 B1 | 6/2004 | Hu |
| 6,748,249 B1 | 6/2004 | Eromaki |
| 6,750,428 B2 | 6/2004 | Okamoto |
| 6,753,909 B1 | 6/2004 | Westerman |
| 6,768,974 B1 | 7/2004 | Nanjundan |
| 6,795,068 B1 | 9/2004 | Marks |
| 6,839,049 B1 | 1/2005 | Koizumi |
| 6,857,553 B1 | 2/2005 | Hartman |
| 6,868,726 B2 | 3/2005 | Lemkin |
| 6,910,971 B2 | 6/2005 | Alsenz |
| 6,927,360 B2 | 8/2005 | Artelsmair |
| 6,937,329 B2 | 8/2005 | Esmiller |
| 6,967,635 B2 | 11/2005 | Hung |
| 6,977,357 B2 | 12/2005 | Hsu |
| 6,995,536 B2 | 2/2006 | Challoner |
| 7,015,419 B2 | 3/2006 | Hackl |
| 7,025,053 B1 | 4/2006 | Altamirano |
| 7,032,814 B2 | 4/2006 | Blankenship |
| 7,045,742 B2 | 5/2006 | Feichtinger |
| 7,081,888 B2 | 7/2006 | Cok |
| 7,120,473 B1 | 10/2006 | Hawkins |
| 7,132,617 B2 | 11/2006 | Lee |
| 7,132,623 B2 | 11/2006 | DeMiranda |
| 7,150,047 B2 | 12/2006 | Fergason |
| 7,173,215 B1 | 2/2007 | Kapoor |
| 7,181,413 B2 | 2/2007 | Hadden |
| 7,226,176 B1 | 6/2007 | Huang |
| 7,261,261 B2 | 8/2007 | Ligertwood |
| 7,342,210 B2 | 3/2008 | Fergason |
| 7,358,458 B2 | 4/2008 | Daniel |
| 7,465,230 B2 | 12/2008 | LeMay |
| 7,474,760 B2 | 1/2009 | Hertzman |
| 7,523,069 B1 | 4/2009 | Friedl |
| 7,564,005 B2 | 7/2009 | Cabanaw |
| 7,574,172 B2 | 8/2009 | Clark |
| 7,577,285 B2 | 8/2009 | Schwarz |
| D614,217 S | 4/2010 | Peters |
| 7,698,094 B2 | 4/2010 | Aratani |
| D615,573 S | 5/2010 | Peters |
| 7,766,213 B2 | 8/2010 | Henrikson |
| 7,789,811 B2 | 9/2010 | Cooper |
| 7,813,830 B2 | 10/2010 | Summers |
| 7,826,984 B2 | 11/2010 | Sjostrand |
| 7,831,098 B2 | 11/2010 | Melikian |
| 7,839,416 B2 | 11/2010 | Ebensberger |
| 7,845,560 B2 | 12/2010 | Emanuel |
| D631,074 S | 1/2011 | Peters |
| 7,899,618 B2 | 3/2011 | Ledet |
| 8,019,144 B2 | 9/2011 | Sugihara |
| 8,044,942 B1 | 10/2011 | Leonhard |
| 8,046,178 B2 | 10/2011 | Dai |
| 8,100,694 B2 | 1/2012 | Portoghese |
| 8,110,774 B2 | 2/2012 | Huonker |
| 8,235,588 B2 | 8/2012 | Louban |
| 8,248,324 B2 | 8/2012 | Nangle |
| 8,274,013 B2 | 9/2012 | Wallace |
| 8,393,519 B2 | 3/2013 | Allehaux |
| 8,406,682 B2 | 3/2013 | Elesseily |
| 8,431,862 B2 | 4/2013 | Kachline |
| 8,432,476 B2 | 4/2013 | Ashforth |
| 8,478,382 B2 * | 7/2013 | Burnside ............... A61B 5/06 600/424 |
| 8,502,866 B2 | 8/2013 | Becker |
| 8,512,043 B2 | 8/2013 | Choquet |
| 8,541,746 B2 | 9/2013 | Andres |
| 8,657,605 B2 | 2/2014 | Wallace |
| 8,681,178 B1 | 3/2014 | Tseng |
| 8,686,318 B2 | 4/2014 | Albrecht et al. |
| 8,692,157 B2 | 4/2014 | Daniel |
| 8,698,843 B2 | 4/2014 | Tseng |
| 8,747,116 B2 | 6/2014 | Zboray |
| 8,777,629 B2 | 7/2014 | Kreindl |
| 8,803,908 B2 | 8/2014 | Van Osten |
| 8,834,168 B2 | 9/2014 | Peters |
| 8,851,896 B2 | 10/2014 | Wallace |
| 8,860,760 B2 | 10/2014 | Chen |
| 8,911,237 B2 | 12/2014 | Postlethwaite |
| 8,915,740 B2 | 12/2014 | Zboray |
| 8,946,595 B2 | 2/2015 | Ishida |
| 8,953,033 B2 | 2/2015 | Yamane |
| 8,953,909 B2 | 2/2015 | Guckenberger |
| RE45,398 E | 3/2015 | Wallace |
| 8,987,628 B2 | 3/2015 | Daniel |
| 8,990,842 B2 | 3/2015 | Rowley |
| 8,992,226 B1 | 3/2015 | Leach |
| 9,011,154 B2 | 4/2015 | Kindig |
| 9,012,802 B2 | 4/2015 | Daniel |
| 9,050,678 B2 | 6/2015 | Daniel |
| 9,050,679 B2 | 6/2015 | Daniel |
| 9,089,921 B2 | 7/2015 | Daniel |
| 9,101,994 B2 | 8/2015 | Albrecht |
| 9,196,169 B2 | 11/2015 | Wallace |
| 9,218,745 B2 | 12/2015 | Choquet |
| 9,230,449 B2 | 1/2016 | Conrardy |
| 9,269,279 B2 | 2/2016 | Penrod |
| 9,293,056 B2 | 3/2016 | Zboray |
| 9,293,057 B2 | 3/2016 | Zboray |
| 9,318,026 B2 | 4/2016 | Peters |
| 9,330,575 B2 | 5/2016 | Peters |
| 9,336,686 B2 | 5/2016 | Peters |
| 9,402,122 B2 | 7/2016 | Richardson |
| 9,573,215 B2 | 2/2017 | Pfeifer |
| 9,685,099 B2 | 6/2017 | Boulware |
| 9,724,787 B2 | 8/2017 | Becker |
| 9,773,429 B2 * | 9/2017 | Boulware ............... B23K 9/173 |
| 9,789,603 B2 | 10/2017 | Jacobsen |
| 9,818,312 B2 * | 11/2017 | Zboray ............... G09B 5/02 |
| 10,068,495 B2 * | 9/2018 | Boulware ............... G09B 19/24 |
| 10,427,239 B2 | 10/2019 | Becker |
| 2001/0026445 A1 | 10/2001 | Naghi |
| 2001/0032508 A1 | 10/2001 | Lemkin |
| 2002/0043607 A1 | 4/2002 | Tajima |
| 2002/0071550 A1 | 6/2002 | Pletikosa |
| 2002/0105797 A1 | 8/2002 | Navid |
| 2002/0114653 A1 | 8/2002 | Gatta |
| 2002/0148745 A1 | 10/2002 | Chang |
| 2002/0153354 A1 | 10/2002 | Norby |
| 2003/0011673 A1 | 1/2003 | Eriksson |
| 2003/0092496 A1 | 5/2003 | Alsenz |
| 2003/0172032 A1 | 9/2003 | Choquet |

(56) References Cited

U.S. PATENT DOCUMENTS

| | | |
|---|---|---|
| 2004/0058703 A1 | 3/2004 | Eromaki |
| 2004/0068335 A1 | 4/2004 | Ferla |
| 2004/0069754 A1 | 4/2004 | Bates |
| 2004/0099648 A1 | 5/2004 | Hu |
| 2004/0175684 A1 | 9/2004 | Kaasa |
| 2004/0223148 A1 | 11/2004 | Takemura |
| 2004/0227730 A1 | 11/2004 | Sugihara |
| 2004/0251910 A1 | 12/2004 | Smith |
| 2005/0006363 A1 | 1/2005 | Hsu |
| 2005/0012598 A1 | 1/2005 | Berquist |
| 2005/0016979 A1 | 1/2005 | Stein |
| 2005/0017152 A1 | 1/2005 | Fergason |
| 2005/0073506 A1 | 4/2005 | Durso |
| 2005/0127052 A1 | 6/2005 | Spencer |
| 2005/0133488 A1 | 6/2005 | Blankenship |
| 2005/0135682 A1 | 6/2005 | Abrams |
| 2005/0179654 A1 | 8/2005 | Hawkins |
| 2005/0197115 A1 | 9/2005 | Clark |
| 2005/0207102 A1 | 9/2005 | Russo |
| 2005/0219206 A1 | 10/2005 | Schena |
| 2005/0227635 A1 | 10/2005 | Hawkins |
| 2005/0256611 A1 | 11/2005 | Pretlove |
| 2006/0010551 A1 | 1/2006 | Bishop |
| 2006/0081740 A1 | 4/2006 | Bellavance |
| 2006/0136183 A1 | 6/2006 | Choquet |
| 2006/0151446 A1 | 7/2006 | Schneider |
| 2006/0163228 A1 | 7/2006 | Daniel |
| 2006/0173619 A1 | 8/2006 | Brant |
| 2006/0212169 A1 | 9/2006 | Luthardt |
| 2006/0241432 A1 | 10/2006 | Herline |
| 2007/0038400 A1 | 2/2007 | Lee |
| 2007/0051711 A1 | 3/2007 | Kachline |
| 2007/0056942 A1 | 3/2007 | Daniel et al. |
| 2007/0114215 A1 | 5/2007 | Bill |
| 2007/0115202 A1 | 5/2007 | Kiesenhofer |
| 2007/0164006 A1 | 7/2007 | Burgstaller |
| 2007/0187378 A1 | 8/2007 | Karakas |
| 2007/0188606 A1 | 8/2007 | Atkinson |
| 2007/0209586 A1 | 9/2007 | Ebensberger |
| 2007/0221636 A1 | 9/2007 | Monzyk |
| 2007/0247793 A1 | 10/2007 | Carnevali |
| 2007/0248261 A1 | 10/2007 | Zhou |
| 2007/0264620 A1 | 11/2007 | Maddix |
| 2007/0278196 A1 | 12/2007 | James |
| 2007/0291166 A1 | 12/2007 | Misawa |
| 2008/0004633 A1 | 1/2008 | Arata |
| 2008/0030631 A1 | 2/2008 | Gallagher |
| 2008/0038702 A1 | 2/2008 | Choquet |
| 2008/0061113 A9 | 3/2008 | Seki |
| 2008/0077422 A1 | 3/2008 | Dooley |
| 2008/0124698 A1 | 5/2008 | Ebensberger |
| 2008/0128395 A1 | 6/2008 | Aigner |
| 2008/0128400 A1 | 6/2008 | Michels |
| 2008/0149602 A1 | 6/2008 | Lenzner |
| 2008/0149608 A1 | 6/2008 | Albrecht |
| 2008/0158502 A1 | 7/2008 | Becker |
| 2008/0168290 A1 | 7/2008 | Jobs |
| 2008/0169277 A1 | 7/2008 | Achtner |
| 2008/0234960 A1 | 9/2008 | Byington |
| 2008/0314887 A1 | 12/2008 | Stoger |
| 2009/0005728 A1 | 1/2009 | Weinert |
| 2009/0057285 A1 | 3/2009 | Bashore |
| 2009/0057286 A1 | 3/2009 | Ihara |
| 2009/0109128 A1 | 4/2009 | Nangle |
| 2009/0146359 A1 | 6/2009 | Canfield |
| 2009/0152251 A1 | 6/2009 | Dantinne |
| 2009/0161212 A1 | 6/2009 | Gough |
| 2009/0173726 A1 | 7/2009 | Davidson |
| 2009/0189974 A1 | 7/2009 | Deering |
| 2009/0190826 A1 | 7/2009 | Tate et al. |
| 2009/0200281 A1 | 8/2009 | Hampton |
| 2009/0200282 A1 | 8/2009 | Hampton |
| 2009/0230107 A1 | 9/2009 | Ertmer |
| 2009/0231423 A1 | 9/2009 | Becker |
| 2009/0236325 A1 | 9/2009 | Gozalbo |
| 2009/0249606 A1 | 10/2009 | Diez |
| 2009/0283021 A1 | 11/2009 | Wong |
| 2009/0298024 A1 | 12/2009 | Batzler |
| 2009/0313549 A1 | 12/2009 | Casner |
| 2009/0323121 A1 | 12/2009 | Valkenburg |
| 2010/0020483 A1 | 1/2010 | Ma |
| 2010/0048273 A1 | 2/2010 | Wallace |
| 2010/0062405 A1 | 3/2010 | Zboray |
| 2010/0062406 A1 | 3/2010 | Zboray |
| 2010/0088793 A1 | 4/2010 | Ghisleni |
| 2010/0123664 A1 | 5/2010 | Shin |
| 2010/0133247 A1 | 6/2010 | Mazumder |
| 2010/0145520 A1 | 6/2010 | Gerio |
| 2010/0201803 A1 | 8/2010 | Melikian |
| 2010/0207620 A1 | 8/2010 | Gies |
| 2010/0224610 A1 | 9/2010 | Wallace |
| 2010/0238119 A1 | 9/2010 | Dubrovsky |
| 2010/0245273 A1 | 9/2010 | Hwang |
| 2010/0283588 A1 | 11/2010 | Gomez |
| 2010/0291313 A1 | 11/2010 | Ling |
| 2010/0314362 A1 | 12/2010 | Albrecht |
| 2011/0000892 A1 | 1/2011 | Mueller |
| 2011/0006047 A1 | 1/2011 | Penrod |
| 2011/0091846 A1 | 4/2011 | Kreindl |
| 2011/0092828 A1 | 4/2011 | Spohn |
| 2011/0114615 A1 | 5/2011 | Daniel |
| 2011/0117527 A1 | 5/2011 | Conrardy |
| 2011/0154699 A1* | 6/2011 | Walsh ................... B65C 3/166 |
| | | 40/306 |
| 2011/0176720 A1 | 7/2011 | VanOsten |
| 2011/0183304 A1 | 7/2011 | Wallace |
| 2011/0198329 A1 | 8/2011 | Davidson |
| 2011/0220616 A1 | 9/2011 | Mehn |
| 2011/0220619 A1 | 9/2011 | Mehn |
| 2011/0240605 A1 | 10/2011 | Takayama |
| 2011/0249090 A1 | 10/2011 | Moore |
| 2011/0284508 A1 | 11/2011 | Miura |
| 2011/0285290 A1 | 11/2011 | Griffin |
| 2011/0286005 A1 | 11/2011 | Yamamoto |
| 2011/0290765 A1 | 12/2011 | Albrecht |
| 2011/0311297 A1* | 12/2011 | Cazzola ............ B05C 17/0242 |
| | | 401/147 |
| 2011/0313731 A1 | 12/2011 | Vock |
| 2012/0007748 A1 | 1/2012 | Forgues |
| 2012/0037600 A1 | 2/2012 | Katoh |
| 2012/0048838 A1 | 3/2012 | Ishida |
| 2012/0072021 A1 | 3/2012 | Walser |
| 2012/0077174 A1 | 3/2012 | DePaul |
| 2012/0105476 A1 | 5/2012 | Tseng |
| 2012/0113512 A1 | 5/2012 | Tsanev |
| 2012/0122062 A1 | 5/2012 | Yang |
| 2012/0175834 A1 | 7/2012 | Hamm |
| 2012/0180180 A1 | 7/2012 | Steve |
| 2012/0188365 A1 | 7/2012 | Stork |
| 2012/0189993 A1* | 7/2012 | Kindig .................. G09B 19/24 |
| | | 434/234 |
| 2012/0205359 A1 | 8/2012 | Daniel |
| 2012/0231894 A1 | 9/2012 | Nicora |
| 2012/0248080 A1 | 10/2012 | Hutchison |
| 2012/0248083 A1 | 10/2012 | Garvey |
| 2012/0291172 A1 | 11/2012 | Wills |
| 2012/0298640 A1* | 11/2012 | Conrardy ................ B23K 9/32 |
| | | 219/130.01 |
| 2012/0323496 A1 | 12/2012 | Burroughs |
| 2013/0040270 A1 | 2/2013 | Albrecht |
| 2013/0064427 A1 | 3/2013 | Picard et al. |
| 2013/0081293 A1 | 4/2013 | Delin |
| 2013/0119037 A1 | 5/2013 | Daniel |
| 2013/0178952 A1 | 7/2013 | Wersborg |
| 2013/0182070 A1 | 7/2013 | Peters |
| 2013/0183645 A1 | 7/2013 | Wallace |
| 2013/0189656 A1 | 7/2013 | Zboray |
| 2013/0189657 A1 | 7/2013 | Wallace |
| 2013/0189658 A1 | 7/2013 | Peters |
| 2013/0200882 A1 | 8/2013 | Almalki |
| 2013/0203029 A1 | 8/2013 | Choquet |
| 2013/0206741 A1* | 8/2013 | Pfeifer ................ B23K 9/0956 |
| | | 219/130.01 |
| 2013/0209976 A1 | 8/2013 | Postlethwaite |

(56) References Cited

U.S. PATENT DOCUMENTS

| | | |
|---|---|---|
| 2013/0230832 A1 | 9/2013 | Peters |
| 2013/0252214 A1 | 9/2013 | Choquet |
| 2013/0256289 A1 | 10/2013 | Knoener |
| 2013/0262000 A1 | 10/2013 | Hutchison |
| 2013/0264315 A1 | 10/2013 | Hung |
| 2013/0264322 A1 | 10/2013 | Bornemann |
| 2013/0265416 A1 | 10/2013 | Enyedy |
| 2013/0288211 A1 | 10/2013 | Patterson |
| 2013/0326842 A1 | 12/2013 | Pearson |
| 2014/0008088 A1 | 1/2014 | Chellew |
| 2014/0017642 A1 | 1/2014 | Postlethwaite |
| 2014/0042135 A1 | 2/2014 | Daniel |
| 2014/0042137 A1 | 2/2014 | Daniel |
| 2014/0069899 A1 | 3/2014 | Mehn |
| 2014/0131337 A1 | 5/2014 | Williams |
| 2014/0134579 A1 | 5/2014 | Becker |
| 2014/0134580 A1 | 5/2014 | Becker |
| 2014/0184496 A1 | 7/2014 | Gribetz |
| 2014/0220522 A1 | 8/2014 | Peters |
| 2014/0234813 A1 | 8/2014 | Peters |
| 2014/0263224 A1 | 9/2014 | Becker |
| 2014/0263227 A1 | 9/2014 | Daniel |
| 2014/0267773 A1 | 9/2014 | Jeung |
| 2014/0272835 A1 | 9/2014 | Becker |
| 2014/0272836 A1 | 9/2014 | Becker |
| 2014/0272837 A1 | 9/2014 | Becker |
| 2014/0272838 A1 | 9/2014 | Becker |
| 2014/0315167 A1 | 10/2014 | Kreindl |
| 2014/0322684 A1 | 10/2014 | Wallace |
| 2014/0346158 A1 | 11/2014 | Matthews |
| 2014/0346163 A1 | 11/2014 | Rajagopalan |
| 2014/0346793 A1 | 11/2014 | DeStories |
| 2014/0374396 A1 | 12/2014 | Luo |
| 2015/0056584 A1 | 2/2015 | Boulware |
| 2015/0056585 A1 | 2/2015 | Boulware |
| 2015/0072323 A1 | 3/2015 | Postlethwaite |
| 2015/0122781 A1 | 5/2015 | Albrecht |
| 2015/0154884 A1 | 6/2015 | Salsich |
| 2015/0170539 A1 | 6/2015 | Barrera |
| 2015/0190875 A1 | 7/2015 | Becker |
| 2015/0190876 A1 | 7/2015 | Becker |
| 2015/0190887 A1 | 7/2015 | Becker |
| 2015/0190888 A1 | 7/2015 | Becker |
| 2015/0194072 A1 | 7/2015 | Becker |
| 2015/0194073 A1 | 7/2015 | Becker |
| 2015/0209887 A1 | 7/2015 | DeLisio |
| 2015/0235565 A1 | 8/2015 | Postlethwaite |
| 2015/0248845 A1 | 9/2015 | Postlethwaite |
| 2015/0325153 A1 | 11/2015 | Albrecht |
| 2015/0328710 A1 | 11/2015 | Kachline |
| 2015/0352653 A1 | 12/2015 | Albrecht |
| 2015/0375323 A1 | 12/2015 | Becker |
| 2015/0375324 A1 | 12/2015 | Becker |
| 2015/0375327 A1 | 12/2015 | Becker |
| 2015/0379894 A1 | 12/2015 | Becker |
| 2016/0049085 A1 | 2/2016 | Beeson |
| 2016/0093233 A1* | 3/2016 | Boulware ............ B23K 9/0026 219/136 |
| 2016/0125592 A1 | 5/2016 | Becker |
| 2016/0125593 A1 | 5/2016 | Becker |
| 2016/0125594 A1 | 5/2016 | Becker |
| 2016/0125653 A1 | 5/2016 | Denis |
| 2016/0125761 A1 | 5/2016 | Becker |
| 2016/0125762 A1 | 5/2016 | Becker |
| 2016/0125763 A1 | 5/2016 | Becker |
| 2016/0125764 A1 | 5/2016 | Becker |
| 2016/0203734 A1 | 7/2016 | Boulware |
| 2016/0203735 A1 | 7/2016 | Boulware |
| 2016/0236303 A1 | 8/2016 | Matthews |
| 2016/0260261 A1 | 9/2016 | Hsu |
| 2016/0267806 A1 | 9/2016 | Hsu |
| 2016/0288236 A1 | 10/2016 | Becker |
| 2016/0358503 A1 | 12/2016 | Batzler |
| 2017/0148352 A1 | 5/2017 | Becker |
| 2017/0165776 A1 | 6/2017 | Becker |
| 2017/0169729 A1 | 6/2017 | Becker |

FOREIGN PATENT DOCUMENTS

| | | |
|---|---|---|
| CA | 2549553 | 7/2004 |
| CA | 2554498 | 4/2006 |
| CN | 1264822 | 8/2000 |
| CN | 100371672 | 12/2004 |
| CN | 1841321 | 10/2006 |
| CN | 1866317 | 11/2006 |
| CN | 1909020 | 2/2007 |
| CN | 101218060 | 7/2008 |
| CN | 201181527 | 1/2009 |
| CN | 101502906 | 8/2009 |
| CN | 101770710 | 7/2010 |
| CN | 102049595 | 5/2011 |
| CN | 102083580 | 6/2011 |
| CN | 102165504 | 8/2011 |
| CN | 102165505 | 8/2011 |
| CN | 102298858 | 12/2011 |
| CN | 202200202 | 4/2012 |
| CN | 102441737 | 5/2012 |
| CN | 103038804 | 4/2013 |
| CN | 202877704 | 4/2013 |
| CN | 103071909 | 5/2013 |
| CN | 103143810 | 6/2013 |
| CN | 103392089 | 11/2013 |
| CN | 203276641 | 11/2013 |
| CN | 103831553 | 6/2014 |
| CN | 203778997 | 8/2014 |
| DE | 202010011064 | 10/2010 |
| DE | 102010038902 | 2/2012 |
| EP | 0323277 A2 | 7/1989 |
| EP | 0878263 | 11/1998 |
| EP | 0963744 A1 | 12/1999 |
| EP | 1029306 | 8/2000 |
| EP | 1295195 | 6/2001 |
| EP | 1573699 | 9/2005 |
| EP | 1797545 | 6/2007 |
| EP | 1864744 | 12/2007 |
| EP | 2022592 | 2/2009 |
| EP | 2415560 | 2/2014 |
| ES | 2438440 | 1/2014 |
| FR | 1456780 | 7/1966 |
| FR | 2827066 | 1/2003 |
| GB | 2454232 A | 5/2009 |
| JP | H11146387 | 5/1999 |
| JP | 2000298427 | 10/2000 |
| JP | 2002317557 | 10/2002 |
| JP | 2004181493 | 7/2004 |
| JP | 2007021542 | 2/2007 |
| JP | 2009125790 | 6/2009 |
| KR | 100876425 B1 | 12/2008 |
| KR | 20110000152 | 1/2011 |
| SU | 846203 | 7/1981 |
| SU | 972552 | 11/1982 |
| SU | 1324050 | 7/1987 |
| SU | 1354234 A1 | 11/1987 |
| SU | 1489933 A1 | 6/1989 |
| SU | 1638145 | 3/1991 |
| WO | 9958286 | 11/1999 |
| WO | 03019349 | 1/2003 |
| WO | 2004057554 | 7/2004 |
| WO | 2005102230 A1 | 11/2005 |
| WO | 2005110658 A2 | 11/2005 |
| WO | 2006004427 | 1/2006 |
| WO | 2006034571 | 4/2006 |
| WO | 2007009131 | 1/2007 |
| WO | 2007044135 | 4/2007 |
| WO | 2008076777 | 6/2008 |
| WO | 2009022443 | 2/2009 |
| WO | 2009053829 | 4/2009 |
| WO | 2009060231 | 5/2009 |
| WO | 2009092944 | 7/2009 |
| WO | 2009146359 | 12/2009 |
| WO | 2010000003 | 1/2010 |
| WO | 2010020867 | 2/2010 |

(56) References Cited

FOREIGN PATENT DOCUMENTS

| WO | 2010020869 | 2/2010 |
|---|---|---|
| WO | 2010020870 | 2/2010 |
| WO | 2010111722 | 10/2010 |
| WO | 2011112493 | 9/2011 |
| WO | 2011150165 | 12/2011 |
| WO | 2012036710 | 3/2012 |
| WO | 2012137060 | 10/2012 |
| WO | 2013138831 | 1/2013 |
| WO | 2013023012 | 2/2013 |
| WO | 2013061518 | 5/2013 |
| WO | 2013186413 | 12/2013 |
| WO | 2014007830 | 1/2014 |
| WO | 2014074296 | 5/2014 |
| WO | 2014074297 | 5/2014 |
| WO | 2014140719 | 9/2014 |

OTHER PUBLICATIONS

Aiteanu Dorin "Virtual and Augmented Reality Supervisor fora New Welding Helmet" Nov. 15, 2005, pp. 1-150 (Year: 2005).*
"Soldamatic: Augmented Training Technology for Welding," Seabery Augmented Training Technology, Seabery Soluciones, 2011.
Hashimoto, Nobuyoshi et al., "Training System for Manual Arc Welding by Using Mixed Reality: Reduction of Position-Perception Error of Electrode Tip," Journal of the Japan Society for Precision Engineering, vol. 72, pp. 249-253, 2006.
Hodgson, et al. "Virtual Reality in the Wild: A Self-Contained and Wearable Simulation System." IEEE Virtual Reality, Mar. 4-8, 2012, Orange County, CA USA.
International Search Report for PCT application No. PCT/US2015/037410, dated Nov. 6, 2015, 10 pgs.
International Search Report from PCT application No. PCT/US2014/018103, dated Jun. 30, 2014, 13 pgs.
International Search Report from PCT application No. PCT/US2015/043370, dated Dec. 4, 2015, 12 pgs.
International Search Report from PCT application No. PCT/US2015/058563, dated Jan. 29, 2016, 13 pgs.
International Search Report from PCT application No. PCT/US2015/058567, dated May 6, 2016, 15 pgs.
International Search Report from PCT application No. PCT/US2015/058569, dated Feb. 10, 2016, 12 pgs.
International Search Report from PCT application No. PCT/US2015/058660, dated Feb. 2, 2016, 14 pgs.
International Search Report from PCT application No. PCT/US2015/058664, dated Apr. 25, 2016, 17 pgs.
International Search Report from PCT application No. PCT/US2015/058666, dated Feb. 1, 2016, 11 pgs.
International Search Report from PCT application No. PCT/US2015/058667, dated Feb. 5, 2016, 14 pgs.
International Search Report from PCT application No. PCT/US2016/023612, dated Jul. 18, 2016, 11 pgs.
Kobayashi, Kazuhiko et al., "Modified Training System for Manual Arc Welding by Using Mixed Reality and Investigation of Its Effectiveness," Journal of the Japan Society for Precision Engineering, vol. 70, pp. 941-945, 2004.
Kobayashi, Kazuhiko et al., "Simulator of Manual Metal Arc Welding with Haptic Display," Chiba University, ICAT 2001, Dec. 2001.
Kobayashi, Kazuhiko et al., "Skill Training System of Manual Arc Welding by Means of Face-Shield HMD and Virtual Electrode," Chiba University, Japan, R. Nakatsu et al. (eds.), Entertainment Computing, Springer Science+Business Media, New York, 2003.
VRTEX 360 Operator's Manual, Lincoln Electric, Oct. 2012.
VRTEX 360, Lincoln Electric, Dec. 2009.
Weld Training Solutions, Realweld, The Lincoln Electric Company, Jul. 2015.
American Welding Society's Virtual Welding Trailer to Debut at FABTECH Careers in Welding Trailer Appeals to New Generation of Welders, Miami, Florida, Nov. 3, 2011.
American Welding Society Forms: typical Procedure Qualification Record and Welding Procedure Specification forms.
ArcSentry Weld Monitoring System, Version 3, Users Manual, Native American Technologies, Golden, CO, Dec. 10, 1999.
Arvika Forum Vorstellung Projeckt PAARA, BMW Group Virtual Reality Center, Nuernberg, 2003.
Ascension Technology Corporation: Tracking 3D Worlds: http://ascension-tech.com/, Dec. 1996.
Barckhoff, J.R.; "Total Welding Managemet," American Welding Society, 2005.
Bender Shipbuilding and Repair, Co., "Virtual Welding—A Low Cost Virtual Reality Welder Training System", Technical Proposal, Jan. 23, 2008.
Byrd, Alex Preston, "Identifying the effects of human factors and training methods on a weld training program" (2014). Graduate Theses and Dissertations. Paper 13991.
Central Welding Supply http://www.welders-direct.com/ Feb. 29, 2000.
Choquet, Claude, ARC+: Today's Virtual Reality Solution for Welders, Jun. 1, 2008.
Choquet, Claude, ARC+& ARC PC Welding Simulators: Teach Welders with Virtual Interactive 3D Technologies; Jul. 2010.
Cybernetics: Enhancing Human Performance found in the DTIC Review dated Mar. 2001, p. 186/19. See http://www.dtic.mil/dtic/tr/fulltext/u2/a385219.pdf.
Echtler, Florian, Fabian Stuurm, Kay Kindermann, Gudrun Klinker, Joachim Stilla, Jorn Trilk, Hesam Najafi, "The Intelligent Welding Gun: Augmented Reality for Experimental Vehicle Construction," Virtual and Augmented Reality Applications in Manufacturing, Ong S.K and Nee A.Y.C., eds., Springer Verlag, 2003, pp. 1-27.
Evaluating Two Novel Tactile Feedback Devices, by Thomas Hulin, Phillipp Kremer, Robert Scheibe, Simon Schaetzle and Carsten Preusche presented at the 4th International Conference on Enactive Interfaces, Grenoble, France, Nov. 19-22, 2007.
EWI, "EWI ArcCheck," marketing brochure, Columbus, Ohio.
EWI, "EWI SkillBuilder," marketing brochure, Columbus, Ohio.
Fast, Kenneth, Jerry Jones, and Valerie Rhoades; "Virtual Welding—A Low Cost Virtual Reality Welder Training System Phase II," National Shipbuilding Research Program (NSRP), NSRP ASE Technology Investment Agreement No. 2010-357, Feb. 29, 2012, http://www.nsrp.org/3-RA-Panel_Final_Reports/FY08_Virtual_Welder_Final_Report.pdf.
Fast et al., Virtual Training for Welding, Proceedings of the Third IEEE and ACM International Symposium on Mixed and Augmented Reality (ISMAR 2004); 0-7695-2191-6/04; 2004.
Fite-Georgel, Pierre; "Is there a Reality in Industrial Augmented Reality?" 10th IEEE International Symposium on Mixed and Augmented Reality (ISMAR), 2011.
Fridenfalk et al., Design and Validation of a Universal 6D Seam Tracking System in Robotic Welding Based on Laser Scanning, Industrial Robotics: Programming, Simulation, and Application, ISBN 3-86611-286-6, pp. 702, ARS/pIV, Germany, Dec. 2006, edited by Kin Huat.
Fronius "The Ghost": http://www.fronius.com/cps/rde/xchg/SID-3202EAB7-AE082518/fronius_interational/hs.xsl/79_15490_ENG_HTML.htm; 2006.
Fronius International GmbH—Focus on Welding—Fronius Virtual Welding; http://www.fronius.com/cps/rde/xchg/SID-99869147-0110E322/fronius_intenational/hs.xsl/79_15490_ENG_HML.htm; 2006.
Fronius Perfect Welding; 06,3082, EN v01 2010 aw05; Virtual Welding—The training method of the future; Feb. 20, 2012.
ftp://www.hitl.washington.edu/pub/scivw/publications/IDS-pdf/HAPTIC1.PDF, (University of Washington): Table 11, Tactile Feedback Actuator Technologies, p. 119, below the table is a. Based on Hasser (1995, 1996).
GAWDA—Welding & Gases Today Online GAWDA Media Blog; Will Games Turn Welding into a Virtual Market? Friday, Dec. 2, 2011; http://www.weldingandgasestoday.org/blogs/Devin-OToole/index.php/ta . . . .
Gundersen, O., et al. "The Use of an Integrated Multiple Neural Network Structure for Simultaneous Prediction of Weld Shape, Mechanical Properties, and Distortion in 6063-T6 and 6082-T6

(56) References Cited

OTHER PUBLICATIONS

Aluminum Assemblies", Mathematical Modelling of Weld Phenomena, vol. 5, Maney Publishing, 2001.
Haptic Feedback for Virtual Reality by Grigore C. Burdea dated 1996.
Hemez, Francois M., Scott W. Doebling, "Uncertainty, Validation of Computer Models an the Myth of Numerical Predictability," Engineering Analysis Group (ESA-EA), Los Alamos National Laboratory, dated 2004.
Hillers, B, and Axel Graeser, "Direct welding arc observation withouth harsh flicker," FABTECH International and AWS Welding Show, 2007.
Hillers, B, and Axel Graeser, "Real time Arc-Welding Video Observation System," 62nd International Conference of IIW, Jul. 12-17, 2009, Singapore, 2009.
Hillers, B., et al.; "TEREBES: Welding Helmet with AR Capabilites," Institute of Automation, University of Bremen, and Institute of Industrial Engineering and Ergonomics, RWTH Aachen Universty, 2004.
Hillers, Bernd, Dorin Aiteanu, Axel Graser, "Augmented Reality—Helmet for the Manual Welding Process," Virtual and Augmented Reality Applications in Manufacturing, Institute of Automation, Universtity of Bremen, 2004.
Himperich, Frederick, "Applications in Augmented Reality in the Automotive Industry," Fachgebiet Augmented Reality, Department of Informatics, Jul. 4, 2007, p. 1-21.
http://www.123arc.com "Simulation and Certification"; 2000.
Image from SimWelder.com—R-V's Welder Training Goes Virtual, www.rvii.com/PDF/simwelder.pdf; Jan. 2010.
IMPACT Spring 2012 vol. 12, No. 2, Undergraduate Research in Information Technology Engineering, University of Virginia School of Engineering & Applied Science; 2012.
IMPACT Welding: miscellaneous examples from current and archived website, trade shows, etc. See, e.g., http://www.impactwelding.com.
Integrated Microelectromechanical Gyrosopes; Journal of Aerospace Engineering, Apr. 2003 pp. 65-75 (p. 65) by Huikai Xie and Garry K. Fedder.
International Search Report for PCT application No. PCT/US2009/045436, dated Nov. 9, 2009, 3 pgs.
International Search Report for PCT application No. PCT/US2012/050059 dated Nov. 27, 2012, 16 pgs.
International Search Report for PCT application No. PCT/US2013/038371 dated Jul. 31, 2013, 8 pgs.
International Search Report for PCT application No. PCT/US2013/066037 dated Mar. 11, 2014, 10 pgs.
International Search Report for PCT application No. PCT/US2013/066040 dated Mar. 11, 2014, 12 pgs.
International Search Report for PCT application No. PCT/US2014/018107, dated Jun. 2, 2014, 3 pgs.
International Search Report for PCT application No. PCT/US2014/018109, dated Jun. 2, 2014, 4 pgs.
International Search Report for PCT application No. PCT/US2014/018113, dated Jun. 2, 2014, 3pgs.
International Search Report for PCT application No. PCT/US2014/018114, dated Jun. 2, 2014, 4 pgs.
International Search Report from PCT application No. PCT/US2014/065498, dated May 11, 2015, 13 pgs.
International Search Report from PCT application No. PCT/US2014/065506, dated Jun. 26, 2015, 16 pgs.
International Search Report from PCT application No. PCT/US2014/065512, dated Jun. 8, 2015, 17 pgs.
International Search Report from PCT application No. PCT/US2014/065525, dated Jul. 23, 2015, 16 pgs.
International Search Report from PCT application No. PCT/US2015/037439, dated Nov. 3, 2015, 12 pgs.
International Search Report from PCT application No. PCT/US2015/037440, dated Nov. 3, 2015, 12 pgs.
International Search Report from PCT application No. PCT/US2015/039680, dated Sep. 23, 2015, 12 pgs.
International Search Report from PCT No. PCT/US2014/067951, dated Feb. 24, 2015, 10 pgs.
Jo et al., Visualization of Virtual Weld Beads, VRST 2009, Kyoto, Japan, Nov. 18-20, 2009; Electronics and Telecommunications Research Institute (ETRI) ACM 978-1 60558-869-8/09/0011.
Kiwinakiful; Holographic TV coming 2012 (as seen on BBC); http://www.youtube.com/watch?v=Ux6aD6vE9sk&feature=related, Jul. 2, 2011.
Kooima, Robert; Kinect +3D TV=Virtual Reality; http://www.youtube.com/watch?v=2MX1RinEXUM&feature=related, Feb. 26, 2011.
Leap Motion; https://www.leapmotion.com/, May 2012.
Lincoln Electric VRTEX Virtual Reality Arc Welding Trainer; http://www.lincolnelectric.com/en-us/equipment/training-equipment/pages/vrtex360.aspx; 1999.
Maccormick, John; How does the Kinect work?; http://users.dickinson.edu/~jmac/selected-talks/kinect.pdf, Dec. 1, 2011.
NAMeS, Native American Technologies Weld Measuring Software, Users Guide, 2000.
National Science Foundation—Where Discoveries Begin—Science and Engineering's Most Powerful Statements Are Not Made From Words Alone—Entry Details for NSF International Science & Engineering Visualization Challenge, Public Voting ended on Mar. 9, 2012; Velu the welder by Muralitharan Vengadasalam—Sep. 30, 2011; https://nsf-scivis.skild.com/skild2/NationalScienceFoundation/viewEntryDetail.action?pid . . . .
Native American Technologies, "ArcDirector Weld Controller" web page, http://web.archive.org/web/20020608125127/http://www.natech-inc.com/arcdirector/index.html, published Jun. 8, 2002.
Native American Technologies, "ArcSentry Weld Quality Monitoring System" web page, http://web.archive.org/web/20020608124903/http://www.natech-inc.com/arcsentry1/index.html, published Jun. 8, 2002.
Native American Technologies, "Official NAMeS Web Site" web page, http://web.archive.org/web/20020903210256/http://www.natech-inc.com/names/names.html, published Sep. 3, 2002.
Native American Technologies, "P/NA.3 Process Modelling and Optimization" web pages, http://web.archive.org/web/20020608125619/http://www.natech-inc.com/pna3/index.html, published Jun. 8, 2002.
Native American Technologies, "Process Improvement Products" web page, http://web.archive.org/web/20020608050736/http://www.natech-inc.com/products.html, published Jun. 8, 2002.
Natural Point, Trackir; http://www.naturalpoint.com/trackir/, Dec. 2003.
Numerical Simulation F Arc Welding Process and its Application Dissertation for Ohio State University by Min Hyun Cho, M.S. 2006: See Internet as this document is security protected) ohttps://etd.ohiolink.edu/ap:0:0:APPLICATION_PROCESS=DOWNLOAD_ETD_SUB_DOC_ACCNUM:::F1501 Id:osu1155741113, attachment.
NZ Manufacturer Game promotes welding trade careers; http://nzmanufacturer.co.nz/2011/11/gme-promotes-welding-trade-careers/ . . . Compentenz Industry Training; www.competenz.org.nz; Game promotes welding trade careers, Nov. 7, 2011.
OptiTrack: Motion Capture Systems: http://www.naturalpoint.com/optitrack/, Mar. 2005.
Penrod, Matt; "New Welder Training Tools," EWI PowerPoint presentation, 2008.
PhaseSpace: Optical Motion Capture: http://phasespace.com/, 2009.
Playstation; Move Motion Controller: http://us.playstation.com/ps3/playstation-move/, Mar. 2010.
Polhemus: Innovation in Motion: http://polhemus.com/?page=researchandtechnology, 1992.
Porter, Nancy C., Edison Welding Institute; J. Allan Cote, General Dynamics Electrict Boat; Timothy D. Gifford, VRSim; and Wim Lam, FCS Controls—Virtual Reality Welder Training—Project No. S1051 Navy Man Tech Program; Project Review for Ship Tech 2005,—Mar. 1, 2005, Biloxi, MS, http://www.nsrp.org/6-Presentations/WD/Virtual_Welder.pdf.
Porter, Nancy C., Edison Welding Institute; J.Allan Cote, General Dynamics Electric Boat; Timoty D. Gifford, VRSim; and Wim Lam, FCS Controls—Virtual Reality Welder Training—Session 5; Joining Technologies for Naval Applications; 2007.

(56) References Cited

OTHER PUBLICATIONS

Porter et al, EWI-CRP Summary Report SR0512, Jul. 2005—Virtual Reality Welder Training.
Quebec International, May 28, 2008 "Video Game" Technology to Fill Growing Need; http://www.mri.gouv.qc.ca/portail/scripts/actualities/viewnew.sap?NewID=5516.
Ryu, Jonghyun, Jaehoon Jung, Seojoon Kim, and Seungmoon Choi, "Perceptually Transparent Vibration Rendering Using a Vibration Motor for Haptic Interaction," 16 IEEE International Conference on Robot & Human Interactive Communication, Jeju, Korea, Aug. 26-29, 2007.
Sandor, Christian, Gudrun Klinker, "PAARTI: Development of an Intelligent Welding Gun for BMW," PIA 2003, Tokyo, Japan, Technical University of Munich Department of Informatics, Oct. 7, 2003.
Sandor, Christian, Gudrun Klinker; "Lessons Learned in Designing Ubiquitous Augmented Reality User Interfaces," Emerging Technologies of Augmented Reality Interfaces, Eds. Haller, M, Billinghurst, M., and Thomas, B., Idea Group Inc., 2006.
ShotOfFuel; Wii Head Tracking for 3D, http://www.youtube.com/watch?v=1x5ffF-0Wr4, Mar. 19, 2008.
Stone, R. T., K. Watts, and P. Zhong, "Virtual Reality Integrated Welder Training, Welding Research," Welding Journal, vol. 90, Jul. 2011, pp. 136-s-141-s, https://app.aws.org/wj/supplement/wj201107_s136.pdf.
TCS News & Events: Press Release: TCS wins the "People Choice" award from National Science Foundation, USA, pp. 1-6; Press Release May 21, 2012; http://www.tsc.com/news_events/press_releases/pages/TCS_People_Choice_award_Natio . . . .
TeachWELD: Welding Simulator/Hands-On Learning for Welding: http://realityworks.com/products/teachweld-welding-simulator; 2012.
Terebes; miscellaneous examples from http://www.terebes.uni-bremen.de.
The Rutgers Master II—New Design Force-Feedback Glove by Mourad Bouzit, Member, IEEE,Grigore Burdea, Senior Member, IEEE, George Popescu, Member, IEEE, and Rares Bolan, Student Member, found in IEEE/ASME Transactions on Mechatronics, vol. 7, No. 2, Jun. 2002.
thefabricator.com—Arc Welding Article; Heston, Tim, Virtual welding—Training in a virtual environment gives welding students a leg up—Mar. 11, 2008.
Tschurner, Petra, Hillers, Bernd, and Graeser, Axel; "A Concept for the Application of Augmented Realty in Manual Gas Metal Arc Welding," Proceedings of the International Symposium on Mixed and Augmented Reality, 2002.
Vicon: Motion Capture Systems: http://vicon.com/, Dec. 1998.
Virtual Reality Training Manual Module 1—Training Overview—A Guide for Gas Metal Arc Welding—EWI 2006.
Welding Journal, American Welding Society, Nov. 2007, https://app.aws.org/wj/2007/11/WJ_2007_11.pdf.
White, S., et al., "Low-Cost Simulated MIG Welding for Advancement in Technical Training," Virtual Reality, 15, 1, 69-81, Mar. 2011. ISSN:13594338 [Retrieved from EBSCOhost, Jun. 15, 2015].
"Low Cost Virtual Reality Welding Training System," NSRP Joint Panel Meeting, Apr. 21, 2010, http://www.nsrp.org/6-Presentations/Joint/042110_Low_Cost_Virtual_Reality_Welder_Training_System_Fast.pdf.
"NJC Technology Displayed at ShipTech 2005", Welding Journal, vol. 84, No. 3, Mar. 2005, p. 54, https://app.aws.org/w/r/www/wj/2005/03/WJ_2005_03.pdf.
"Sheet Metal Conference XXII," Conference Program, American Welding Society, May 2006, Detroit.
"Virtual Reality Program to Train Welders for Shipbuilding", American Welding Society, Navy Joining Center, https://app.aws.org/wj/2004/04/052/.
"Virtual Reality Welder Training Initiatives: Virtual Welding Lab Pilot," Paul D. Camp Community College, Advanced Science & Automation Corporation, Northrop Grumman Newport News, Nov. 22, 2006, http://www.nsrp.org/6-Presentations/WD/103106_Virtual_Reality_Welder.pdf.
"Virtual Welding: A Low Cost Virtual Reality Welder Training System," NSRP ASE, Feb. 19, 2009, http://www.nsrp.org/6-Presentations/WD/020409_Virtual_Welding_Wilbur.pdf.
"Virtual Welding—A Low Cost Virtual Reality Welder Training System", Interim Status Report # 4, Technology Investment Agreement 2008-600, Feb. 18, 2009, http://www.nsrp.org/3-Key_Deliverables/FY08_Low-Cost_Virtual_Reality_Welder_Trainer/FY08_Low-Cost_Virtual_Reality_Welder_Trainer-Interim2.pdf.
"Vision for Welding Industry," American Welding Society, Apr. 22, 1999, http://www.aws.org/library/doclib/vision.pdf.
"Welding in Defense Industy," American Welding Society conference schedule, 2004. https://app.aws.org/conferences/defense/live_index.html.
"Welding Technology Roadmap," prepared by Energetics, Inc., Columbia, MD, in cooperation with The American Welding Society and the Edison Welding Institute, Sep. 2000.
123arc.com—"Weld into the future"; 2000.
Advance Program of American Welding Society Programs and Events, Nov. 11-14, 2007, Chicago.
Aiteanu, Dorian, and Axel Graeser; "Generation and Rendering of a Virtual Welding Seam in an Augmented Reality Training Environment," Proceedings of the Sixth IASTED International Conference on Visualization, Imaging, and Image Processing, Aug. 28-30, 2006, Palma de Mallorca, Spain, ED. J.J. Villaneuva, ACTA Press, 2006.
Aiteanu, Dorin, and Axel Graser, "Computer-Aided Manual Welding Using an Augmented Reality Supervisor," Sheet Metal Welding Conference XII, Livoinia, MI, May 9-12, 2006, pp. 1-14.
Aiteanu, Dorin, et al., "A Step Forward in Manual Welding: Demonstration of Augmented Reality Helmet," Institute of Automation, University of Bremen, Germany, 2003.
Aiteanu, Dorin, "Virtual and Augmented Reality Supervisor for a New Welding Helmet" Nov. 15, 2005, pp. 1-150.
Canadian Office Action Appln No. 2,952,496 dated Jul. 11, 2019 (4 pgs).
Canadian Office Action Appln No. 2,961,093 dated Mar. 5, 2018 (4 pgs).
Canadian Office Action Appln No. 2,961,806 dated Jan. 8, 2018 (3 pgs).
Communication from European Patent Office Appln. No. 15798269.5 dated Mar. 13, 2019.
European Patent Office, Communication Pursuant to Article 94(3) EPC, in Application No. 16 715 672.8 dated May 20, 2019 (5 pages).

* cited by examiner

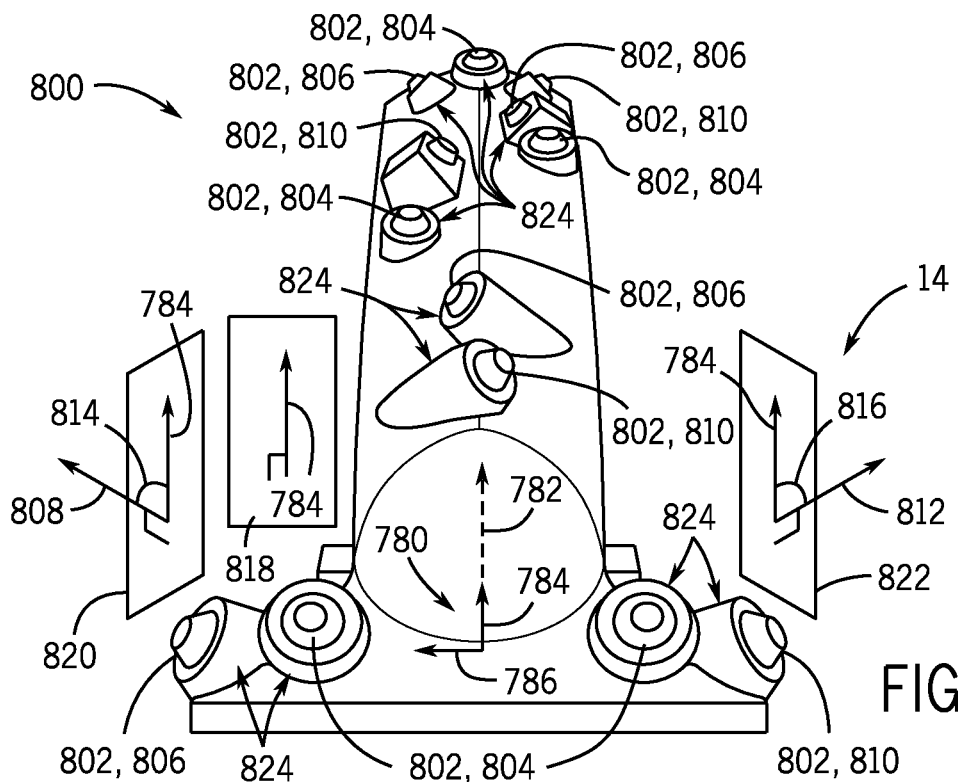
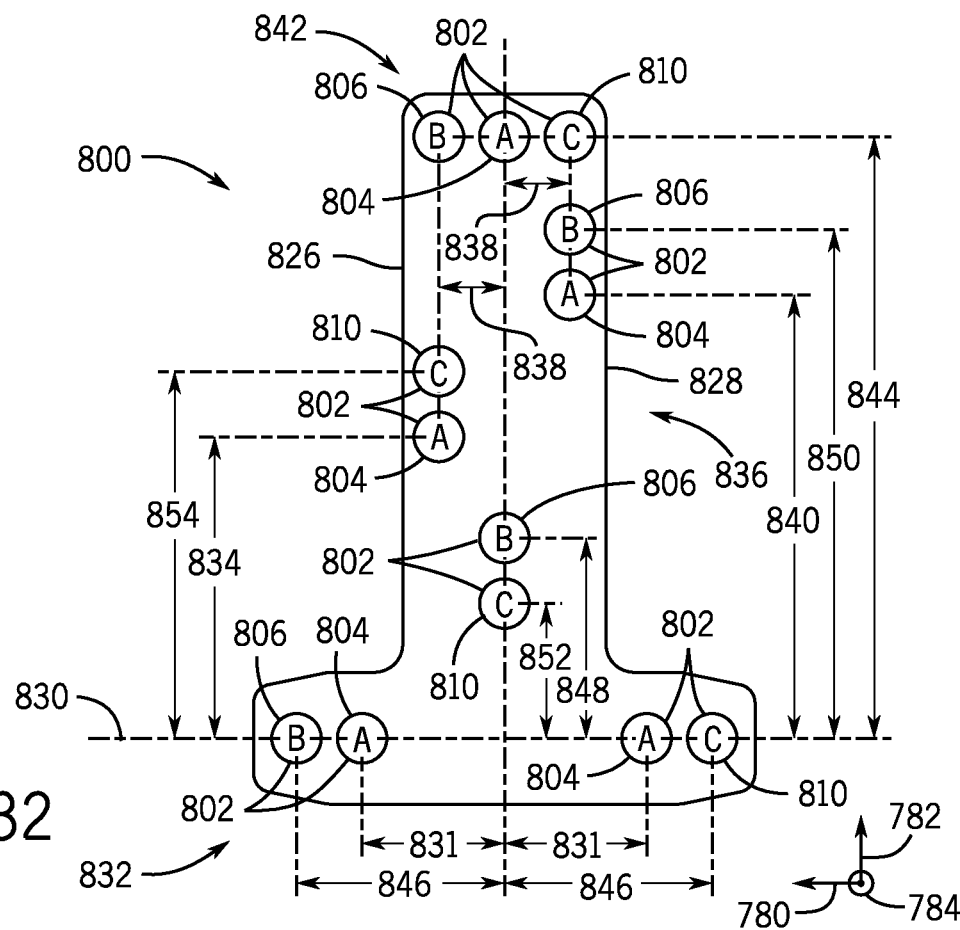
FIG. 31
FIG. 32

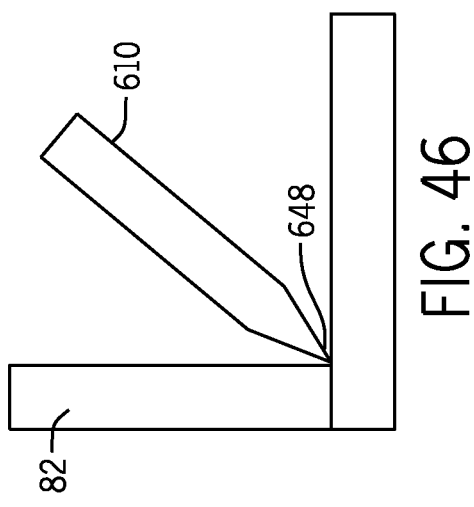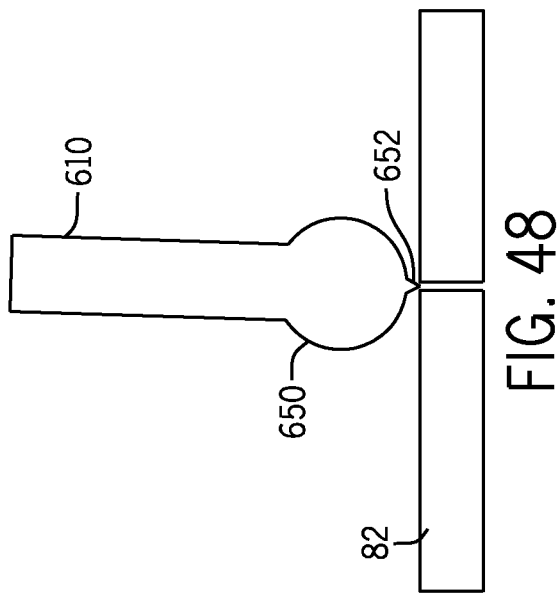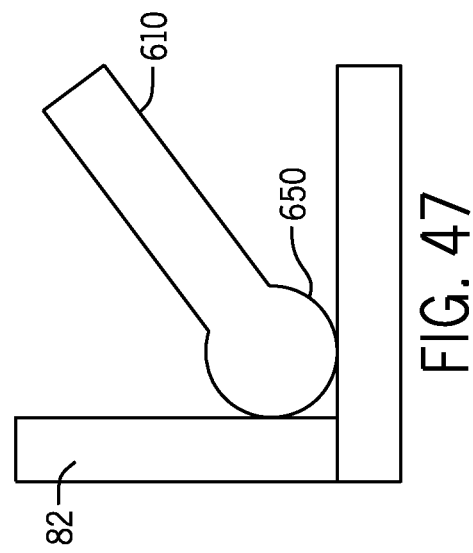

SYSTEM AND METHOD OF MARKING A WELDING WORKPIECE

CROSS REFERENCE TO RELATED APPLICATIONS

This application claims priority from and the benefit of U.S. Provisional Application Ser. No. 62/034,642, entitled "SYSTEM AND METHOD OF DETERMINING A WELD JOINT SHAPE," filed Aug. 7, 2014, which is hereby incorporated by reference in its entirety for all purposes.

BACKGROUND

The invention relates generally to welding and, more particularly, to a welding system that may be used for monitoring a weld environment and managing welding data associated with the weld environment, such as welding data collected from the weld environment during and/or preceding welding.

Welding is a process that has increasingly become utilized in various industries and applications. Such processes may be automated in certain contexts, although a large number of applications continue to exist for manual welding operations. In both cases, such welding operations rely on a variety of types of equipment to ensure the supply of welding consumables (e.g., wire feed, shielding gas, etc.) is provided to the weld in appropriate amounts at the desired time.

In preparation for performing manual welding operations, welding operators may be trained using a welding system (e.g., a welding training system). The welding system may be designed to train welding operators with the proper techniques for performing various welding operations. Certain welding systems may use various training methods. As may be appreciated, these training systems may be expensive to acquire and operate. Accordingly, welding training institutions may only acquire a limited number of such training systems. Furthermore, certain welding systems may not adequately train welding operators to perform high quality welds.

DRAWINGS

These and other features, aspects, and advantages of the present invention will become better understood when the following detailed description is read with reference to the accompanying drawings in which like characters represent like parts throughout the drawings, wherein:

FIG. 31 is perspective view of an embodiment of the welding torch, taken along line 31-31 of FIG. 30 in accordance with aspects of the present disclosure;

FIG. 32 is a top view of an embodiment of the welding torch and visual markers in accordance with aspects of the present disclosure;

FIG. 46 is a side view of an embodiment of a pointed tip of a calibration tool in accordance with aspects of the present disclosure;

FIG. 47 is a side view of an embodiment of a rounded tip of a calibration tool in accordance with aspects of the present disclosure;

FIG. 48 is a side view of an embodiment of a rounded tip of a calibration tool having a small pointed tip in accordance with aspects of the present disclosure;

FIG. 65 is an embodiment of a screen illustrating properties relating to a welding procedure in accordance with aspects of the present disclosure;

FIG. 68 is an embodiment of a screen illustrating a summary of weld test parameters in accordance with aspects of the present disclosure;

DETAILED DESCRIPTION

Figure 1:
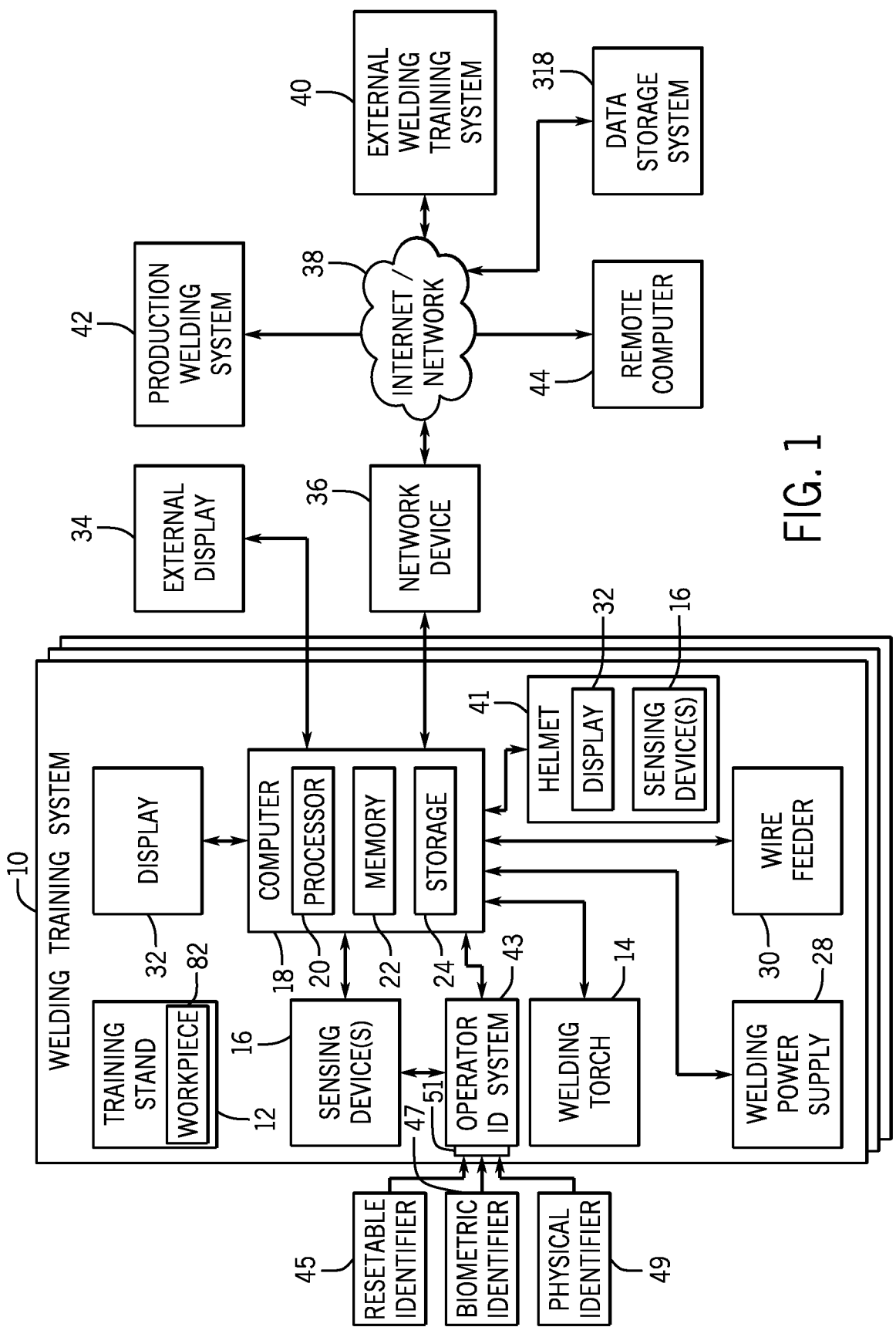
FIG. 1 is a block diagram of an embodiment of a welding system in accordance with aspects of the present disclosure.

FIG. 1 is a block diagram of an embodiment of one or more welding systems 10. As used herein, a welding system may include any suitable welding related system, including, but not limited to, a welding training system, a live welding system, a remote welding training system (e.g., helmet training system), a simulated welding system, a virtual reality welding system, and so forth. For example, the welding system 10 may include, but is not limited to, a LiveArc™ Welding Performance Management System available from Miller Electric of Appleton, Wis. The welding system 10 may include a welding stand 12 for providing support for various training devices. For example, the stand 12 may be configured to support a welding surface, a workpiece 82, a fixture, one or more training arms, and so forth. The welding system 10 includes a welding torch 14 that may be used by a welding operator (e.g., welding student) to perform welding operations (e.g., training operations). As described in greater detail below, the welding torch 14 may be configured with a user interface configured to receive inputs from the welding operator, control circuitry configured to process the inputs, and a communication interface configured to provide the inputs to another device. Furthermore, the welding torch 14 may include one or more display and/or indicators to provide data to the welding operator.

Moreover, the welding system 10 includes one or more sensing devices 16 (e.g., sensor, sensing assembly, and so forth) used to sense a position of one or more welding devices and/or to sense an orientation of one or more welding devices. For example, the sensing device 16 may be used to sense a position and/or an orientation of the stand 12, the welding torch 14, a welding surface, the workpiece 82, a fixture, one or more training arms, the operator, an identification token, and so forth. The one or more sensing devices 16 may include any suitable sensing device, such as an inertial sensing device or a motion tracking device. Furthermore, the sensing device 16 may include one or more cameras, such as one or more infrared cameras, one or more visible spectrum cameras, one or more high dynamic range (HDR) cameras, and so forth. Additionally, or in the alternative, the sensing device 16 may include one or more depth sensors to determine relative distances between the respective depth sensors 16 and an object (e.g., welding torch 14, workpiece 82, operator, and so forth). The sensing devices 16 may be positioned in various locations about the welding environment of the training system 10, thereby enabling some sensing devices 16 to monitor the welding environment (e.g., track movement of an object) when other sensing devices 16 are obscured. For example, a sensing device 16 (e.g., camera, depth sensor) integrated with a welding helmet 41 may facilitate tracking the position, orientation, and/or movement of the welding torch 14 relative to the workpiece 82 when the welding torch 14 is at least partially obscured from other sensing devices 16 by the workpiece 82 or the operator. For example, markers disposed on the welding torch 14 that facilitate tracking the welding torch 14 may be partially obscured from a first sensing device 16, yet be observable by another sensing device 16 of the helmet 41. The other sensing device 16 of the helmet 41 may be independent of the first sensing device 16. Furthermore, a sensing device 16 (e.g., accelerometer) integrated with the welding torch 14 may facilitate tracking the position, orientation, and/or movement of the welding torch 14 relative to the workpiece 82 when the welding torch 14 is at least partially obscured from other sensing devices 16 (e.g., cameras, depth sensors) by the workpiece 82 or the operator.

The sensing device 16 is communicatively coupled to a computer 18. The sensing device 16 is configured to provide data (e.g., image data, acoustic data, sensed data, six degrees of freedom (6DOF) data, etc.) to the computer 18. Furthermore, the sensing device 16 may be configured to receive data (e.g., configuration data, setup data, commands, register settings, etc.) from the computer 18. The computer 18 includes one or more processors 20, memory devices 22, and storage devices 24. The computer 18 may include, but is not limited to, a desktop, a laptop, a tablet, a mobile device, a wearable computer, or any combination thereof. The processor(s) 20 may be used to execute software, such as welding software, image processing software, sensing device software, and so forth. Moreover, the processor(s) 20 may include one or more microprocessors, such as one or more "general-purpose" microprocessors, one or more special-purpose microprocessors and/or application specific integrated circuits (ASICS), or some combination thereof. For example, the processor(s) 20 may include one or more reduced instruction set (RISC) processors.

The storage device(s) 24 (e.g., nonvolatile storage) may include ROM, flash memory, a hard drive, or any other suitable optical, magnetic, or solid-state storage medium, or a combination thereof. The storage device(s) 24 may store data (e.g., data corresponding to a welding operation, video and/or parameter data corresponding to a welding operation, data corresponding to an identity and/or a registration number of the operator, data corresponding to past operator performance, etc.), instructions (e.g., software or firmware for the welding system, the sensing device 16, etc.), and any other suitable data. As will be appreciated, data that corresponds to a welding operation may include a video recording of the welding operation, a simulated video, an orientation of the welding torch 14, a position of the welding torch 14, a work angle, a travel angle, a distance between a contact tip of the welding torch 14 and a workpiece, a travel speed, an aim, a voltage, a current, a traversed path, a discontinuity analysis, welding device settings, and so forth.

The memory device(s) 22 may include a volatile memory, such as random access memory (RAM), and/or a nonvolatile memory, such as read-only memory (ROM). The memory device(s) 22 may store a variety of information and may be used for various purposes. For example, the memory device(s) 22 may store processor-executable instructions (e.g., firmware or software) for the processor(s) 20 to execute, such as instructions for a welding training simulation, for the sensing device 16, and/or for an operator identification system 43. In addition, a variety of control regimes for various welding processes, along with associated settings and parameters may be stored in the storage device(s) 24 and/or memory device(s) 22, along with code configured to provide a specific output (e.g., initiate wire feed, enable gas flow, capture welding current data, detect short circuit parameters, determine amount of spatter, etc.) during operation. The welding power supply 28 may be used to provide welding power to a live-arc welding operation, and the wire feeder 30 may be used to provide welding wire to the live-arc welding operation.

The welding system 10 includes a display 32 for displaying data and/or screens associated with welding (e.g., to display data corresponding to a welding software). For example, the display 32 may provide a graphical user interface to a welding operator (e.g., welding instructor, welding student). The graphical user interface may provide various screens to enable the welding instructor to organize a class, provide assignments to the class, analyze assignments performed by the class, provide assignments to an individual, analyze assignments performed by the individual, add, change, and/or delete parameters for a welding assignment, and so forth. Furthermore, the graphical user interface may provide various screens to enable a welding operator (e.g., welding student) to perform a welding assignment, view results from prior welding assignments, and so forth. In certain embodiments, the display 32 may be a touch screen display configured to receive touch inputs, and to provide data corresponding to the touch inputs to the computer 18.

An external display 34 is coupled to the computer 18 to enable an individual located remotely from the welding system 10 to view data corresponding to the welding system 10. Furthermore, a network device 36 is coupled to the computer 18 to enable the computer 18 to communicate with other devices connected to the Internet or another network 38 (e.g., for providing test results to another device and/or for receiving test results from another device). For example, the network device 36 may enable the computer 18 to communicate with an external welding system 40, a production welding system 42, a remote computer 44, and/or a data storage system (e.g., cloud storage system) 318. As may be appreciated, the welding system 10 described herein may be used to train welding students in a cost effective manner. In some embodiments, the one or more welding systems 10 may include a helmet 41 having a display 32 and one or more sensing devices 16, such as optical or acoustic sensing devices. As described in detail below, the helmet 41 is communicatively coupled to the computer 18, and the helmet 41 may facilitate welding training and/or welding monitoring without the training stand 12. In some embodiments, the one or more sensing devices 16 integrated with the helmet 41 may facilitate welding training and/or welding monitoring without separate sensing devices 16 external to the helmet 41. Furthermore, the welding system 10 is configured to integrate real welding with simulated welding in a manner that prepares welding students for high quality production welding.

An operator identification system 43 is coupled to the computer 18 to enable an operator utilizing the welding system 10 to be identified. The operator identification system 43 utilizes one or more types of operator information (e.g., identifiers) to identify the operator. Operator information may include, but is not limited to, a resettable identifier 45 (e.g., password, motion sequence, operator-performed action), a biometric identifier 47 (e.g., retinal scan, fingerprint, palm print, facial profile, voice profile, inherent operator trait), information based at least in part on a biometric identifier 47, a token 49 (e.g., key, key fob, radio frequency identification (RFID) tag, passcard, barcode, physical identifier), or any combination thereof. Additionally, or in the alternative, an instructor or manager may provide an input to the operator identification system 43 to verify the identity of the operator, thereby authorizing the operator for the welding session (e.g., welding assignment) and the associated weld data. That is, the identification of an operator may involve one or more steps, such as operator identification via information received from the operator, and operator verification via information received from the instructor and/or manager of the operator. In some embodiments, the operator identification system 43 may utilize the one or more sensing devices 16 to facilitate operator identification. For example, a camera or microphone of the welding system 10 may receive the biometric identifier 47. Moreover, the operator identification system 43 may have an input device 51 (e.g., keypad, touch screen, retinal scanner, fingerprint sensor, camera, microphone, barcode scanner, radio transceiver, and so forth) configured to receive the one or more types of operator identification information.

The operator identification system 43 may identify the operator prior to performing a weld process (e.g., live process, training process, simulated process, virtual reality process) or after performing the weld process. In some embodiments, the operator identification system 43 may enable or lock out an operator from utilizing the welding system 10 based on the one or more identifiers received at the input device 51. For example, the operator identification system 43 may lock out a first operator (e.g., student) from utilizing the welding system 10 until the operator identification system 43 receives a first input from the first operator that may identify the first operator. In some embodiments, the welding system 10 may enable the first operator to perform a welding session with the welding system 10 without verification of the identity of the first operator; however, the welding system 10 may store and/or transmit the welding data associated with such a welding session only upon verification of the identity of the first operator based at least in part on a second input from a second operator (e.g., instructor, administrator). That is, the operator identification system 43 may disable the storage or transmission of the welding data associated with a welding session until the identity of the first operator that performed the welding session is verified by the second operator. Moreover, some embodiments of the welding system 10 may lock out the first operator from utilizing the welding system until a second input is received from the second operator that verifies the identity of the first operator, which was preliminarily determined based on the first input from the first operator. In some embodiments, the operator identification system 43 may identify the operator during a weld process, such as via an identifying characteristic of an operator during the weld process. For example, a first operator may hold the welding torch differently than a second operator, and a sensing device 16 (e.g., camera) coupled to the operator identification system 43 may facilitate distinguishing the first operator from the second operator. Additionally, or in the alternative, the operator identification system 43 may include a sensor (e.g., fingerprint scanner, camera, microphone) on the welding torch 14 or the helmet 41. In some embodiments, an instructor and/or a manager may confirm upon completion of a weld process that the identified operator performed the weld process.

The operator identification system 43 may communicate with the computer 18 to determine the identity of the operator utilizing the received identification information. In some embodiments, the computer 18 may communicate with the network 38 and/or a remote computer 44 to determine the identity of the operator. The computer 18 may control the display 32 to display at least some of the information associated with the operator upon identification of the operator. For example, the display 32 may present the name, a photo, registration number, experience level, or any combination thereof. In some embodiments, the operator identification system 43 may be utilized with one or more welding systems 10.

The computer 18 may receive welding data (e.g., welding parameters, arc parameters) corresponding to a welding session (e.g., welding assignment) during and/or after the respective welding session is performed by the operator. The computer 18 may receive the welding data from the network 38, one or more sensing devices 16, the welding torch 14, the welding power supply 28, the wire feeder 30, or the helmet 41, or any combination thereof. Additionally, or in the alternative, the computer 18 may associate the received welding data with the identity of the operator, such as via a registration number unique to the operator, the operator's name, and/or a photograph of the operator. Moreover, the computer 18 may transmit the associated welding data and identity of the operator (e.g., registration number) to a data storage system within the welding system 10 or located remotely via the network 38. Association of the welding data with the identity of the operator (e.g., via the registration number) enables significantly more than the collection of unassociated welding data from operators. That is, association of the welding data with a registration number unique to the operator enables someone (e.g., the operator, instructor, manager) that is either local or remote from the operator to track the performance, progress, and skills of the operator over time via the registration number.

Figure 2:
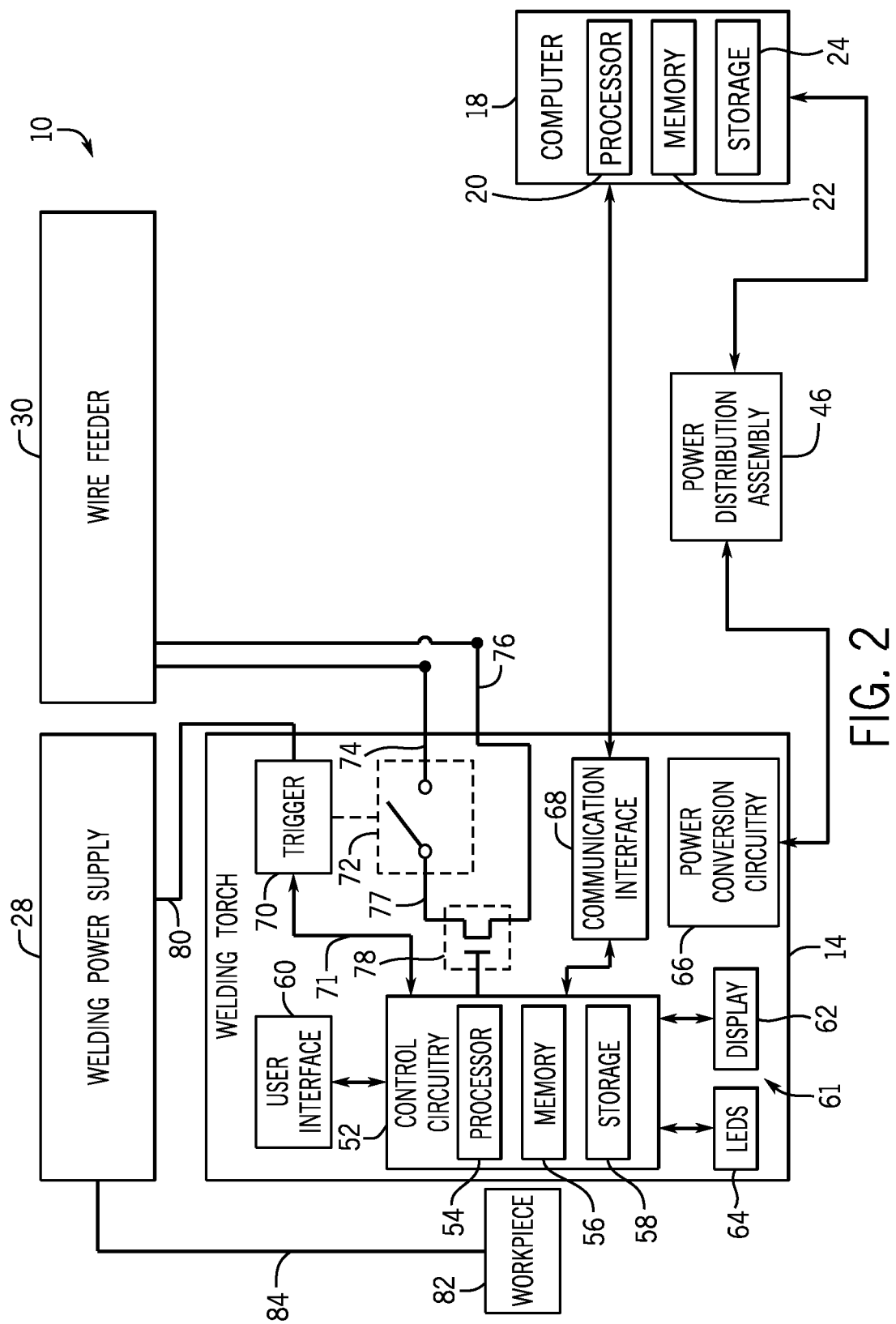
FIG. 2 is a block diagram of an embodiment of portions of the welding system of FIG. 1 in accordance with aspects of the present disclosure.

FIG. 2 is a block diagram of an embodiment of portions of the welding system 10 of FIG. 1. As illustrated, a power distribution assembly 46 provides power to the welding torch 14 and the computer 18. Moreover, the welding torch 14 includes control circuitry 52 configured to control the operation of the welding torch 14. In the illustrated embodiment, the control circuitry 52 includes one or more processors 54, memory devices 56, and storage devices 58. In other embodiments, the control circuitry 52 may not include the processors 54, the memory devices 56, and/or the storage devices 58. The processor(s) 54 may be used to execute software, such as welding torch software. Moreover, the processor(s) 54 may be similar to the processor(s) 20 described previously. Furthermore, the memory device(s) 56 may be similar to the memory device(s) 22, and the storage device(s) 58 may be similar to the storage device(s) 24.

The welding torch 14 includes a user interface 60 to enable a welding operator (e.g., welding student, welding instructor, etc.) to interact with the welding torch 14 and/or to provide inputs to the welding torch 14. For example, the user interface 60 may include buttons, switches, touch screens, touchpads, scanners, and so forth. The inputs provided to the welding torch 14 by the welding operator may be provided to the computer 18. For example, the inputs provided to the welding torch 14 may be used to control welding software being executed by the computer 18. As such, the welding operator may use the user interface 60 on the welding torch 14 to navigate the welding software screens, setup procedures, data analysis, welding courses, make selections within the welding software, configure the welding software, and so forth. Thus, the welding operator can use the welding torch 14 to control the welding software (e.g., the welding operator does not have to put down the welding torch 14 to use a different input device). The welding torch 14 also includes visual indicators 61, such as a display 62 and LEDs 64. The visual indicators 61 may be configured to indicate or display data and/or images corresponding to a weld, welding training, and/or welding software. For example, the visual indicators 61 may be configured to indicate a welding torch orientation, a welding torch travel speed, a welding torch position, a contact tip to workpiece distance, an aim of the welding torch 14, training information for the welding operator, and so forth. Moreover, the visual indicators 61 may be configured to provide visual indications before a weld, during a weld, and/or after a weld. In certain embodiments, the LEDs 64 may illuminate to facilitate their detection by the sensing device 16. In such embodiments, the LEDs 64 may be positioned to enable the sensing device 16 to determine a position and/or an orientation of the welding torch 14 based on a spatial position of the LEDs 64.

Figure 71:
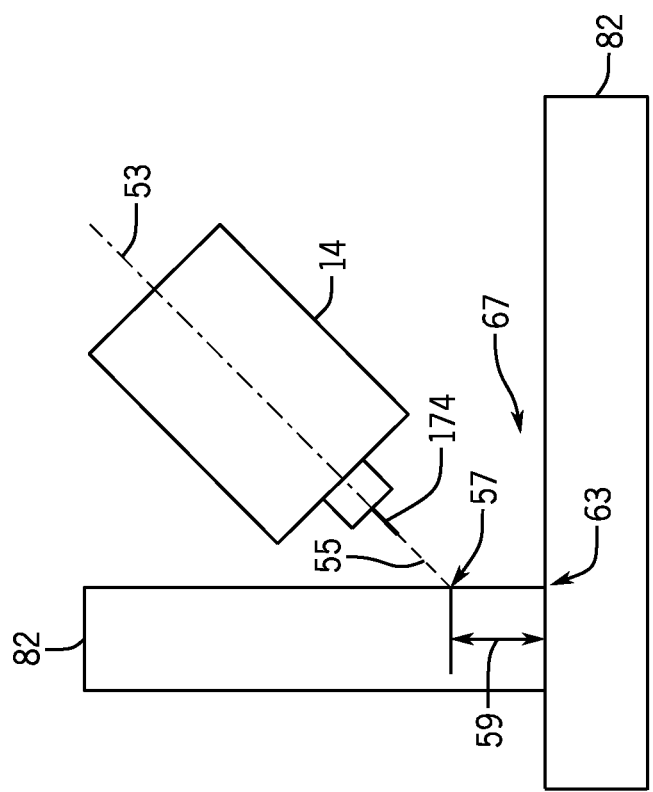
FIG. 71 is a diagram of an embodiment of the aim of a welding torch relative to a workpiece in accordance with aspects of this present disclosure.
Figure 72:
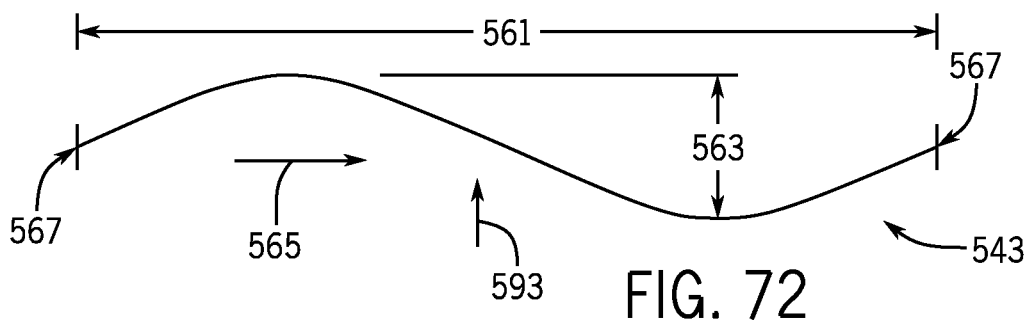
FIG. 72 is an embodiment of a marker that may be applied to the workpiece by a marking tool in accordance with aspects of this present disclosure.
Figure 73:
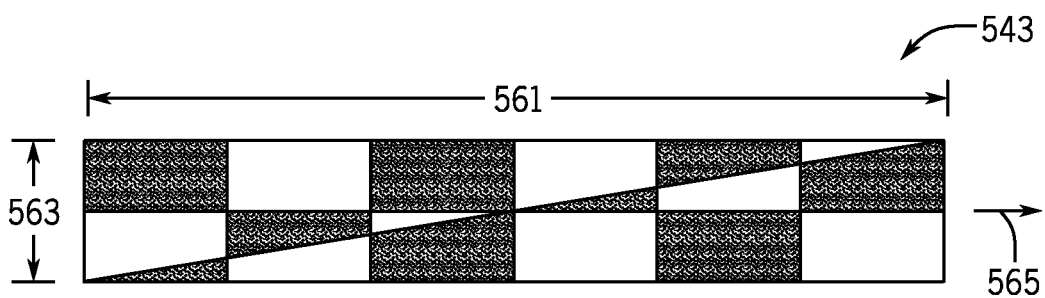
FIG. 73 is an embodiment of a marker that may be applied to the workpiece by a marking tool in accordance with aspects of this present disclosure.
Figure 74:
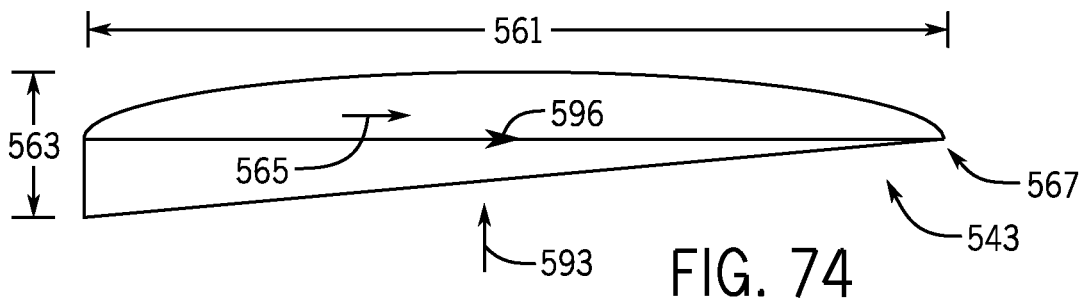
FIG. 74 is an embodiment of a marker that may be applied to the workpiece by a marking tool in accordance with aspects of this present disclosure.
Figure 75:
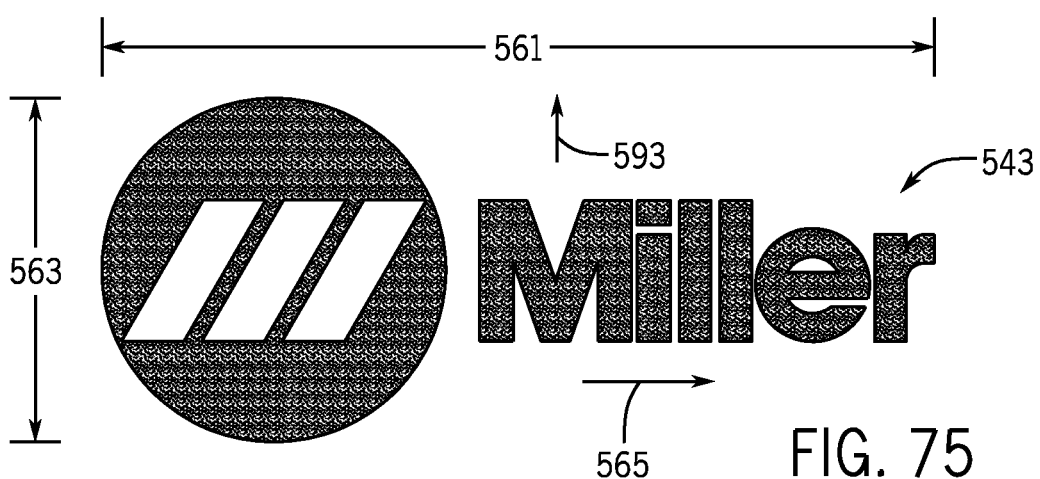
FIG. 75 is an embodiment of a marker that may be applied to the workpiece by a marking tool in accordance with aspects of this present disclosure.

As may be appreciated, FIG. 71 illustrates an embodiment of the aim of the welding torch 14. Where a wire electrode 174 extends along an axis 53 of the torch 14, a projected line 55 along the axis 53 extending from the wire electrode intersects the workpiece 82 at an intersection point 57. As utilized herein, the term "aim" may be defined as the shortest distance 59 along the workpiece 82 between the intersection point 57 and a center 63 of a joint 67 of the workpiece 82.

Returning to FIG. 2, in certain embodiments, the welding torch 14 includes power conversion circuitry 66 configured to receive power from the power distribution assembly 46, the computer 18, or another device, and to convert the received power for powering the welding torch 14. In certain embodiments, the welding torch 14 may receive power that is already converted and/or does not utilize power conversion. Moreover, in some embodiments, the welding torch 14 may be powered by a battery or any suitable powering mechanism. The welding torch 14 also includes a communication interface 68 (e.g., RS-232 driver) to facilitate communication between the welding torch 14 and the computer 18. Accordingly, inputs provided to the welding torch 14 may be provided to the computer 18.

The welding torch 14 includes a trigger 70 configured to mechanically actuate a trigger switch 72 between an open position (as illustrated) and a closed position. The trigger 70 provides a conductor 71 to carry a signal to the control circuitry 52 to indicate whether the trigger switch 72 is in the open position or the closed position. The wire feeder 30, the welding power supply 28, and/or the computer 18 may determine whether there is continuity through the welding torch 14 across a first trigger conductor 74 and a second trigger conductor 76. The trigger switch 72 is electrically coupled between the first trigger conductor 74 and the second trigger conductor 76. Continuity across the first trigger conductor 74 and the second trigger conductor 76 may be determined by applying a voltage across the conductors 74 and 76, applying a current across the conductors 74 and 76, measuring a resistance across the conductors 74 and 76, and so forth. In certain embodiments, portions of the first trigger conductor 74 and/or portions of the second trigger conductor 76 may be disposed within a connector of the welding torch 14. Furthermore, in certain embodiments, the arrangement of switches and/or conductors within the welding torch 14 may be different than illustrated in FIG. 2.

The welding power supply 28 may determine whether to enable welding power to flow through the welding torch 14 based on whether there is continuity across the conductors 74 and 76. For example, the welding power supply 28 may enable welding power to flow through the welding torch 14 while there is continuity across the conductors 74 and 76, and the welding power supply 28 may block welding power from flowing through the welding torch 14 while there is an open circuit across the conductors 74 and 76. Furthermore, the wire feeder 30 may provide welding wire to the welding torch 14 while there is continuity across the conductors 74 and 76, and may block welding wire from being provided to the welding torch 14 while there is an open circuit across the conductors 74 and 76. Moreover, the computer 18 may use the continuity across the conductors 74 and 76 and/or the position of the trigger 70 or trigger switch 72 to start and/or stop a welding operation, a welding simulation, data recording, and so forth.

With the trigger switch 72 in the open position, there is an open circuit across the conductors 74 and 76, thus, the open position of the trigger switch 72 blocks electron flow between the conductors 74 and 76. Accordingly, the welding power supply 28 may block welding power from flowing through the welding torch 14 and the wire feeder 30 may block welding wire from being provided to the welding torch 14. Pressing the trigger 70 directs the trigger switch 72 to the closed position where the trigger switch 72 remains as long as the trigger 70 is pressed. With the trigger switch 72 in the closed position, there is continuity between the first trigger conductor 74 and a conductor 77 electrically connected to the trigger switch 72 and a training switch 78.

The training switch 78 is electrically coupled between the first trigger conductor 74 and the second trigger conductor 76. Moreover, the training switch 78 is electrically controlled by the control circuitry 52 to an open position or to a closed position. In certain embodiments, the training switch 78 may be any suitable electrically controlled switch, such as a transistor, relay, etc. The control circuitry 52 may selectively control the training switch 78 to the open position or to the closed position. For example, while welding software of the welding system 10 is operating in a live-arc mode, the control circuitry 52 may be configured to control the training switch 78 to the closed position to enable a live welding arc while the trigger 70 is pressed. In contrast, while welding software of the welding system 10 is operating in any mode other than the live-arc mode (e.g., simulation, virtual reality, augmented reality, etc.), the control circuitry 52 may be configured to control the training switch 78 to the open position to block a live welding arc (by blocking electron flow between the conductors 74 and 76).

In certain embodiments, the training switch 78 may default to the open position, thereby establishing an open circuit across the conductors 74 and 76. As may be appreciated, while the training switch 78 is in the open position, there will be an open circuit across the conductors 74 and 76 regardless of the position of the trigger switch 72 (e.g., electron flow between the conductors 74 and 76 is blocked by the open position of the training switch 78). However, while the training switch 78 is controlled to the closed position, and the trigger switch 72 is in the closed position, conductivity is established between the conductors 74 and 76 (e.g., electron flow between the conductors 74 and 76 is enabled). Accordingly, the welding power supply 28 may enable welding power to flow through the welding torch 14 only while the training switch 78 is in the closed position and while the trigger switch 72 is in the closed position. For example, welding power may flow from the welding power supply 28, through a weld cable 80, the welding torch 14, a workpiece 82, and return to the welding power supply 28 via a work cable 84 (e.g., electrode-negative, or straight polarity). Conversely, welding power may flow from the welding power supply 28, through the work cable 84, the workpiece 82, the welding torch 14, and return to the welding power supply 28 via the weld cable 80 (e.g., electrode-positive, or reverse polarity).

As may be appreciated, the training switch 78 may be physically located in any suitable portion of the welding system 10, such as the computer 18, and so forth. Furthermore, in certain embodiments, the functionality of the training switch 78 may be replaced by any suitable hardware and/or software in the welding system 10.

Figure 2A:
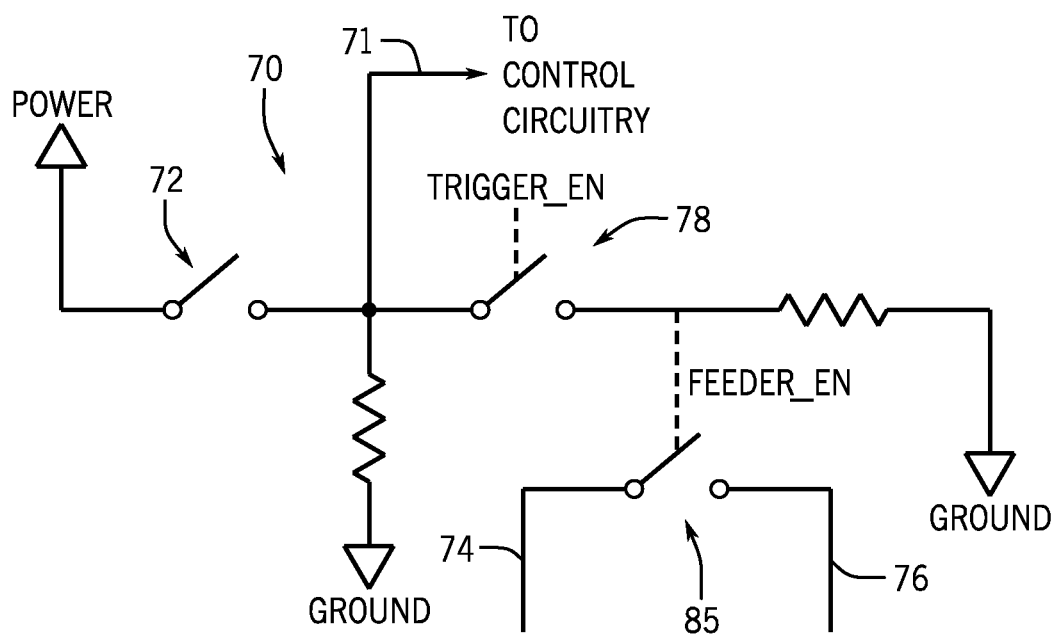
FIG. 2A is a schematic diagram of an embodiment of circuitry of the welding torch of FIG. 1 in accordance with aspects of the present disclosure.

FIG. 2A is a schematic diagram of an embodiment of circuitry of the welding torch 14 of FIG. 1. In the illustrated embodiment, the trigger switch 72 selectively connects a power supplying conductor (e.g., voltage source, etc.) to the conductor 71. Accordingly, while the trigger switch 72 is open, no voltage is applied to the conductor 71, and while the trigger switch 72 is closed, voltage from the power supplying conductor is supplied to the conductor 71. A trigger enable signal (e.g., TRIGGER_EN) may be provided by the control circuitry 52 to selectively control the training switch 78, and thereby control a feeder enable switch 85. For example, when the trigger enable signal controls the training switch 78 to an open position, no voltage is applied to the feeder enable switch 85 (e.g., via the FEEDER_EN connection), thereby maintaining the feeder enable switch 85 in the open position. Conversely, when the trigger enable signal controls the training switch 78 to a closed position, voltage is applied to the feeder enable switch 85, thereby controlling the feeder enable switch 85 to the closed position. With the feeder enable switch 85 in the closed position, conductivity between the conductors 74 and 76 is established. While one example of welding torch 14 circuitry is provided, any suitable circuitry may be used within the welding torch 14. A microprocessor of the control circuitry 52 may pulse the trigger enable signal at predetermined intervals to provide an indication to detection circuitry of the control circuitry 52 that the trigger enable signal is working properly. If the detection circuitry does not detect the trigger enable signal, the trigger may not be enabled.

Figure 3:
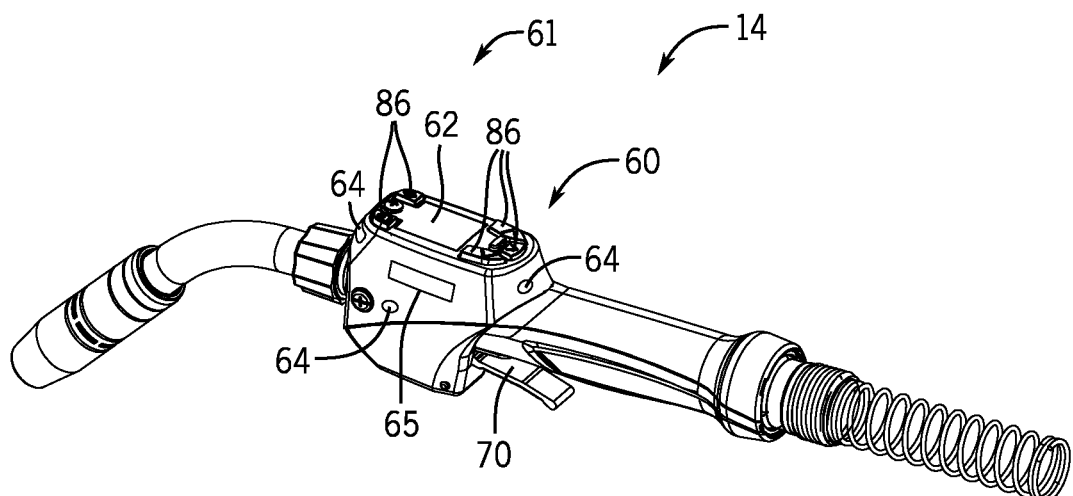
FIG. 3 is a perspective view of an embodiment of the welding torch of FIG. 1 in accordance with aspects of the present disclosure.

FIG. 3 is a perspective view of an embodiment of the welding torch 14 of FIGS. 1 and 2. As illustrated, the user interface 60 includes multiple buttons 86 which may be used to provide inputs to the welding torch 14. For example, the buttons 86 may enable a welding operator to navigate through welding software. Furthermore, the welding torch 14 includes the display 62 which may show the welding operator data corresponding to the welding software, data corresponding to a welding operation, and so forth. As illustrated, the LEDs 64 may be positioned at various locations on the welding torch 14. Accordingly, the LEDs 64 may be illuminated to facilitate detection by the sensing device 16. As discussed in detail below, one or more sets of LEDs 64 may be arranged on the welding torch 14 to facilitate detection by the sensing device 16 regardless of the position of the welding torch in the welding environment. For example, one or more sets of LEDs 64 may be arranged about the welding torch 14 and oriented in directions that enable the sensing device 16 to detect the position and orientation of the welding torch 14 in a flat welding position, a horizontal welding position, a vertical welding position, and an overhead position. Moreover, the one or more sets of LEDs 64 may enable the sensing device 16 to substantially continuously detect the movement of the welding torch 14 between various welding positions in the welding environment prior to initiating a welding process, movement of the welding torch during a welding process, and movement of the welding torch after completing a welding process, or any combination thereof. In some embodiments, a scanning device 65, such as a finger print scanner, may be arranged on the welding torch 14. The scanning device 65 may be a part of the operator identification system 43. The operator may utilize the scanning device 65 to provide identification information to the operator identification system 43 of the welding system 10. For example, the operator may scan a finger before and/or after performing a weld process to facilitate verification that the identified operator performed the weld process. In some embodiments, the operator may utilize the scanning device 65 within a relatively brief window (e.g., approximately 3, 5, 10, or 15 seconds) of initiating or completing a weld process to verify the identity of the operator. That is, the welding system 10 and/or the welding torch 14 may lock out the operator from initiating or completing a weld process if the weld process is not initiated within the brief window after verification of the identity of the operator. Accordingly, the operator identification system 43 may be utilized to reduce or eliminate instances in which the performance of a given weld process by a second operator and the associated weld data from the given weld process is erroneously attributed to a first operator that did not perform the given weld process.

Figure 4:
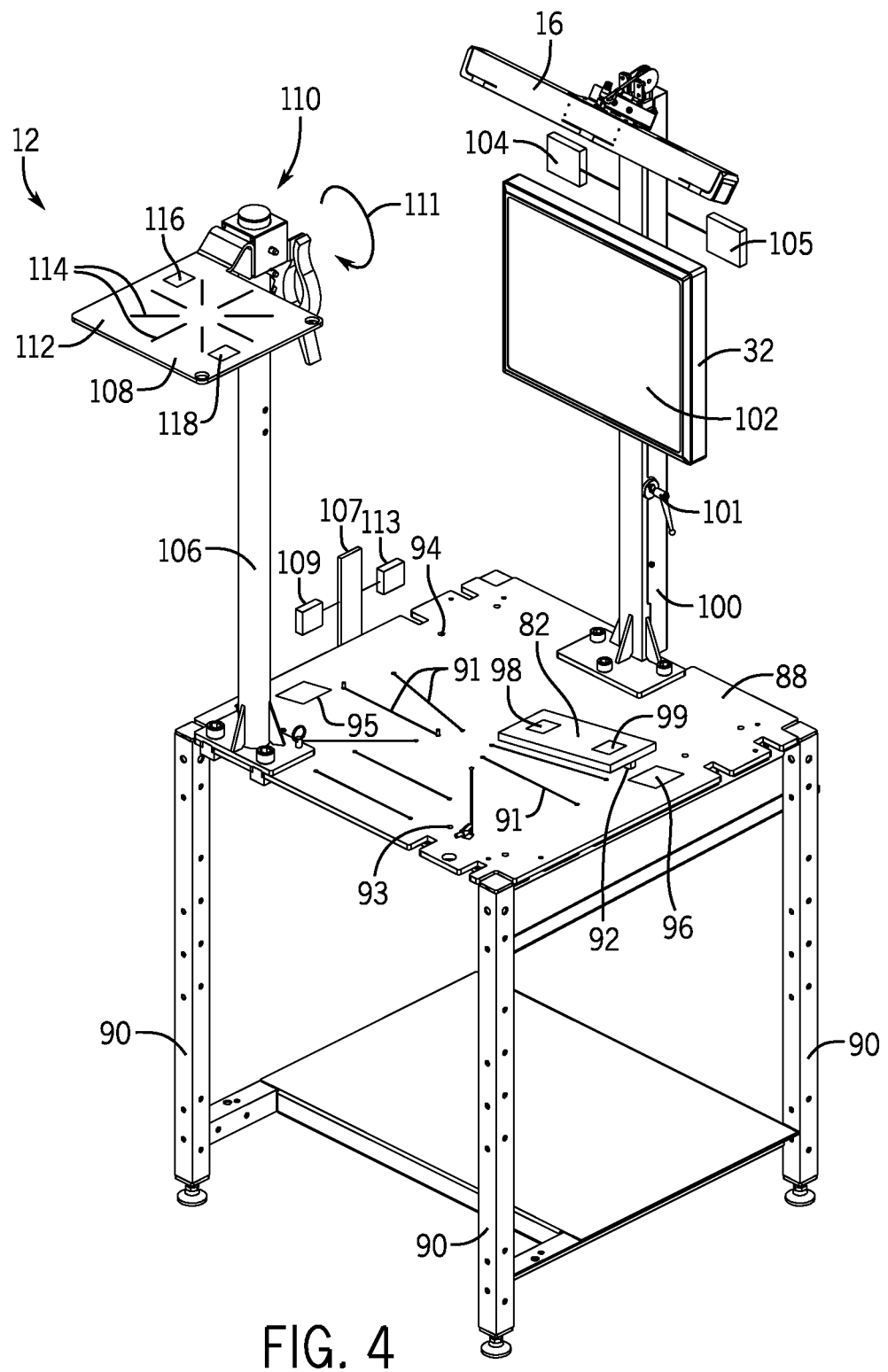
FIG. 4 is a perspective view of an embodiment of the welding stand of FIG. 1 in accordance with aspects of the present disclosure.

FIG. 4 is a perspective view of an embodiment of the stand 12 of FIG. 1. The stand 12 includes a welding surface 88 on which live welds (e.g., real welds, actual welds) and/or simulated welds may be performed. Legs 90 provide support to the welding surface 88. In certain embodiments, the welding surface 88 may include slots 91 to aid a welding operator in positioning and orienting the workpiece 82. In certain embodiments, the position and orientation of the workpiece 82 may be provided to welding software of the welding system 10 to calibrate the welding system 10. For example, a welding operator may provide an indication to the welding software identifying which slot 91 of the welding surface 88 the workpiece 82 is aligned with. Furthermore, a predefined welding assignment may direct the welding operator to align the workpiece 82 with a particular slot 91. In certain embodiments, the workpiece 82 may include an extension 92 configured to extend into one or more of the slots 91 for alignment of the workpiece 82 with the one or more slots 91. As may be appreciated, each of the slots 91 may be positioned at a location corresponding to a respective location defined in the welding software.

The welding surface 88 includes a first aperture 93 and a second aperture 94. The first and second apertures 93 and 94 may be used together to determine a position and/or an orientation of the welding surface 88. As may be appreciated, in certain embodiments at least three apertures may be used to determine the position and/or the orientation of the welding surface 88. In some embodiments, more than three apertures may be used to determine the position and/or the orientation of the welding surface 88. The first and second apertures 93 and 94 may be positioned at any suitable location on the welding surface 88, and may be any suitable size. In certain embodiments, the position and/or orientation of the welding surface 88 relative to the sensing device 16 may be calibrated using the first and second apertures 93 and 94. For example, as described in greater detail below, a calibration device configured to be sensed by the sensing device 16 may be inserted into the first aperture 93, or touched to the first aperture 93. While the calibration device is inserted into, or touching, the first aperture 93, a user input provided to the welding software (or other calibration software) may indicate that the calibration device is inserted into the first aperture 93. As a result, the welding software may establish a correlation between a first data set (e.g., calibration data) received from the sensing device 16 (e.g., position and/or orientation data) at a first time and the location of first aperture 93. The calibration device may next be inserted into the second aperture 94, or touched to the second aperture 94. While the calibration device is inserted into, or touching, the second aperture 94, a user input provided to the welding software may indicate that the calibration device is inserted into the second aperture 94. As a result, the welding software may establish a correlation between a second data set (e.g., calibration data) received from the sensing device 16 at a second time and the location of second aperture 94. Thus, the welding software may be able to calibrate the position and/or orientation of the welding surface 88 relative to the sensing device 16 using the first data set received at the first time and the second data set received at the second time.

The welding surface 88 also includes a first marker 95 and a second marker 96. The first and second markers 95 and 96 may be used together to determine a position and/or an orientation of the welding surface 88. As may be appreciated, in certain embodiments at least three markers may be used to determine the position and/or the orientation of the welding surface 88. In some embodiments, more than three markers may be used to determine the position and/or the orientation of the welding surface 88. The first and second markers 95 and 96 may be formed from any suitable material. Moreover, in certain embodiments, the first and second markers 95 and 96 may be built into the welding surface 88, while in other embodiments, the first and second markers 95 and 96 may be attached to the welding surface 88. For example, the first and second markers 95 and 96 may be attached to the welding surface 88 using an adhesive and/or the first and second markers 95 and 96 may be stickers (e.g., tape). The first and second markers 95 and 96 may have any suitable shape, size, and/or color. Furthermore, in certain embodiments, the first and second markers 95 and 96 may be a reflector formed from a reflective material. The first and second markers 95 and 96 may be used by the welding system 10 to calibrate the position and/or orientation of the welding surface 88 relative to the sensing device 16 without a separate calibration device. Accordingly, the first and second markers 95 and 96 are configured to be detected by the sensing device 16. In certain embodiments, the first and second markers 95 and 96 may be positioned at predetermined locations on the welding surface 88. Furthermore, the welding software may be programmed to use the predetermined locations to determine the position and/or the orientation of the welding surface 88. In other embodiments, the location of the first and second markers 95 and 96 may be provided to the welding software during calibration. With the first and second markers 95 and 96 on the welding surface 88, the sensing device 16 may sense the position and/or orientation of the first and second markers 95 and 96 relative to the sensing device 16. Using this sensed data in conjunction with the location of the first and second markers 95 and 96 on the welding surface 88, the welding software may be able to calibrate the position and/or orientation of the welding surface 88 relative to the sensing device 16. In some embodiments, the welding surface 88 may be removable and/or reversible. In such embodiments, the welding surface 88 may be flipped over, such as if the welding surface 88 become worn.

In the illustrated embodiment, the workpiece 82 includes a first marker 98 and a second marker 99. The first and second markers 98 and 99 may be used together to determine a position and/or an orientation of the workpiece 82. As may be appreciated, at least two markers are used to determine the position and/or the orientation of the workpiece 82. In certain embodiments, more than two markers may be used to determine the position and/or the orientation of the workpiece 82. The first and second markers 98 and 99 may be formed from any suitable material. Moreover, in certain embodiments, the first and second markers 98 and 99 may be built into the workpiece 82, while in other embodiments, the first and second markers 98 and 99 may be attached to the workpiece 82. For example, the first and second markers 98 and 99 may be attached to the workpiece 82 using an adhesive and/or the first and second markers 98 and 99 may be stickers. As a further example, the first and second markers 98 and 99 may be clipped or clamped onto the workpiece 82. The first and second markers 98 and 99 may have any suitable shape, size, and/or color. Furthermore, in certain embodiments, the first and second markers 98 and 99 may be a reflector formed from a reflective material. The first and second markers 98 and 99 may be used by the welding system 10 to calibrate the position and/or orientation of the workpiece 82 relative to the sensing device 16 without a separate calibration device. Accordingly, the first and second markers 98 and 99 are configured to be detected by the sensing device 16. In certain embodiments, the first and second markers 98 and 99 may be positioned at predetermined locations on the workpiece 82. Furthermore, the welding software may be programmed to use the predetermined locations to determine the position and/or the orientation of the workpiece 82. In other embodiments, the location of the first and second markers 98 and 99 may be provided to the welding software during calibration. With the first and second markers 98 and 99 on the workpiece 82, the sensing device 16 may sense the position and/or orientation of the first and second markers 98 and 99 relative to the sensing device 16. Using this sensed data in conjunction with the location of the first and second markers 98 and 99 on the workpiece 82, the welding software may be able to calibrate the position and/or orientation of the workpiece 82 relative to the sensing device 16. While the markers 95, 96, 98, and 99 have been described herein as being detected by the sensing device 16, in certain embodiments, the markers 95, 96, 98, and 99 may indicate locations where a calibration device is to be touched for calibration using the calibration device, as described previously.

The stand 12 includes a first arm 100 extending vertically from the welding surface 88 and configured to provide support for the sensing device 16 and the display 32. A knob 101 is attached to the first arm 100 and may be used to adjust an orientation of the sensing device 16 relative to the first arm 100. For example, as the knob 101 is adjusted, mechanical components extending through the first arm 100 may adjust an angle of the sensing device 16. The display 32 includes a cover 102 to protect the display 32 from welding emissions that may occur during a live welding operation. The cover 102 may be made from any suitable material, such as a transparent material, a polymer, and so forth. By using a transparent material, a welding operator may view the display 32 while the cover 102 is positioned in front of the display 32, such as before, during, and/or after a welding operation. The sensing device 16 may include a camera 104 coupled to the first arm 100 for recording welding operations. In certain embodiments, the camera 104 may be a high dynamic range (HDR) camera. Furthermore, the sensing device 16 may include an emitter 105 coupled to the first arm 100. The emitter 105 may be used to calibrate the position and/or orientation of the welding surface 88 relative to the sensing device 16. For example, the emitter 105 may be configured to emit a visible pattern onto the welding surface 88, the workpiece 82, the welding torch 14, or the operator, or any combination thereof. That is, the pattern emitted by the emitter 105 is visible to the camera 104. The emitter 105 may emit the visible pattern at a desired wavelength, such as a wavelength in the infrared, visible, or ultraviolet spectrum (e.g., approximately 1 mm to 120 nm). The visible pattern may be shown onto the welding surface 88 and/or the workpiece 82. Furthermore, the visible pattern may be detected by the sensing device 16 to calibrate the position and/or the orientation of the welding surface 88 relative to the sensing device 16. For example, based on particular features of the visible pattern alignments and/or orientations may be determined by the sensing device 16 and/or the welding software. Moreover, the visible pattern emitted by the emitter 105 may be used to facilitate positioning of the workpiece 82 on the welding surface 88. As discussed in greater detail below, the visible pattern may be detected by the sensing device 16 (e.g., camera 104) to determine a shape (e.g., tube, S-shape, I-shape, U-shape) of the workpiece 82, the operator, or position of the welding torch 14 prior to welding. In some embodiments, the visible pattern may be detected by the sensing device 16 during welding to detect workpiece 82, the operator, the welding torch 14, or any combination thereof.

In some embodiments, the one or more sensing devices 16 of the stand 12 may include a second camera 109 coupled to a third arm 107 for recording welding operations in a similar manner to the camera 104. Furthermore, a second emitter 113 coupled to the third arm 107 may emit a visible pattern onto the welding surface 88, the workpiece 82, the welding torch 14, or the operator, or any combination thereof. The second emitter 113 may emit the visible pattern at a desired wavelength, such as a wavelength in the infrared, visible, or ultraviolet spectrum. The visible pattern emitted from the second emitter 113 may be approximately the same wavelength or a different wavelength than the visible pattern emitted by the emitter 105. As may be appreciated, the second camera 109 and the second emitter 113 may be positioned to have a different orientation (e.g., perpendicular, greater than approximately 5, 10, 20, 30, 45, 50, 60, 75, or 80 or degrees or more) relative to the workpiece 82 than the camera 104 and the emitter 105, thereby enabling the determination of the shape of the workpiece 82, the position of the operator, or the position of the welding torch 14 in the event that the sensing device 16 of either arm 100, 107 is obscured from view of a portion of the welding environment. In some embodiments, the sensing devices 16 may include multiple sets of cameras and emitters arranged at various points about the welding environment on or off the stand 12 to facilitate the monitoring of the position and movement of objects in the welding environment if one or more sensing devices are obscured from view of the welding environment. As discussed in greater detail below, the receiver (e.g., camera 104) and the emitter 105 may be integrated with the welding helmet 41, thereby enabling the training system 10 to monitor the position and/or orientation of the welding torch 14 and the workpiece relative to the welding helmet 41.

The stand 12 also includes a second arm 106 extending vertically from the welding surface 88 and configured to provide support for a welding plate 108 (e.g., vertical welding plate, horizontal welding plate, overhead welding plate, etc.). The second arm 106 may be adjustable to facilitate overhead welding at different heights. Moreover, the second arm 106 may be manufactured in a number of different ways to facilitate overhead welding at different heights. The welding plate 108 is coupled to the second arm 106 using a mounting assembly 110. The mounting assembly 110 facilitates rotation of the welding plate 108 as illustrated by arrow 111. For example, the welding plate 108 may be rotated from extending generally in the horizontal plane (e.g., for overhead welding), as illustrated, to extend generally in the vertical plane (e.g., for vertical welding). The welding plate 108 includes a welding surface 112. The welding surface 112 includes slots 114 that may aid a welding operator in positioning the workpiece 82 on the welding surface 112, similar to the slots 91 on the welding surface 88. In certain embodiments, the position of the workpiece 82 may be provided to welding software of the welding system 10 to calibrate the welding system 10. For example, a welding operator may provide an indication to the welding software identifying which slot 114 of the welding surface 112 the workpiece 82 is aligned with. Furthermore, a predefined welding assignment may direct the welding operator to align the workpiece 82 with a particular slot 114. In certain embodiments, the workpiece 82 may include an extension configured to extend into one or more of the slots 114 for alignment of the workpiece 82 with the one or more slots 114. As may be appreciated, each of the slots 114 may be positioned at a location corresponding to a respective location defined in the welding software.

The welding surface 112 also includes a first marker 116 and a second marker 118. The first and second markers 116 and 118 may be used together to determine a position and/or an orientation of the welding surface 112. As may be appreciated, at least two markers are used to determine the position and/or the orientation of the welding surface 112. In certain embodiments, more than two markers may be used to determine the position and/or the orientation of the welding surface 112. The first and second markers 116 and 118 may be formed from any suitable material. Moreover, in certain embodiments, the first and second markers 116 and 118 may be built into the welding surface 112 (or another part of the welding plate 108), while in other embodiments, the first and second markers 116 and 118 may be attached to the welding surface 112 (or another part of the welding plate 108). For example, the first and second markers 116 and 118 may be attached to the welding surface 112 using an adhesive and/or the first and second markers 116 and 118 may be stickers (e.g., tape). As a further example, the first and second markers 116 and 118 may be clipped or clamped onto the welding surface 112. In some embodiments, the first and second markers 116 and 118 may be integrated into a holding clamp that is clamped onto a welding coupon. The first and second markers 116 and 118 may have any suitable shape, size, and/or color. Furthermore, in certain embodiments, the first and second markers 116 and 118 may be a reflector formed from a reflective material.

The first and second markers 116 and 118 may be used by the welding system 10 to calibrate the position and/or orientation of the welding surface 112 relative to the sensing device 16 without a separate calibration device. Accordingly, the first and second markers 116 and 118 are configured to be detected by the sensing device 16. In certain embodiments, the first and second markers 116 and 118 may be positioned at predetermined locations on the welding surface 112. Furthermore, the welding software may be programmed to use the predetermined locations to determine the position and/or the orientation of the welding surface 112. In other embodiments, the location of the first and second markers 116 and 118 may be provided to the welding software during calibration. With the first and second markers 116 and 118 on the welding surface 112, the sensing device 16 may sense the position and/or orientation of the first and second markers 116 and 118 relative to the sensing device 16. Using this sensed data in conjunction with the location of the first and second markers 116 and 118 on the welding surface 112, the welding software may be able to calibrate the position and/or orientation of the welding surface 112 relative to the sensing device 16. Furthermore, the sensing device 16 may sense and/or track the first and second markers 116 and 118 during a weld to account for any movement of the welding plate 108 that may occur during the weld. While the markers 116 and 118 have been described herein as being detected by the sensing device 16, in certain embodiments, the markers 116 and 118 may indicate locations where a calibration device is to be touched or inserted for calibration using the calibration device, as described previously.

Figure 5:
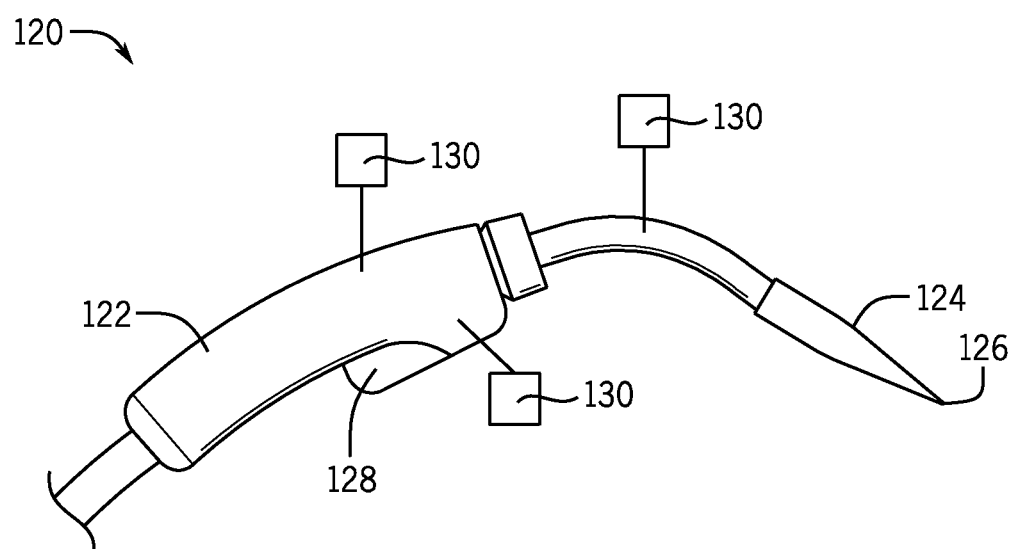
FIG. 5 is a perspective view of an embodiment of a calibration device in accordance with aspects of the present disclosure.

FIG. 5 is a perspective view of an embodiment of a calibration device 120. In some embodiments, the calibration device 120 is shaped like a torch and may be used for calibrating the position and/or orientation of the welding surfaces 88 and 112 relative to the sensing device 16. In other embodiments, the calibration device 120 may be used for calibrating the position and/or orientation of a welding joint. The calibration device 120 includes a handle 122 and a nozzle 124. The nozzle 124 includes a pointed end 126 that may be used to touch a location for calibration and/or to be inserted into an aperture for calibration. The calibration device 120 also includes a user interface 128 that enables the welding operator to provide input corresponding to a time that the calibration device 120 is touching a location for calibration and/or is being inserted into an aperture for calibration. Moreover, in certain embodiments, the calibration device 120 includes markers 130 configured to be sensed by the sensing device 16. As illustrated, the markers 130 extend from the calibration device 120. However, in other embodiments, the markers 130 may not extend from the calibration device 120. The markers 130 may be any suitable marker configured to be detected by the sensing device 16 (e.g., camera). Moreover, the markers 130 may be any suitable size, shape, and/or color.

During calibration, the sensing device 16 may sense a position of the calibration device 120 and/or an orientation of the calibration device 120. The position and/or orientation of the calibration device 120 may be used by the welding software to determine a position and/or orientation of one or more of the welding surfaces 88 and 112 relative to the sensing device 16, a position and/or orientation of the workpiece 82 relative to the sensing device 16, a position and/or orientation of a fixture relative to the sensing device 16, and so forth. Thus, the calibration device 120 may facilitate calibration of the welding system 10. In some embodiments, a tray may be positioned beneath the welding surface 88 for storing the calibration device 120. Moreover, in certain embodiments live welding may be disabled if the calibration device 120 is able to be tracked by the sensing device 16 (e.g., to block spatter from contacting the calibration device 120).

Figure 6:
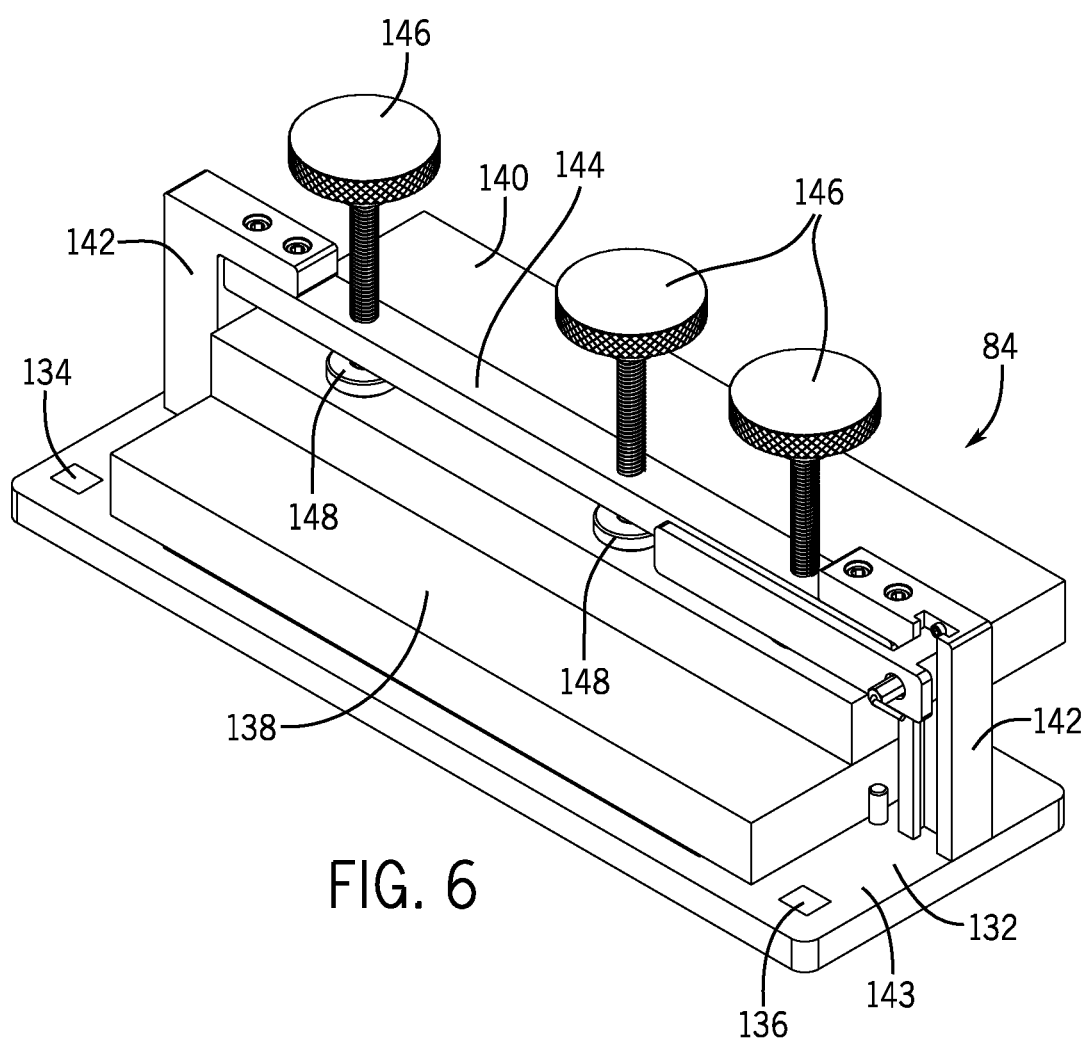
FIG. 6 is a perspective view of an embodiment of a fixture assembly in accordance with aspects of the present disclosure.

FIG. 6 is a perspective view of an embodiment of a fixture assembly 132. The fixture assembly 132 may be positioned on the welding surface 88 and/or the welding surface 112, and may secure the workpiece 82 thereon. In certain embodiments, the fixture assembly 132 may be configured to align with one or more of the slots 92 and 114. In other embodiments, the fixture assembly 132 may be placed at any location on the welding surface 88 and/or the welding surface 122. The fixture assembly 132 also includes a first marker 134 and a second marker 136. The first and second markers 134 and 136 may be used together to determine a position and/or an orientation of the fixture assembly 132. As may be appreciated, at least two markers are used to determine the position and/or the orientation of the fixture assembly 132. The first and second markers 134 and 136 may be formed from any suitable material. Moreover, in certain embodiments, the first and second markers 134 and 136 may be built into the fixture assembly 132, while in other embodiments, the first and second markers 134 and 136 may be attached to the fixture assembly 132. For example, the first and second markers 134 and 136 may be attached to the fixture assembly 132 using an adhesive and/or the first and second markers 134 and 136 may be stickers (e.g., tape). The first and second markers 134 and 136 may have any suitable shape, size, and/or color. Furthermore, in certain embodiments, the first and second markers 134 and 136 may be a reflector formed from a reflective material. The first and second markers 134 and 136 may be used by the welding system 10 to calibrate the position and/or orientation of the fixture assembly 132 relative to the sensing device 16 without a separate calibration device. Accordingly, the first and second markers 134 and 136 are configured to be detected by the sensing device 16. In certain embodiments, the first and second markers 134 and 136 may be positioned at predetermined locations on the fixture assembly 132. Furthermore, the welding software may be programmed to use the predetermined locations to determine the position and/or the orientation of the fixture assembly 132. In other embodiments, the location of the first and second markers 134 and 136 may be provided to the welding software during calibration. With the first and second markers 134 and 136 on the fixture assembly 132, the sensing device 16 may sense the position and/or orientation of the first and second markers 134 and 136 relative to the sensing device 16. Using this sensed data in conjunction with the location of the first and second markers 134 and 136 on the fixture assembly 132, the welding software may be able to calibrate the position and/or orientation of the fixture assembly 132 relative to the sensing device 16. While the first and second markers 134 and 136 have been described herein as being detected by the sensing device 16, in certain embodiments, the first and second markers 134 and 136 may indicate locations where a calibration device is to be touched or inserted for calibration using the calibration device 120, as described previously.

In the illustrated embodiment, the fixture assembly 132 is configured to secure a lower portion 138 of the workpiece 82 to an upper portion 140 of the workpiece 82 for performing a lap weld. In other embodiments, the fixture assembly 132 may be configured to secure portions of the workpiece 82 for performing a butt weld, a fillet weld, and so forth, to aid a welding operator in performing a weld. The fixture assembly 132 includes vertical arms 142 extending from a base 143. A cross bar 144 extends between the vertical arms 142, and is secured to the vertical arms 142. Adjustment mechanisms 146 (e.g., knobs) may be adjusted to direct locking devices 148 toward the workpiece 82 for securing the workpiece 82 between the locking devices 148 and the base 143 of the fixture assembly 132. Conversely, the adjustment mechanisms 146 may be adjusted to direct the locking devices 148 away from the workpiece 82 for removing the workpiece 82 from being between the locking devices 148 and the base 143. Accordingly, the workpiece 82 may be selectively secured to the fixture assembly 132.

Figure 7:
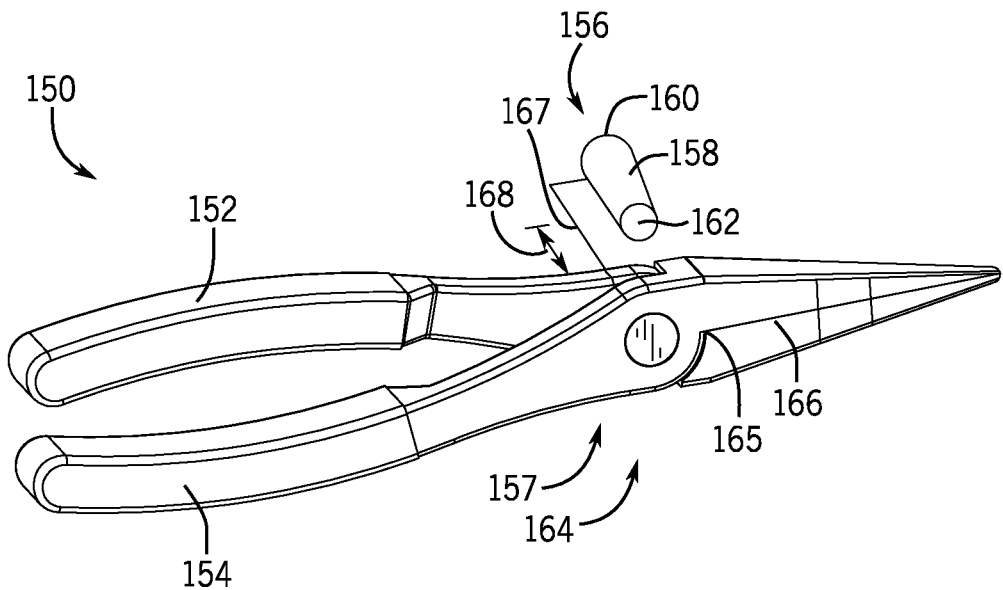
FIG. 7 is a perspective view of a welding wire stickout calibration tool in accordance with aspects of the present disclosure.

FIG. 7 is a perspective view of a welding wire stickout calibration tool 150. The tool 150 is configured to calibrate a length of welding wire extending out of a torch nozzle to a selectable length. Accordingly, the tool 150 includes a first handle 152 and a second handle 154. The tool 150 also includes a torch nozzle holder 156 attached to a central portion 157 of the tool 150 and extending outward from the central portion 157 a selected distance. In the illustrated embodiment, the torch nozzle holder 156 has a generally cylindrical body 158 (e.g., cup shape); however, in other embodiments, the body 158 of the torch nozzle holder 156 may have any suitable shape. Moreover, the torch nozzle holder 156 is configured to receive the torch nozzle through a nozzle inlet 160 such that the torch nozzle extends into the body 158. Furthermore, the torch nozzle holder 156 includes an opening 162 configured to enable welding wire to extend out the end of the torch nozzle holder 156, and to block the torch nozzle from extending through the opening 162. As the torch nozzle extends into the torch nozzle holder 156, the welding wire extends out of the opening 162 of the torch nozzle holder 156 toward a blade assembly 164 of the tool 150. The blade assembly 164 includes one or more sides 165 and 166 configured to contact the welding wire. In certain embodiments, both of sides 165 and 166 include blades to cut opposing sides of the welding wire, while in other embodiments, only one of the sides 165 and 166 includes a blade to cut one side of the welding wire and the other side includes a surface to which the blade is directed toward. For calibrating the length of the welding wire, the welding wire may extend through the opening 162 and into the blade assembly 164. The welding wire may be cut to a selectable length by pressing the first handle 152 and the second handle 154 toward one another, thereby calibrating the length of wire extending from the torch nozzle. The calibration length may be selected using an adjustment mechanism 167 to adjust a distance 168 between the blade assembly 164 and the opening 162 of the torch nozzle holder 156. Thus, using the tool 150, the length of wire extending from the torch nozzle may be calibrated.

Figure 8:
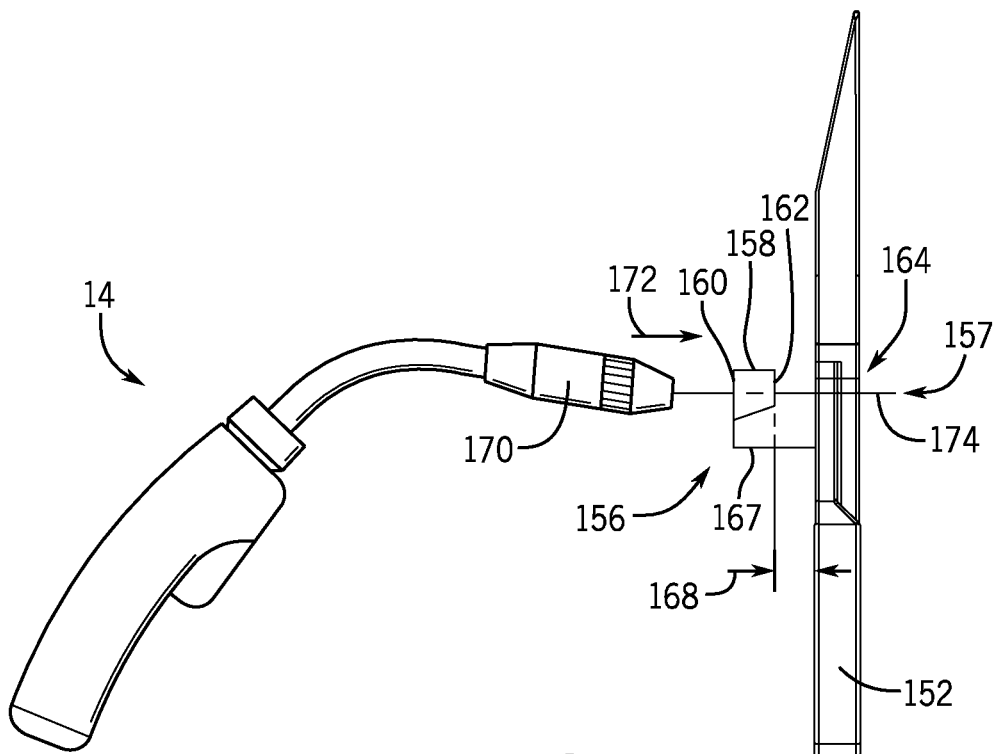
FIG. 8 is a top view of the welding wire stickout calibration tool of FIG. 7 in accordance with aspects of the present disclosure.

FIG. 8 is a top view of the welding wire stickout calibration tool 150 of FIG. 7. As illustrated, the welding torch 14 may be used with the tool 150. Specifically, a nozzle 170 of the welding torch 14 may be inserted into the torch nozzle holder 156 in a direction 172. Welding wire 174 extending from the welding torch 14 is directed through the nozzle inlet 160, the opening 162, and the blade assembly 164. Accordingly, the first and second handles 152 and 154 may be pressed together to cut the welding wire 174 to the distance 168 (e.g., the calibration length) set by the adjustment mechanism 167.

Figure 9:
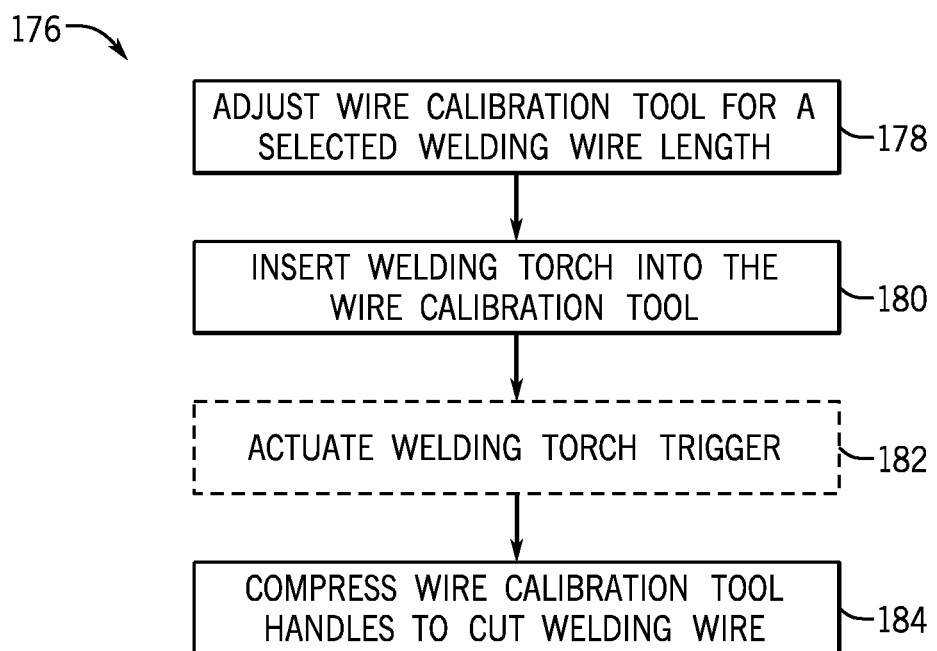
FIG. 9 is an embodiment of a method for calibrating wire stickout from a welding torch in accordance with aspects of the present disclosure.

FIG. 9 is an embodiment of a method 176 for calibrating wire stickout from the welding torch 14. The tool 150 may be used to calibrate the length of welding wire 174 extending from the nozzle 170 using a variety of methods. In the method 176, the adjustment mechanism 167 of the welding wire stickout calibration tool 150 may be adjusted for a selected welding wire 174 length (block 178). For example, the distance 168 of the torch nozzle holder 156 from the tool 150 may be set to a range of between approximately 0.5 to 2.0 cm, 1.0 to 3.0 cm, and so forth. The welding torch 14 may be inserted into the torch nozzle holder 156 of the tool 150, such that the nozzle 170 of the welding torch 14 abuts the torch nozzle holder 156, and that the welding wire 174 extends through the opening 162 of the torch nozzle holder 156 (block 180). In certain embodiments, the welding wire 174 may be long enough to extend through the blade assembly 164. However, if the welding wire 174 does not extend through the blade assembly 164, a welding operator may actuate the trigger 70 of the welding torch 14 to feed welding wire 174 such that the welding wire 174 extends through the blade assembly 164 (block 182). Accordingly, the welding operator may compress handles 152 and 154 of the tool 150 to cut the welding wire 174 extending through the blade assembly 164 and thereby calibrate the length of the welding wire 174 (block 184).

Figure 10:
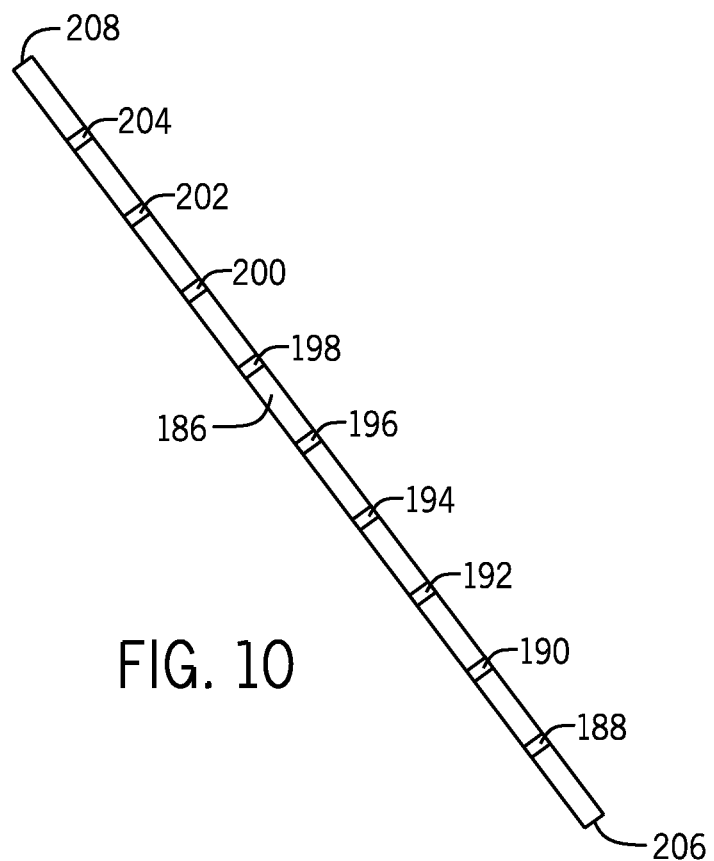
FIG. 10 is a perspective view of an embodiment of a welding consumable having physical marks in accordance with aspects of the present disclosure.

FIG. 10 is a perspective view of an embodiment of a welding consumable 186 having physical marks. The welding consumable 186 may be any suitable welding consumable, such as a welding stick, welding rod, or a welding electrode. The welding consumable 186 includes physical marks 188, 190, 192, 194, 196, 198, 200, 202, and 204. The physical marks 188, 190, 192, 194, 196, 198, 200, 202, and 204 may be any suitable physical mark. For example, the physical marks 188, 190, 192, 194, 196, 198, 200, 202, and 204 may include a bar code, an image, a shape, a color, text, a set of data, and so forth. In certain embodiments, the physical marks 188, 190, 192, 194, 196, 198, 200, 202, and 204 may be laser etched. Furthermore, in certain embodiments, the physical marks 188, 190, 192, 194, 196, 198, 200, 202, and 204 may be visible with the natural eye (e.g., within the visible spectrum), while in other embodiments the physical marks 188, 190, 192, 194, 196, 198, 200, 202, and 204 may not be visible with the natural eye (e.g., not within the visible spectrum).

Each of the physical marks 188, 190, 192, 194, 196, 198, 200, 202, and 204 indicates a location on the welding consumable 186 relative to either a first end 206, or a second end 208 of the welding consumable 186. For example, the physical mark 188 may indicate a distance from the first end 206, a distance from the second end 208, or some other location relative to the welding consumable 186. In certain embodiments, the physical marks 188, 190, 192, 194, 196, 198, 200, 202, and 204 may indicate a number that corresponds to the first end 206 and/or the second end 208. For example, the physical mark 188 may indicate a number "1" indicating that it is the first physical mark from the first end 206 and/or the physical mark 188 may indicate a number "9" indicating that it is the ninth physical mark from the second end 208. A processing device may use a lookup table to determine a distance from the first end 206 or the second end 208 based on the number indicated by the physical mark.

A camera-based detection system, which may include the sensing device 16, or another type of system is configured to detect the physical marks 188, 190, 192, 194, 196, 198, 200, 202, and 204 during live arc welding or a welding simulation. Moreover, the camera-based detection system is configured to determine a remaining length of the welding consumable 186, a consumed length of the welding consumable 186, a rate of use of the welding consumable 186, a dipping rate of the welding consumable 186, and so forth, based on the detected physical marks. Accordingly, data corresponding to use of the welding consumable 186 may be tracked by the welding system 10 for training and/or analysis.

Figure 11:
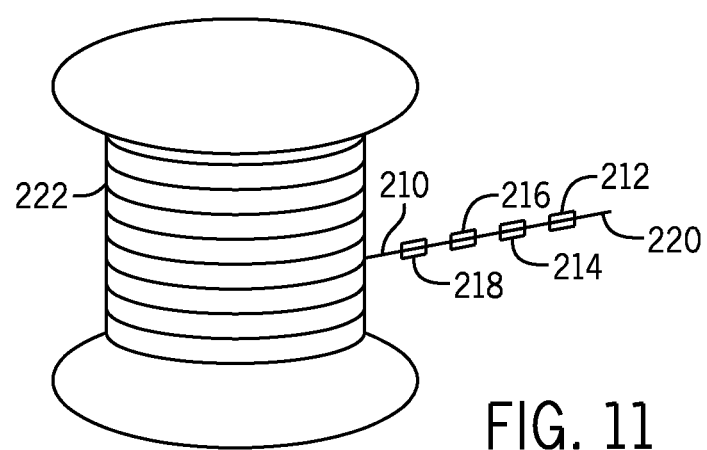
FIG. 11 is a perspective view of an embodiment of welding wire having physical marks in accordance with aspects of the present disclosure.

FIG. 11 is a perspective view of an embodiment of welding wire 210 having physical marks 212, 214, 216, and 218. The physical marks 212, 214, 216, and 218 may be any suitable physical mark. For example, the physical marks 212, 214, 216, and 218 may include a bar code, an image, a shape, text, a set of data, and so forth. In certain embodiments, the physical marks 212, 214, 216, and 218 may be laser etched. Furthermore, in certain embodiments, the physical marks 212, 214, 216, and 218 may be visible with the natural eye (e.g., within the visible spectrum), while in other embodiments the physical marks 212, 214, 216, and 218 may not be visible with the natural eye (e.g., not within the visible spectrum).

Each of the physical marks 212, 214, 216, and 218 indicates a location on the welding wire 210 relative to either a first end 220, or a second end 222 of the welding wire 210. For example, the physical mark 212 may indicate a distance from the first end 220, a distance from the second end 222, or some other location relative to the welding wire 210. In certain embodiments, the physical marks 212, 214, 216, and 218 may indicate a number that corresponds to the first end 220 and/or the second end 222. For example, the physical mark 212 may indicate a number "1" indicating that it is the first physical mark from the first end 220 and/or the physical mark 212 may indicate a number "4" indicating that it is the fourth physical mark from the second end 222. A processing device may use a lookup table to determine a distance from the first end 220 or the second end 222 based on the number indicated by the physical mark.

A camera-based detection system, which may include the sensing device 16, or another type of system is configured to detect the physical marks 212, 214, 216, and 218 during live arc welding or a welding simulation. Moreover, the camera-based detection system is configured to determine a remaining length of the welding wire 210, a consumed length of the welding wire 210, a rate of use of the welding wire 210, a dipping rate of the welding wire 210, and so forth, based on the detected physical marks. Accordingly, data corresponding to use of the welding wire 210 may be tracked by the welding system 10 for training and/or analysis.

Figure 12:
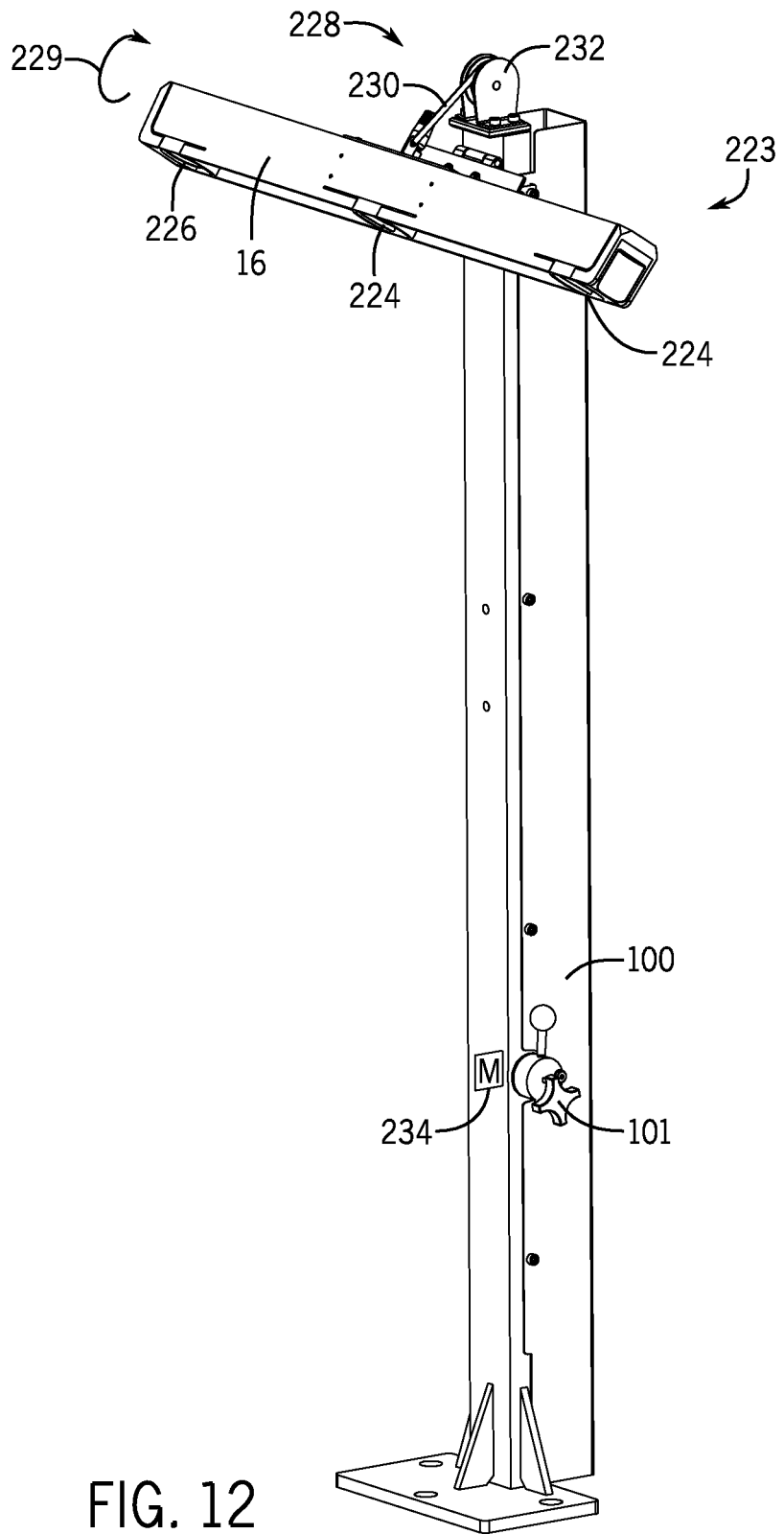
FIG. 12 is a perspective view of an embodiment of a vertical arm assembly of the welding stand of FIG. 1 in accordance with aspects of the present disclosure.

FIG. 12 is a perspective view of an embodiment of a vertical arm assembly 223 of the stand 12 of FIG. 4. As illustrated, the sensing device 16 is attached to the first arm 100. Furthermore, the sensing device 16 includes cameras 224, and an infrared emitter 226. However, in other embodiments, the sensing device 16 may include any suitable number of cameras, emitters, and/or other sensing devices. A pivot assembly 228 is coupled to the first arm 100 and to the sensing device 16, and enables an angle of the sensing device 16 to be adjusted while the sensing device 16 rotates as illustrated by arrow 229. As may be appreciated, adjusting the angle of the sensing device 16 relative to the first arm 100 changes the field of view of the sensing device 16 (e.g., to change the portion of the welding surface 88 and/or the welding surface 112 sensed by the sensing device 16). In some embodiments, the sensing device 16 may be arranged to observe at least a portion (e.g., hands, face) of the operator prior to and/or after completion of a weld process. Observation of the operator by the sensing device 16, such as by a camera, may facilitate operator identification and verification that the identified operator performed the observed weld process.

A cord 230 extends between the knob 101 and the sensing device 16. The cord 230 is routed through a pulley 232 to facilitate rotation of the sensing device 16. Thus, a welding operator may rotate the knob 101 to manually adjust the angle of the sensing device 16. As may be appreciated, the combination of the cord 230 and the pulley 232 is one example of a system for rotating the sensing device 16. It should be noted that any suitable system may be used to facilitate rotation of the sensing device 16. While one embodiment of a knob 101 is illustrated, it may be appreciated that any suitable knob may be used to adjust the angle of the sensing device 16. Furthermore, the angle of the sensing device 16 may be adjusted using a motor 234 coupled to the cord 230. Accordingly, a welding operator may operate the motor 234 to adjust the angle of the sensing device 16. Moreover, in certain embodiments, control circuitry may be coupled to the motor 234 and may control the angle of the sensing device 16 based on a desired field of view of the sensing device 16 and/or based on tracking of an object within the field of view of the sensing device 16.

Figure 13:
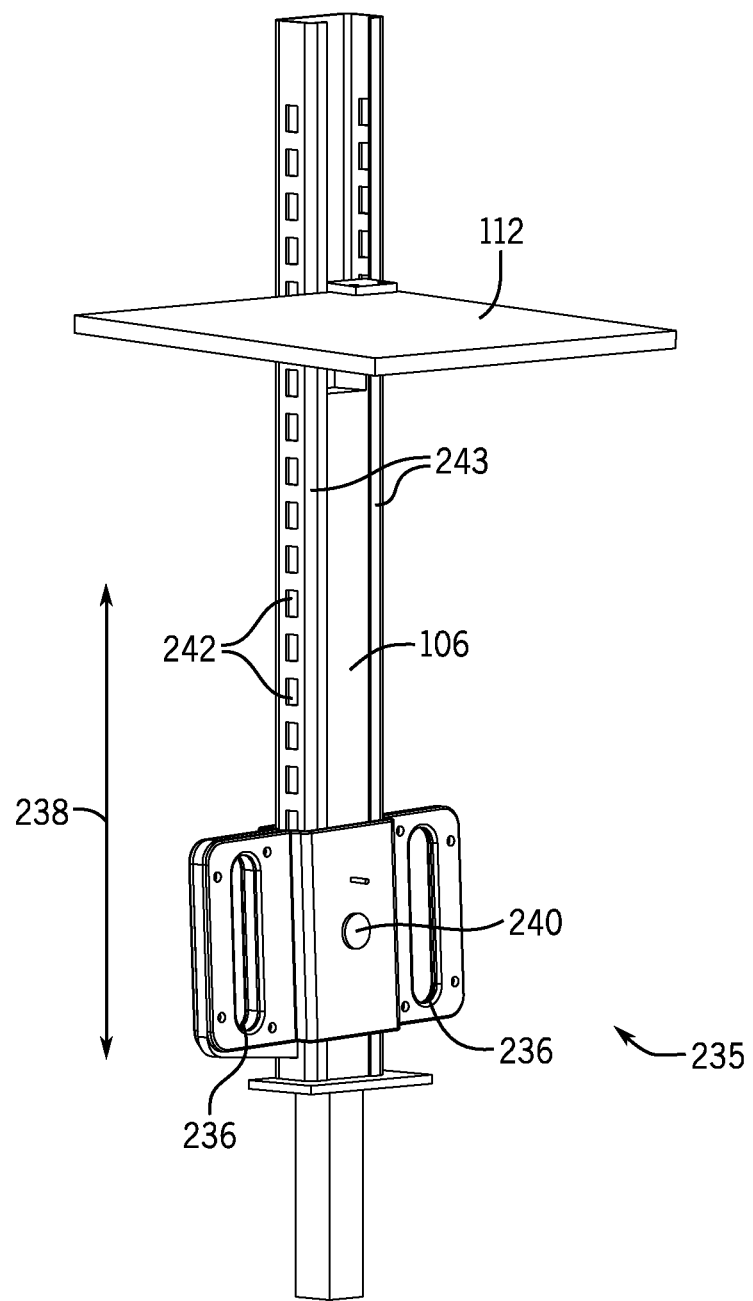
FIG. 13 is a perspective view of an embodiment of an overhead welding arm assembly in accordance with aspects of the present disclosure.

FIG. 13 is a perspective view of an embodiment of an overhead welding arm assembly 235. The overhead welding arm assembly 235 illustrates one embodiment of a manufacturing design that enables the second arm 106 to have an adjustable height. Accordingly, as may be appreciated, the second arm 106 may be manufactured to have an adjustable height in a number of ways. As illustrated, the overhead welding assembly 235 includes handles 236 used to vertically raise and/or lower the second arm 106 as illustrated by arrows 238. The overhead welding arm assembly 235 includes a locking device 240 to lock the second arm 106 at a desired height. For example, the locking device 240 may include a button that is pressed to disengage a latch configured to extend into openings 242, thus unlocking the second arm 106 from being secured to side rails 243. With the second arm 106 unlocked from the side rails 243, the handles 236 may be vertically adjusted to a desired height, thereby adjusting the plate 112 to a desired height. As may be appreciated, releasing the button may result in the latch extending into the openings 242 and locking the second arm 106 to the side rails 243. As may be appreciated, the locking device 240 may operate manually as described and/or the locking device 240 may be controlled by a control system (e.g., automatically controlled). Furthermore, the second arm 106 may be vertically raised and/or lowered using the control system. For example, in certain embodiments, the welding software may control the second arm 106 to move to a desired position automatically. Thus, the plate 112 may be adjusted to a desired height for overhead welding.

Figure 14:
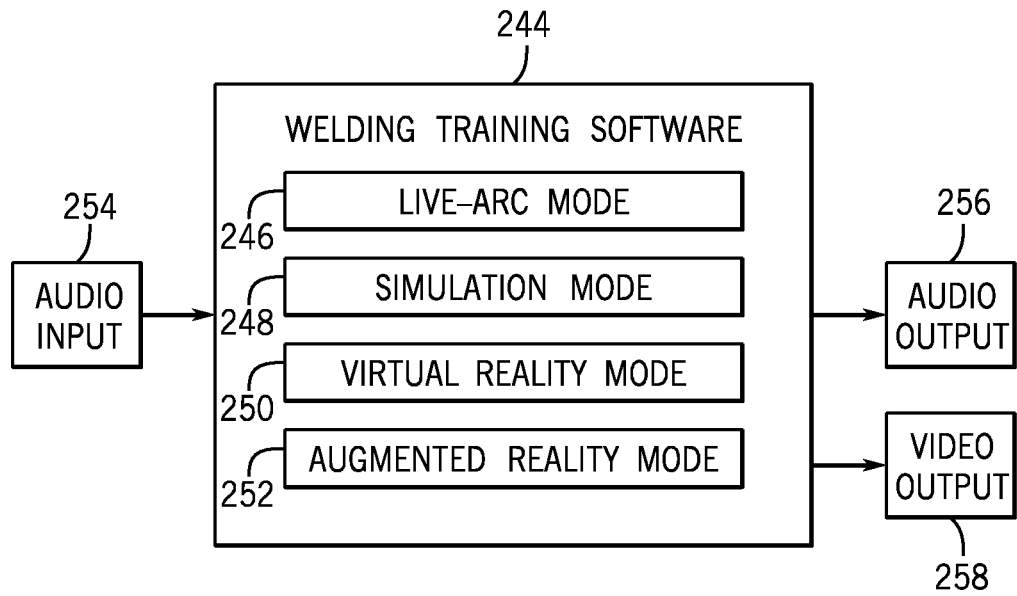
FIG. 14 is a block diagram of an embodiment of welding software having multiple training modes in accordance with aspects of the present disclosure.

FIG. 14 is a block diagram of an embodiment of welding software 244 (e.g., welding training software) of the welding system 10 having multiple modes. As illustrated, the welding software 244 may include one or more of a live-arc mode 246 configured to enable training using a live (e.g., actual) welding arc, a simulation mode 248 configured to enable training using a welding simulation, a virtual reality (VR) mode 250 configured to enable training using a VR simulation, and/or an augmented reality mode 252 configured to enable training using augmented reality simulation.

The welding software 244 may receive signals from an audio input 254. The audio input 254 may be configured to enable a welding operator to operate the welding software 244 using audible commands (e.g., voice activation). Furthermore, the welding software 244 may be configured to provide an audio output 256 and/or a video output 258. For example, the welding software 244 may provide audible information to a welding operator using the audio output 256. Such audible information may include instructions for configuring (e.g., setting up) the welding system 10, real-time feedback provided to a welding operator during a welding operation, instructions to a welding operator before performing a welding operation, instructions to a welding operator after performing a welding operation, warnings, and so forth.

Figure 15:
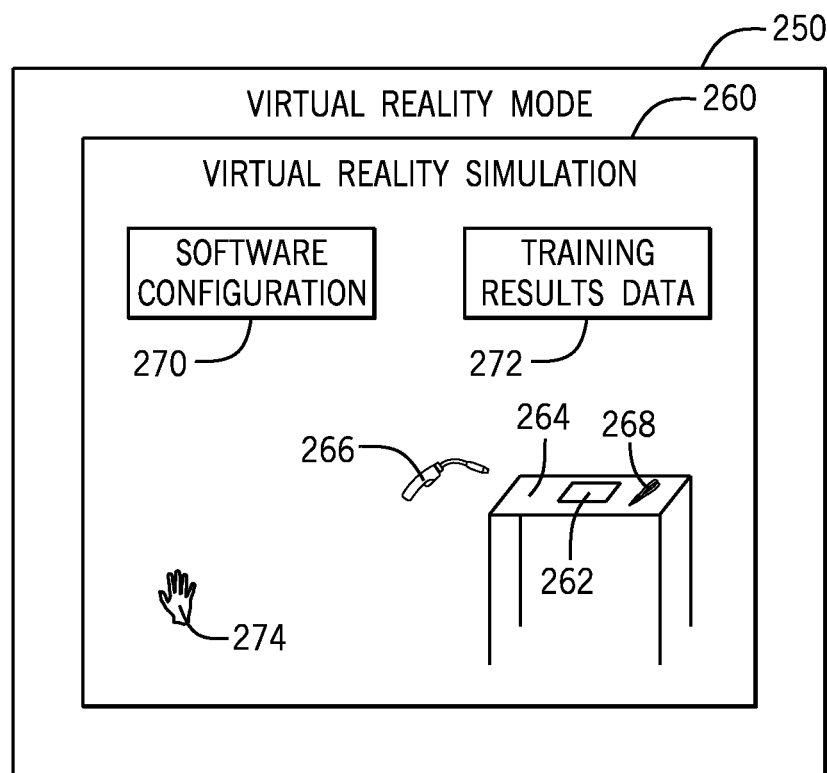
FIG. 15 is a block diagram of an embodiment of a virtually reality mode of welding software in accordance with aspects of the present disclosure.

FIG. 15 is a block diagram of an embodiment of the VR mode 250 of the welding software 244. The VR mode 250 is configured to provide a welding operator with a VR simulation 260. The VR simulation 260 may be displayed to a welding operator through a VR headset, VR glasses, a VR display, or any suitable VR device. In some embodiments, the display 32 of the helmet 41 of the welding system 10 may facilitate the VR simulation 260. The VR simulation 260 may be configured to include a variety of virtual objects, such as the objects illustrated in FIG. 15, that enable interaction between a welding operator and a selected virtual object of the variety of virtual objects within the VR simulation 260. For example, virtual objects may include a virtual workpiece 262, a virtual welding stand 264, a virtual welding torch 266, virtual wire cutters 268, virtual software configuration 270, virtual training data results 272, and/or a virtual glove 274.

In certain embodiments, the welding operator may interact with the virtual objects without touching a physical object. For example, the sensing device 16 may detect movement of the welding operator and may result in similar movements occurring in the VR simulation 260 based on the welder operator's movements in the real world. In other embodiments, the welding operator may use a glove or the welding torch 14 to interact with the virtual objects. For example, the glove or the welding torch 14 may be detected by the sensing device 16, and/or the glove or the welding torch 14 may correspond to a virtual object in the VR simulation 260. Furthermore, the welding operator may be able to operate the welding software 244 within the VR simulation 260 using the virtual software configuration 270 and/or the virtual training data results 272. For example, the welding operator may use their hand, the glove, or the welding torch 14 to select items within the welding software 244 that are displayed virtually within the VR simulation 260. Moreover, the welding operator may perform other actions such as picking up wire cutters and cutting virtual welding wire extending from the virtual torch 266, all within the VR simulation 260.

Figure 16:
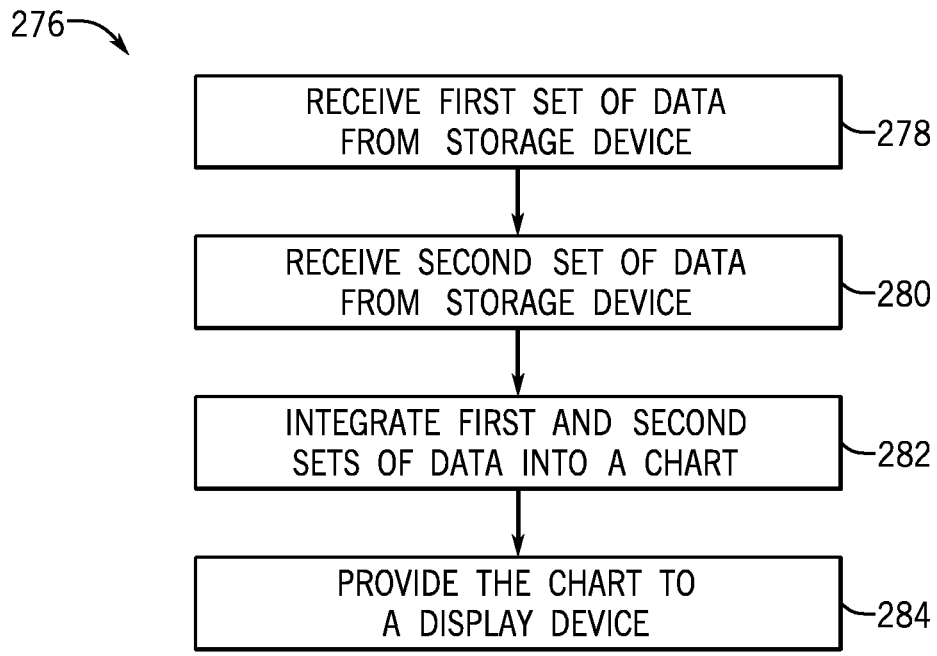
FIG. 16 is an embodiment of a method for integrating training results data in accordance with aspects of the present disclosure.

FIG. 16 is an embodiment of a method 276 for integrating training results data, non-training results data, simulation results data, and so forth. The method 276 includes the welding software 244 of the computer 18 receiving a first set of welding data from a storage device (e.g., storage device 24) (block 278). The first set of welding data may include welding data corresponding to a first welding session (e.g., welding assignment). The method 276 also includes the welding software 244 receiving a second set of welding data from the storage device (block 280). In certain embodiments, the first set and/or second set of welding data may be received from a network storage device. The network storage device may be configured to receive welding data from and/or to provide welding data to the welding system 10 and/or the external welding system 40. The welding software 244 may integrate the first and second sets of welding data into a chart to enable a visual comparison of the first set of welding data with the second set of welding data (block 282). As may be appreciated, the chart may be a bar chart, a pie chart, a line chart, a histogram, and so forth. In certain embodiments, integrating the first set of welding data with the second set of welding data includes filtering the first set of welding data and the second set of welding data to display a subset of the first set of welding data and a subset of the second set of welding data. The welding software 244 may provide the chart to a display device (e.g., the display 32) (block 284). In certain embodiments, providing the chart to the display device includes providing selectable elements on the chart that when selected display data corresponding to a respective selected element of the selectable elements (e.g., selecting wire speed from the chart may change the screen to display the wire speed history for a particular welding session (e.g., welding assignment)).

The first set of welding data and/or the second set of welding data may include a welding torch orientation, a welding torch travel speed, a welding torch position, a contact tip to workpiece distance, an aim of the welding torch, a welding score, a welding grade, and so forth. Moreover, the first set of welding data and the second set of welding data may correspond to training performed by one welding operator and/or by a class of welding operators. Furthermore, the first welding session (e.g., welding assignment) and the second welding session (e.g., welding assignment) may correspond to training performed by one welding operator and/or by a class of welding operators. In certain embodiments, the first welding assignment may correspond to training performed by a first welding operator, and the second welding assignment may correspond to welding performed by a second welding operator. Moreover, the first assignment and the second assignment may correspond to the same welding scenario. Additionally, or in the alternative, the first set of welding data and the second set of welding data may correspond to welding sessions (e.g., welding assignments) performed by one welding operator and/or a class of welding operators outside of a training environment (e.g., production floor).

Figure 17:
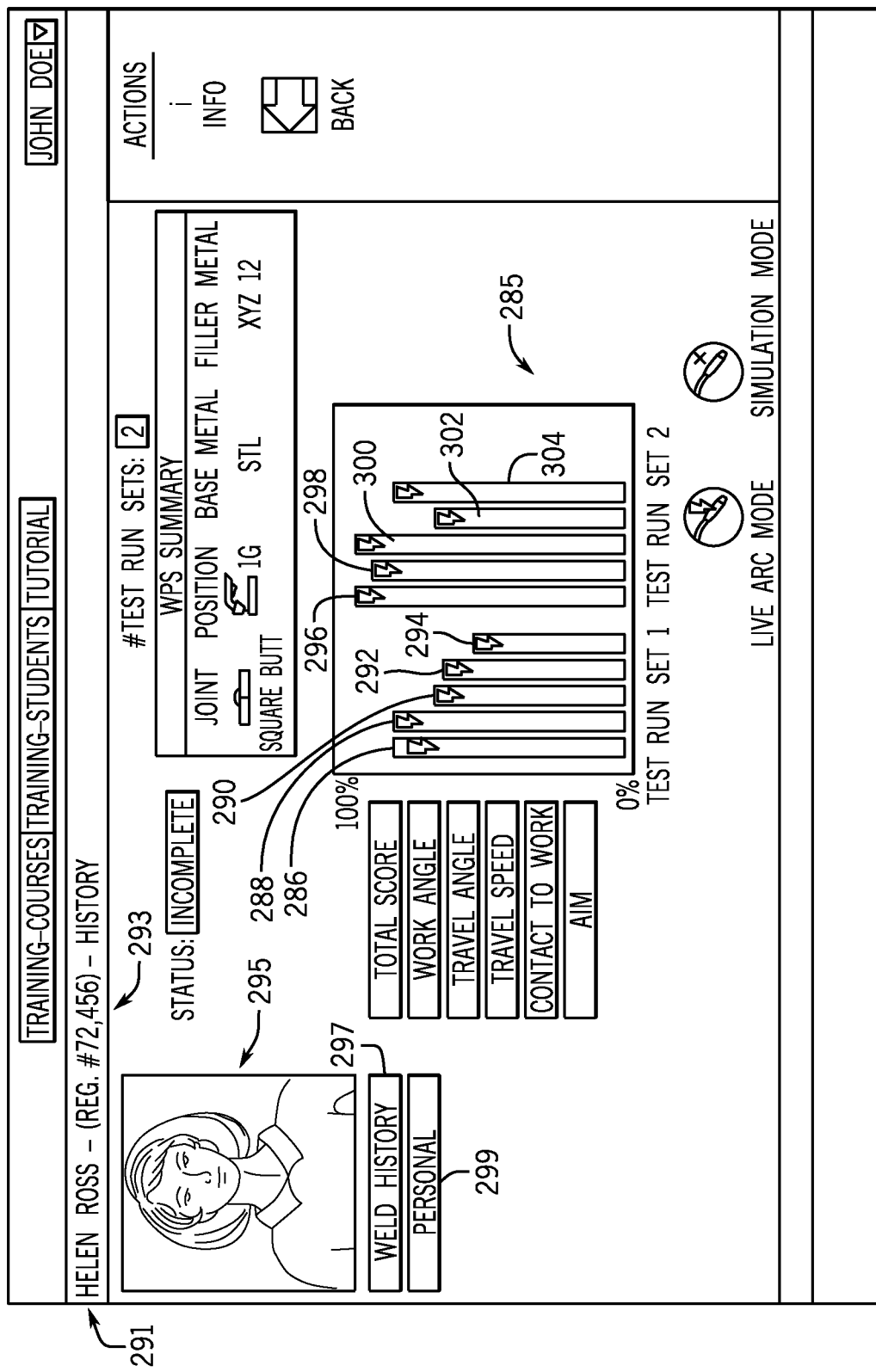
FIG. 17 is an embodiment of a chart illustrating multiple sets of welding data for a welding operator in accordance with aspects of the present disclosure.

FIG. 17 is an embodiment of a chart 285 illustrating multiple sets of welding data for a welding operator. The chart 285 may be produced by the welding software 244 and may be provided to the display 32 to be used by a welding instructor to review welding operations performed by a welding student, and/or may be provided to the display 32 to be used by a welding student to review welding operations performed by that welding student. The chart 285 illustrates a bar graph comparison between different sessions (e.g., assignments) of a first set of welding assignments performed by a welding operator. The first set of welding sessions (e.g., welding assignments) includes sessions (e.g., assignments) 286, 288, 290, 292, and 294. The chart 285 also illustrates a bar graph comparison between different assignments of a second set of welding sessions (e.g., welding assignments) performed by the welding operator. The second set of welding sessions (e.g., welding assignments) includes sessions (e.g., assignments) 296, 298, 300, 302, and 304. Accordingly, welding sessions (e.g., welding assignments) may be compared to one another for analysis, instruction, certification, and/or training purposes. As illustrated, the welding sessions (e.g., welding assignments) may be compared to one another using one of any number of criteria, such as a total score, a work angle, a travel angle, a travel speed, a contact to work distance, an aim, a mode (e.g., live-arc mode, simulation mode, etc.), a completion status (e.g., complete, incomplete, partially complete, etc.), a joint type (e.g., fillet, butt, T, lap, etc.), a welding position (e.g., flat, vertical, overhead, etc.), a type of metal used, a type of filler metal, and so forth.

The welding software 244 may associate an operator with welding data (e.g., arc parameters, welding parameters) acquired during a welding session (e.g., live arc welding assignment, simulated welding assignment, and so forth). For example, the welding software 244 may identify the welding operator by an operator name 291, an operator registration number 293, an operator photograph 295, and so forth. For example, the operator identification system 43 discussed above with FIG. 1 may be utilized to determine the operator registration number 293. That is, each operator registration number 293 may correspond to the operator name 291 and a set of identification information (e.g., resettable information 45, biometric information 47, token 49). In some embodiments, the registration number 293 may be reset or reassigned to another operator after a period (e.g., 1, 3, 5, 10, or more years) of inactivity associated with the registration number 293. The registration number 293 may be unique for each operator. In some embodiments, the registration number 293 may be retained by the operator for an extended period of time (e.g., career, life) regardless of activity level associated with the registration number 293. That is, the registration number 293 may be a permanent identifier associated with each operator across one welding system 10 or a network of welding systems 10 coupled via the network 38. Welding data associated with the registration number 293 may be maintained locally or within one or more data storage systems, such as a cloud storage system or database of the network 38 coupled to the welding system 10. The data storage system 318 (e.g., cloud storage system) of the network 38 may be maintained by the manufacturer or another party, thereby enabling the welding data associated with a certain registration number 293 to be retained independent of an employment status of the operator with the certain registration number 293. For example, the operator registration number 293 and the data storage system (e.g., cloud storage system) may facilitate the retention of welding data associated with the operator from weld processes performed during training, during a simulation, during a first employment, during a second employment, during personal time, or any combination thereof. In some embodiments, welding data stored within the memory 22 or the storage 24 of the computer 18 of the welding system 10 for a particular welding operator (e.g., operator registration number 293) may be selectively or automatically synchronized with the data storage system (e.g., cloud storage system).

Weld history data, such as the data of the chart 285, is associated with each registration number 293. In some embodiments, the weld history data is automatically acquired and stored in the data storage system (e.g., cloud storage system) by the welding software 244 of the welding system 10. Additionally, or in the alternative, weld history data may be loaded directly to the data storage system (e.g., cloud storage system) of the network 38 via a remote computer 44. The welding software 244 may facilitate access to the welding history data via a welding history control 297. Additionally, the welding software 244 may enable the operator to associate personal information with the registration number 293 via a personal user control 299. The operator associated with the registration number 293 may input one or more organizations (e.g., training center, school, employer, trade organization) with which the operator is affiliated, experience, certifications for various welding processes and/or welding positions, a résumé, or any combination thereof. Furthermore, the registration umber 293 may remain associated with the operator despite changes in affiliated organizations, experience, certifications, or any combination thereof.

Figure 18:
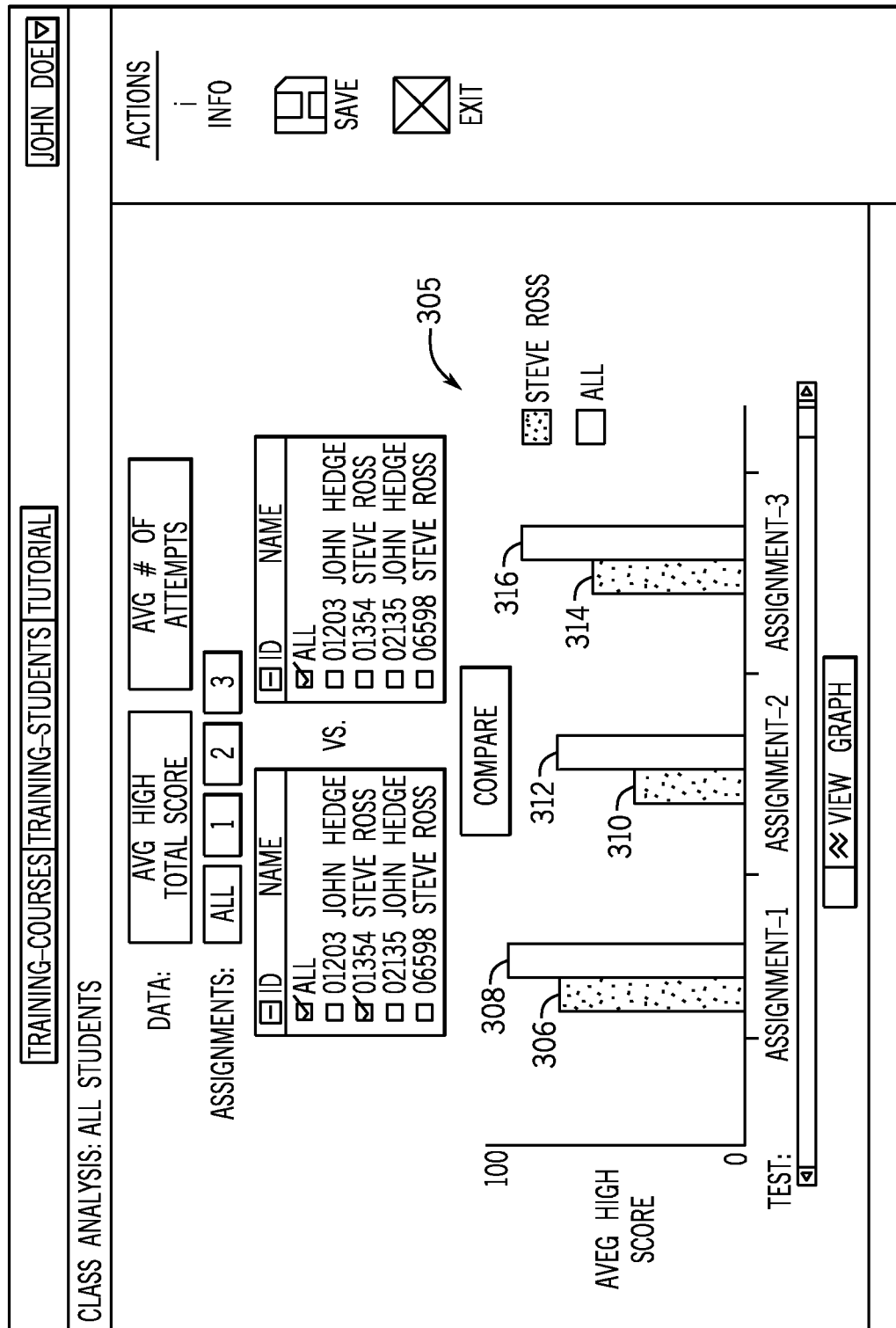
FIG. 18 is an embodiment of a chart illustrating welding data for a welder compared to welding data for a class in accordance with aspects of the present disclosure.

FIG. 18 is an embodiment of a chart 305 illustrating welding data for a welder compared to welding data for a class. For example, the chart 305 illustrates a score 306 of a welding operator compared to a score 308 (e.g., average, median, or some other score) of a class for a first assignment. Furthermore, a score 310 of the welding operator is compared to a score 312 (e.g., average, median, or some other score) of the class for a second assignment. Moreover, a score 314 of the welding operator is compared to a score 316 (e.g., average, median, or some other score) of the class for a third assignment. As may be appreciated, scores from one or more welding operators may be compared to scores of the entire class. Such a comparison enables a welding instructor to assess the progress of individual welding students as compared to the class of welding students. Furthermore, scores from one or more welding operators may be compared to scores of one or more other welding operators. In certain embodiments, scores from one class may be compared to scores of another class. Moreover, scores from the first assignment, the second assignment, and/or the third assignment may be selected for comparison.

Figure 19:
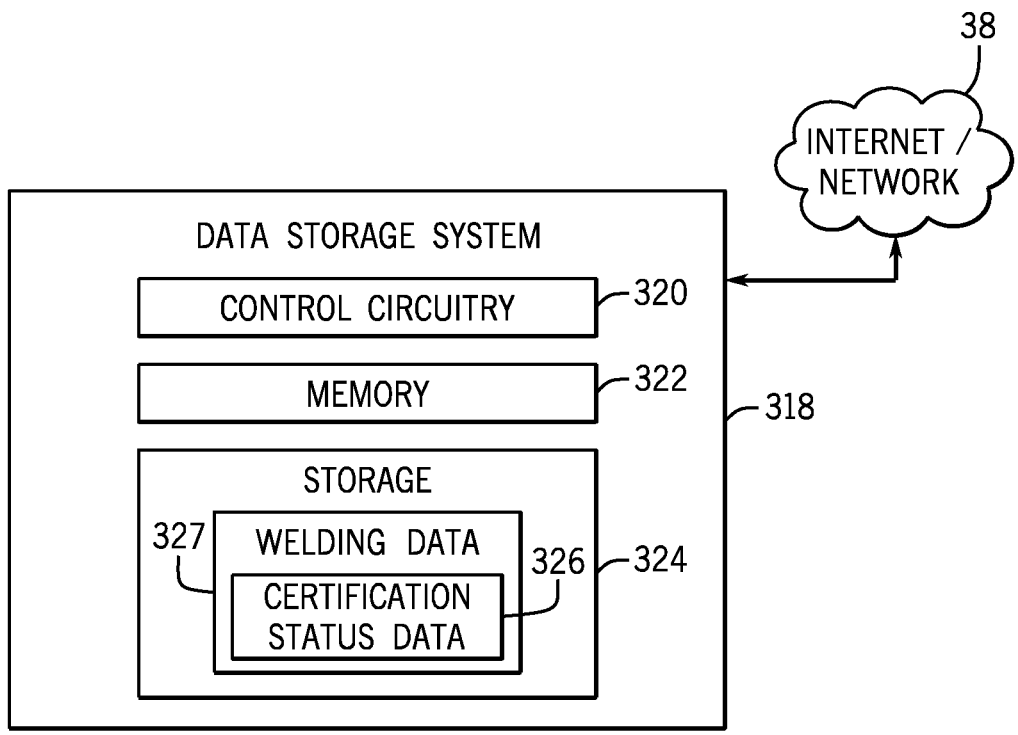
FIG. 19 is a block diagram of an embodiment of a data storage system (e.g., cloud storage system) for storing certification status data in accordance with aspects of the present disclosure.

FIG. 19 is a block diagram of an embodiment of a data storage system 318 (e.g., cloud storage system) for storing welding data 327, such as certification status data 326. The data storage system 318 may include, but is not limited to, the computer 18 of the welding system 10, a remote computer 44 (e.g., server) coupled to the welding system 10 via the internet or a network 38, or any combination thereof. The certification status data may be produced as a welding operator completes various assignments in the welding system 10. For example, a predetermined set of assignments may certify a welding operator for a particular welding device and/or welding process. The data storage system 318 (e.g., cloud storage system) includes control circuitry 320, one or more memory devices 322, and one or more storage devices 324. The control circuitry 320 may include one or more processors, which may be similar to the processor(s) 20. Furthermore, the memory device(s) 322 may be similar to the memory device(s) 22, and the storage device(s) 324 may be similar to the storage device(s) 24. The memory device(s) 322 and/or the storage device(s) 324 may be configured to store certification status data 326 corresponding to a welding certification (e.g., welding training certification) of a welding operator.

The welding data 327 may include any data acquired by the welding system 10 associated with the registration number 293 of the welding operator (e.g., any data that is related to the assignments to certify the welding operator, training welding data, simulated welding data, virtual reality welding data, live welding data), any data related to an actual certification (e.g., certified, not certified, qualified, not qualified, etc.), a quantity of one or more welds performed by the welding operator, a timestamp for one or more welds performed by the welding operator, a location and/or facility that the welding operator performs the one or more welds, the components of the welding system utilized by the welding operator for the one or more welds, the organization with which the welding operator is affiliated, the organization for whom the welding operator is performing the one or more welds, welding parameter data for one or more welds performed by the welding operator, a quality ranking of the welding operator, a quality level of the welding operator, a history of welds performed by the welding operator, a history of production welds performed by the welding operator, a first welding process (e.g., a metal inert gas (MIG) welding process, a tungsten inert gas (TIG) welding process, a stick welding process, etc.) certification status (e.g., the welding operator is certified for the first welding process, the welding operator is not certified for the first welding process), a second welding process certification status (e.g., the welding operator is certified for the second welding process, the welding operator is not certified for the second welding process), a first welding device (e.g., a wire feeder, a power supply, a model number, etc.) certification status (e.g., the welding operator is certified for the first welding device, the welding operator is not certified for the first welding device), and/or a second welding device certification status (e.g., the welding operator is certified for the second welding device, the welding operator is not certified for the second welding device).

The control circuitry 320 may be configured to receive a request for the first welding process certification status, the second welding process certification status, the first welding device certification status, and/or the second welding device certification status of the welding operator. Furthermore, the control circuitry 320 may be configured to provide a response to the request. The response to the request may include the first welding process certification status, the second welding process certification status, the first welding device certification status, and/or the second welding device certification status of the welding operator. In certain embodiments, the welding operator may be authorized to use a first welding process, a second welding process, a first welding device, and/or a second welding device based at least partly on the response. Furthermore, in some embodiments, the first welding process, the second welding process, the first welding device, and/or the second welding device of a welding system may be enabled or disabled based at least partly on the response. Moreover, in certain embodiments, the first welding process, the second welding process, the first welding device, and/or the second welding device of a welding system may be enabled or disabled automatically. Thus, a welding operator's certification data may be used to enable and/or disable that welding operator's ability to use a particular welding system, welding device, and/or welding process. For example, a welding operator may have a certification for a first welding process, but not for a second welding process. Accordingly, in certain embodiments, a welding operator may verify their identity at a welding system (e.g., by logging in, by utilizing the operator identification system 43, providing the registration number 293, or some other form of authentication). After the identity of the welding operator is verified, the welding system may check the welding operator's certification status. The welding system may enable the welding operator to perform operations using the first welding process based on the welding operator's certification status, but may block the welding operator from performing the second welding process based on the welding operator's certification status.

The storage 324 of the data storage system 318 (e.g., cloud storage system) may have welding data 327 of multiple operators. The data storage system 318 may be a database that retains welding data 327 associated with registration numbers 293 to enable analysis and tracking of the weld history of the operator over extended durations (e.g., career, lifetime), even across one or more organizations. As may be appreciated, the data storage system 318 (e.g., cloud storage system) may facilitate aggregation of certification status data 326 and/or welding data 327 to identify usage trends, anticipate supply or maintenance issues, and so forth. Moreover, coupling the data storage system 318 to the internet or other network 38 enables instructors or managers to monitor and analyze weld data remote from the operator and the respective welding system 10.

Figure 20:
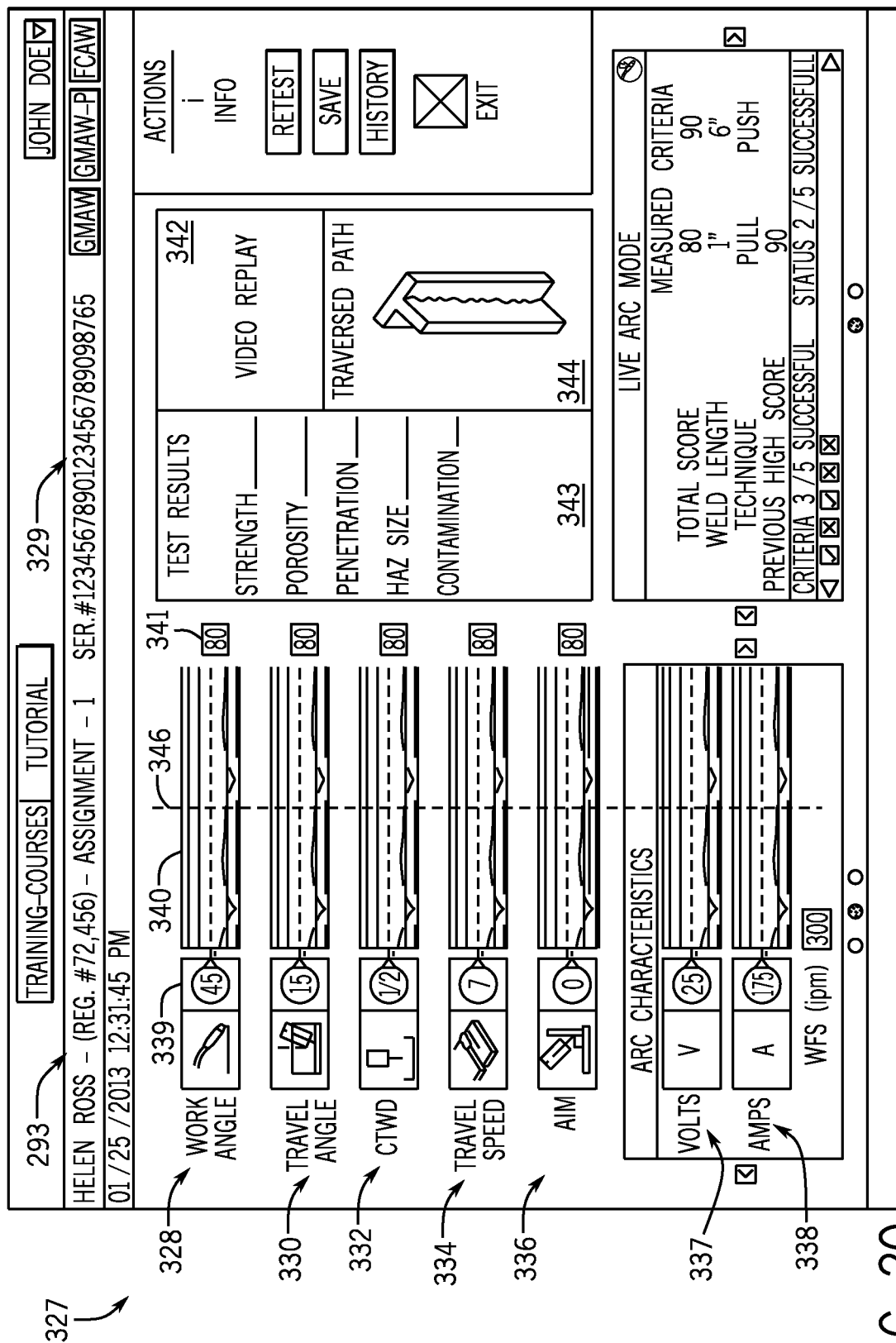
FIG. 20 is an embodiment of a screen illustrating data corresponding to a weld in accordance with aspects of the present disclosure.

FIG. 20 is an embodiment of a screen illustrating data corresponding to a weld by an operator identified on the screen by the registration number 293. In some embodiments, each weld session (e.g., weld test, assignment) performed by an operator and monitored by the welding system 10 is assigned a unique serial number 329. The serial number 329 may be associated with the registration number 293 within one or more local and/or remote data storage systems, such as a cloud storage system or database of the network 38 coupled to the welding system 10. The serial number 329 may be used to associate the physical weld sample with the captured weld test results. The format of the serial number 329 may include, but is not limited to a decimal number, a hexadecimal number, or a character string. Moreover, the serial numbers 329 for the same assignment may be different for each operator. In some embodiments, the serial number 329 is affixed to the workpiece 82. For example, the serial number 329 may attached to, stamped, etched, engraved, embossed, or printed on the workpiece 82. In some embodiments, the serial number 329 is encoded as a barcode affixed to the workpiece 82. Additionally, or in the alternative, the operator may write the serial number 329 on the workpiece 82.

As discussed below, a search feature enables an instructor to enter the serial number 329 to recall the test results for the associated weld session (e.g., weld test, assignment) without the instructor needing to know the user (e.g., registration number 293), the assignment, or any other details about the weld. Accordingly, the instructor may review the data corresponding to each serial number 329, then provide feedback to the respective operator. Furthermore, an inspector or technician may review the serial number 329 of a workpiece 82 to aid in a quality review of the performed weld relative to welding procedure specifications (WPS) and/or to determine a maintenance schedule related to the workpiece 82. That is, the serial number 329 may be utilized to track the workpiece 82, the welding data, the arc data, and the operator (e.g., registration number 293) through a life of the respective workpiece 82. In some embodiments, the serial number 329 may be stored within one or more local and/or remote data storage systems, such as a cloud storage system or database of the network 38 coupled to the welding system 10. The screen may be produced by the welding software 244 and may be displayed on the display 32. The screen illustrates parameters that may be graphically displayed to a welding operator before, during, and/or after performing a welding operation. For example, the parameters may include a work angle 328, a travel angle 330, a contact tip to workpiece distance 332, a welding torch travel speed 334, an aim of the welding torch in relation to the joint of the workpiece 336, a welding voltage 337, a welding current 338, a welding torch orientation, a welding torch position, and so forth.

As illustrated, graphically illustrated parameters may include an indication 339 of a current value of a parameter (e.g., while performing a welding session). Furthermore, a graph 340 may show a history of the value of the parameter, and a score 341 may show an overall percentage that corresponds to how much time during the welding session that the welding operator was within a range of acceptable values. In certain embodiments, a video replay 342 of a welding session may be provided on the screen. The video replay 342 may show live video of a welding operator performing a real weld, live video of the welding operator performing a simulated weld, live video of the welding operator performing a virtual reality weld, live video of the welding operator performing an augmented reality weld, live video of a welding arc, live video of a weld puddle, and/or simulated video of a welding operation.

In certain embodiments, the welding system 10 may capture video data during a welding session (e.g., welding assignment), and store the video data on the storage device 24 and/or the data storage system 318 (e.g., cloud storage system) via the network 38. Moreover, the welding software 244 may be configured to retrieve the video data from the storage device 24 or the data storage system 318, to retrieve welding parameter data from the storage device 24 or the data storage system 318, to synchronize the video data with the welding parameter data, and to provide the synchronized video and welding parameter data to the display 32.

In some embodiments, the welding system 10 may receive test data from previously performed welds. Test results 343 based at least in part on the test data may be displayed on the screen. Test data may include properties of the performed welding session (e.g., welding assignment), such as strength, porosity, penetration, hardness, heat affected zone size, appearance, and contamination, or any combination thereof. The test data may be obtained via destructive or non-destructive testing performed after completion of the welding session. For example, strength of a weld may be determined via a destructive test, whereas the porosity and penetration may be obtained via non-destructive testing, such as x-ray or ultrasonic inspection.

In some embodiments, the welding system 10 may determine the test data (e.g., properties of the welding assignment) based at least in part on welding parameter data. Additionally, or in the alternative, the welding system 10 may utilize arc parameter data to determine the test data. The test data (e.g., properties of the welding assignment) may be associated with the welding parameter data and any arc parameter data, such that the test data, welding parameter data, and arc parameter data corresponding to the same welding session (e.g., welding assignment) are stored together. Where the welding session (e.g., welding assignment) is a live welding assignment, the arc parameters (e.g., weld voltage, weld current, wire feed speed) may include measured arc parameters and/or set arc parameters. Where the welding session is a simulated, virtual reality, or augmented reality welding assignment, the arc parameters may include simulated arc parameters. In some embodiments, the arc parameters associated with non-live welding sessions (e.g., simulated, virtual reality, augmented reality) may include a null set stored in the data storage.

In some embodiments, the determined properties of the welding session (e.g., welding assignment) are based at least in part on a comparison with welding data (e.g., welding parameters, arc parameters) corresponding to previously performed welding sessions. The welding data corresponding to previously performed welding sessions may be stored in the data storage system 318. The welding system 10 may determine (e.g., estimate, extrapolate) properties of a simulated welding assignment, a virtual reality welding assignment, or an augmented reality welding assignment through comparison with welding data (e.g., welding parameters, arc parameters) and associated test data corresponding to previously performed live welding session (e.g., live welding assignments). For example, the welding system 10 may determine the penetration of a virtual reality welding assignment through comparison of the welding parameters (e.g., contact tip to work distance, travel speed) of the virtual reality welding assignment to the welding parameters associated with previously performed live welding assignments. Accordingly, the welding system 10 may facilitate training an operator through providing determined one or more properties of the welding assignment despite the welding assignment (e.g., simulated, virtual reality, augmented reality) being performed without a tangible workpiece produced to test.

The computer 18 of the welding system 10 may determine one or more properties of the welding session (e.g., welding assignment) via executing processor-executable instructions to compare the received welding data with welding data corresponding to previously performed welding sessions. In some embodiments, the one or more properties of the welding session are determined remotely from the welding system 10, such as on a remote computer 44 or data storage system 318 coupled to the welding system 10 via the network 38. Additionally, or in the alternative, the one or more determined properties may be transmitted to the data storage system 318, such as via the network 38. In some embodiments, the computer 18 may determine properties of the welding session (e.g., welding assignment) while receiving the welding data associated with the welding session. That is, the computer 18 may determine properties (e.g., penetration, porosity, strength, appearance) substantially in real-time while the operator is performing the welding session. The determined properties may be displayed via the display 32 as test results. As may be appreciated, the determined properties may be adjusted upon obtaining results from testing (e.g., destructive testing, non-destructive testing) of the welding session (e.g., welding assignment).

The welding software 244 may analyze welding parameter data to determine a traversed path 344 that may be shown on the display 32. In some embodiments, a time during a weld may be selected by a welding operator, as shown by an indicator 346. By adjusting the selected time indicator 346, the welding operator may view the video replay 342 and/or the traversed path 344 in conjunction with the welding parameters as they were at the selected time in order to establish a correlation between the welding parameters, the video replay 342, and/or the traversed path 344. Additionally, or in the alternative, the welding operator may select (e.g., via a cursor on the display 32) a location of the traversed path 344 displayed to review the welding data 327 corresponding to the one or more times the welding torch 14 traversed the selected location. Moreover, the video replay 342 may show frames of video (e.g., captured images, pictures) corresponding to the selected time 346 and/or selected location. As may be appreciated, a selected location may correspond to multiple frames or captured images when the welding operator utilized a weaving or whipping technique and/or when the welding session includes multiple passes. Accordingly, the display 32 may show the multiple frames (e.g., captured images, pictures), and the welding operator may select one or more for additional review. In some embodiments, the test results 343 (e.g., one or more determined properties of the welding assignment) displayed may correspond to the selected time shown by the indicator 346 and/or to one or more locations along the traversed path 344. That is, the test results 343 may display tested characteristics (e.g., porosity, penetration) of the weld corresponding to the selected time indicator 346 and/or the selected location along the traversed path 344. The welding software 244 may be configured to recreate welding data based at least partly on welding parameter data, to synchronize the video replay 342 with the recreated welding data, and to provide the synchronized video replay 342 and recreated welding data to the display 32. In certain embodiments, the recreated welding data may be weld puddle data and/or a simulated weld. In some embodiments, the welding software 244 may correlate various aspects (e.g., determined properties, video, non-destructive test results, destructive test results) of the weld data acquired for positions along the traversed path 344 of the weld and/or for selected times during the weld process. The welding software 244 may facilitate correlation of the welding parameters (e.g., work angle 328, travel angle 330, CTWD 332, travel speed 334, and aim 336 of the welding torch in relation to the joint of the workpiece, a welding torch orientation, a welding torch position) with arc parameters (e.g., voltage 337, current 338, wire feed speed), the video replay 342, and test results 343, or any combination thereof. The weld data associated with the registration number 293 for an operator may enable the operator, the instructor, or a manager, to review the welding parameters, the arc parameters, the video replay 342, and the test results 343 (e.g., determined properties) corresponding to the selected time indicator 346 and/or position along the traversed path 344 of the weld process. For example, the operator may review the weld data to identify relationships between changes in the welding parameters (e.g., work angle 328, CTWD 332) and changes to the arc parameters (e.g., current, voltage) at the selected time shown by the indicator 346 or a selected position. Moreover, the operator may review the weld data to identify relationships between changes in the welding parameters and changes to the test results 343 of the weld.

In some embodiments, the welding torch 14 (e.g., MIG welding torch, stick electrode holder, TIG torch) may be utilized as a pointer, where pointing the welding torch 14 at a specific location of the weld displays weld data 327 on the display 32 corresponding to the specific location. In some embodiments, the welding torch 14 may contact the workpiece 82 at the specific location. Moreover, the welding software 244 may determine the specific location from the operator based on the point along the weld that is nearest to where the operator is pointing the welding torch 14 (e.g., electrode). The welding software 244 may produce a location bar 346 (e.g., indicator) to be displayed along the weld data 327 when the welding torch 14 is pointed at locations along the weld upon completion of the session. That is, the location bar may extend across the graphs of the welding parameters (e.g., work angle 328, travel angle 330, CTWD 332, travel speed 334, and aim 336 of the welding torch in relation to the joint of workpiece) in a similar manner as the selected time line 346 described above and illustrated in FIG. 20. The welding software 244 may be configured to display the video replay 342 (e.g., one or more video frames, captured images) that was captured when the welding torch 14 was at the specific location. For example, the welding software 244 may display between 0 to 30 frames before and/or after when the welding torch 14 was at the specific location. Additionally, or in the alternative, the welding software 244 may display a cross-sectional view of the weld at the specific location. The cross-sectional view may be based on one or more sets of data including, but not limited to, an x-ray scan, an ultrasonic scan, a generated model based at least in part on the welding data 327, or any combination thereof. Moreover, the cross-sectional view may enable the welding operator or an instructor to review various quality characteristics of the weld at the specific location, including, but not limited to, porosity, undercut, spatter, underfill, and overfill. While the welding torch 14 may be readily used to point to and select specific locations of the weld before the workpiece 82 is moved upon completion of the session, the welding torch 14 may be used as a pointer for previously completed sessions with moved workpieces 82 upon recalibration of respective workpieces 82.

In certain embodiments, the storage device 24 may be configured to store a first data set corresponding to multiple welds performed by a welding operator, and to store a second data set corresponding to multiple non-training welds performed by the welding operator. Furthermore, the control circuitry 320 may be configured to retrieve at least part of the first data set from the storage device 24, to retrieve at least part of the second data set from the storage device 24, to synchronize the at least part of the first data set with the at least part of the second data set, and to provide the synchronized at least part of the first data set and at least part of the second data set to the display 32.

Figure 21:
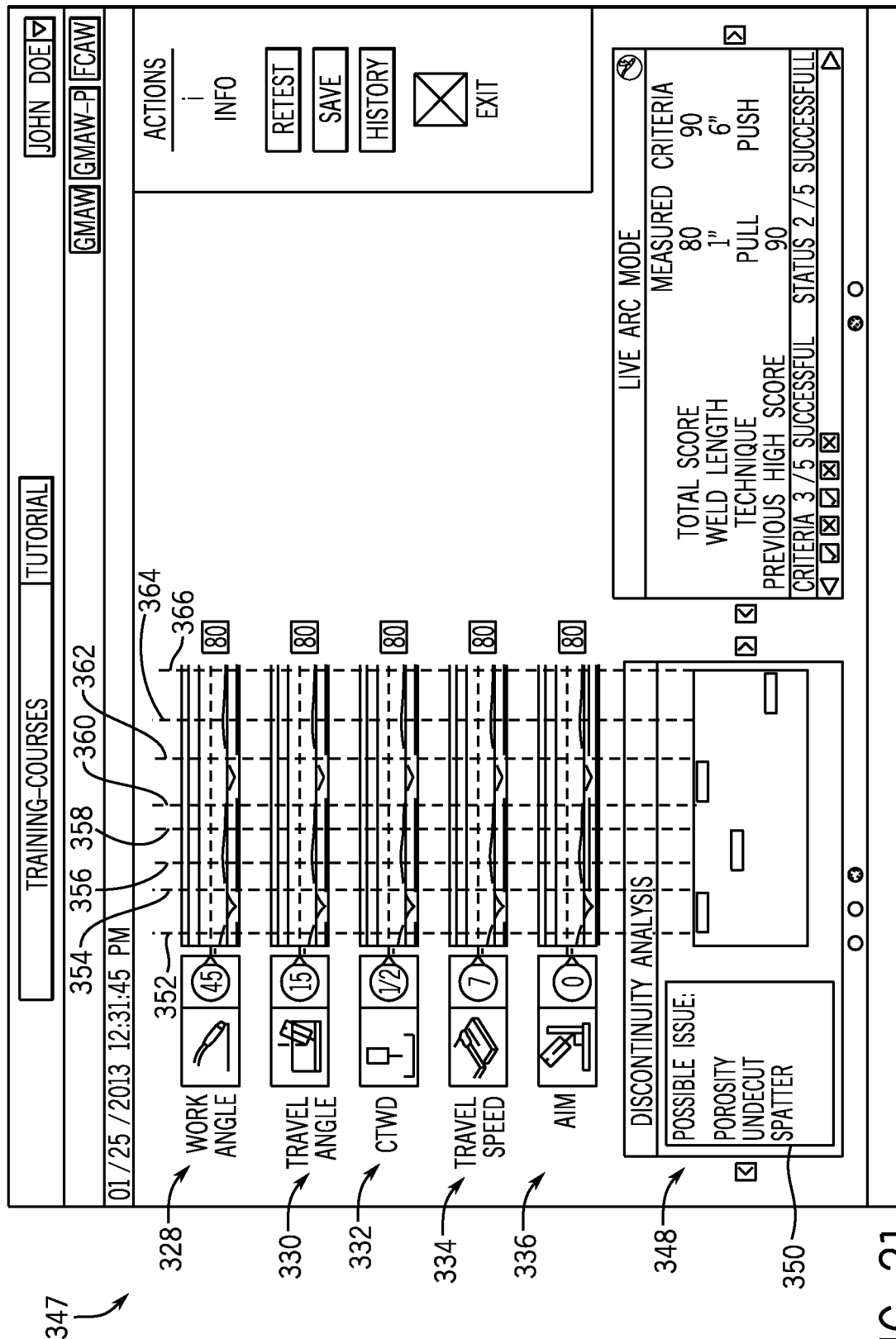
FIG. 21 is an embodiment of a screen illustrating a discontinuity analysis of a weld in accordance with aspects of the present disclosure.

FIG. 21 is an embodiment of a screen 347 illustrating a discontinuity analysis 348 of a weld. The discontinuity analysis 348 includes a listing 350 that may itemize potential issues with a welding operation. The discontinuity analysis 348 provides feedback to the welding operator regarding time periods within the welding operation in which the weld does not meet a predetermined quality threshold. For example, between times 352 and 354, there is a high discontinuity (e.g., the welding quality is poor, the weld has a high probability of failure, the weld is defective). Furthermore, between times 356 and 358, there is a medium discontinuity (e.g., the welding quality is average, the weld has a medium probability of failure, the weld is partially defective). Moreover, between times 360 and 362, there is a high discontinuity, and between times 364 and 366, there is a low discontinuity (e.g., the welding quality is good, the weld has a low probability of failure, the weld is not defective). With this information a welding operator may be able to quickly analyze the quality of a welding operation.

Figure 22:
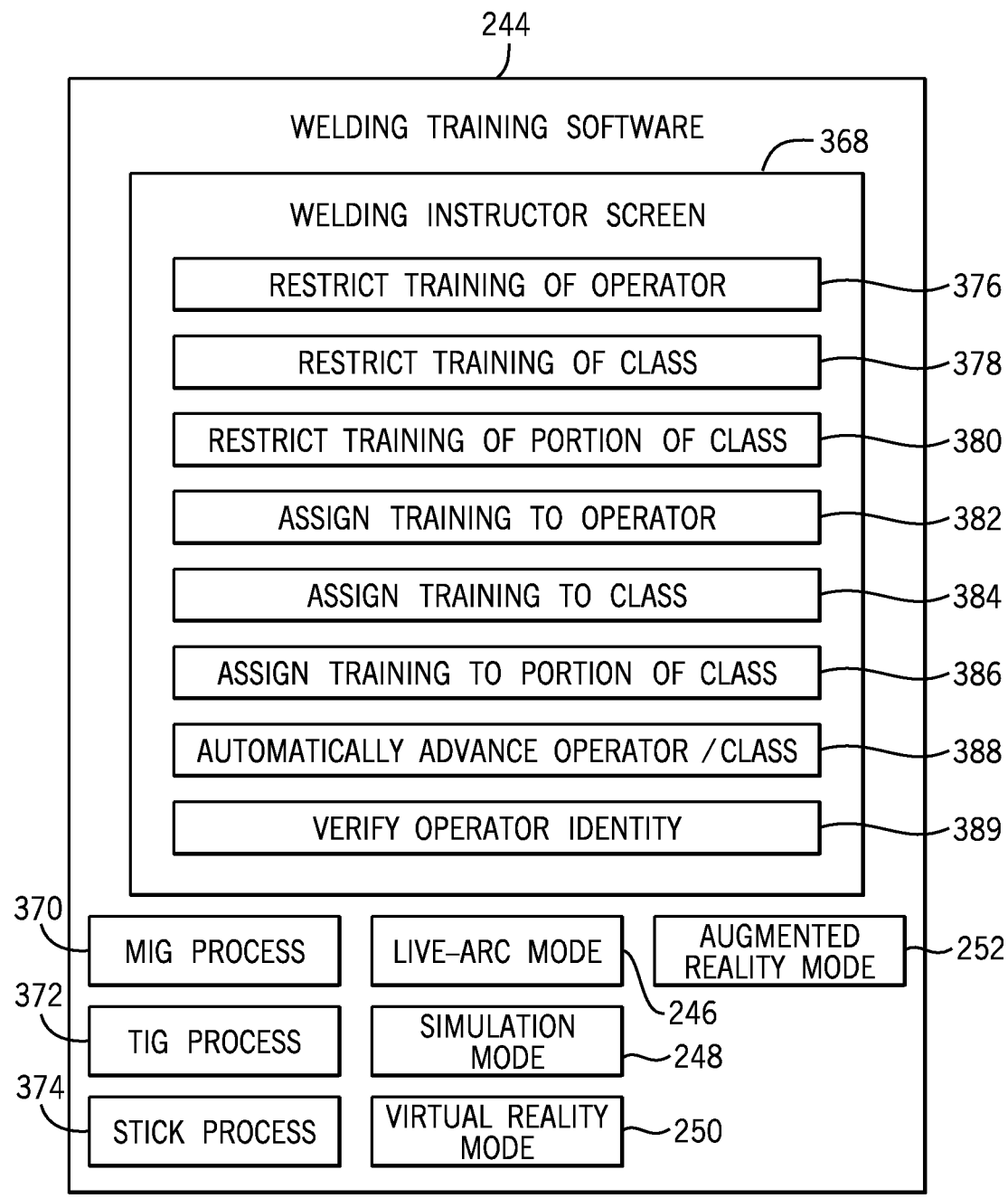
FIG. 22 is a block diagram of an embodiment of a welding instructor screen of welding software in accordance with aspects of the present disclosure.

FIG. 22 is a block diagram of an embodiment of a welding instructor screen 368 of the welding software 244. The welding software 244 is configured to provide training simulations for many different welding configurations. For example, the welding configurations may include a MIG welding process 370, a TIG welding process 372, a stick welding process 374, the live-arc welding mode 346, the simulation welding mode 248, the virtual reality welding mode 250, and/or the augmented reality welding mode 252.

The welding instructor screen 368 may be configured to enable a welding instructor to restrict training of a welding operator 376 (e.g., to one or more selected welding configurations), to restrict training of a class of welding operators 378 (e.g., to one or more selected welding configurations), and/or to restrict training of a portion of a class of welding operators 380 (e.g., to one or more selected welding configurations). Moreover, the welding instructor screen 368 may be configured to enable the welding instructor to assign selected training assignments to the welding operator 382, to assign selected training assignments to a class of welding operators 384, and/or to assign selected training assignments to a portion of a class of welding operators 386. Furthermore, the welding instructor screen 368 may be configured to enable the welding instructor to automatically advance the welding operator (or a class of welding operators) from a first assignment to a second assignment 388. For example, the welding operator may advance from a first assignment to a second assignment based at least partly on a quality of performing the first assignment. Moreover, the welding instructor screen 368 may be configured to verify the identity of an operator 389 (e.g., to ensure welding data is associated with the proper registration number 293). In some embodiments, the operator identification system 43 identifies the operator, and the instructor verifies the identity of the operator via the welding instructor screen 368. For example, the instructor may provide a verification input (e.g., resettable identifier, biometric identifier, physical identifier) to the operator identification system 43 to authorize that the identity of the operator is properly recognized by the operator identification system 43. In some embodiments, the instructor (e.g., second operator) provides a second identifier input (e.g., resettable identifier, biometric identifier, token) to the welding system 10, such as via the operator identification system 43, thereby verifying the identity of the operator that provided a first identifier input to the operator identification system 43. The second identifier input may be stored with the welding data (e.g., identity of operator performing the welding session), such as in the memory 56 of the computer 18 or the data storage system 318). Additionally, or in the alternative, the welding instructor may verify the identity of an operator 389 via a two-step identification process in which the operator identification system 43 separately identifies both the operator and the instructor prior to ensure that welding data is associated with the proper registration number 293.

Figure 23:
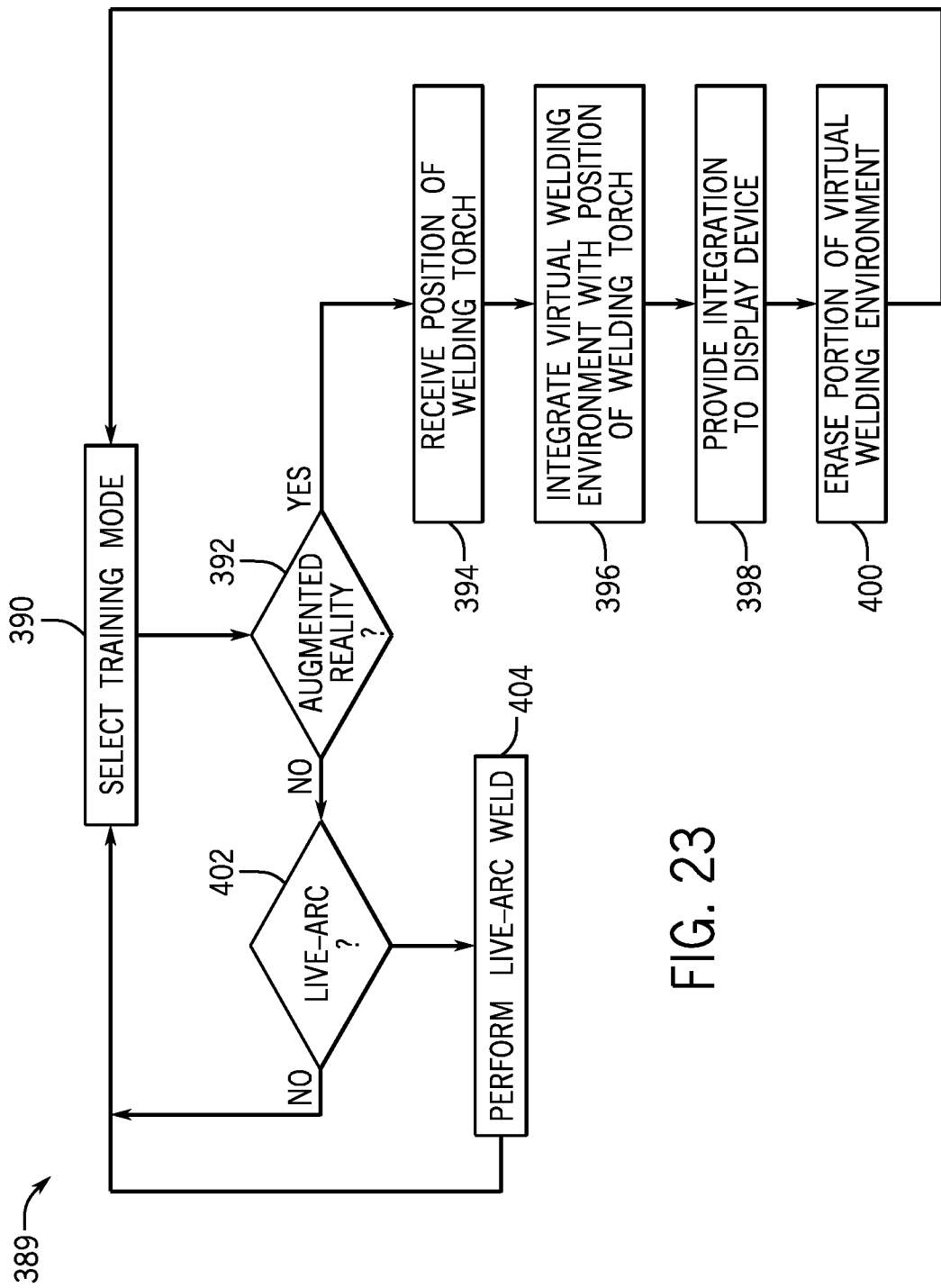
FIG. 23 is an embodiment of a method for weld training using augmented reality in accordance with aspects of the present disclosure.

FIG. 23 is an embodiment of a method 389 for weld training using augmented reality. A welding operator may select a mode of the welding software 244 (block 390). The welding software 244 determines whether the augmented reality mode 252 has been selected (block 392). If the augmented reality mode 252 has been selected, the welding software 244 executes an augmented reality simulation. It should be noted that the welding operator may be wearing a welding helmet and/or some other headgear configured to position a display device in front of the welding operator's view. Furthermore, the display device may generally be transparent to enable the welding operator to view actual objects; however, a virtual welding environment may be portrayed on portions of the display device. As part of this augmented reality simulation, the welding software 244 receives a position and/or an orientation of the welding torch 14, such as from the sensing device 16 (block 394). The welding software 244 integrates the virtual welding environment with the position and/or the orientation of the welding torch 14 (block 396). Moreover, the welding software 244 provides the integrated virtual welding environment to the display device (block 398). For example, the welding software 244 may determine where a weld bead should be positioned within the welding operator's field of view, and the welding software 244 may display the weld bead on the display device such that the weld bead appears to be on a workpiece. After completion of the weld, the augmented reality simulation may enable the welding operator to erase a portion of the virtual welding environment (e.g., the weld bead) (block 400), and the welding software 244 returns to block 390.

If the augmented realty mode 252 has not been selected, the welding software 244 determines whether the live-arc mode 246 has been selected (block 402). If the live-arc mode 246 has been selected, the welding software 244 enters the live-arc mode 246 and the welding operator may perform the live-arc weld (block 404). If the live-arc mode 246 has not been selected and/or after executing block 404, the welding software 244 returns to block 390. Accordingly, the welding software 244 is configured to enable a welding operator to practice a weld in the augmented reality mode 252, to erase at least a portion of the virtual welding environment from the practice weld, and to perform a live weld in the live-arc mode 246. In certain embodiments, the welding operator may practice the weld in the augmented reality mode 252 consecutively a multiple number of times.

Figure 24:
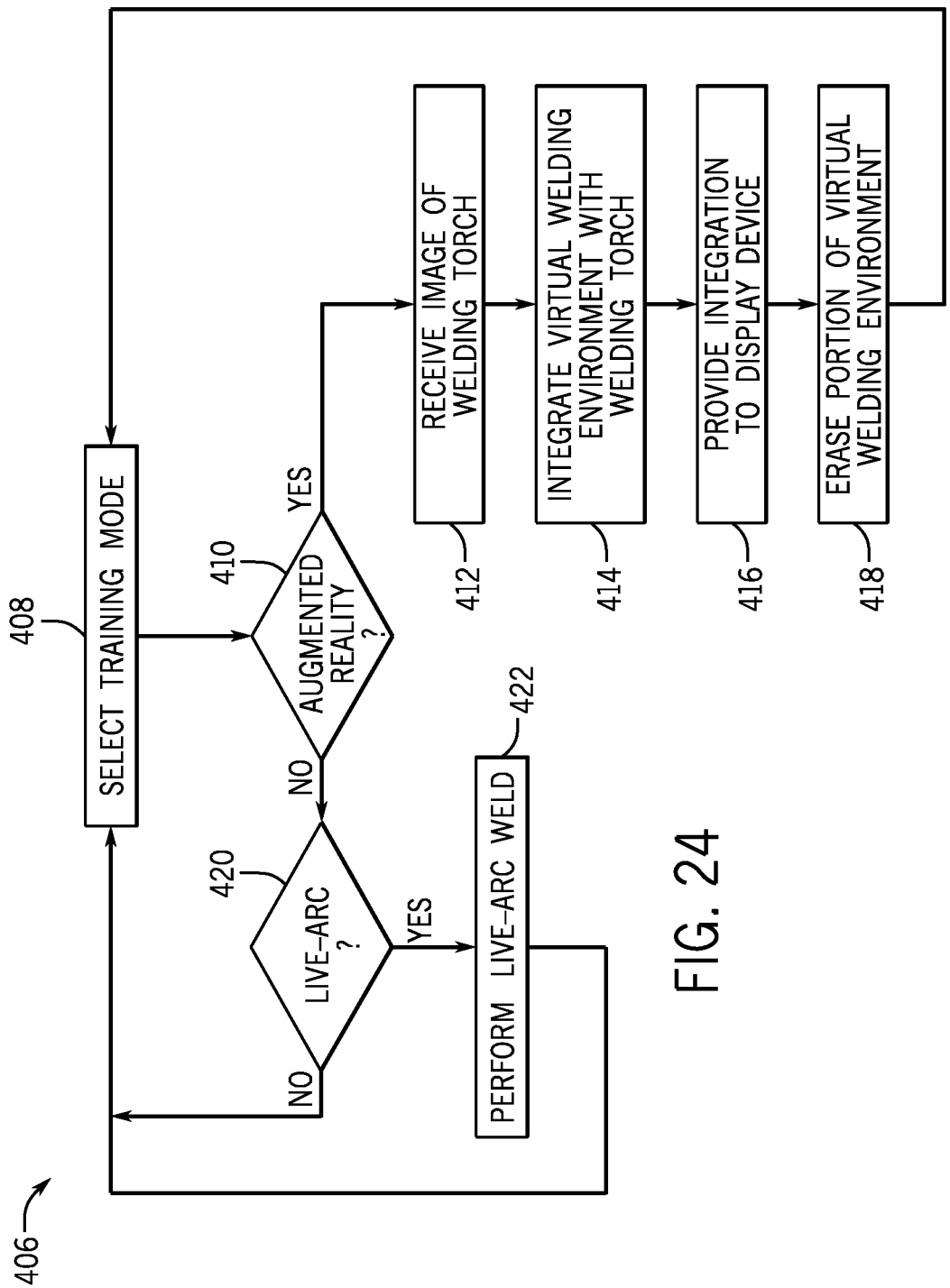
FIG. 24 is an embodiment of another method for weld training using augmented reality in accordance with aspects of the present disclosure.

FIG. 24 is an embodiment of another method 406 for weld training using augmented reality. A welding operator may select a mode of the welding software 244 (block 408). The welding software 244 determines whether the augmented reality mode 252 has been selected (block 410). If the augmented reality mode 252 has been selected, the welding software 244 executes an augmented reality simulation. It should be noted that the welding operator may be wearing a welding helmet and/or some other headgear configured to position a display device in front of the welding operator's view. Furthermore, the display device may completely block the welding operator's field of vision such that images observed by the welding operator have been captured by a camera and displayed on the display device. As part of this augmented reality simulation, the welding software 244 receives an image of the welding torch 14, such as from the sensing device 16 (block 412). The welding software 244 integrates the virtual welding environment with the image of the welding torch 14 (block 414). Moreover, the welding software 244 provides the integrated virtual welding environment with the image of the welding torch 14 to the display device (block 416). For example, the welding software 244 may determine where a weld bead should be positioned within the welding operator's field of view and the welding software 244 displays the weld bead on the display device with the image of the welding torch 14 and other objects in the welding environment. After completion of the weld, the augmented reality simulation may enable the welding operator to erase a portion of the virtual welding environment (e.g., the weld bead) (block 418), and the welding software 244 returns to block 408.

If the augmented realty mode 252 has not been selected, the welding software 244 determines whether the live-arc mode 246 has been selected (block 420). If the live-arc mode 246 has been selected, the welding software 244 enters the live-arc mode 246 and the welding operator may perform the live-arc weld (block 422). If the live-arc mode 246 has not been selected and/or after executing block 422, the welding software 244 returns to block 408. Accordingly, the welding software 244 is configured to enable a welding operator to practice a weld in the augmented reality mode 252, to erase at least a portion of the virtual welding environment from the practice weld, and to perform a live weld in the live-arc mode 246. In certain embodiments, the welding operator may practice the weld in the augmented reality mode 252 consecutively a multiple number of times.

Figure 25:
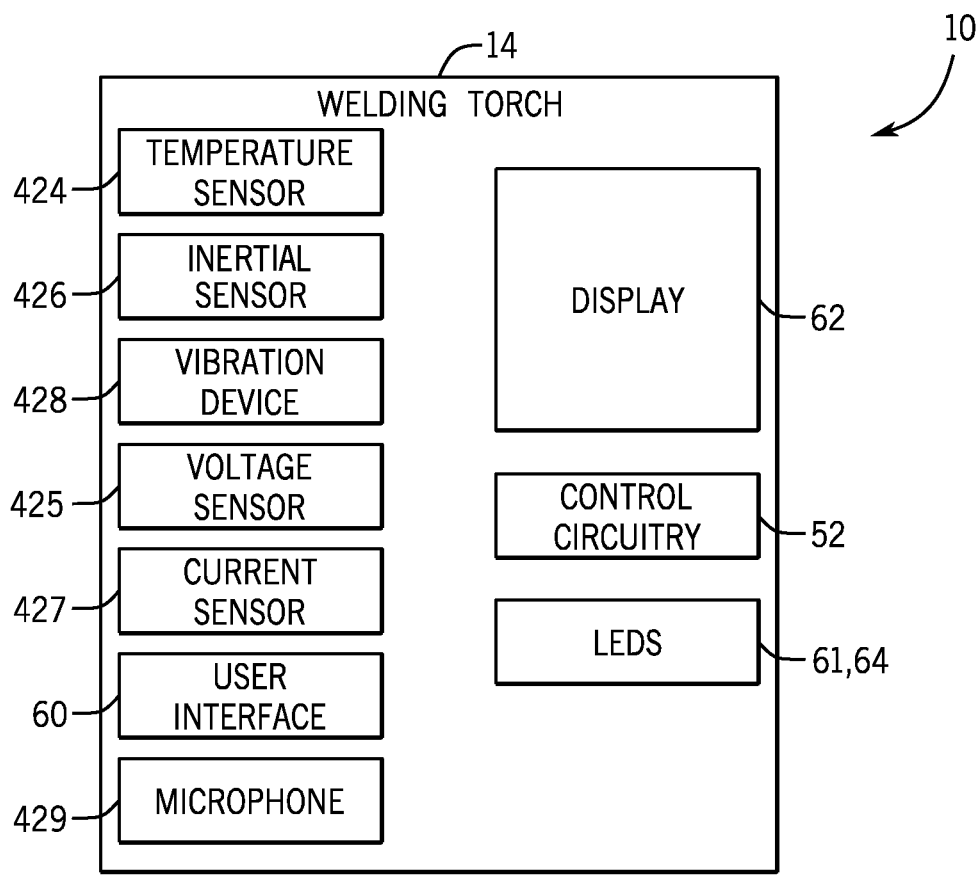
FIG. 25 is a block diagram of an embodiment of a welding torch in accordance with aspects of the present disclosure.

FIG. 25 is a block diagram of an embodiment of the welding torch 14. The welding torch 14 includes the control circuitry 52, the user interface 60, and the display 62 described previously. Furthermore, the welding torch 14 includes a variety of sensors and other devices. The welding torch 14 may include a temperature sensor 424 (e.g., thermocouple, thermistor, etc.), an inertial sensor 426 (e.g., accelerometer, gyroscope, magnetometer, etc.), a vibration device 428 (e.g., vibration motor), a microphone 429, one or more visual indicators 61 (e.g., LEDs 64), or any combination thereof. In addition, in certain embodiments, the welding torch 14 may include a voltage sensor 425 and/or a current sensor 427 to sense voltage and/or current, respectively, of the arc produced by the welding torch 14. As discussed in detail below, one or more sets of LEDs 64 may be arranged about the welding torch 14 to enable the sensing device 16 to detect the position and orientation of the welding torch 14 relative to the training stand 12 and the workpiece 82. For example, sets of LEDs 64 may be arranged on a top side, a left side, and a right side of the welding torch 14 to enable the sensing device 16 to detect the position and orientation of the welding torch 14 regardless of which side of the welding torch 14 is facing the sensing device 16. In certain embodiments, the welding torch 14 may include more than one temperature sensor 424, inertial sensor 426, vibration device 428, voltage sensor 425, current sensor 427, and/or microphone 429.

During operation, the welding torch 14 may be configured to use the temperature sensor 424 to detect a temperature associated with the welding torch 14 (e.g., a temperature of electronic components of the welding torch 14, a temperature of the display 62, a temperature of a light-emitting device, a temperature of the vibration device, a temperature of a body portion of the welding torch 14, etc.). The control circuitry 52 (or control circuitry of another device) may use the detected temperature to perform various events. For example, the control circuitry 52 may be configured to disable use of the live-arc mode 246 (e.g., live welding) by the welding torch 14 if the detected temperature reaches and/or surpasses a predetermined threshold (e.g., such as 85° C.). Moreover, the control circuitry 52 may also be configured to disable various heat producing devices of the welding torch 14, such as the vibration device 428, light-emitting devices, and so forth. The control circuitry 52 may also be configured to show a message on the display 62, such as "Waiting for torch to cool down. Sony for the inconvenience." In certain embodiments, the control circuitry 52 may be configured to disable certain components or features if the detected temperature reaches a first threshold and to disable additional components or features if the detected temperature reaches a second threshold.

Moreover, during operation, the welding torch 14 may be configured to use the inertial sensor 426 to detect a motion (e.g., acceleration, etc.) associated with the welding torch 14. The control circuitry 52 (or control circuitry of another device) may use the detected acceleration to perform various events. For example, the control circuitry 52 may be configured to activate the display 62 (or another display) after the inertial sensor 426 detects that the welding torch 14 has been moved. Accordingly, the control circuitry 52 may direct the display 62 to "wake up," such as from a sleep mode and/or to exit a screen saver mode to facilitate a welding operator of the welding torch 14 using a graphical user interface (GUI) on the display 62. Furthermore, the control circuitry 52 may utilize feedback from the one or more inertial sensors 426 to determine the position of the welding torch 14 in the welding environment and/or the movement of the welding torch 14 within the welding environment. As discussed in detail below, the sensing devices 16 (e.g., camera) may utilize markers 474 on the torch to determine the position, orientation, and/or movement of the welding torch 14 in the welding environment. In some embodiments, the control circuitry 52 (or control circuitry of another device) may utilize the feedback from the one or more inertial sensors 426 to augment the determination with the sensing devices 16 of the position, orientation, and/or movement of the welding torch 14. That is, the control circuitry 52 may determine the position and orientation of the welding torch 14 based on the feedback from the one or more inertial sensors 426 when the workpiece 82 or the operator obscures (e.g., blocks) one or more markers 474 of the welding torch 14 from the view of the sensing device 16.

Returning to FIG. 21 for an example, the one or more inertial sensors 426 may enable the control circuitry 52 to determine the work angle 328, the travel angle 330, and the travel speed 334 for an interval between times 360 and 362 when other sensing devices 16 may be unable to monitor the position and orientation of the welding torch 14 for any reason (e.g., one or more markers of a set utilized to optically track the welding torch 14 is obscured from a camera). The one or more inertial sensors 426 may provide an output regarding the position and/or the orientation of the welding torch 14 that is independent of another position detection system (e.g., optical detection system, magnetic detection system, acoustic detection system). The control circuitry 52 may determine the work angle 328, the travel angle 330, and the travel speed 334 based at least in part on the feedback from the one or more inertial sensors 426 of the welding torch 14 with the assumption that the CTWD 332 and the aim of the welding torch 14 relative to the joint of the workpiece 82 are approximately constant for the interval.

Returning to FIG. 25, in certain embodiments, the control circuitry 52 may be configured to determine that a high impact event (e.g., dropped, used as a hammer, etc.) to the welding torch 14 has occurred based at least partly on the detected motion. Upon determining that a high impact event has occurred, the control circuitry 52 may store (e.g., log) an indication that the welding torch 14 has been impacted. Along with the indication, the control circuitry 52 may store other corresponding data, such as a date, a time of day, an acceleration, a user name, welding torch identification data, and so forth. The control circuitry 52 may also be configured to show a notice on the display 62 to a welding operator requesting that the operator refrain from impacting the welding torch 14. In some embodiments, the control circuitry 52 may be configured to use the motion detected by the inertial sensor 426 to enable the welding operator to navigate and/or make selections within a software user interface (e.g., welding software, welding training software, etc.). For example, the control circuitry 52 may be configured to receive the acceleration and to make a software selection if the acceleration matches a predetermined pattern (e.g., the acceleration indicates a jerky motion in a certain direction, the acceleration indicates that the welding torch 14 is being shaken, etc.).

The vibration device 428 is configured to provide feedback to a welding operator by directing the welding torch 14 to vibrate and/or shake (e.g., providing vibration or haptic feedback). The vibration device 428 may provide vibration feedback during live welding and/or during simulated welding. As may be appreciated, vibration feedback during live welding may be tuned to a specific frequency to enable a welding operator to differentiate between vibration that occurs due to live welding and the vibration feedback. For example, vibration feedback may be provided at approximately 3.5 Hz during live welding. Using such a frequency may enable a welding operator to detect when vibration feedback is occurring at the same time that natural vibration occur due to live welding. Conversely, vibration feedback may be provided at approximately 9 Hz during live welding. However, the 9 Hz frequency may be confused with natural vibration that occurs due to live welding.

The one or more microphones 429 are configured to facilitate determination of the position of the welding torch 14 with a local positioning system. The one or more microphones 429 of the welding torch 14 receive emitted signals (e.g., ultrasonic, RF) from beacons disposed at known locations about the welding environment. As may be appreciated, a local positioning system enables the determination of a location of an object when the object receives the emitted signals (i.e., via unobstructed line of sight) from three or more beacons at known positions. The control circuitry 52 (or control circuitry of another device) may determine the position of the welding torch 14 from the received signals via triangulation, trilateration, or multilateration. In some embodiments, the microphones 429 may facilitate the determination of the position of the welding torch 14 during welding when one or more of the sensing devices 16 (e.g., cameras) are obstructed by the workpiece 82 and/or the operator.

Figure 26:
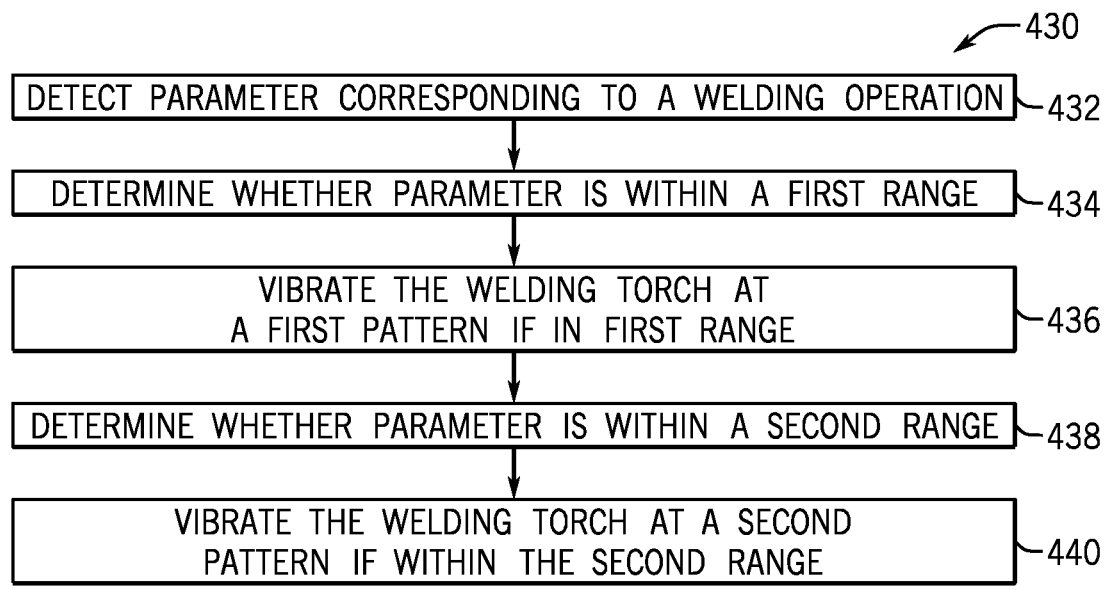
FIG. 26 is an embodiment of a method for providing vibration feedback to a welding operator using a welding torch in accordance with aspects of the present disclosure.

FIG. 26 is an embodiment of a method 430 for providing vibration feedback to a welding operator using the welding torch 14. The control circuitry 52 (or control circuitry of another device) detects a parameter (e.g., work angle, travel angle, travel speed, tip-to-work distance, aim, etc.) corresponding to a welding operation (block 432). As may be appreciated, the welding operation may be a live welding operation, a simulated welding operation, a virtual reality welding operation, and/or an augmented reality welding operation. The control circuitry 52 determines whether the parameter is within a first predetermined range (block 434). As may be appreciated, the first predetermined range may be a range that is just outside of an acceptable range. For example, the parameter may be work angle, the acceptable range may be 45 to 50 degrees, and the first predetermined range may be 50 to 55 degrees. Accordingly, in such an example, the control circuitry 52 determines whether the work angle is within the first predetermined range of 50 to 55 degrees.

Figure 27:
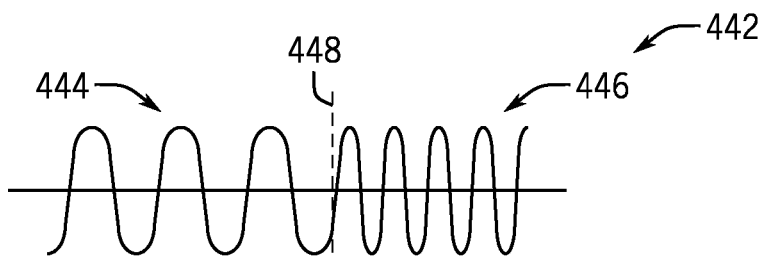
FIG. 27 is a graph of an embodiment of two patterns each including a different frequency for providing vibration feedback to a welding operator in accordance with aspects of the present disclosure.
Figure 28:
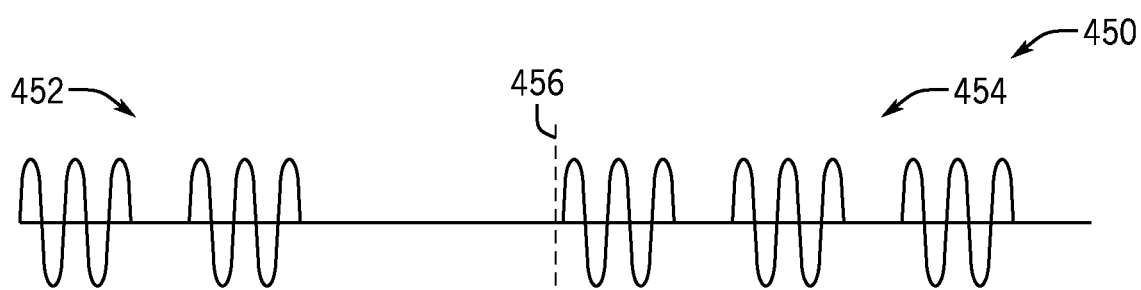
FIG. 28 is a graph of an embodiment of two patterns each including a different modulation for providing vibration feedback to a welding operator in accordance with aspects of the present disclosure.
Figure 29:
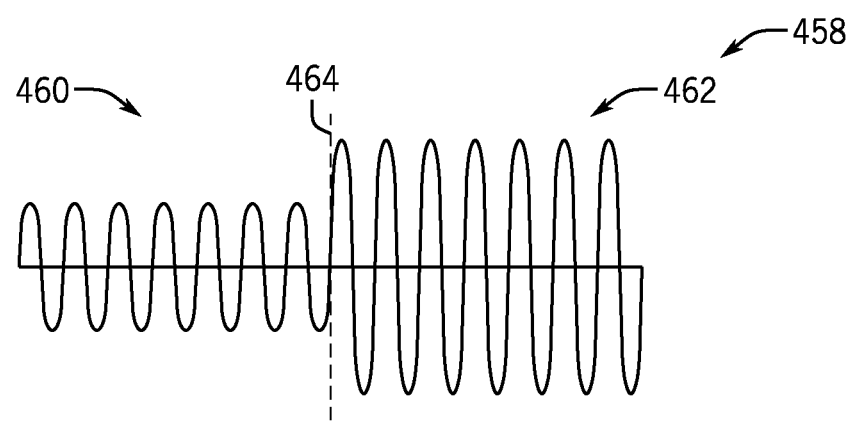
FIG. 29 is a graph of an embodiment of two patterns each including a different amplitude for providing vibration feedback to a welding operator in accordance with aspects of the present disclosure.

If the parameter is within the first predetermined range, the control circuitry 52 vibrates the welding torch at a first pattern (block 436). The first pattern may be a first frequency, a first frequency modulation, a first amplitude, and so forth. Moreover, if the parameter is not within the first predetermined range, the control circuitry 52 determines whether the parameter is within a second predetermined range (block 438). The second predetermined range may be a range that is just outside of the first predetermined range. For example, continuing the example discussed above, the second predetermined range may be 55 to 60 degrees. Accordingly, in such an example, the control circuitry 52 determines whether the work angle is within the second predetermined range of 55 to 60 degrees. If the parameter is within the second predetermined range, the control circuitry 52 vibrates the welding torch at a second pattern (block 440). The second pattern may be a second frequency, a second frequency modulation, a second amplitude, and so forth. It should be noted that the second pattern is typically different than the first pattern. In certain embodiments, the first and second patterns may be the same. Furthermore, audible indications may be provided to the welding operator to indicate whether the parameter is within the first predetermined range or within the second predetermined range. In addition, audible indications may be used to indicate a parameter that is not within an acceptable range. In such embodiments, vibration may be used to indicate that a welding operator is doing something wrong, and audible indications may be used to identify what the welding operator is doing wrong and/or how to fix it. The parameter may be any suitable parameter, such as a work angle, a travel angle, a travel speed, a tip-to-work distance, and/or an aim. FIGS. 27 through 29 illustrate embodiments of various patterns.

FIG. 27 is a graph 442 of an embodiment of two patterns each including a different frequency for providing vibration feedback to a welding operator. A first pattern 444 is separated from a second pattern 446 by time 448. In the illustrated embodiment, the first pattern 444 is a first frequency and the second pattern 446 is a second frequency that is different from the first frequency. The first and second frequencies may be any suitable frequency. As may be appreciated, the first and second frequencies may be configured to be different than a natural frequency produced during live welding to facilitate a welding operator differentiating between the natural frequency and the first and second frequencies. Although the illustrated embodiment shows the first frequency being lower than the second frequency, in other embodiments, the second frequency may be lower than the first frequency.

FIG. 28 is a graph 450 of an embodiment of two patterns each including a different modulation for providing vibration feedback to a welding operator. A first pattern 452 is separated from a second pattern 454 by time 456. In the illustrated embodiment, the first pattern 452 is a first modulation and the second pattern 454 is a second modulation that is different from the first modulation. The first and second modulation may be any suitable modulation. For example, the first modulation may include a first number of vibration pulses (e.g., two pulses) and the second modulation may include a second number of vibration pulses (e.g., three pulses). Moreover, the modulation may vary a number of pulses, a time between pulses, etc. In certain embodiments, a number of vibration pulses and/or a time between pulses may be configured to gradually increase or decrease as a parameter moves toward or away from acceptable parameter values. Although the illustrated embodiment shows the first modulation as having fewer pulses than the second modulation, in other embodiments, the second modulation may have fewer pulses than the first modulation.

FIG. 29 is a graph 458 of an embodiment of two patterns each including a different amplitude for providing vibration feedback to a welding operator. A first pattern 460 is separated from a second pattern 462 by time 464. In the illustrated embodiment, the first pattern 460 is a first amplitude and the second pattern 462 is a second amplitude that is different from the first amplitude. The first and second amplitudes may be any suitable amplitude. Although the illustrated embodiment shows the first amplitude being lower than the second amplitude, in other embodiments, the second amplitude may be lower than the first amplitude.

The welding torch 14 may provide varied levels of vibration and visual feedback to the operator during simulated welding or live welding. For example, a first feedback mode of the welding torch 14 may provide visual feedback (e.g., via display 62) and vibration feedback to the operator until the operator initiates a simulated or live welding process, and the welding torch 14 may not provide visual or vibration feedback during the simulated or live welding process. A second feedback mode of the welding torch 14 may provide visual and vibration feedback to the operator both prior to and during the simulated or live welding process. A third feedback mode of the welding torch may provide visual and vibration feedback to the operator both prior to and during only simulated welding processes. As may be appreciated, some modes may provide only visual feedback prior to or during a simulated welding process, and other modes may provide only vibration feedback prior to or during a simulated welding process. In some embodiments, an instructor may specify the level of feedback that may be provided to the operator during simulated or live welding sessions to be evaluated. Moreover, the operator may selectively disable vibration and/or visual feedback provided by the welding torch prior to and during simulated or live welding.

Figure 30:
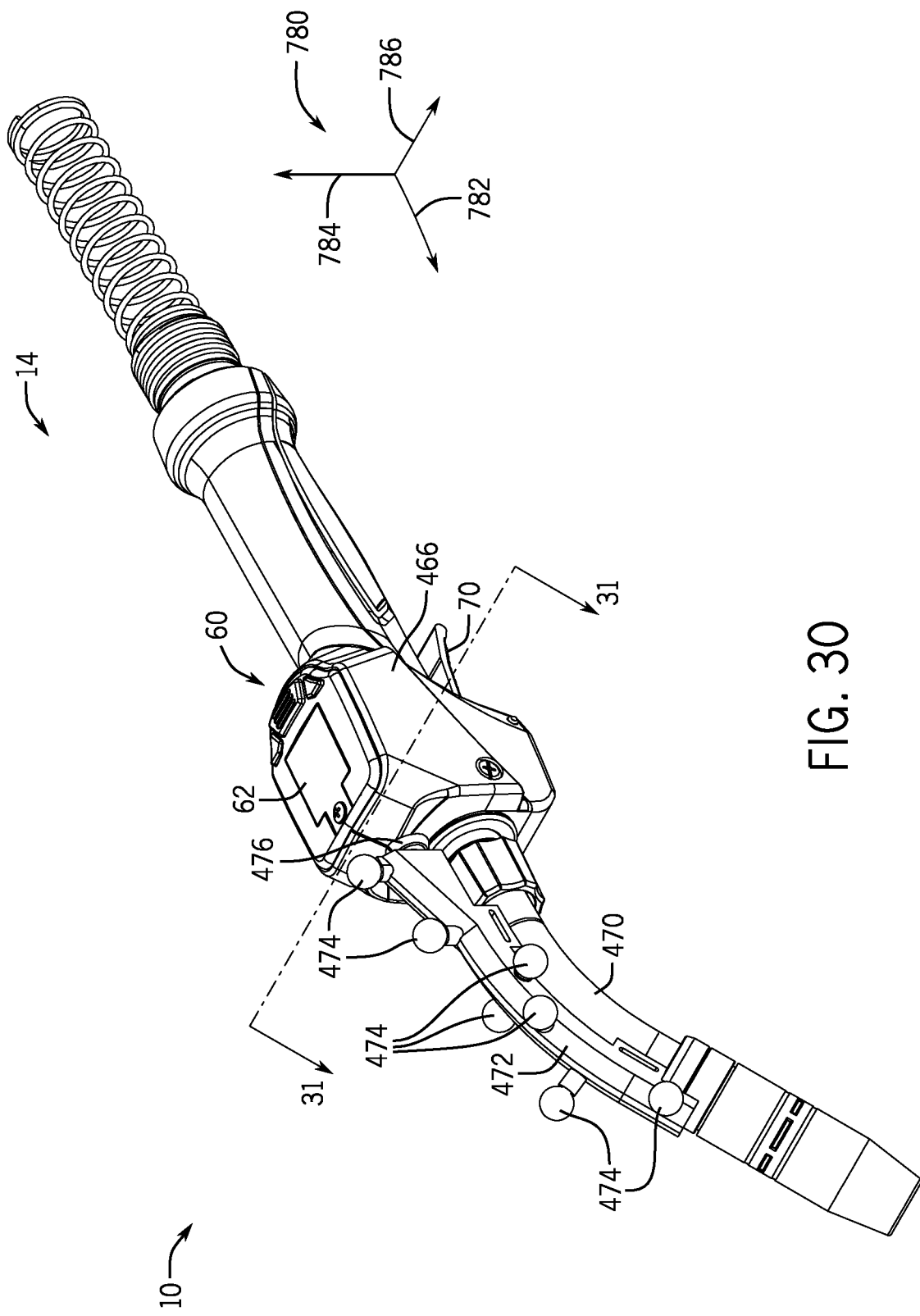
FIG. 30 is a perspective view of an embodiment of a welding torch having spherical markers that may be used for tracking the welding torch in accordance with aspects of the present disclosure.

FIG. 30 is a perspective view of an embodiment of the welding torch 14 having markers that may be used for tracking the welding torch 14. In some embodiments, the position of the welding torch 14 may be tracked prior to live welding to determine (i.e., calibrate) the shape of the welding joint. For example, the welding torch 14 may be utilized to trace the shape of a workpiece 82 in various positions including, but not limited, to welding positions 1G, 2G, 3G, 4G, 5G, 6G, 1F, 2F, 3F, 4F, 5F, or 6F. The determined shape of the welding joint may be stored in the data storage system 318 for comparison with a subsequent live welding process along the welding joint. In some embodiments, the position of the welding torch 14 may be tracked during live welding and compared with the shape of the welding joint stored in the data storage system 318. The control circuitry 52 of the welding torch 14 and/or any other component of the training system 10 may provide approximately real-time feedback to the operator regarding the position (e.g., location) and/or orientation of the welding torch 14 relative to the welding joint. The welding torch 14 includes a housing 466 that encloses the control circuitry 52 of the welding torch 14 and/or any other components of the welding torch 14. The display 62 and user interface 60 are incorporated into a top portion of the housing 466.

As illustrated, a neck 470 extends from the housing 466 of the welding torch 14. Markers for tracking the welding torch 14 may be disposed on the neck 470. Specifically, a mounting bar 472 is used to couple markers 474 to the neck 470. The markers 474 are spherical markers in the illustrated embodiment; however, in other embodiments, the markers 474 may be any suitable shape (e.g., such as a shape of an LED). The markers 474 are used by the sensing device 16 for tracking the position and/or the orientation of the welding torch 14. As may be appreciated, three of the markers 474 are used to define a first plane. Moreover, the markers 474 are arranged such that a fourth marker 474 is in a second plane different than the first plane. Accordingly, the sensing device 16 may be used to track the position and/or the orientation of the welding torch 14 using the four markers 474. It should be noted that while the illustrated embodiment shows four markers 474, the mounting bar 472 may have any suitable number of markers 474.

In certain embodiments, the markers 474 may be reflective markers, while in other embodiments the markers 474 may be light-emitting markers (e.g., light-emitting diodes LEDs). In embodiments in which the markers 474 are light-emitting markers, the markers 474 may be powered by electrical components within the housing 466 of the welding torch 14. For example, the markers 474 may be powered by a connection 476 between the mounting bar 472 and the housing 466. Furthermore, the control circuitry 52 (or control circuitry of another device) may be used to control powering on and/or off (e.g., illuminating) the markers 474. In certain embodiments, the markers 474 may be individually powered on and/or off based on the position and/or the orientation of the welding torch 14. In other embodiments, the markers 474 may be powered on and/or off in groups based on the position and/or the orientation of the welding torch 14. It should be noted that in embodiments that do not include the mounting bar 472, the connection 476 may be replaced with another marker 468 on a separate plane than the illustrated markers 468. Embodiments of the welding torch 14 are described herein relative to a consistent set of coordinate axes 780. An X-axis 782 is a horizontal direction along a longitudinal axis of the welding torch 14, a Y-axis 784 is the vertical direction relative to the longitudinal axis, and a Z-axis 786 is a horizontal direction extending laterally from the welding torch 14.

FIG. 31 is an embodiment of a neck 800 of the welding torch 14, taken along line 31-31 of FIG. 30. Visual markers 802 are arranged at predefined locations on the neck 800 to facilitate detection of the position and orientation of the welding torch 14 by the sensing device 16. In some embodiments, the visual markers 802 are LEDs 64. Additionally, or in the alternative, the visual markers 802 are directional, such that the sensing device 16 detects visual markers 802 that are oriented toward the sensing device 16 more readily than visual markers 802 that are less oriented toward the sensing device 16. For example, LEDs 64 arranged on a surface may be directed to emit light primarily along an axis substantially perpendicular to the surface. In some embodiments, multiple sets of visual markers 802 are arranged on the neck 800.

The visual markers 802 of each set may be oriented in substantially the same direction as the other visual markers 802 of the respective set. In some embodiments, a first set 804 of visual markers 802 is directed substantially vertically along the Y-axis 784, a second set 806 of visual markers 802 is directed in a second direction 808, and a third set 810 of visual markers 802 is directed in a third direction 812. That is, the visual markers 802 of each set are oriented to emit light in substantially parallel directions as other visual markers 802 of the respective set. The second direction 808 is substantially perpendicular to the X-axis 782 along the welding torch 14, and is offset a second angle 814 from the Y-axis 784. The third direction 812 is substantially perpendicular to the X-axis 782 along the welding torch 14, and is offset a third angle 816 from the Y-axis 784. In some embodiments, the second angle 814 and the third angle 816 have approximately the same magnitude. For example, the second set 806 of visual indicators 802 may be offset from the Y-axis 784 by 45°, and the third set 810 of visual indicators 802 may be offset from the Y-axis 784 by 45°, such that the second angle 814 is substantially perpendicular with the third angle 816. The second angle 814 and the third angle 816 may each be between approximately 5° to 180°, 15° to 135°, 25° to 90°, or 30° to 75°. As may be appreciated, the neck 800 may have 1, 2, 3, 4, 5, 6, 7, 8, 9, 10, or more sets of visual markers 802, with each set oriented in a particular direction to facilitate detection by the sensing device 16.

The visual markers 802 of each set may be arranged on the same or substantially parallel planes. For example, the first set 804 of visual markers 802 may be arranged on a first plane 818 or a plane substantially parallel to the first plane 818 that is perpendicular to the Y-axis 784. The second set 806 of visual markers 802 may be arranged on a second plane 820 or a plane substantially parallel to the second plane 820 that is perpendicular to the second direction 808. The third set 810 of visual markers 802 may be arranged on a third plane 822 or a plane substantially parallel to the third plane 822 that is perpendicular to the third direction 812. As used herein, the term "substantially parallel" includes orientations within 10 degrees of parallel, and the term "substantially perpendicular" includes orientations within 10 degrees of perpendicular. The arrangements of the visual markers 802 of each set may facilitate tracking the welding torch 14 during simulated and/or live out of position welding processes including, but not limited to, vertical or overhead welding positions.

Structures 824 of the neck 800 may facilitate the orientation of the sets of the visual markers 802. For example, a mounting surface of each structure 824 may be substantially parallel to a respective plane for the corresponding set of visual markers 802. Moreover, the structures 824 may reduce or eliminate the detection of the respective visual marker 802 by the sensing device 16 when the respective visual marker 802 is oriented relative to the sensing device 16 at an angle greater than a threshold angle. For example, the second set 806 of visual markers 802 may be configured to be detected by the sensing device 16 when the operator holds the welding torch 14 with the sensing device 16 to the left of the operator (i.e., a left-handed operator), and the third set 810 of visual markers 802 may be configured to be detected by the sensing device 16 when the operator holds the welding torch 14 with the sensing device 16 to the right of the operator (i.e., a right-handed operator). The neck 800 and/or the structures 824 for the second set 806 of visual markers 802 may reduce or eliminate the detection of the second set 806 of visual markers 802 when a right-handed operator uses the welding torch 14, and vice versa for the third set 810 of visual markers when a left-handed operator uses the welding torch 14.

FIG. 32 is a top view of an arrangement of visual markers 80 on the neck 800 of the welding torch 14, similar to the embodiment of the neck 800 illustrated in FIG. 31. The visual markers 802 of the first set 804 (e.g., "A"), the second set 806 (e.g., "B"), and the third set 810 (e.g., "C") are arranged at different predefined positions on the neck 800 that enable the sensing device 16 to determine which side of the welding torch 14 is most directed towards the sensing device 16 via detecting a distinct pattern or arrangement that corresponds to each side (e.g., top, left 826, right 828, bottom, front) of the welding torch 14. Additionally, or in the alternative, the visual markers 802 (e.g., LEDs 64) of each set may be respectively colored, thereby enabling the sensing device 16 to determine which side of the welding torch 14 is most directed towards the sensing device 16 via color detection.

The sensing device 16 may track the position and orientation of the welding torch 14 relative to the training stand 12 and the workpiece 82 when the sensing device 16 detects a threshold quantity of visual markers 802 of a set. The threshold quantity of visual markers 802 of a set may be less than or equal to the quantity of visual markers 802 of the respective set. For example, the sensing device 16 may detect the right side of the welding torch 14 when detecting the four visual markers 802 of the third set 810, the sensing device 16 may detect the top side of the welding torch 14 when detecting the five visual markers 802 of the first set 804, and the sensing device 16 may detect the left side of the welding torch when detecting the four visual markers 802 of the second set. In some embodiments, each set of visual markers 802 may have redundant visual markers, such that sensing device 16 may track the position and the orientation of the welding torch 14 when one or more of the redundant visual markers are obscured from view. The sensing device 16 may track the position and the orientation with substantially the same accuracy, regardless of which set is detected by the sensing device 16.

The visual markers 802 may be arranged on the neck 800 of the welding torch 14 at positions relative to the X-axis 782 along the welding torch 14, and relative to a baseline 830. For example, the first set 804 may have five visual markers 802: two visual markers 802 along the baseline 830 near a first end 832 of the neck 800 and spaced a first offset 831 from the X-axis 782, a visual marker 802 spaced a first distance 834 from the baseline 830 in a midsection 836 of the neck 800 and spaced a second offset 838 from the X-axis 782 to the left side 826, a visual marker 802 spaced a third distance 840 from the baseline 830 in the midsection 836 and spaced the second offset 838 to the right side 828, and a visual marker 802 near a second end 842 of the neck 800 along the X-axis 782 and spaced a fourth distance 844 from the baseline 830. The second set 806 may have four visual markers 802: a visual marker 802 along the baseline 830 and spaced a third offset 846 from the X-axis 782 on the left side 826, a visual marker 802 spaced a fifth distance 848 from the baseline 830 along the X-axis 782 in the midsection 836, a visual marker 802 spaced a sixth distance 850 from the baseline 830 in the midsection 836 and spaced the second offset 838 from the X-axis 782 on the right side 828, and a visual marker 802 near the second end 842 of the neck 800 spaced the fourth distance 844 from the baseline 830 and spaced the second offset 838 on the left side 826. The third set 810 may have four visual markers 802: a visual marker 802 along the baseline 830 and spaced the third offset 846 from the X-axis 782 on the right side 828, a visual marker 802 spaced a seventh distance 852 from baseline 830 along the X-axis 782 in the midsection 836, a visual marker 802 spaced an eighth distance 854 from the baseline 830 in the midsection 836 and spaced the second offset 838 from the X-axis 782 on the left side 826, and a visual marker 802 near the second end 842 of the neck 800 spaced the fourth distance 844 from the baseline 830 and spaced the second offset 838 on the right side 828.

The arrangements (e.g., distances and offsets relative to the baseline 830 and X-axis 782) of the visual markers 802 for each set 804, 806, 810 may be stored in a memory of the welding system 10. For example, the arrangements may be stored in a memory as calibrations corresponding to a particular welding torch coupled to the welding system 10. As discussed in detail below, the welding system 10 may detect the arrangement of the visual markers 802 directed to the sensing device 16, and determine the position and orientation of the welding torch 14 relative to the training stand 12 and the workpiece 82 based at least in part on a comparison of the detected arrangement and the arrangements stored in memory. Each set of visual markers 802 may be calibrated, such as prior to an initial use, after reconnecting the welding torch 14, or at a predetermined maintenance interval. To calibrate a set of visual markers 802, the welding torch 14 may be mounted to the training stand 12 in a predetermined position and orientation such that the respective set of visual markers 802 is substantially directed toward the sensing device 16. For example, the first set 804 may be calibrated when the welding torch 14 is mounted such that the Y-axis 784 of the welding torch 14 is generally directed toward the sensing device 16, the second set 806 may be calibrated when the welding torch 14 is mounted such that the second direction 808 is generally directed toward the sensing device 16, and the third set 810 may be calibrated when the welding torch 14 is mounted such that the third direction 812 is generally directed toward the sensing device 16. In some embodiments, the sets of visual markers 802 are calibrated when a calibration tool (e.g., calibration tool 610 discussed below) is coupled to the welding torch 14. The operator may verify the calibrations by moving the welding torch 14 about the welding environment relative to the training stand 12 and the sensing device 16.

Figure 33:
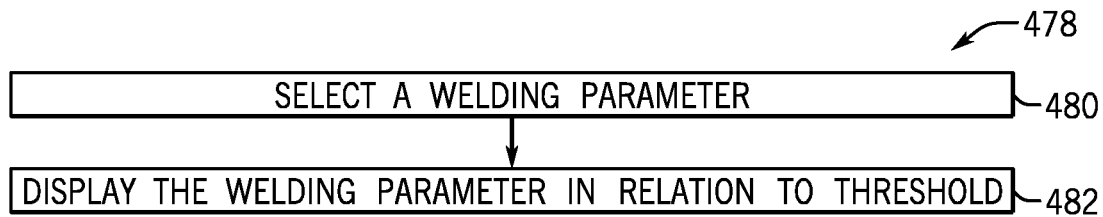
FIG. 33 is an embodiment of a method for displaying on a display of a welding torch a welding parameter in relation to a threshold in accordance with aspects of the present disclosure.

FIG. 33 is an embodiment of a method 478 for displaying on a display of a welding torch a welding parameter in relation to a threshold. In the illustrated embodiment, the control circuitry 52 (or control circuitry of another device) receives a selection made by a welding operator of a welding parameter associated with a position, an orientation, and/or a movement of the welding torch 14 (block 480). For example, the welding operator may select a button on the user interface 60 of the welding torch 14 to select a welding parameter. The welding parameter may be any suitable welding parameter, such as a work angle, a travel angle, a travel speed, a tip-to-work distance, an aim, and so forth. As may be appreciated, the welding system 10 may select the welding parameter automatically without input from a welding operator. After the selection is made, the display 62 of the welding torch 14 displays or shows a representation of the welding parameter in relation to a predetermined threshold range and/or target value for the welding parameter (block 482). The displayed welding parameter is configured to change as the position of the welding torch 14 changes, as the orientation of the welding torch 14 changes, and/or as movement of the welding torch 14 changes. Thus, the welding operator may use the welding torch 14 to properly position and/or orient the welding torch 14 while performing (e.g., prior to beginning, starting, stopping, etc.) a welding operation, thereby enabling the welding operator to perform the welding operation with the welding parameter within the predetermined threshold range or at the target value.

For example, the welding operator may desire to begin the welding operation with a proper work angle. Accordingly, the welding operator may select "work angle" on the welding torch 14. After "work angle" is selected, the welding operator may position the welding torch 14 at a desired work angle. As the welding operator moves the welding torch 14, a current work angle is displayed in relation to a desired work angle. Thus, the welding operator may move the welding torch 14 around until the current work angle matches the desired work angle and/or is within a desired range of work angles. As may be appreciated, the display 62 may be turned off and/or darkened so that it is blank during a welding operation. However, a welding operator may select a desired welding parameter prior to performing the welding operation. Even with the display 62 blank, the control circuitry 52 may be configured to monitor the welding parameter and provide feedback to the welding operator during the welding operation (e.g., vibration feedback, audio feedback, etc.).

Figure 34:
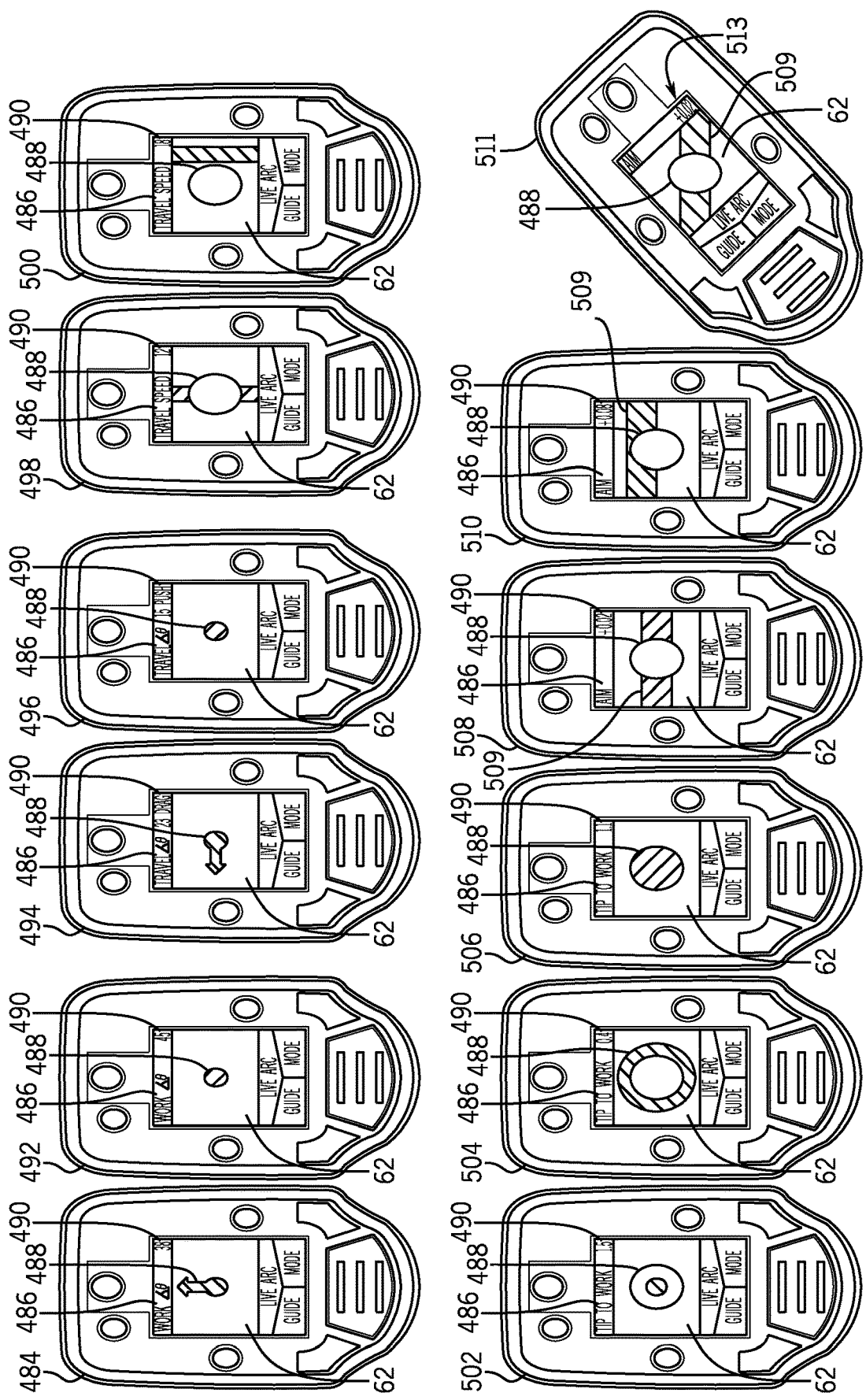
FIG. 34 is an embodiment of a set of screenshots of a display of a welding torch for showing a welding parameter in relation to a threshold in accordance with aspects of the present disclosure.

FIG. 34 is an embodiment of a set of screenshots of the display 62 of the welding torch 14 for showing a welding parameter in relation to a threshold. The set of screenshots illustrate various ways that welding parameters are displayed for a welding operator for performing a welding operation. As may be appreciated, in certain embodiments, the welding parameters may be displayed to the welding operator before, during, and/or after the welding operation. Screen 484 illustrates a work angle that is not within a predetermined threshold range. A parameter portion 486 of the display 62 indicates the selected parameter. Moreover, a range section 488 indicates whether the selected parameter is within the predetermined threshold range. Furthermore, a parameter value section 490 indicates the value of the selected parameter. On the screen 484, the work angle of 38 is out of range as indicated by the arrow extending outward from the central circle. Screen 492 illustrates a work angle of 45 that is within the predetermined threshold range as indicated by no arrow extending from the central circle.

As may be appreciated, the sensing device 16 may be configured to detect whether the travel angle is a drag angle (e.g., the travel angle is ahead of the welding arc) or a push angle (e.g., the travel angle follows behind the welding arc). Accordingly, screen 494 illustrates a drag travel angle of 23 that is outside of a predetermined threshold range as indicated by an arrow extending outward from a central circle. Conversely, screen 496 illustrates a push travel angle of 15 that is within the predetermined threshold range as indicated by no arrow extending from the central circle. Furthermore, screen 498 illustrates a travel speed of 12 that is within of a predetermined threshold range as indicated by a vertical line aligned with the central circle. Conversely, screen 500 illustrates a travel speed of 18 that is outside of (i.e., greater than) the predetermined threshold range as indicated by the vertical line to the right of the central circle. As may be appreciated, a travel speed that is less than a predetermined threshold range may be indicated by a vertical line to the left of the central circle. The travel speed indicator may dynamically move relative to the central circle in real-time during a weld process based at least in part on the determined travel speed, thereby guiding the operator to perform the weld process with a travel speed within the predetermined threshold range.

Screen 502 illustrates a tip-to-work distance of 1.5 that is greater than a predetermined threshold range as indicated by a small circle within an outer band. Moreover, screen 504 illustrates the tip-to-work distance of 0.4 that is less than a predetermined threshold range as indicated by the circle outside of the outer band. Furthermore, screen 506 illustrates the tip-to-work distance of 1.1 that is within the predetermined threshold range as indicated by the circle substantially filling the area within the outer band. Moreover, screen 508 illustrates an aim of 0.02 that is within a predetermined threshold range as indicated by a line 509 aligned with a central circle. Conversely, screen 510 illustrates an aim of 0.08 that is not within the predetermined threshold range as indicated by the line 509 toward the top part of the central circle. In some embodiments, the line 509 of screens 508 and 510 represents the joint relative to the tip of the welding torch 14. For example, screens 508 and 510 illustrate the aim of the welding torch 14 when the welding torch 14 is oriented substantially perpendicular to the joint (as illustrated by the line 509). Screen 511 illustrates the aim of the welding torch 14 when the welding torch 14 is at least partially angled relative to the joint, as indicated by the line 509 and the tilted orientation of the welding torch 14. That is, while the positions of the welding torch 14 relative to the joint (e.g., line 509) corresponding to screens 508 and 511 are substantially the same, the orientation of the line 509 of screen 508 on the display corresponds to a perpendicular orientation of the welding torch 14 relative to the joint and the orientation of the line 509 of screen 511 on the display 62 corresponds to a non-perpendicular orientation of the welding torch 14 relative to the joint. The orientation of the range section 488 (e.g., aim indicator, angle indicator, CTWD indicator) may be rotated on the display by a rotation angle defined as the angle difference between a front edge 513 of the display 62 and the joint. The graphical representations on the display 62 may correspond to the orientation of the welding torch 14 to the joint rather than to the orientation of the display 62 relative to the operator. For example, when the welding torch 14 is positioned near a vertical joint such that the welding torch 14 is substantially parallel with the joint, the line 509 on the display 62 may be oriented vertically. The joint indicator line 509 may be substantially perpendicular to the travel speed indicator discussed above with screens 498 and 500.

While specific graphical representations have been shown on the display 62 in the illustrated embodiment for showing a welding parameter in relation to a threshold, other embodiments may use any suitable graphical representations for showing a welding parameter in relation to a threshold. Moreover, in certain embodiments individual parameter visual guides may be combined so that multiple parameters are visually displayed together.

Furthermore, in certain embodiments, the welding system 10 may detect if the welding torch 14 is near and/or far from a welding joint. Being near the welding joint is a function of the contact tip-to-work distance (CTWD) and aim parameters. When both the CTWD and aim parameters are within suitable predetermined ranges (e.g., less than 3.0, 2.0, 1.5, 1.0, or 0.5 inches each), the welding system 10 may consider the welding torch 14 near the welding joint. Furthermore, the control circuitry 52 of the welding torch 14 or another device may determine the work angle, the travel angle, and the travel speed based at least in part on the position of the welding torch 14 relative to a known (e.g., calibrated) welding joint of the workpiece 82 when the CTWD and the aim are substantially constant along the welding joint. As may be appreciated, the position and orientation of the welding torch 14 may be determined via the sensing devices 16 and the markers 474, the one or more inertial sensors 426, and/or the one or more microphones 429 of the welding torch 14. In some embodiments, a second position detection system (e.g., inertial sensor(s) 426 of the welding torch 14, microphone(s) 429 of the welding torch 14) may only be activated when the welding torch 14 is positioned near the welding joint. The second position detection system may be deactivated when the welding torch 14 is not near the welding joint, such that the sensing devices 16 and the markers 474 may be utilized to determine the position and/or orientation of the welding torch 14 within the welding environment. Moreover, when the welding torch 14 is near the welding joint, the visual guides may be displayed on the welding torch 14. When the welding torch 14 is near the welding joint and in the live welding mode, a message (e.g., warning message) may be displayed on a display indicating that proper welding equipment (e.g., welding helmet, etc.) should be in place as a safety precaution for onlookers. However, an external display may continue to display the real-time data at a safe distance from the welding operation. Moreover, in some embodiments, when the welding torch 14 is near the welding joint and in the live welding mode, the display of the welding torch 14 may be changed (e.g., to substantially blank and/or clear, to a non-distracting view, to a predetermined image, etc.) while a welding operator actuates the trigger of the welding torch 14. When the welding torch 14 is far from the welding joint, actuating the trigger of the welding torch 14 will not perform (e.g., begin) a test run. Furthermore, when the welding torch 14 is far from the welding joint, actuating the welding torch 14 will have no effect in a non-live welding mode, and may feed welding wire in the live welding mode without beginning a test run.

Figure 35:
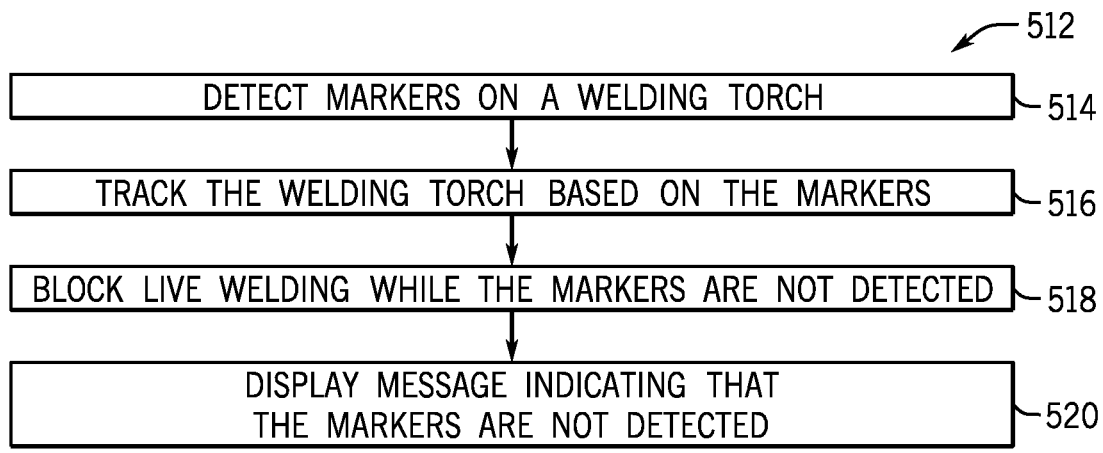
FIG. 35 is an embodiment of a method for tracking a welding torch in a welding system using at least four markers in accordance with aspects of the present disclosure.

FIG. 35 is an embodiment of a method 512 for tracking the welding torch 14 in the welding system 10 using at least four markers. One or more cameras (e.g., such as one or more cameras of the sensing system 16) are used to detect the markers of the welding torch 14 (block 514). As discussed above, the markers may be reflective markers and/or light-emitting markers. Furthermore, the markers may include four or more markers to facilitate determining an accurate position and/or orientation of the welding torch 14. One or more processors 20 of the computer 18 (or other processors) may be used with the sensing system 16 to track the position of the welding torch 14 and/or the orientation of the welding torch 14 based on the detected markers (block 516). If the one or more cameras are unable to detect one or more of the markers, the one or more processors 20 (or control circuitry, such as the control circuitry 52) may be configured to block live welding while the one or more cameras are unable to detect the markers (block 518). However, in some embodiments of the welding system 10, one or more cameras integrated with the helmet 41 may enable detection of four or more markers to facilitate determining an accurate position and/or orientation of the welding torch 14 with respect to the welding helmet 41. Thus, one or more cameras integrated with the helmet 41 may facilitate detection of the position and/or orientation of the welding torch 14 for welding processes that would otherwise obscure the one or more markers from cameras mounted to the stand 12. As may be appreciated, the position and/or orientation of the welding helmet 41 in the welding environment may be determined via the one or more sensing devices 16 of the welding system 10 in a similar manner as described above for the welding torch 14 where the markers are observable. In some embodiments, the display 62 of the welding torch 14 may be configured to display a message indicating that the markers are not detected while the one or more cameras are unable to detect the markers of the welding torch 14 (block 520). Accordingly, live welding using the welding torch 14 may be blocked if the welding torch 14 is unable to be tracked by the sensing system 16.

Some embodiments of the welding system 10 may track the welding torch 14 in the welding environment during periods where one or more of the markers 474 are obscured and not detected. Some embodiments may utilize position detection systems that directly observe a portion of the welding torch 14 without the markers 474. Furthermore, the welding system 10 may include one or more of various types (e.g., line-of-sight based (i.e., infrared, visible light, or acoustic), electromagnetic radiation based, radio signal based, inertial based) of position detection systems that may be used independently or in combination to facilitate tracking the position, orientation, and/or movement of the welding torch 14 relative to the workpiece 82. In some embodiments, control circuitry (e.g., computer 18) of the welding system 10 may independently store output from each position detection system, thereby facilitating separate analysis and/or weighting of the respective outputs to determine the position and orientation of the welding torch within the welding environment. For example, output from different position detection systems may be weighted based on an accuracy of the output, a reliability of the output, a calibration of the respective position detection system, or any combination thereof. As described above, the welding system 10 may track the position and/or the orientation of the welding torch 14 based at least in part on feedback from one or more inertial sensors 426 (e.g., accelerometers, gyroscopes) of the welding torch 14. Moreover, embodiments of the welding system 10 with beacons of a local positioning system and one or more microphones 429 on the welding torch 14 may determine a position of the welding torch 14 within the welding environment when the portions (e.g., markers 474) of the welding torch 14 are obscured from the line of sight of some sensing devices 16 (e.g., cameras). Accordingly, block 518 of method 512 (to block live welding while the markers are not detected) may be optional during intervals when the control circuitry 52 may otherwise determine the position of the welding torch 14 within the welding environment. Additionally, or in the alternative, the welding system 10 may track the welding torch 14 in the welding environment when the welding torch 14 does not have markers 474 as described above. Therefore, in some embodiments, the control circuitry 52 permits live welding while the markers are not detected or not present on the welding torch 14.

Figure 36:
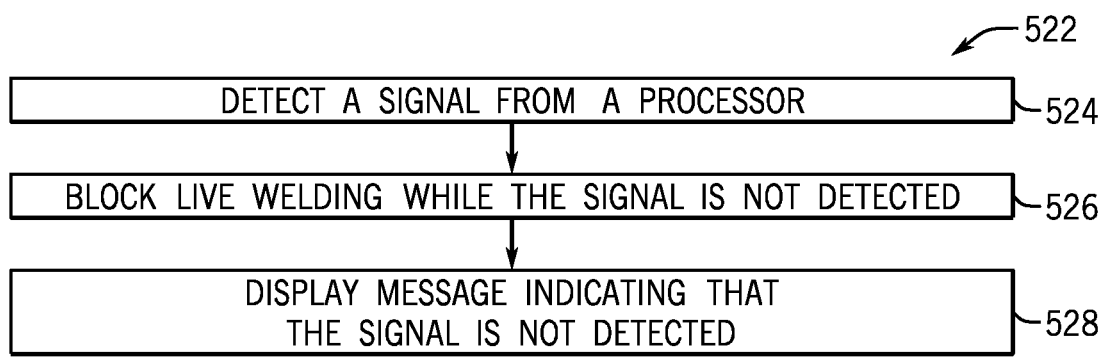
FIG. 36 is an embodiment of a method for detecting the ability for a processor to communicate with a welding torch in accordance with aspects of the present disclosure.

FIG. 36 is an embodiment of a method 522 for detecting the ability for the processor 20 (or any other processor) to communicate with the welding torch 14. The welding torch 14 is configured to detect a signal from the processor 20 (block 524). The signal is provided from the processor 20 to the welding torch 14 at a predetermined interval. In certain embodiments, the signal may be a pulsed signal provided from the processor 20 to the welding torch 14 at the predetermined interval. Moreover, the signal is provided to the welding torch 14 so that the welding torch 14 is able to determine that the welding torch 14 is able to communicate with the processor 20. If the welding torch 14 does not receive the signal from the processor 20 within the predetermined interval, control circuitry 52 (or control circuitry of another device) is configured to block live welding using the welding torch 14 while the signal is not detected (block 526). Moreover, the display 62 may be configured to display a message indicating that the signal from the processor 20 is not detected while the live welding is blocked (block 528). Accordingly, the welding torch 14 may detect the ability for the processor 20 to communicate with the welding torch 14.

Figure 37:
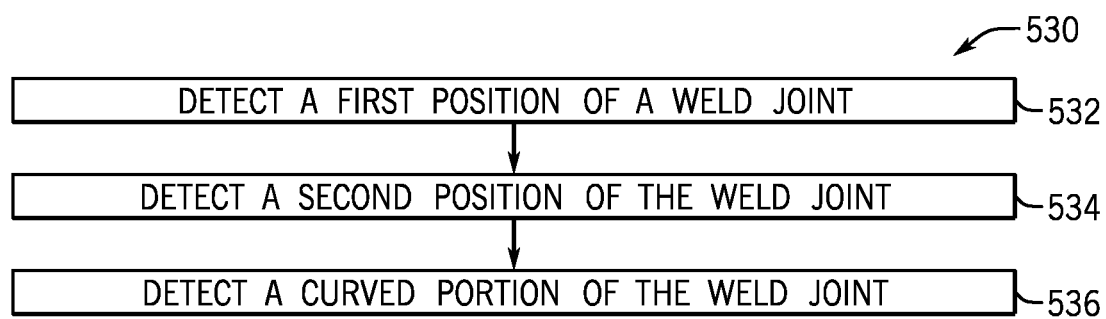
FIG. 37 is an embodiment of a method for calibrating a curved weld joint that may be used with a welding system in accordance with aspects of the present disclosure.

FIG. 37 is an embodiment of a method 530 for calibrating a curved weld joint that may be used with the welding system 10. One or more cameras (e.g., such as one or more cameras of the sensing system 16) are used to detect a first position (e.g., first calibration point) of the curved weld joint (block 532). For example, a calibration tool and/or the welding torch 14 may be used to identify the first position of the curved weld joint to the one or more cameras (e.g., such as by touching a tip of the calibration tool and/or the welding torch 14 to the first position). In addition, the one or more cameras may be used to track the calibration tool and/or the welding torch 14 to determine a position and/or an orientation of the calibration tool and/or the welding torch 14 for detecting the first position of the curved weld joint.

Moreover, the one or more cameras are used to detect a second position (e.g., second calibration point) of the curved weld joint (block 534). For example, the calibration tool and/or the welding torch 14 may be used to identify the second position of the curved weld joint to the one or more cameras. In addition, the one or more cameras may be used to track the calibration tool and/or the welding torch 14 to determine a position and/or an orientation of the calibration tool and/or the welding torch 14 for detecting the second position of the curved weld joint. Furthermore, the one or more cameras are used to detect a curved portion of the curved weld joint between the first and second positions of the curved weld joint (block 536). For example, the calibration tool and/or the welding torch 14 may be used to identify the curved weld joint between the first and second positions of the curved weld joint. In addition, the one or more cameras may be used to track the calibration tool and/or the welding torch 14 to determine a position and/or an orientation of the calibration tool and/or the welding torch 14 for detecting the curved portion of the curved weld joint. As may be appreciated, during operation, the first position may be detected, then the curved weld joint may be detected, and then the second position may be detected. However, the detection of the first position, the second position, and the curved weld joint may occur in any suitable order. In certain embodiments, a representation of the curved portion of the curved weld joint may be stored for determining a quality of a welding operation by comparing a position and/or an orientation of the welding torch 14 during the welding operation to the stored representation of the curved portion of the curved weld joint. As may be appreciated, in certain embodiments, the welding operation may be a multi-pass welding operation.

Moreover, calibration for some joints, such as circular weld joints (e.g., pipe joints) may be performed by touching the calibration tool to three different points around the circumference of the circular weld joint. A path of the circular weld joint may then be determined by calculating a best-fit circle that intersects all three points. The path of the circular weld joint may be stored and used to evaluate welding parameters of training welds. For a more complex geometry, the calibration tool and/or the welding torch 14 might be dragged along the entire joint in order to indicate the joint to the system so that all of the parameters may be calculated.

In some embodiments, the method 530 for calibrating a curved weld joint that may be used with the welding system 10 may not utilize the welding torch 14 or the calibration tool to determine the path of the weld joint. That is, the control circuitry 52 may utilize one or more images captured by cameras (e.g., such as one or more cameras of the sensing system 16) to detect the first position (block 532), the second position (block 534), and the curved portion (block 536) of the weld joint. Additionally, or in the alternative, the control circuitry 52 may utilize one or more emitters (e.g., emitters 105, 109) to emit a visible pattern (e.g., grid, point field) onto the workpiece 82 and weld joint. Cameras configured to detect the visible pattern may determine the shape of the workpiece 82 and/or the path of the weld joint based on particular features of the shape and orientation of the visible pattern on the workpiece 82 and weld joint. The control circuitry 52 may determine the shape of the weld joint and/or the workpiece 82 utilizing object recognition algorithms (e.g., edge detection) applied to the one or more captured images or visible pattern. The operator may provide input to aid the object recognition, such as selecting a type of joint (e.g., butt, tee, lap, corner, edge) and/or the shape (e.g., planar, tubular, curved) of the workpiece 82.

Figure 38:
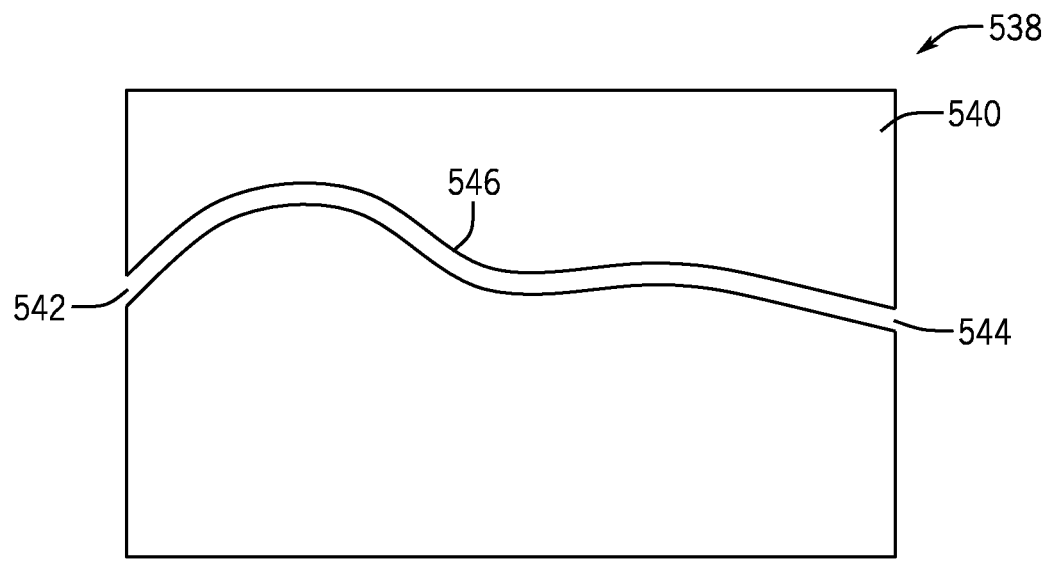
FIG. 38 is a diagram of an embodiment of a curved weld joint in accordance with aspects of the present disclosure.

FIG. 38 is a diagram of an embodiment of a curved weld joint 538. Such a curved weld joint 538 may be calibrated using the method 530 described in FIG. 37. The curved weld joint 538 is on a workpiece 540. Specifically, the curved weld joint 538 includes a first position 542, a second position 544, and a curved portion 546. Using the method 530, a shape of the curved weld joint 538 may be determined and/or stored for evaluating a welding operator performing a welding operation on the curved weld joint 538.

Figure 39:
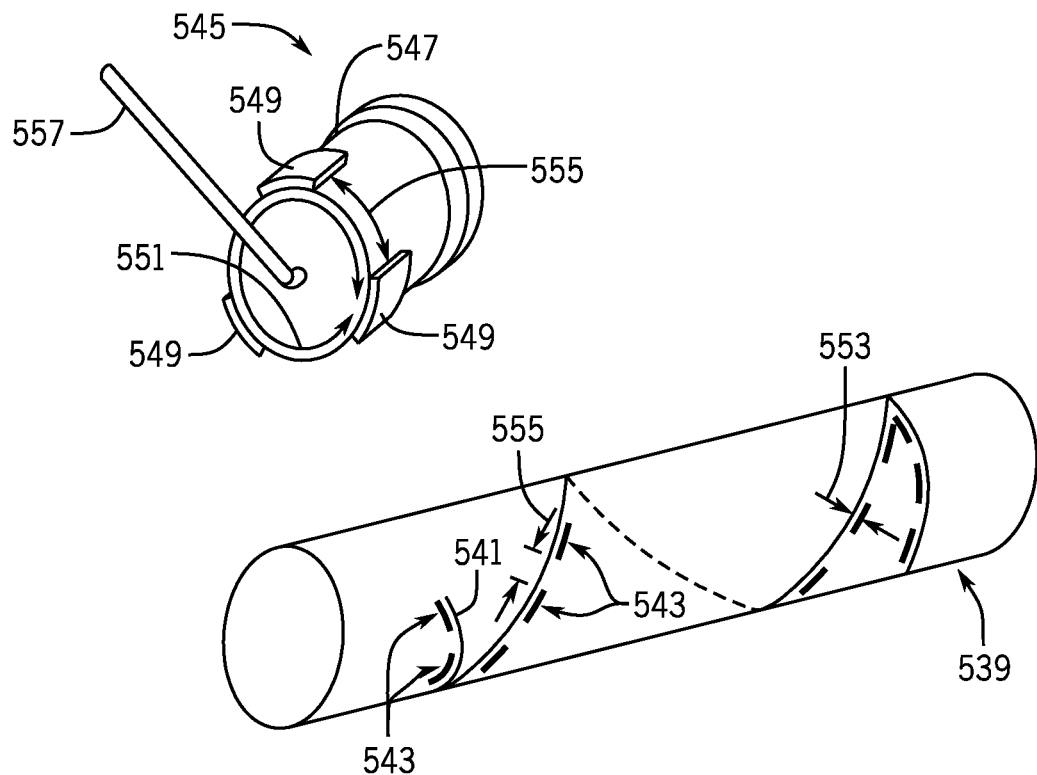
FIG. 39 is a diagram of an embodiment of a curved weld joint and a marking tool in accordance with aspects of the present disclosure.

FIG. 39 is a diagram of an embodiment of a complex shape workpiece 539 with a curved weld joint 541. The curved weld joint 541 may be calibrated via markers 543 added to the workpiece 539 (e.g., near the curved weld joint 541). A marking tool 545 may apply the markers 543 to the workpiece 539. The marking tool 545 may be a manual marking tool 545 with a handle 557. The markers 543 may include, but are not limited to paints, inks, pigments, stickers (e.g., tape), or reflectors applied to the workpiece 539 via the marking tool 545. The operator may roll a marking wheel 547 of the marking tool 545 along the curved weld joint 541, depositing (e.g., transferring) the markers 543 on the workpiece 539 to be utilized during a live welding session. For example, one or more applicators 549 on the marking wheel 547 may apply the markers 543 to the workpiece 539. In some embodiments, the markers 543 (e.g., paint, ink, pigment) may be removed from the workpiece 539 upon completion of performing the weld along the weld joint 541. That is, the markers 543 may be washed or scrubbed off the workpiece 539. The one or more applicators 549 are arranged about the marking tool 545 to facilitate placing one or more markers in a repeating pattern along a path of the workpiece. For example, the one or more applicators 549 may be arranged about a circumference 551 of the marking wheel 547 such that one period of the pattern of the one or more markers 543 is applied to the workpiece 539 for each revolution of the marking wheel 547. In some embodiments, the applicators 549 are configured to apply paint (e.g., reflective paint, fluorescent paint) from a reservoir of the marking tool 545 as each applicator 549 interfaces with the workpiece 539. Moreover, the applicators 549 may be a sorbent material that stores paint or ink.

Cameras of the sensing device 16 on the stand 12 and/or integrated with the helmet 41 of the welding system 10 may detect the markers 543. Control circuitry of the welding system 10 may determine the shape of the complex shape workpiece 539 and/or the welding system 10 may determine the welding path along the curved weld joint 541 based at least in part on the detected markers 543. The shape of the complex shape workpiece 539 and/or the welding path of the curved weld joint 541 may be stored for evaluating a welding operator performing a welding operation on the curved weld joint 541. While the markers 543 shown in FIG. 39 are discontinuous, some embodiments of the markers 543 may be continuous along the curved weld joint 541.

As may be appreciated, embodiments of the one or more markers 543 may include various geometric shapes, curves, lines, pictures, text, logos, or any combination thereof. FIGS. 72-75 illustrate embodiments of markers 543 that may be applied to the workpiece 539 by the marking tool 545. Each of FIGS. 72-75 illustrates a respective embodiment of a marker 543 having known properties (e.g., length 561, width 563, direction 565, shape, radius). In some embodiments, markers 543 are asymmetric about the direction 565 (e.g., markers of FIGS. 73-75), asymmetric in about a transverse direction 593 (e.g., marker of FIG. 72), or asymmetric about both directions 565 and 593. For example, the logo marker embodiment of FIG. 75 includes a picture and text that corresponds to the tool manufacturer and/or seller. In some embodiments, each marker 543 has an endpoint 567 that demarcates the beginning and/or the end of the respective marker 543. Moreover, features (e.g., arrows 569, text direction, unique portions) of the marker 543 may facilitate correspondence of the known properties of the marker 543 with images captured by the sensing device 16 (e.g., camera). In some embodiments, the period of each marker 543 includes one or more unmarked lengths 555 (e.g., gaps), as shown by the dashed line markers 543 proximate the joint 541 of FIG. 39. As discussed below, comparison of observed properties of a pattern of markers 543 with the known properties of the markers 543 facilitates the determination of the shapes of workpiece components with the pattern of markers 543 and the determination of the weld joint 541 between the workpiece components. In some embodiments, the pattern of markers 543 may be a continuous line with known properties (e.g., length, width).

Figure 76:
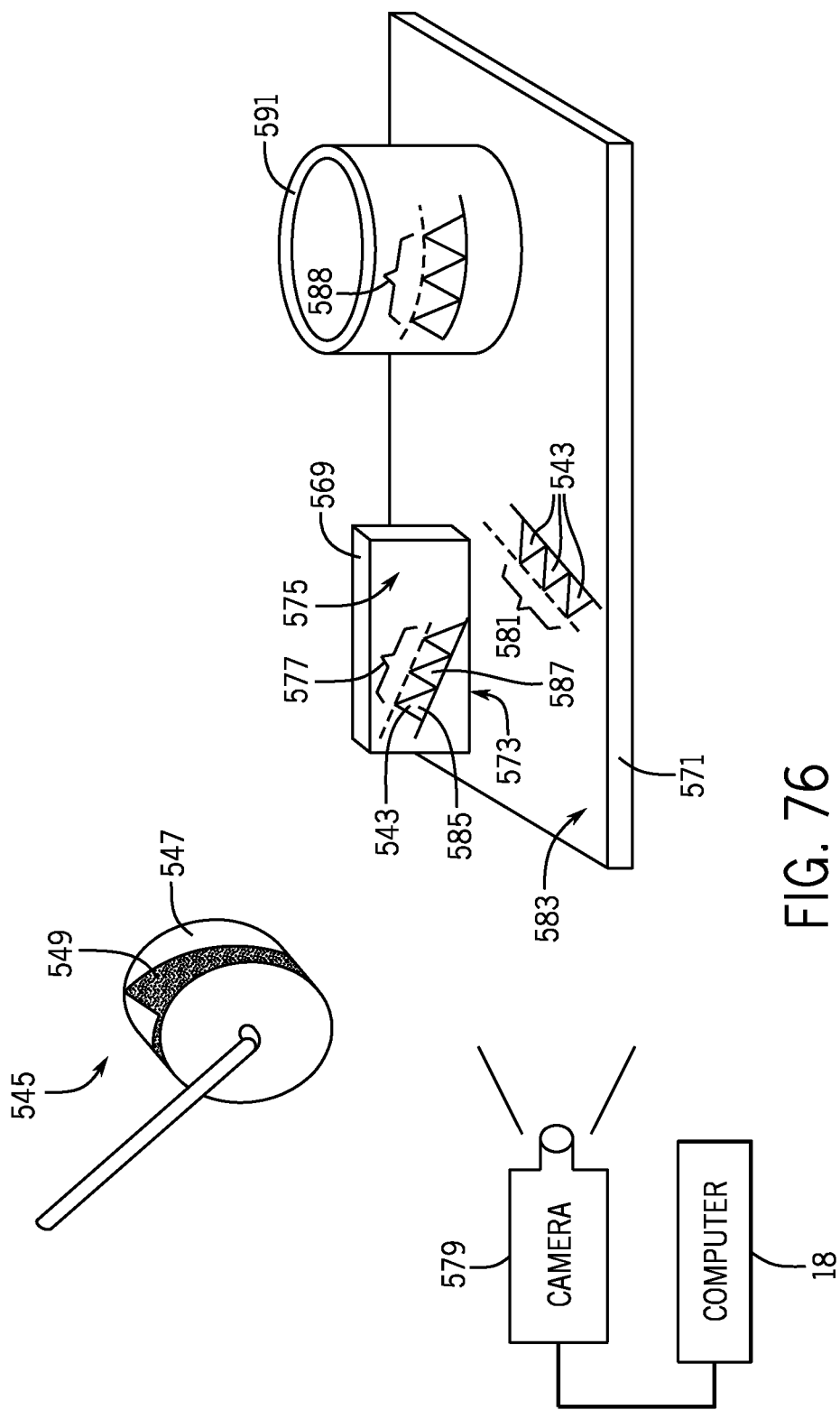
FIG. 76 is a perspective view of an embodiment of a welding system with a marking tool and markers applied to surfaces of a workpiece with the marking tool in accordance with aspects of this present disclosure.

FIG. 76 illustrates an embodiment of a welding system with workpiece components 569, 571 to be joined along a weld joint 573. As discussed herein, the term workpiece includes embodiments of separate pieces (e.g., first component 569, second component 571) to be welded together. A first surface 575 of the first component 569 has a first pattern 577 of markers 543 (e.g., triangles) observable by the camera 579. As may be appreciated, the camera 579 may be a camera of the sensing device 16, such as a camera 579 coupled to and/or integrated with the welding helmet 41. In some embodiments, the camera 579 is coupled to the welding torch 14. Captured images of the first pattern 577 of markers 543 may be used to determine the plane of the first surface 575. Comparison of observed properties (e.g., marker length, marker width, marker radius) of a marker 543 of the first pattern 577 with the known properties of the marker 543 may be utilized to determine the position (e.g., radial distance, height, azimuth) of the marker 543 relative to the camera 579. In some embodiments, the known properties of the marker 543 may include the marker width for each point along the marker length. Comparison of the observed marker width at a point with the known marker width at the point may facilitate determining the position and/or the orientation of the respective marker 543 relative to the camera 579. The determined position of multiple markers (or points within the markers) of the first pattern 577 may facilitate the determination of the plane of the first surface 575. In a similar manner, captured images of a second pattern 581 of markers 543 on a second surface 583 of the second component 571 may facilitate the determination of the plane of the second surface 583. The location of the joint 573 may then be determined as the intersection of the determined plane of the first surface 575 with the determined plane of the second surface 583. While the embodiments of the first pattern 577 and the second pattern 581 each have a plurality (e.g., three) of full length adjacent markers 543, it may be appreciated that patterns of markers 543 with portions of a period of a marker 543 may be utilized to determine the plane and the location of the joint 573. Moreover, the positions of the markers 543, the planes of the surfaces 575 and 583, and the location of the joint 573 may be determined by one or more algorithms executed by the computer 18.

In some embodiments, the respective surface of the components and the joint 573 may be determined by comparing observed properties of the markers 543 with the known properties of the markers 543. For example, the computer 18 may determine the position of a first marker 585 by comparing the observed length and width of the first marker 585 to the known length 561 and width 563 of the first marker 585. The computer 18 may also determine the direction 565 of the first marker 585, thereby enabling the computer 18 to estimate the position of an adjacent second marker 587. That is, the markers 543 of a pattern (e.g., first pattern 577) applied to a workpiece component may be detected by the camera 579 in substantially any orientation (e.g., parallel, perpendicular, askew) relative to the joint 573. Comparison of the observed properties of the second marker 587 with estimated or observed properties of the second marker 587 may facilitate the determination of the shape of the first surface 575. For example, the observed differences of the markers 543 of the first pattern 577 applied to a planar component (e.g., first surface 575) may be recognizably different than the observed differences of the markers 543 of a third pattern 589 applied to a curved (e.g., circular) component 591. The differences (e.g., distortion) between the observed properties of the markers 543 relative to the known properties of the markers 543 may be utilized to determine the position and/or the orientation of the markers 543 on the surface of the workpiece. Moreover, differences (e.g., distortion) between the observed properties of the markers 543 within a repeating pattern on the same surface may be utilized to determine the shape of the workpiece.

Figure 40:
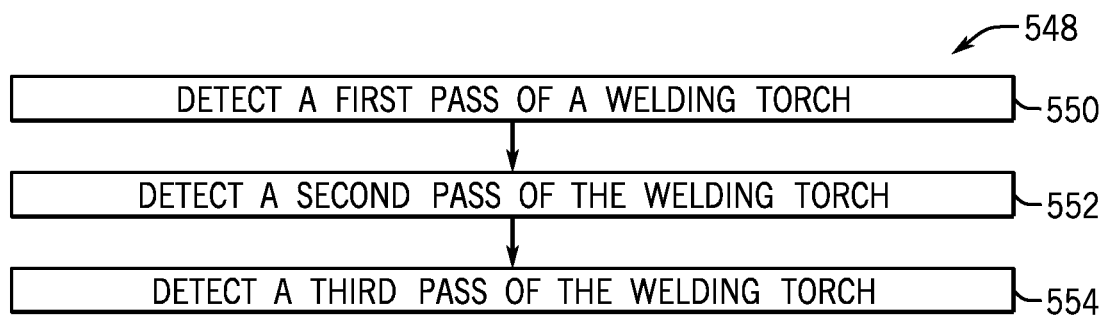
FIG. 40 is an embodiment of a method for tracking a multi-pass welding operation in accordance with aspects of the present disclosure.

FIG. 40 is an embodiment of a method 548 for tracking a multi-pass welding operation. One or more cameras (e.g., such as one or more cameras of the sensing system 16) are used to detect a first pass of the welding torch 14 along a weld joint during the multi-pass welding operation (block 550). Moreover, the one or more cameras are used to detect a second pass of the welding torch 14 along the weld joint during the multi-pass welding operation (block 552). Furthermore, the one or more cameras are used to detect a third pass of the welding torch 14 along the weld joint during the multi-pass welding operation (block 554). The control circuitry 52 (or control circuitry of another device) may be configured to store a representation of the first pass, the second pass, and/or the third pass together as a single welding operation for determining a quality of the multi-pass welding operation. As may be appreciated, the multi-pass welding operation may be a live welding operation, a training welding operation, a virtual reality welding operation, and/or an augmented reality welding operation.

Figure 41:
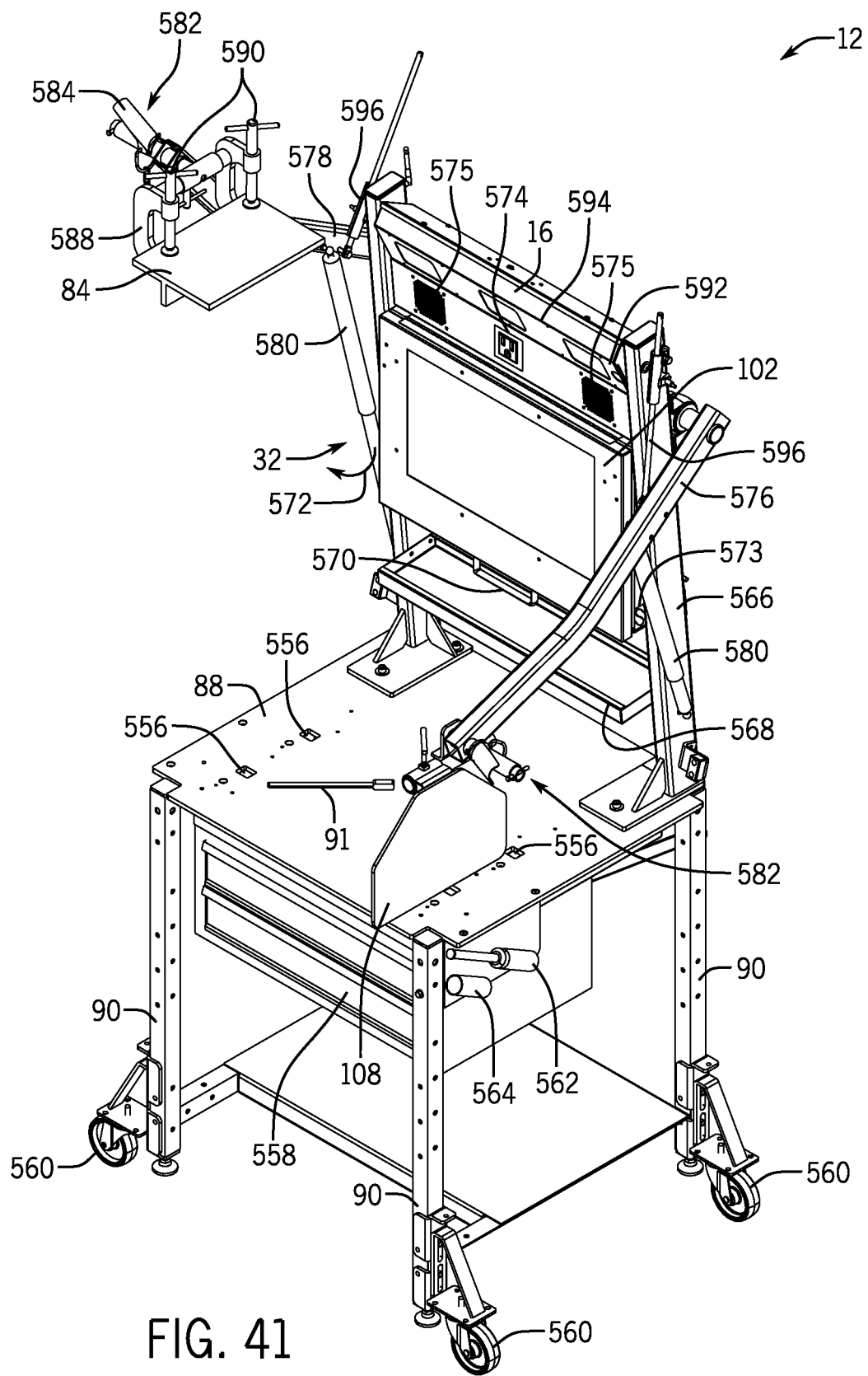
FIG. 41 is a perspective view of an embodiment of a welding stand in accordance with aspects of the present disclosure.

FIG. 41 is a perspective view of an embodiment of the welding stand 12. The welding stand 12 includes the welding surface 88 supported by the legs 90. Moreover, the welding surface 88 includes one or more slots 91 to facilitate positioning of a workpiece on the welding surface 88. Furthermore, the welding surface 88 includes multiple apertures 556 (e.g., holes or openings) that extend through the welding surface 88. The apertures 556 may be used to enable the sensing device 16 to determine a position and/or an orientation of the welding surface 88. Specifically, markers may be arranged below the apertures 556, yet within the view of the sensing device 16 to enable the sensing device 16 to determine the position and/or the orientation of the welding surface 88. The markers may be arranged below the welding surface 88 to facilitate longer lasting markers and/or to block debris from covering the markers, as explained in greater detail in relation to FIG. 42.

Drawers 558 are attached to the welding stand 12 to enable storage of various components with the welding stand 12. Moreover, wheels 560 are coupled to the welding stand 12 to facilitate easily moving the welding stand 12. Adjacent to the drawers 558, a calibration tool holder 562 and a welding torch holder 564 enable storage of a calibration tool and the welding torch 14. In certain embodiments, the welding system 10 may be configured to detect that the calibration tool is in the calibration tool holder 562 at various times, such as before performing a welding operation. A support structure 566 extending vertically from the welding surface 88 is used to provide structure support to the sensing device 16 and the display 32. Moreover, a tray 568 is coupled to the support structure 566 to facilitate storage of various components.

The protective cover 102 is positioned over the display 32 to block certain environmental elements from contacting the display 32 (e.g., weld spatter, smoke, sparks, heat, etc.). A handle 570 is coupled to the protective cover 102 to facilitate rotation of the protective cover 102 from a first position (as illustrated) used to block certain environmental elements from contacting the display 32 to a second raised position away from the display 32, as illustrated by arrows 572. The second position is not configured to block the environmental elements from contacting the display 32. In certain embodiments, the protective cover 102 may be held in the first and/or the second position by a latching device, a shock, an actuator, a stop, and so forth.

A switch 573 is used to detect whether the protective cover 102 is in the first position or in the second position. Moreover, the switch 573 may be coupled to the control circuitry 52 (or control circuitry of another device) and configured to detect whether the protective cover 102 is in the first or the second position and to block or enable various operations (e.g., live welding, auxiliary power, etc.) while the switch 573 detects that the protective cover 102 is in the first and/or the second position. For example, if the switch 573 detects that the protective cover 102 is in the second position (e.g., not properly covering the display 32), the control circuitry 52 may block live welding and/or simulation welding (with the protective cover 102 in the second position the sensing device 16 may be unable to accurately detect markers). As another example, if the switch 573 detects that the protective cover 102 is in the second position, control circuitry of the welding stand 12 may block the availability of power provided to an outlet 574 of the welding stand 12. In certain embodiments, the display 32 may show an indication that the protective cover 102 is in the first and/or the second position. For example, while the protective cover 102 is in the second position, the display 32 may provide an indication to the welding operator that live welding and/or power at the outlet 574 are unavailable. The welding stand 12 includes speakers 575 to enable audio feedback to be provided to a welding operator using the welding stand 12. Furthermore, in certain embodiments, if the trigger of the welding torch 14 is actuated while the protective cover 102 is in the second position, the welding system 10 may provide visual and/or audio feedback to the operator (e.g., the welding system 10 may provide a visual message and an audible sound effect).

As illustrated, the support structure 566 includes a first arm 576 and a second arm 578. The first and second arms 576 and 578 are rotatable about the support structure 566 to enable the first and second arms 576 and 578 to be positioned at a selected height for vertical and/or overhead welding. In the illustrated embodiment, the first and second arms 576 and 578 are independently (e.g., separately) rotatable relative to one another so that the first arm 576 may be positioned at a first vertical position while the second arm 578 may be positioned at a second vertical position different from the first vertical position. In other embodiments, the first and second arms 576 and 578 are configured to rotate together. Moreover, in certain embodiments, the first and second arms 576 and 578 may be rotated independently and/or together based on a selection by a welding operator. As may be appreciated, in other embodiments, arms may not be coupled to the support structure 566, but instead may be positioned at other locations, such as being positioned to extend vertically above one or more front legs, etc. Furthermore, in some embodiments, a structure may be coupled to the welding stand 12 to facilitate a welding operator leaning and/or resting thereon (e.g., a leaning bar).

Each of the first and second arms 576 and 578 includes a shock 580 (or another supporting device) that facilitates holding the first and second arms 576 and 578 in selected vertical positions. Moreover, each of the first and second arms 576 and 578 includes a braking system 582 configured to lock the first and second arms 576 and 578 individually in selected positions. In certain embodiments, the braking system 582 is unlocked by applying a force to a handle, a switch, a pedal, and/or another device.

The workpiece 82 is coupled to the second arm 578 for overhead and/or vertical welding. Moreover, the first arm 576 includes the welding plate 108 for overhead, horizontal, and/or vertical welding. As may be appreciated, the workpiece 82, the welding plate 108, and/or a clamp used to hold the welding plate 108 may include multiple markers (e.g., reflective and/or light emitting) to facilitate tracking by the sensing device 16. For example, in certain embodiments, the workpiece 82, the welding plate 108, and/or the clamp may include three markers on one surface (e.g., in one plane), and a fourth marker on another surface (e.g., in a different plane) to facilitate tracking by the sensing device 16. As illustrated, a brake release 584 is attached to each of the first and second arms 576 and 578 for unlocking each braking system 582. In certain embodiments, a pull chain may extend downward from each brake release 584 to facilitate unlocking and/or lowering the first and second arms 576 and 578, such as while the brake release 584 of the first and second arms 576 and 578 are vertically above the reach of a welding operator. Thus, the welding operator may pull a handle of the pull chain to unlock the braking system 582 and/or to lower the first and second arms 576 and 578.

As illustrated, the second arm 578 includes a clamp assembly 588 for coupling the workpiece 82 to the second arm 578. Moreover, the clamp assembly 588 includes multiple T-handles 590 for adjusting, tightening, securing, and/or loosening clamps and other portions of the clamp assembly 588. In certain embodiments, the first arm 576 may also include various T-handles 590 for adjusting, tightening, securing, and/or loosening the welding plate 108. As may be appreciated, the clamp assembly 588 may include multiple markers (e.g., reflective and/or light emitting) to facilitate tracking by the sensing device 16. For example, in certain embodiments, the clamp assembly 588 may include three markers on one surface (e.g., in one plane), and a fourth marker on another surface (e.g., in a different plane) to facilitate tracking by the sensing device 16. It should be noted that the welding system 10 may include the clamp assembly 588 on one or both of the first and second arms 576 and 578.

The sensing device 16 includes a removable cover 592 disposed in front of one or more cameras of the sensing device 16 to block environmental elements (e.g., spatter, smoke, heat, etc.) or other objects from contacting the sensing device 16. The removable cover 592 is disposed in slots 594 configured to hold the removable cover 592 in front of the sensing device 16. In certain embodiments, the removable cover 592 may be inserted, removed, and/or replaced without the use of tools. As explained in detail below, the removable cover 592 may be disposed in front of the sensing device 16 at an angle to facilitate infrared light passing therethrough.

As illustrated, a linking assembly 596 may be coupled between the first and/or second arms 576 and 578 and the sensing device 16 to facilitate rotation of the sensing device 16 as the first and/or second arms 576 and 578 are rotated. Accordingly, as the first and/or second arms 576 and 578 are rotated, the sensing device 16 may also rotate such that one or more cameras of the sensing device 16 are positioned to track a selected welding surface. For example, if the first and/or second arms 576 and 578 are positioned in a lowered position, the sensing device 16 may be configured to track welding operations that occur on the welding surface 88. On the other hand, if the first and/or second arms 576 and 578 are positioned in a raised position, the sensing device 16 may be configured to track vertical, horizontal, and/or overhead welding operations. In some embodiments, the first and/or second arms 576 and 578 and the sensing device 16 may not be mechanically linked, yet rotation of the first and/or second arms 576 and 578 may facilitate rotation of the sensing device 16. For example, markers on the first and/or second arms 576 and 578 may be detected by the sensing device 16 and the sensing device 16 may move (e.g., using a motor) based on the sensed position of the first and/or second arms 576 and 578.

In some embodiments, movement of the first and/or second arms 576, 578 may at least partially invalidate previous calibrations of the sensing device 16 with components of the training stand 12. For example, after the sensing device 16 is calibrated with the main (e.g., horizontal) welding surface 88 of the training stand 12, subsequent movement of the first and second arms 576, 578 may invalidate the calibration of the main welding surface 88 based at least in part on movement of the sensing device 16. Accordingly, the sensing device 16 may be recalibrated with the main welding surface 88 after the operator performs welding sessions that utilize the first and/or second arms 576, 578. In some embodiments, the computer 18 notifies the operator via the display 32 and/or audible notifications when the sensing device 16 is to be recalibrated based on detected movement of the sensing device 16 relative to the welding surface 88. Additionally, or in the alternative, the display 62 of the welding torch 14 may notify the operator when the sensing device 16 is to be recalibrated.

Figure 42:
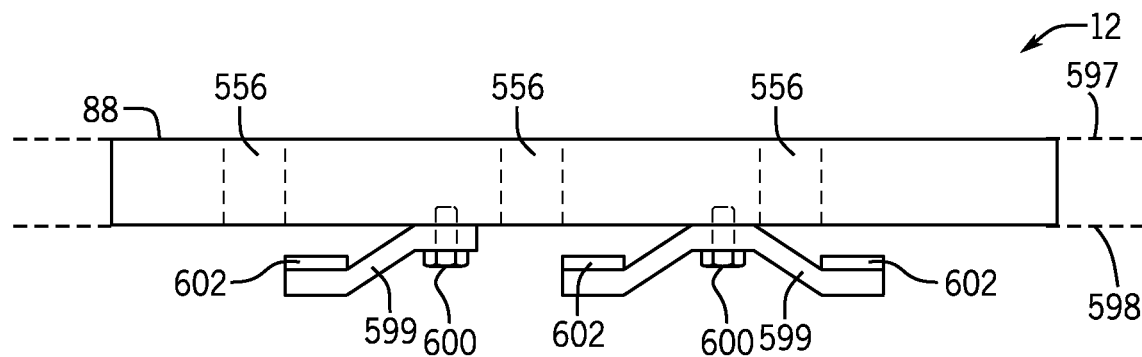
FIG. 42 is a cross-sectional view of an embodiment of a welding surface of the welding stand of FIG. 41 in accordance with aspects of the present disclosure.

FIG. 42 is a cross-sectional view of an embodiment of the welding surface 88 of the welding stand 12 of FIG. 41. As illustrated, the welding surface 88 includes multiple apertures 556 extending therethrough between an upper plane 597 of the welding surface 88 and a lower plane 598 of the welding surface 88. A bracket 599 is positioned beneath each aperture 556. The brackets 599 may be coupled to the welding surface 88 using any suitable fastener or securing means. In the illustrated embodiment, the brackets 599 are coupled to the welding surface 88 using fasteners 600 (e.g., bolts, screws, etc.). In other embodiments, the brackets 599 may be welded, bonded, or otherwise secured to the welding surface 88. Moreover, in certain embodiments, the brackets 599 may be mounted to a lateral side of the welding stand 12 rather than the welding surface 88. Markers 602 are coupled to the brackets 599 and positioned vertically below the apertures 556, but the markers 602 are horizontally offset from the apertures 556 to block dust and/or spatter from contacting the markers 602 and to enable the sensing device 16 to sense the markers 602. In some embodiments, the markers 602 may be positioned within the apertures 556 and/or at any location such that the motion tracking system is positioned on one side of the upper plane 597 and the markers 602 are positioned on the opposite side of the upper plane 597. As may be appreciated, the markers 602 may be light reflective and/or light-emissive. For example, in certain embodiments, the markers 602 may be formed from a light reflective tape. In some embodiments, the markers 602 may be spherical markers. Accordingly, the sensing device 16 may detect the markers 602 to determine a position and/or an orientation of the welding surface 88.

Figure 43:
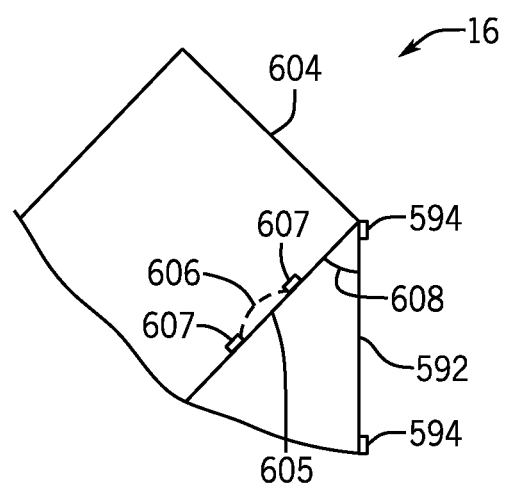
FIG. 43 is a cross-sectional view of an embodiment of a sensing device having a removable cover in accordance with aspects of the present disclosure.

FIG. 43 is a cross-sectional view of an embodiment of the sensing device 16 having the removable cover 592. As illustrated, the removable cover 592 is disposed in the slots 594. The sensing device 16 includes a camera 604 (e.g., infrared camera) having a face 605 on a side of the camera 604 having a lens 606. The removable cover 592 is configured to enable infrared light to pass therethrough and to block environmental elements (e.g., spatter, smoke, heat, etc.) or other objects from contacting the lens 606 of the camera 604. As may be appreciated, the camera 604 may include one or more infrared emitters 607 configured to emit infrared light. If the removable cover 592 is positioned directly in front of the face 605, a large amount of the infrared light from the infrared emitters 607 may be reflected by the removable cover 592 toward the lens 606 of the camera 604. Accordingly, the removable cover 592 is positioned at an angle 608 relative to the face 605 of the camera 604 to direct a substantial portion of the infrared light from being reflected toward the lens 606. Specifically, in certain embodiments, the removable cover 592 may be positioned with the angle 608 between approximately 10 to 60 degrees relative to the face 605 of the camera 604. Moreover, in other embodiments, the removable cover 592 may be positioned with the angle 608 between approximately 40 to 50 degrees (e.g., approximately 45 degrees) relative to the face 605 of the camera 604. The removable cover 592 may be manufactured from any suitable light-transmissive material. For example, in certain embodiments, the removable cover 592 may be manufactured from a polymeric material, or any other suitable material.

Figure 44:
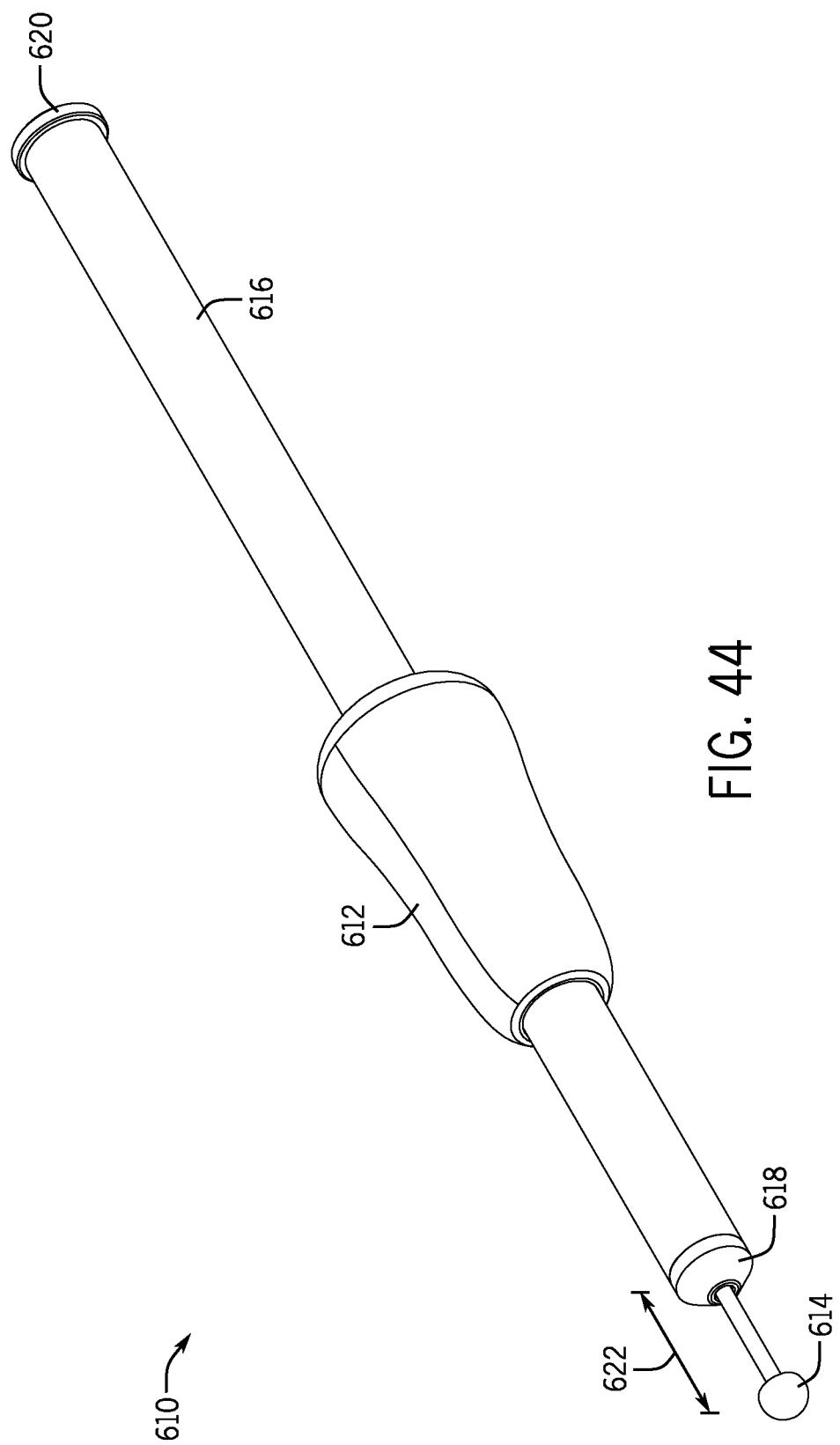
FIG. 44 is a perspective view of an embodiment of a calibration tool in accordance with aspects of the present disclosure.

FIG. 44 is a perspective view of an embodiment of a calibration tool 610. As may be appreciated, the calibration tool 610 may be used to calibrate a workpiece, a work surface, a weld joint, and so forth, for a welding operation. The calibration tool 610 includes a handle 612 to facilitate gripping the calibration tool 610. Moreover, the calibration tool 610 is configured to be detected by the sensing device 16 for determining a spatial position that a tip 614 of the calibration tool 610 is contacting. In certain embodiments, the computer 18 coupled to the sensing device 16 may be configured to determine a calibration point merely by the tip 614 contacting a specific surface. In other embodiments, the computer 18 is configured to determine a calibration point by a welding operator providing input indicating that the tip 614 is contacting a calibration point. Furthermore, in the illustrated embodiment, the computer 18 is configured to detect a calibration point by the tip 614 contacting the calibration point while a downward force is applied to the calibration tool 610 via the handle. The downward force directs a distance between two adjacent markers to decrease below a predetermined threshold thereby indicating a selected calibration point. The sensing device 16 is configured to detect the change in distance between the two adjacent markers and the computer 18 is configured to use the change in distance to identify the calibration point.

The handle 612 is coupled to a light-transmissive cover 616. Moreover, a gasket 618 is coupled to one end of the light-transmissive cover 616, while an end cap 620 is coupled to an opposite end of the light-transmissive cover 616. During operation, as a downward force is applied to the calibration tool 610 using the handle 612, a distance 622 between the tip 613 and the gasket 618 decreases.

Figure 45:
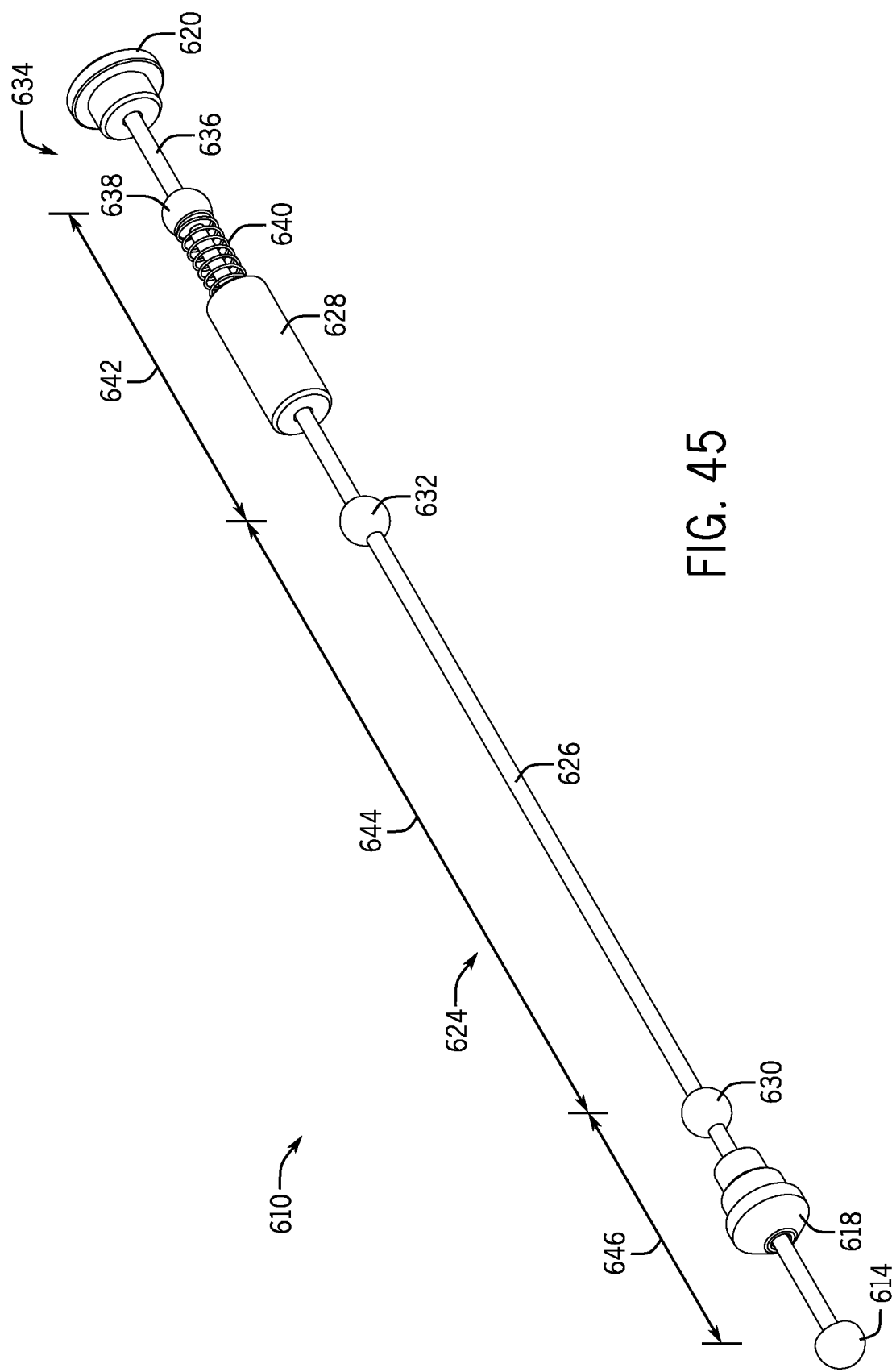
FIG. 45 is a perspective view of the calibration tool of FIG. 44 having an outer cover removed in accordance with aspects of the present disclosure.

FIG. 45 is a perspective view of the calibration tool 610 of FIG. 43 having the outer cover 616 removed. The calibration tool 610 includes a first portion 624 having a first shaft 626. Moreover, the first shaft 626 includes the tip 614 on one end, and a bearing 628 (or mounting structure) on an opposite end. In certain embodiments, the bearing 628 has a cup like structure configured to fit around a contact tip of the welding torch 14. Furthermore, the first shaft 626 includes a first marker 630 and a second marker 632 coupled thereto. The calibration tool 610 also includes a second portion 634 having a second shaft 636 with a third marker 638 coupled thereto. A spring 640 is disposed around the second shaft 636 between the third marker 638 and the bearing 628. As may be appreciated, the spring 640 facilitates the third marker 638 being directed toward the second marker 632. For example, as a downward force is applied to the calibration tool 610 using the handle 612, the spring 640 is compressed to decrease a first distance 642 between the second and third markers 632 and 638. In contrast, as the downward force is removed from the calibration tool 610, the spring 640 is decompressed to increase the first distance 642 between the second and third markers 632 and 638. A second distance 644 between the first and second markers 630 and 632 is fixed, and a third distance 646 between the first marker 630 and the tip 614 is also fixed.

In certain embodiments, the welding system 10 uses the calibration tool 610 to detect calibration points using a predetermined algorithm. For example, the third distance 646 between the tip 614 and the closest marker to the tip 614 (e.g., the first marker 630) is measured. The third distance 646 is stored in memory. The second distance 644 between two fixed markers (e.g., the first marker 630 and the second marker 632) is measured. The second distance 644 is also stored in memory. Furthermore, a compressed distance between the markers (e.g., the second and third markers 632 and 638) with the spring 640 disposed therebetween is measured. A line is calculated between the two fixed markers using their x, y, z locations. The line is used to project a vector along that line with a length of the third distance 646 starting at the first marker 630 closest to the tip 614. The direction of the vector may be selected to be away from the compressed markers. Accordingly, the three dimensional location of the tip may be calculated using the markers. In some embodiments, only two markers may be used by the calibration tool 610. In such embodiments, an assumption may be made that the marker closest to the tip 614 is the marker closest to the work surface (e.g., table or clamp). Although the calibration tool 610 in the illustrated embodiment uses compression to indicate a calibration point, the calibration tool 610 may indicate a calibration point in any suitable manner, such as by uncovering a marker, covering a marker, turning on an LED (e.g., IR LED), turning off an LED (e.g., IR LED), enabling and/or disabling a wireless transmission to a computer, and so forth.

The first, second, and third markers 630, 632, and 638 are spherical, as illustrated; however, in other embodiments, the first, second, and third markers 630, 632, and 638 may be any suitable shape. Moreover, the first, second, and third markers 630, 632, and 638 have a reflective outer surface and/or include a light-emitting device. Accordingly, the first, second, and third markers 630, 632, and 638 may be detected by the sensing device 16. Therefore, the sensing device 16 is configured to detect the first, second, and third distances 642, 644, and 646. As the first distance 642 decreases below a predetermined threshold, the computer 18 is configured to identify a calibration point. As may be appreciated, the first, second, and third distances 642, 644, and 646 are all different to enable the sensing device 16 and/or the computer 18 to determine a location of the tip 614 using the location of first, second, and third markers 630, 632, and 638.

To calibrate a workpiece, the workpiece may first be clamped to the welding surface 88. After the workpiece is clamped to the welding surface 88, a welding operator may provide input to the welding system 10 to signify that the workpiece is ready to be calibrated. In certain embodiments, the clamp used to secure the workpiece to the welding surface 88 may include markers that facilitate the welding system 10 detecting that the workpiece is clamped to the welding surface 88. After the welding system 10 receives an indication that the workpiece is clamped to the welding surface 88, the welding operator uses the calibration tool 610 to identify two calibration points on the workpiece 82. Where the clamp assembly 588 securing the workpiece has markers (e.g., visual markers 802), the measurements of the joint calibration tool 610 may be relative to the markers of the clamp assembly 588. Accordingly, the computer 18 may compensate for movement of the workpiece 82 and/or clamp assembly 588 after the joint has been calibrated based on identification of the clamp markers. Specifically, in the illustrated embodiment, the welding operator touches the tip 614 to a first calibration point and applies downward force using the handle 612 until the welding system 10 detects a sufficient change in distance between adjacent markers, thereby indicating the first calibration point. Furthermore, the welding operator touches the tip 614 to a second calibration point and applies downward force using the handle 612 until the welding system 10 detects a sufficient change in distance between adjacent markers, thereby indicating the second calibration point. In certain embodiments, the welding system 10 will only detect a calibration point if the calibration tool 610 is pressed and held at the calibration point for a predetermine period of time (e.g., 0.1, 0.3, 0.5, 1.0, 2.0 seconds, and so forth). The welding system 10 may be configured to capture multiple calibration points (e.g., 50, 100, etc.) over the predetermined period of time and average them together. If movement of the multiple calibration points greater than a predetermined threshold is detected, the calibration may be rejected and done over. Furthermore, if a first point is successfully calibrated, a second point may be required to be a minimum distance away from the first point (e.g., 2, 4, 6 inches, etc.). If the second point is not the minimum distance away from the first point, calibration of the second point may be rejected and done over. The welding system 10 uses the two calibration points to calibrate the workpiece.

In certain embodiments, the welding system 10 may determine a virtual line between the first and second calibration points. The virtual line may be infinitely long and extend beyond the first and second calibration points. The virtual line represents a weld joint. Various welding parameters (e.g., work angle, travel angle, contact tip-to-work distance (CTWD), aim, travel speed, etc.) may be in reference to this virtual line. Accordingly, the virtual line may be important for calculating the various welding parameters.

It should be noted that in certain embodiments the first, second, and third markers 630, 632, and 638 are all disposed vertically above the handle 612, while in other embodiments, one or more of the first, second, and third markers 630, 632, and 638 are disposed vertically below the handle 612 to enable a greater distance between adjacent markers. In certain embodiments, the first portion 624 may be removed from the calibration tool 610 and coupled to a contact tip of the welding torch 14 for calibrating the welding torch 14. As may be appreciated, the tip 614 of the calibration tool 610 may be any suitable shape. FIGS. 46 through 48 illustrate a few embodiments of shapes the tip 614 may have.

Specifically, FIG. 46 is a side view of an embodiment of a pointed tip 648 of the calibration tool 610. Using the pointed tip 648, the calibration tool 610 may be used for calibrating various joints on the workpiece 82, such as the illustrated fillet joint, a lap joint, a butt joint with no root opening, and so forth. Moreover, FIG. 47 is a side view of an embodiment of a rounded tip 650 of the calibration tool 610. Using the rounded tip 650, the calibration tool 610 may be used for calibrating various joints on the workpiece 82, such as the illustrated fillet joint, a butt joint with a root opening, a lap joint, and so forth. Furthermore, FIG. 48 is a side view of an embodiment of the rounded tip 650 of the calibration tool 610 having a small pointed tip 652. Using the small pointed tip 652 on the end of the rounded tip 650, the calibration tool 610 may be used for calibrating various joints on the workpiece 82, such as the illustrated butt joint with no root opening, a filled joint, a lap joint, and so forth. In certain embodiments, the tip of the calibration tool 610 may be removable and/or reversible, such that the tip includes two different types of tips (e.g., one type of tip on each opposing end). Accordingly, a welding operator may select the type of tip used by the calibration tool 610. In certain embodiments, one or more markers may be coupled to the calibration tool 610 if the calibration tool 610 is reversible. The one or more markers may be used to indicate which side of the tip is being used so that the welding system 10 may use a suitable marker-tip distance for calibration calculations.

Figure 49:
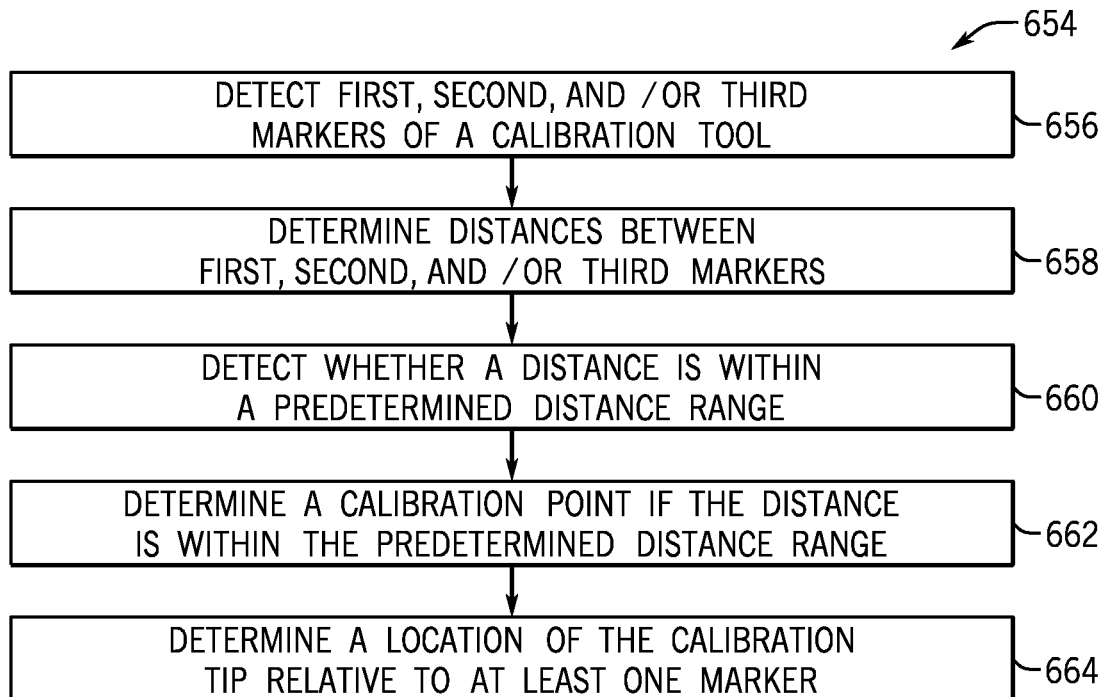
FIG. 49 is an embodiment of a method for detecting a calibration point in accordance with aspects of the present disclosure.

FIG. 49 is an embodiment of a method 654 for detecting a calibration point. The sensing device 16 (or another component of the welding system 10) detects a first marker of the calibration tool 610, a second marker of the calibration tool 610, and/or a third marker of the calibration tool 610 (block 656). Moreover, the welding system 10 determines a first distance between the first marker and the second marker and/or a second distance between the second marker and the third marker (block 658). Furthermore, the welding system 10 detects whether the first distance or the second distance is within a predetermined distance range (e.g., signifying a compressed distance) (block 660).

The welding system 10 determines a position of a calibration point if the first distance or the second distance is within the predetermined distance range (e.g., signifying a compressed distance) (block 662). In addition, the welding system 10 determines a location of a calibration tip of the calibration tool 610 relative to at least one of the first, second, and third markers to determine the spatial position of the calibration point (block 664).

Figure 50:
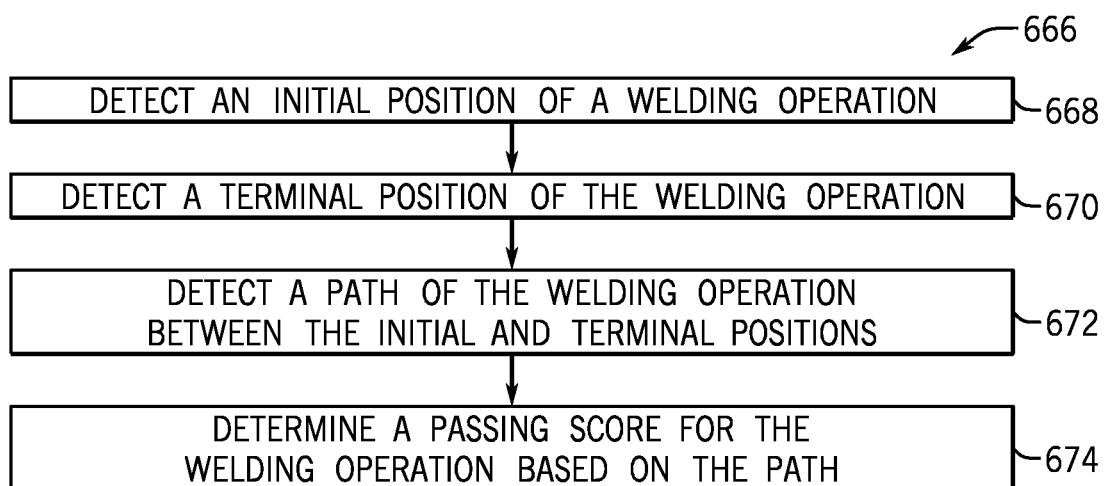
FIG. 50 is an embodiment of a method for determining a welding score based on a welding path in accordance with aspects of the present disclosure.

FIG. 50 is an embodiment of a method 666 for determining a welding score based on a welding path. Accordingly, the method 666 may be used for evaluating a welding operation. The sensing device 16 (or any suitable motion tracking system) detects an initial position of the welding operation (block 668). Moreover, the sensing device 16 detects a terminal position of the welding operation (block 670). In addition, the sensing device 16 detects a spatial path of the welding operation between the initial position and the terminal position (block 672). For example, the sensing device 16 tracks a position and/or an orientation of the welding operation. The welding system 10 determines a score of the welding operation based at least partly on the spatial path of the welding operation (e.g., whether the welding operation receives a passing score based on the spatial path of the welding operation) (block 674). For example, in certain embodiments, the spatial path of the welding operation may alone be used to determine whether a welding score fails. In some embodiments, the sensing device 16 may be used to detect a calibration point that corresponds to the initial position and/or a calibration point that corresponds to the terminal position.

For example, in certain embodiments, the welding system 10 determines whether the welding operation receives a passing score by determining whether: a distance of the path of the welding operation is greater than a predetermined lower threshold, the distance of the path of the welding operation is less than the predetermined lower threshold, the distance of the path of the welding operation is greater than a predetermined upper threshold, the distance of the path of the welding operation is less than the predetermined upper threshold, the path of the welding operation deviates substantially from a predetermined path of the welding operation, the path of the welding operation indicates that multiple welding passes occurred at a single location along a weld joint, a time of welding along the path of the welding operation is greater than a predetermined lower threshold, the time of welding along the path of the welding operation is less than the predetermined lower threshold, the time of welding along the path of the welding operation is greater than a predetermined upper threshold, and/or the time of welding along the path of the welding operation is less than the predetermined upper threshold.

Moreover, in some embodiments, for the welding system 10 to determine a score, the welding system 10 may disregard a first portion of the path adjacent to the initial position and a second portion of the path adjacent to the terminal position. For example, the first portion of the path and the second portion of the path may include a distance of approximately 0.5 inches. Moreover, in other embodiments, the first portion of the path and the second portion of the path may include portions of the path formed during a time of approximately 0.5 seconds.

Figure 51:
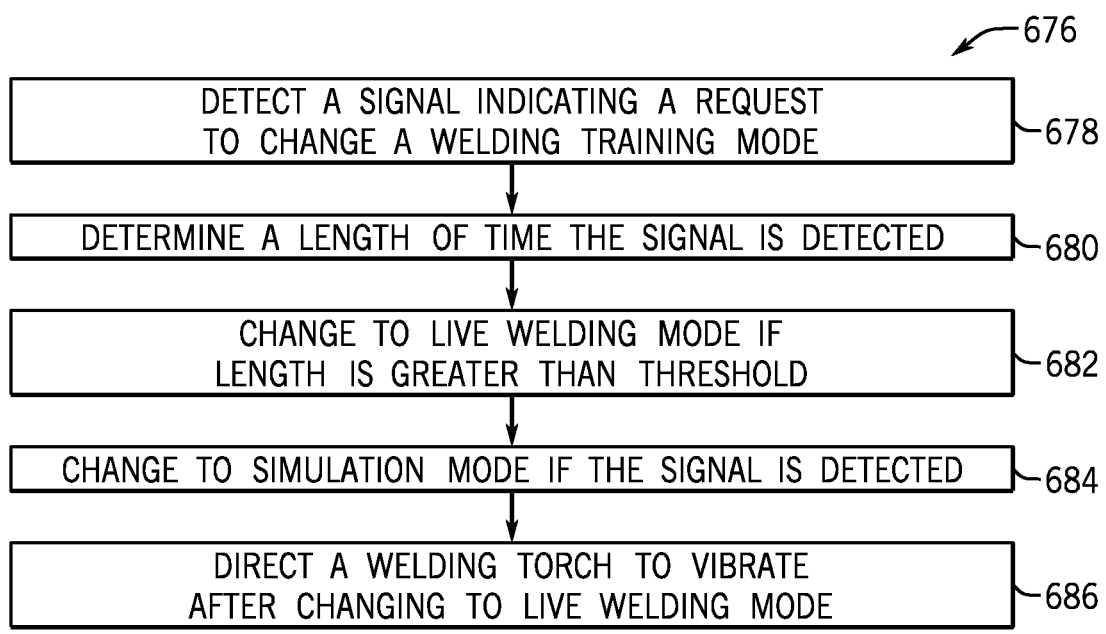
FIG. 51 is an embodiment of a method for transitioning between welding modes using a user interface of a welding torch in accordance with aspects of the present disclosure.

FIG. 51 is an embodiment of a method 676 for transitioning between welding modes using a user interface of the welding torch 14. The control circuitry 52 of the welding torch 14 (or control circuitry of another device) detects a signal produced by a user interface of the welding torch 14 indicating a request to change the welding mode (e.g., welding training mode) (block 678). Moreover, the control circuitry 52 determines a length of time that the signal is detected (block 680). The control circuitry 52 is configured to change the welding mode from a simulation mode (e.g., virtual reality mode, augmented reality mode, etc.) to a live welding mode if the length of time that the signal is detected is greater than a predetermined threshold (block 682). Conversely, the control circuitry 52 is configured to change the welding mode from the live welding mode to the simulation mode merely if the signal is detected (block 684) (e.g., there is no length of time that the signal is to be detected before a transition from the live welding mode is made). The control circuitry 52 is configured to direct the welding torch 14 to vibrate after changing to the live welding mode (block 686). For example, the control circuitry 52 may be configured to direct the welding torch 14 to vibrate two or more times (e.g., vibration pulses) to indicate a change to the live welding mode.

Moreover, the control circuitry 52 may be configured to direct the welding torch 14 to vibrate any suitable number of times (e.g., predetermined number of times) to indicate a change to the live welding mode. As may be appreciated, the signal indicating the request to change the welding mode may be produced by pressing a button on the user interface of the welding torch 14. As such, the welding mode may be changed from the live welding mode by pressing and releasing the button (e.g., the button does not have to be held down for a predetermined period of time). In contrast, the welding mode may be changed from the simulation mode to the live welding mode by pressing and holding the button for a predetermined period of time. In certain embodiments, an audible sound may be produced after changing welding modes. Furthermore, in some embodiments an audible sound and a vibration may accompany any change between welding modes. In addition, a display of the welding torch 14 may show the welding mode after changing the welding mode. In some embodiments, the display may flash the welding mode on the display a predetermined number of times.

Figure 52:
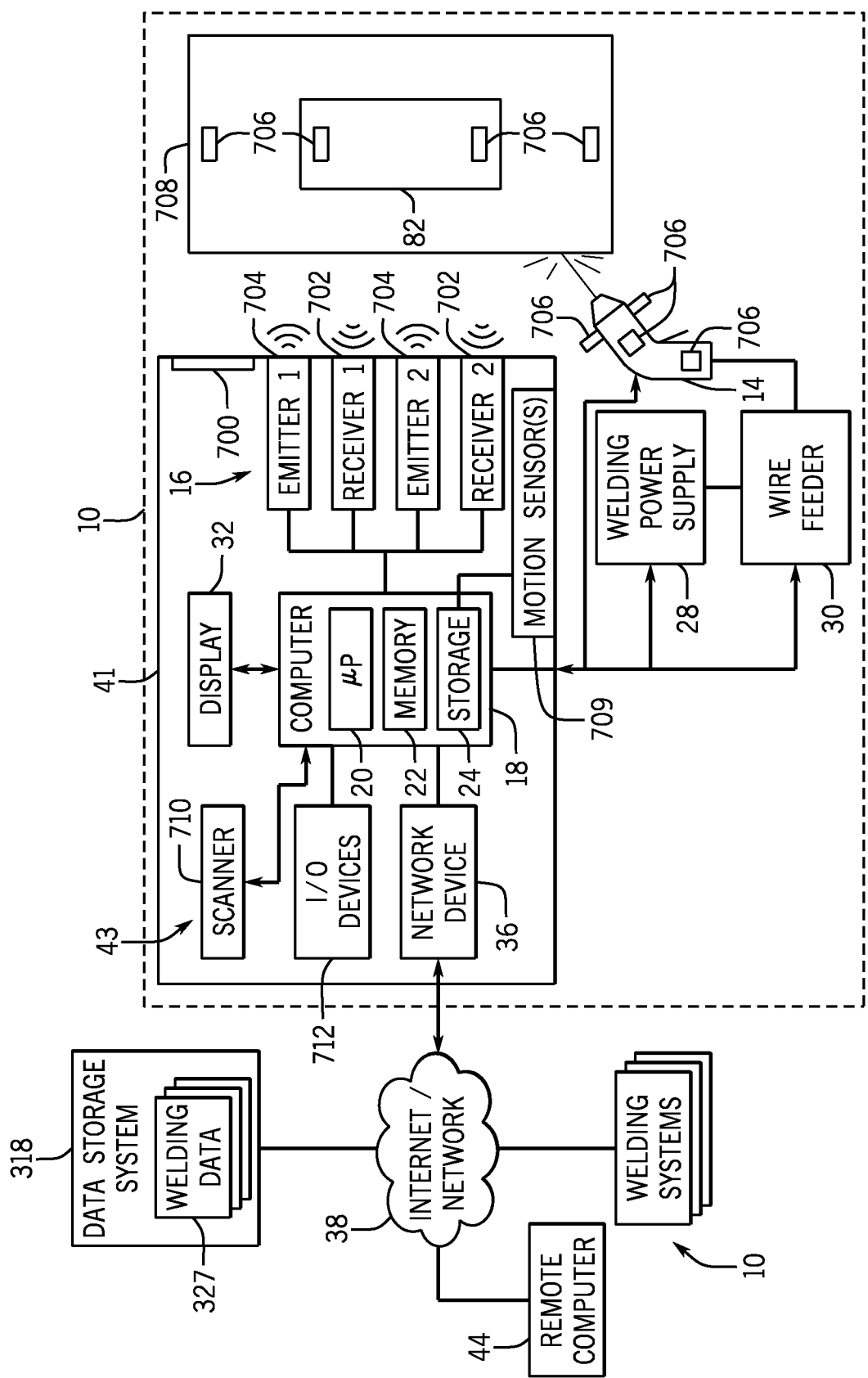
FIG. 52 is an embodiment of a remote welding training system in accordance with aspects of the present disclosure.

FIG. 52 is a block diagram of an embodiment of a remote training system, such as a helmet training system 41. In some embodiments, the helmet training system 41 facilitates acquisition of welding parameters (e.g., a work angle, a travel angle, a contact tip to workpiece distance, a welding torch travel speed, a welding torch orientation, a welding torch position, an aim of the welding torch relative to the joint of the workpiece, and so forth) of a weld process and/or arc parameters (e.g., a welding voltage, a welding current, wire feed speed) without utilizing the stand 12 described above. As may be appreciated, operators utilize helmets during welding, and the helmet training system 41 integrates the one or more sensing devices 16 (e.g., emitters, receivers) into the helmet. Various embodiments of the helmet 41 may incorporate the computer 18 (e.g., as a controller), couple to the computer 18 via a wired connection, or couple to the computer via a wireless connection. In some embodiments, the helmet training system 41 utilizes a lens 700 to shield the operator from the arc during a weld process. In some embodiments, the display 32 is disposed within the helmet training system 41 such that the operator may view the display 32 and the lens 700 in preparation for or during a weld process. The display 32 may be a heads-up display that is at least partially overlaid with the operator's view through the helmet training system 41. As may be appreciated, the welding software may utilize the display 32 disposed within the helmet training system 41 to present information to the operator in a similar manner as described above with the display 32 external to the helmet 41. For example, the display 32 of the helmet 41 may shows a visual representation (e.g., number, text, color, arrow, graph) of one or more arc parameters, one or more welding parameters, or any combination thereof. That is, the display 32 of the helmet 41 may display a visual representation of a welding parameter in relation to a predetermined threshold range and/or to a target value for the welding parameter according to a selected welding assignment. In some embodiments, the display 32 may show a graphical representation of a welding parameter or an arc parameter in relation to a threshold similar to the displays 62 of the torch 14 described above with FIG. 34. Additionally, the display 32 of the helmet 41 may show one or more parameters (e.g., arc parameters, welding parameters) before, during, or after the operator using the helmet 41 performs a welding session (e.g., welding assignment).

The helmet training system 41 utilizes one or more integrated sensing devices 16 to determine the welding parameters from observations of the welding torch 14 and the workpiece 82. The one or more sensing devices 16 of the helmet training system 41 may include one or more receivers 702 including, but not limited to, microphones, cameras, infrared receivers, or any combination thereof. Moreover, in some embodiments, one or more emitters 704 may emit energy signals (e.g., infrared light, visible light, electromagnetic waves, acoustic waves), and reflections of the energy signals may be received by the one or more receivers 702. In some embodiments, fiducial points 706 (e.g., markers) of the welding torch 14 and/or the workpiece 82 are active markers (e.g., LEDs) that emit energy signals, as discussed above with FIGS. 31 and 32. Accordingly, the one or more receivers 702 of the helmet training system 41 may receive energy signals emitted from active markers. In particular, the receivers 702 may identify fiducial points (e.g., markers) 706 disposed on the workpiece 82, the work environment 708, and/or the welding torch 14, and the receivers 702 may send feedback signals to the computer 18 (e.g., controller) that correspond to the identified fiducial points. As discussed above, arrangements of the identified fiducial points 706 may enable the sensing device 16 to determine the position and orientation of the welding torch 14 in the work environment 708. The computer 18 (e.g., controller) may determine the distances between the fiducial points 706 and may determine the welding parameters based at least in part on the feedback from the receivers 702. Additionally, the computer 18 (e.g., controller) may be coupled to sensors within the welding power supply 28, the wire feeder 30, and/or the welding torch 14 to determine the arc parameters of the welding process.

In some embodiments, the helmet training system 41 may determine the types of components of the welding system 10 from the identified fiducial points. For example, the fiducial points of a TIG welding torch are different than the fiducial points of a MIG welding torch. Moreover, the welding software 244 executed by the computer 18 may control the welding power supply 28 and/or the wire feeder 30 based at least in part on the determined types of components of the welding system 10. For example, the helmet training system 41 may control the arc parameters (e.g., weld voltage, weld current) based on the type of welding torch 14, the welding position of the workpiece 82, and/or the workpiece material. The helmet training system 41 may also control the arc parameters based on the experience or certification status of the operator associated with the registration number 293. For example, the helmet training system 41 may control the welding power supply 28 to reduce the weld current available for selection by an operator with less than a predetermined threshold of experience with weld processes on relatively thin workpieces or in the overhead welding position. In some embodiments, the one or more sensing devices 16 of the helmet training system 41 include inertial sensors 709 (e.g., gyroscopes and accelerometers) that are coupled to the computer 18. The inertial sensors 709 may enable the computer 18 to determine the orientation and relative movement of the helmet training system 41 within the environment.

In some embodiments, the helmet training system 41 includes the operator identification system 43. The operator identification system 43 may utilize a scanner 710 (e.g., fingerprint scanner, retinal scanner, barcode scanner) or an input/output device 712 (e.g., keyboard, touch screen) to receive the identification information from the operator. As discussed above, the identification information may be associated with the registration number 293 unique to the operator. Welding data received by the computer 18 (e.g., controller) may be stored in the memory 22 or storage 24, as discussed above. The computer 18 (e.g., controller) may associate the received and stored welding data with the registration number 293 of the identified operator. The network device 36 couples to the network 38 via a wired or wireless connection to store the welding data 327 from the helmet training system 41 in the data storage system 318 (e.g., cloud storage system). In some embodiments the helmet training system 41 may store welding data locally within the storage 24 of the computer 18 while the helmet training system 41 is operated remotely (e.g., production floor, worksite). The helmet training system 41 may be configured to upload stored welding data to the data storage system 318 (e.g., cloud storage system) upon connection with the network 38, such as when the operator stows the helmet training system 41 at the end of a shift or at the end of a work week. In some embodiments, the network device 36 of the helmet training system 41 may stream welding data to the data storage system 318 (e.g., cloud storage system) via the network 38 during and/or after the operator performs a welding session.

As may be appreciated, using the systems, devices, and techniques described herein, a welding system 10 may be provided for training welding operators. The welding system 10 may be cost efficient and may enable welding students to receive high quality hands on training. While the welding systems 10 described herein may be utilized for receiving and correlating weld data 327 for training and educational purposes, it may be appreciated that the welding systems 10 described herein may be utilized to monitor operators and obtain weld data 327 from non-training weld processes. That is, weld data obtained from non-training weld processes may be utilized to monitor weld quality and/or weld productivity of previously trained operators. For example, the weld data 327 may be utilized to verify that welding procedures for a particular weld process were executed. As illustrated in FIG. 52, multiple welding systems 10 may be coupled to the data storage system 318 (e.g., cloud storage system) via the network 38. Accordingly, the data storage system 318 may receive welding data 327 associated with registration numbers 293 from multiple welding systems 10 (e.g., systems with training stands 12, helmet training systems 41). Moreover, welding data associated with each registration number 293 may include serial numbers 329 corresponding to other welding sessions performed by the respective operator. Moreover, as utilized herein, the term "assignment" is not to be limited to weld tests performed by the operator for training and educational purposes. That is, assignments may include non-training weld processes, training simulated weld processes, and training live weld processes, among others. Moreover, the term "welding session" may include, but is not limited to, welding assignments, welds performed on a production floor, welds performed at a worksite, or any combination thereof.

Figure 53:
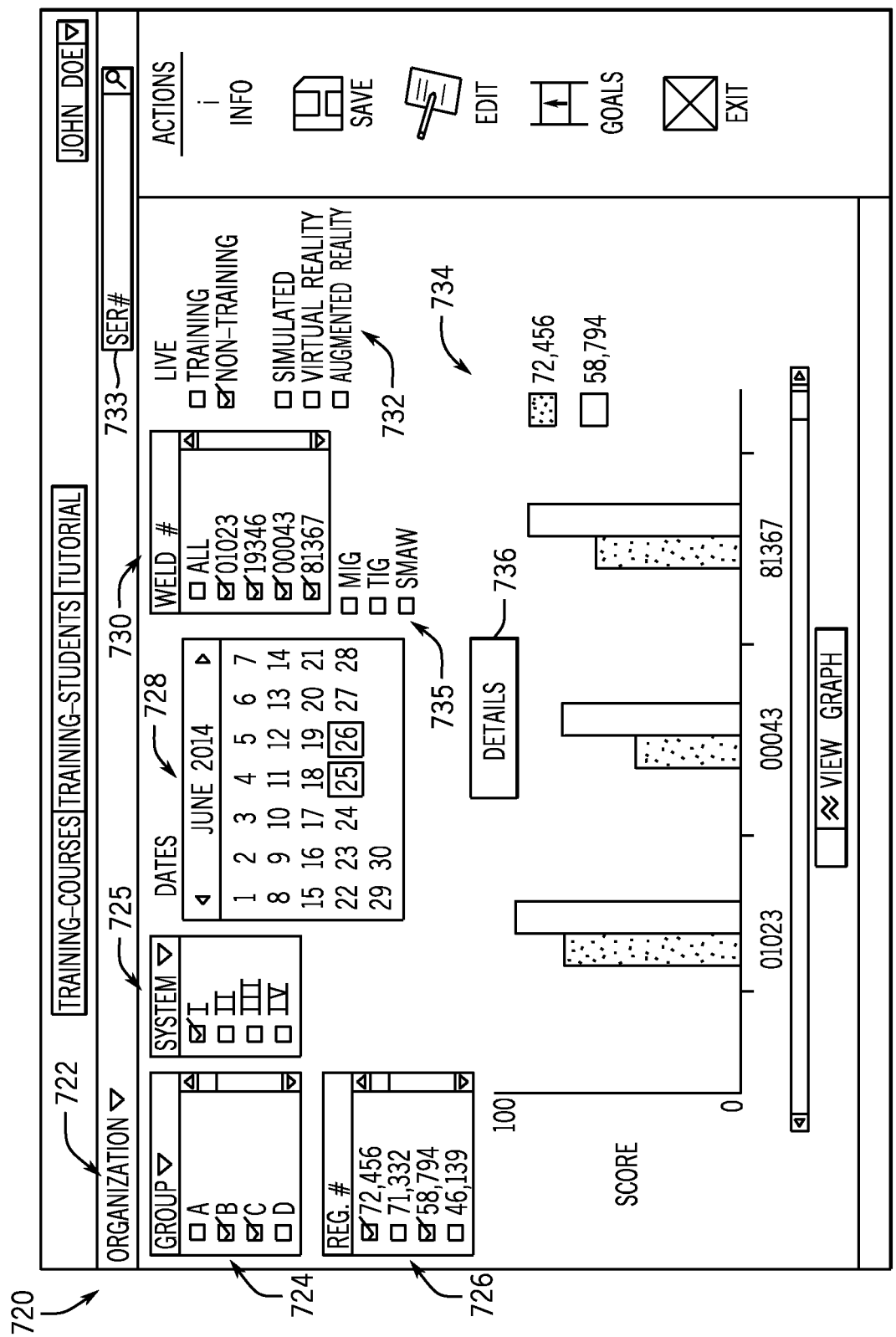
FIG. 53 is an embodiment of a dashboard page with welding data from different operators, in accordance with aspects of the present disclosure.

The welding data 327 of the data storage system 318 (e.g., cloud storage system) may be monitored and/or managed via a remote computer 44 coupled to the network 38. The stored welding data 327 corresponds to weld processes (e.g., live, simulated, virtual reality) performed by various operators at one or more locations. FIG. 53 illustrates an embodiment of a user viewable dashboard screen 720 that may be utilized by a manager or instructor to monitor and/or analyze the stored welding data 327 in the data storage system 318. The welding data 327 may be organized by characteristics (e.g., filter criteria) of the welding data 327. Characteristics of the welding data 327 that may be utilized for sorting the welding data 327 may include, but are not limited to, one or more organizations 722 (e.g., training center, employer, work site), one or more groups 724 (e.g., shift) within the organization, one or more registration numbers 726 of operators within the selected organizations 722 or groups 724, time (e.g., dates 728, time of day) welding processes were performed, systems 725, and weld identifications 730 (e.g., particular welding assignments, unique identifier associated with a welding session, workpiece part number, or types of welds). For example, welding data 327 associated with one or more registration numbers 293 over a period of time (e.g., dates 728) and across different organizations 722 or different groups 724 may be displayed on the dashboard screen 720. Accordingly, the manager or instructor may track the progress of an operator over time across different organizations via welding data associated with the registration number 293 of the operator. In some embodiments, a welding data type 732 (e.g., live training, live non-training, simulated, virtual reality) may be used to filter the viewed welding data. Moreover, a welding process type 735 (e.g., GMAW, TIG, SMAW) may be used to filter the viewed welding data in some embodiments. As may be appreciated, welding data for each welding session (e.g., welding assignment) may be sorted (e.g., filtered) into various subsets. As illustrated in FIG. 53, live, non-training welds performed by an operator with registration number 58,794 on Jun. 25, 2014 with system I may be displayed on the dashboard screen 720 via selection of one or more of the appropriate fields for registration numbers 726, systems 725, dates 728, and welding data types 732.

Additionally, or in the alternative, the instructor may utilize a search control 733 to search for welding data 327 associated with various parameters (e.g., serial numbers 329, organization 722, group 724, operator name, registration number 726, time, welding data type) corresponding to welding sessions performed by operators. Upon selection of a set of welding data, a section 734 of the dashboard screen 720 may display graphical indicia (e.g., a score) associated with the selected welding data and/or at least a portion of the welding data. Moreover, details of the welding data 327 may be viewed upon selection of the welding data 327 and a user control 736. The dashboard screen 720 may enable the manager or instructor to save or edit the arrangement of the welding data on the dashboard screen 720. Furthermore, the dashboard screen 720 may enable the manager or instructor to export at least a portion of the welding data 327. For example, the manager may export the welding data 327 corresponding to the sessions performed by a set of operators over the course of a day or a week. The dashboard screen 720 may enable the manager or instructor to export the welding data 327 in various formats, including but not limited to a comma-separated values (CSV) file, a spreadsheet file, and a text file. In some embodiments, the manager or instructor may remove a subset of welding data (e.g., demonstration welding data) from the data storage system (e.g., cloud storage system). Additionally, or in the alternative, the manager or instructor may edit the welding data type 732, such as to revise training weld data as non-training weld data, revise the operator associated with welding data, revise the time associated with welding data, and so forth.

As may be appreciated, the dashboard screen 720 may enable the manager or instructor to monitor, compare, and analyze the welding data associated with one or more registration numbers 726. In some embodiments, the performance, experience, and historical data of welding operators may be compared across organizations or groups via the registration numbers 726. In some embodiments, the dashboard screen 720 may enable the manager or instructor to set goals or provide assignments to desired registration numbers 726. Furthermore, the manager or instructor may monitor and adjust previously established goals. The dashboard screen 720 may enable notes or comments regarding the welding performance associated with one or more registration numbers to be entered and stored with the welding data.

Figure 54:
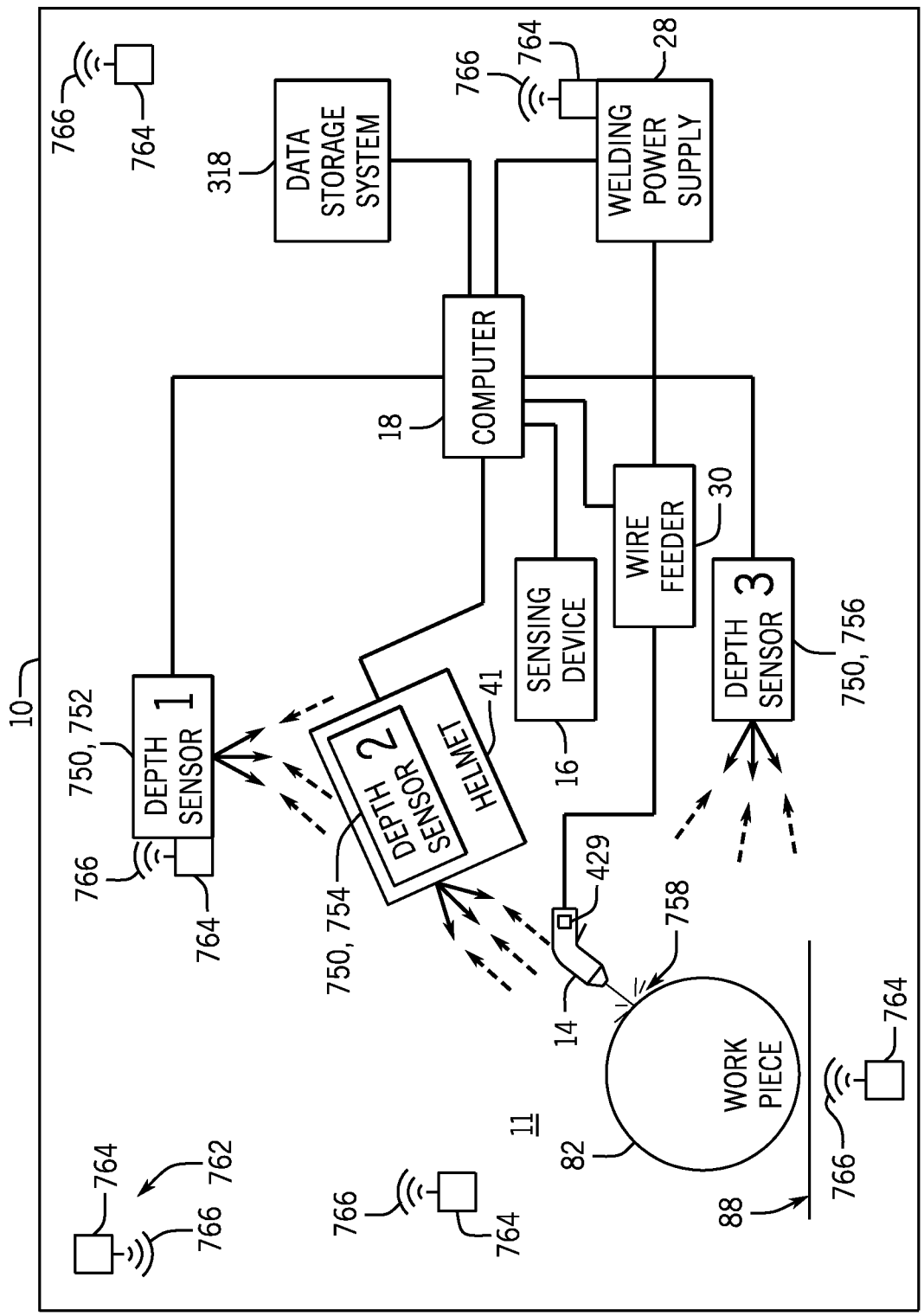
FIG. 54 is an embodiment of a welding system with depth sensors and a local positioning system, in accordance with aspects of the present disclosure.

FIG. 54 illustrates an embodiment of the welding system 10 in the welding environment 11 that may track the position and/or orientation of the welding torch 14 without utilizing the markers 474 on the welding torch 14 discussed above in FIGS. 30-32. The welding system 10 of FIG. 54 may track the position and/or orientation of the welding torch 14 prior to conducting a welding process. In some embodiments, the welding system 10 of FIG. 54 may track the position and/or orientation of the welding torch 14 during the welding process. One or more depth sensors 750 are arranged at various positions in the welding environment 11, such as a first depth sensor 752 above the workpiece 82, a second depth sensor 754 integrated with the welding helmet 41 (e.g., helmet training system), or a third depth sensor 756 horizontal with the workpiece 82, or any combination thereof. Each depth sensor 750 may have an emitter configured to emit a visible pattern at a desired wavelength and a camera configured to monitor the visible pattern in the welding environment 11. The visible pattern emitted by each depth sensor 750 may be the same or different than the visible pattern emitted by other depth sensors 750. Moreover, the desired wavelength of the visible pattern for each depth sensor 750 may be the same or different among the depth sensors 750. FIG. 54 illustrates respective emitted visible patterns from each depth sensor 750 with solid arrows, and FIG. 54 illustrates the patterns reflected toward each depth sensor 750 with dashed arrows. The wavelength of the visible patterns may be within the infrared, visible, or ultraviolet spectrum (e.g., approximately 1 mm to 120 nm). The emitter of each depth sensor emits the respective visible pattern into the welding environment 11 onto the welding surface 88, the workpiece 82, the welding torch 14, or the operator, or any combination thereof. By observing the visible pattern reflected in the welding environment 11, the computer 18 may track objects (e.g., welding torch 14, operator) moving within the welding environment. Additionally, the computer 18 may identify the shape of the workpiece 82 or a welding joint path on the workpiece 82 based upon observations of the visible pattern in the welding environment 11.

As may be appreciated, an arc 758 struck by the welding torch 14 with the workpiece 82 emits electromagnetic radiation. The wavelengths and the intensity of the emissions at each wavelength of the electromagnetic radiation emitted by the arc may be based on a variety of factors including, but not limited to, the workpiece material, the electrode material, the shielding gas composition, the weld voltage, the weld current, the type of welding process (e.g., SMAW, MIG, TIG). In some embodiments, the sensing device 16 includes a light sensor configured to detect the wavelengths electromagnetic radiation of the welding environment 11 prior to and during welding processes. The computer 18 of the welding system 10 may determine the emitted wavelengths and the intensity of the emitted wavelengths from the emitted based on feedback received from the sensing device 16. Additionally, or in the alternative, the computer 18 may determine the emitted wavelengths and the intensity of the emitted wavelengths from data stored in memory of the computer 18 or the data storage system 318, the welding parameters, and the arc parameters. For example, the computer 18 may determine that the arc for steel MIG welding has different predominant wavelengths than the arc for aluminum TIG welding.

In some embodiments, the wavelengths of the one or more visible patterns emitted by the depth sensors 750 may be selected to reduce noise from the arc 758 during welding processes. Furthermore, in some embodiments, the depth sensors 750 can vary the wavelength of the emitted visible pattern. Accordingly, the computer 18 may adaptively control the wavelengths of the emitted visible patterns to improve the accuracy of the position and orientation determinations from the depth sensor feedback. That is, the computer 18 may control the depth sensors 750 to emit the visible pattern in a first range for steel MIG welding, and to emit the visible pattern in a different second range for aluminum TIG welding. Additionally, or in the alternative, the computer 18 may filter the signals received by the depth sensors 750 to reduce or eliminate the effects of the emissions by the arc 758.

Furthermore, the arc 758 may not be continuous during the weld formation for some welding processes (e.g., short circuit MIG). The emitted electromagnetic radiation when the arc 758 is out (e.g., during a short circuit phase of the welding process) may be substantially less than the emitted electromagnetic radiation when the arc 758 is live. The computer 18 may control the depth sensors 750 to emit the respective visible patterns when the arc 758 is out (e.g., extinguished) rather than when the arc 758 is live, thereby enabling the depth sensors 750 to track the position and/or orientation of the welding torch 14 during the weld process. That is, the computer 18 may synchronize the emitted visible patterns to substantially coincide with the short circuit phases of the welding process. The short circuit frequency may be greater than 30 Hz, thereby enabling the computer 18 to determine the position and/or the orientation of the welding torch 14 in the welding environment 11 at approximately 30 Hz or more.

Additionally, or in the alternative to the depth sensors 750, the welding system 10 may utilize a local positioning system 762 to determine the position of the welding torch 14 within the welding environment 11. Beacons 764 of the local positioning system 762 are arranged at known locations about the welding environment and emit signals 766 (e.g., ultrasonic, RF) received via one or more microphones 429 on the welding torch. The computer 18 coupled to the one or more microphones 429 may determine the location of the welding torch 14 within the welding environment 11 based at least in part on received signals from three or more beacons 764. The computer may determine the position of the welding torch 14 via triangulation, trilateration, or multilateration. More than three beacons 764 of the local positioning system 762 distributed about the welding environment 11 increase the robustness of the local positioning system 762 and increase the likelihood that the welding torch 14 is within a line of sight of at least three beacons 764 at any point along a workpiece 82 having a complex shape (e.g., pipe). In some embodiments, beacons 764 may be positioned with depth sensors 750 or components of the welding system 10, such as the welding power supply 28.

Returning to FIGS. 31 and 32, embodiments of the welding torch 14 may have multiple sets of visual markers 802 to facilitate detection of the position and the orientation of the welding torch 14 relative to the training stand 12 and to the workpiece 82. In some embodiments, the visual markers 802 are LEDs 64 that may be independently controlled. For example, each set (e.g., first set 804, second set 806, third set 810) of LEDs 64 may be separately controlled so that only one set is turned on and emits light at a time. Reducing the quantity of visual markers 802 detectable by the sensing device 16 may reduce the complexity of the determination of the position and the orientation of the welding torch 14. That is, the sensing device 16 may readily determine which side (e.g., top, left, right) of the welding torch 14 is facing the sensing device 16 based on the arrangement of the detected LEDs 64 when only one set of LEDs 64 is turned on at a time. The control circuitry 52 of the welding torch 14 may control the LEDs 64 so that at least one set of the LEDs 64 is detectable by the sensing device 16 during a simulated or live welding session (e.g., live welding assignment).

Figure 55:
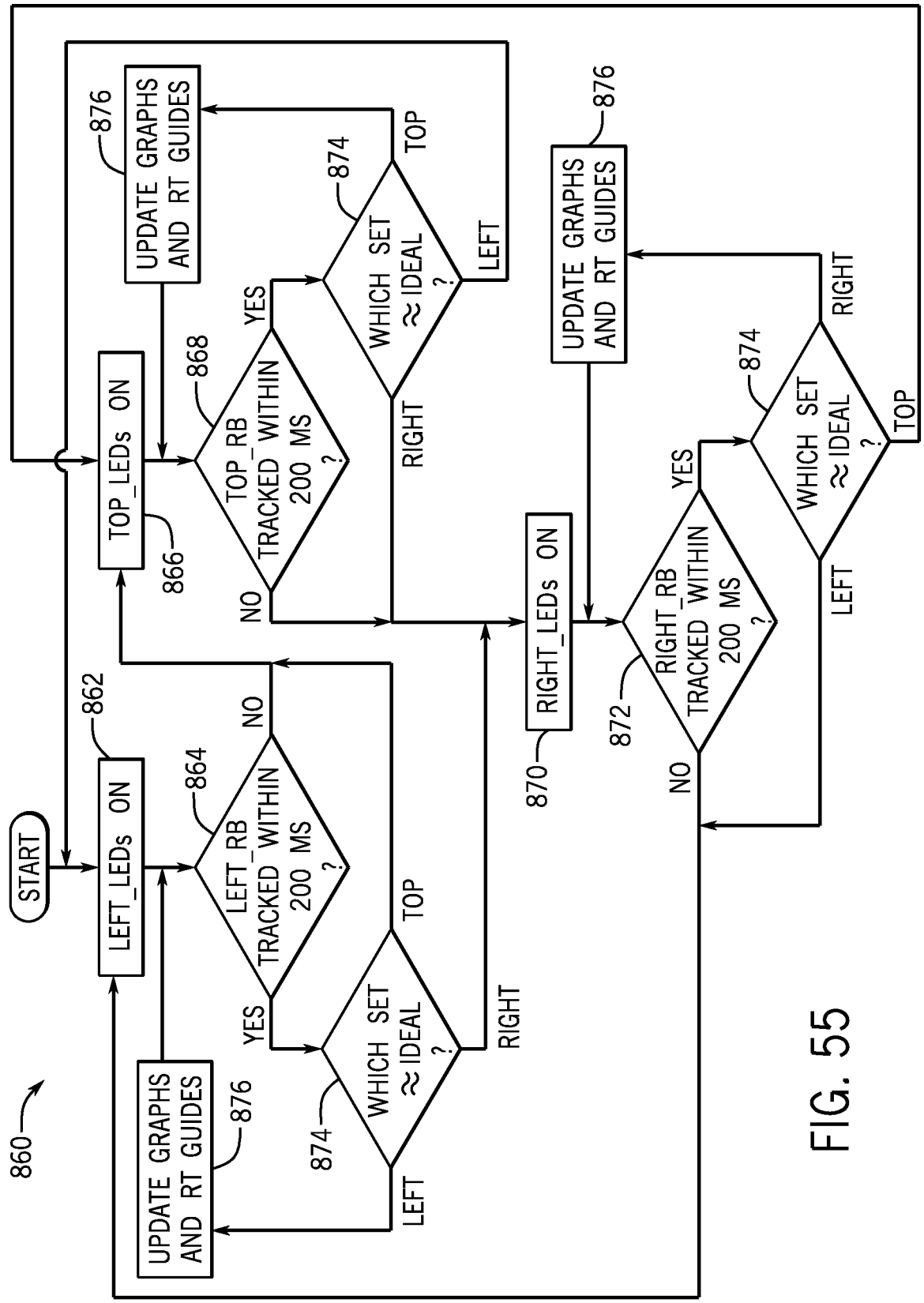
FIG. 55 is an embodiment of a method of controlling visual markers of the welding torch to track the movement and position of the welding torch, in accordance with aspects of the present disclosure.

The processor 20 coupled to the sensing device 16 and/or the control circuitry 52 may determine which set of LEDs 64 to turn on to track the movement and position of the welding torch 14 utilizing a method 860 illustrated in FIG. 55. As may be appreciated, the method 860 may be performed by a controller, which includes, but is not limited to the processor 20, the control circuitry 52, or a combination thereof. Generally, the controller may turn on each set of LEDs 64 sequentially for a detection interval, then compare the response detected by the sensing device 16 from each set to determine which set of LEDs 64 enables better tracking data. For example, the controller may turn on (block 862) the left set (e.g., second set 806) of LEDs 64. The controller determines (node 864) whether the left set of LEDs 64 is detected within the detection interval (e.g., approximately 50 to 500 ms). If the left set of LEDs 64 is not detected at node 864, the controller may turn on (block 866) the top set (e.g., first set 802) of LEDs 64. The controller then determines (node 868) whether the top set of LEDs 64 is detected. If the top set of LEDs 64 is not detected at node 868, the controller may turn on (block 870) the right set (e.g., third set 810) of LEDs 64. The controller then determines (node 872) whether the right set of LEDs 64 is detected. If the right set of LEDs 64 is not detected at node 872, then the controller may return to the start of the method 860, and turn on (block 862) the left set of LEDs 64. In some embodiments, the controller may repeat method 860 to turn on each set of LEDs 64 in sequence until at least one set of LEDs 64 is detected during the detection interval.

As discussed herein, when the controller determines whether a set of LEDs 64 is detected (e.g., nodes 864, 868, 872), the controller may determine whether the threshold quantity of LEDs 64 for the respective set is detected. As discussed above, the threshold quantity may be less than or equal to the total quantity of visual markers (e.g., LEDs 64) of a respective set. In some embodiments, the controller is configured to determine a rigid body (RB) model of the welding torch 14 upon detection of the threshold quantity of LEDs 64. The controller determines (nodes 874) which rigid body model corresponding to tracked sets of LEDs 64 is the closest to an ideal model. As may be appreciated, the ideal model may correspond to when a set of LEDs 64 is directed directly towards the sensing device 16 within a predetermined range of angles (e.g., approximately 20, 30, 45, or 60 degrees). Furthermore, each set of LEDs 64 side may have its own predetermined range of angles, such as approximately 45 degrees for the top set of LEDs 64 and approximately 30 degrees for the left and right sets of LEDs 64. In some embodiments, the first set 802 of LEDs 64 may approximate the ideal model when the Y-axis 784 relative to the welding torch 14 is directed to the sensing device 16. If the determined rigid body model of the welding torch 14 corresponding to one set of LEDs 64 (e.g., second set 806) does not approximate the ideal model, the controller may turn off the one set and turn on the next set (e.g., first set 802) of LEDs 64 to determine if an approximately ideal rigid body model may be detected with the next set. Additionally, or in the alternative, the controller may utilize the detected non-ideal angle of one set (e.g., first set 804) of LEDs 64 and the predetermined relative angles of the other sets (e.g., second set 806, third set 810) of LEDs 64 to determine which set (e.g., third set 810) of LEDs 64 corresponds closest to the ideal model, thereby enabling the controller to turn on that set (e.g., third set 810) of LEDs 64 directly without turning on other sets (e.g., second set 806). The controller may be configured to latch to a set of turned on LEDs 64 when the determined rigid body model approximates the ideal model.

In some embodiments, a set of LEDs 64 may approximate the ideal model when LEDs 64 are oriented within approximately 20 to 60 degrees or approximately 30 to 50 degrees of the sensing device 16. Accordingly, based on the orientation of the sets of LEDs 64, some embodiments of the controller may be able to determine a rigid body model corresponding to more than one set of LEDs 64 at a time. Where multiple rigid body models may be determined, the controller may determine which set of LEDs 64 is most oriented toward the sensing device 16. Moreover, the controller may utilize a hysteresis control when the welding torch orientation fluctuates near an angle threshold where multiple rigid body models may be determined respective sets of LEDs 64. As discussed above, the first set 802 of LEDs 64 may be oriented approximately along the Y-axis 784, and the second set 806 of LEDs 64 may be oriented so that the second direction 808 is offset approximately 45 degrees from the Y-axis 784. In some embodiments, rigid body models may be determined for each respective set of LEDs 64 oriented within approximately 30° of the sensing device 16, such that rigid body models for each respective set may be determined for an overlapping range of approximately 15°. Utilizing the hysteresis control, the controller may remain latched to the first set 802 of LEDs 64 when the first set 802 is oriented within approximately 25° offset from the Y-axis 784 and within approximately 20° offset from the second direction 808. That is, the hysteresis control may reduce the turning off and on sets of LEDs 64 when multiple sets of LEDs 64 may be detectable by the sensing device 16 and prevents rapid oscillation between sets of LEDs 64 when the welding torch 14 is oriented near the threshold between sets of LEDs 64.

Upon latching to a set of LEDs 64 that approximate the ideal model, the controller (blocks 876) may update the items displayed on the display 32 of the welding system 10, the display 32 of the helmet 41, and/or the display 62 of the welding torch 14 based at least in part on the position and orientation determined from the tracked set of LEDs 64. The controller may maintain the status (e.g., on, off) of each set of LEDs 64 while the determined rigid body model approximates the ideal model. In some embodiments, the controller may repeat method 860 at intervals during operation, thereby turning on each set of LEDs 64 sequentially to verify that the determined rigid body model of the latched set of LEDs 64 most approximates the ideal model. For example, the controller may repeat method 860 every 1, 5, or 15 minutes. Additionally, or in the alternative, the controller may repeat method 860 upon receipt of an assignment, selection of an assignment, upon lifting the welding torch 14 from the training stand 12, or any combination thereof.

Figure 56:
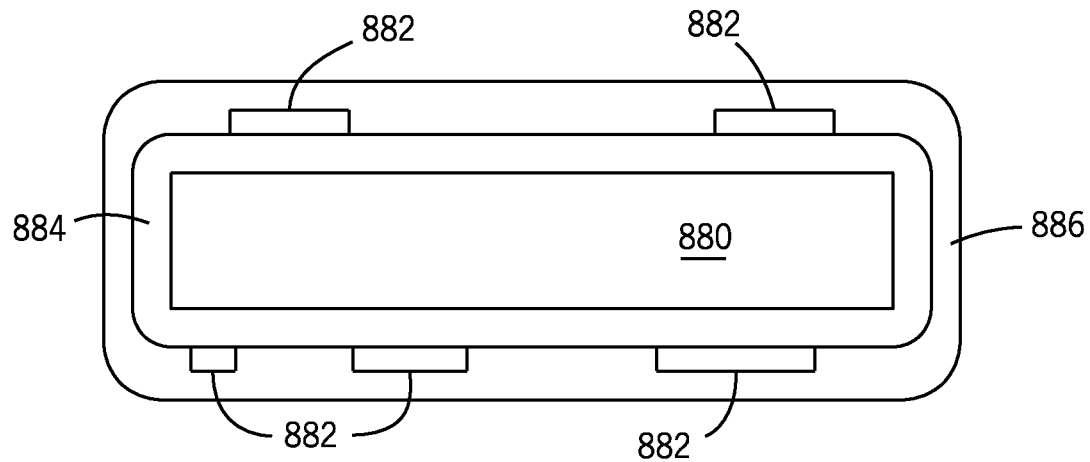
FIG. 56 is a cross-sectional view of a base component with visual markers, in accordance with aspects of the present disclosure.

As discussed above, various elements of the welding system 10 may have markers that for utilization to track movement of the respective element within the welding environment in real-time and/or to calibrate the position and orientation of the element relative to the training stand 12 or to the workpiece 82. For example, the training stand 12 of FIG. 4 may have the first and second markers 95, 96, the welding surface 112 may have the markers 116, 118, the calibration tool 120 of FIG. 5 may have the markers 130, the fixture assembly 132 of FIG. 6 may have the first and second markers 134, 136, the welding torch 14 of FIG. 30 may have the markers 474, and the welding torch 14 of FIG. 31 may have the visual markers 802. FIG. 56 illustrates a cross-sectional view of a base component 880 that may be provided with visual markers 882. The base component 880 may include, but is not limited to, the training stand 12, the workpiece 82, the welding surface 112, the calibration tool 120, the fixture assembly 132, the welding torch 14, the clamp assembly 588, or any combination thereof.

The base component 880 may be coated with a thermally insulating layer 884 (e.g., plastic, fabric, ceramic, resin, glass). The thermally insulating layer 884 may be wrapped about, molded to, mechanically fastened to, or bonded to the base component 880. As may be appreciated, the base component 880 may receive or conduct thermal heat from the welding process. The visual markers 882 may be positioned at distinct locations on the insulating layer 884 of the base component 880. The visual markers 882 may be readily detectable by the sensing device 16. For example, the visual markers 882 may be reflective to one or more electromagnetic waves. For example, the visual markers 882 may reflect visible and/or infrared (IR) light. The position of the each visual marker 882 may be configured to enable the sensing device 16 to determine the position and the orientation of the base component 880 within the welding environment. The visual markers 882 may be positioned on one or more faces of the base component 880. Different quantities and/or arrangements of the visual markers 882 on each side of the base component 880 may facilitate identification of the respective sides based on detection of the arrangement of the visual markers 882.

A cover layer 886 (e.g., cover plate) is coupled to the insulating layer 884 and to the visual markers 882. The cover layer 886 may cover the visual markers 882, thereby shielding the visual markers 882 from some environmental factors, such as spatter, dust, unintentional removal, and so forth. In some embodiments, the cover layer 886 does not cover or only partially covers the visual markers 882. In some embodiments, the cover layer 86 is a plastic, such as polycarbonate. The cover layer 886 may be a material that is not substantially reflective of one or more electromagnetic waves that are reflected by the markers 882. Additionally, or in the alternative, the cover layer 886 may be conditioned to reduce or eliminate reflections of electromagnetic waves. For example, the cover layer 886 may be painted, coated, or roughened (e.g., sandblasted), or any combination thereof. In some embodiments, the cover layer 886 is substantially non-reflective except in an area immediately covering the visual markers 882.

Figure 57:
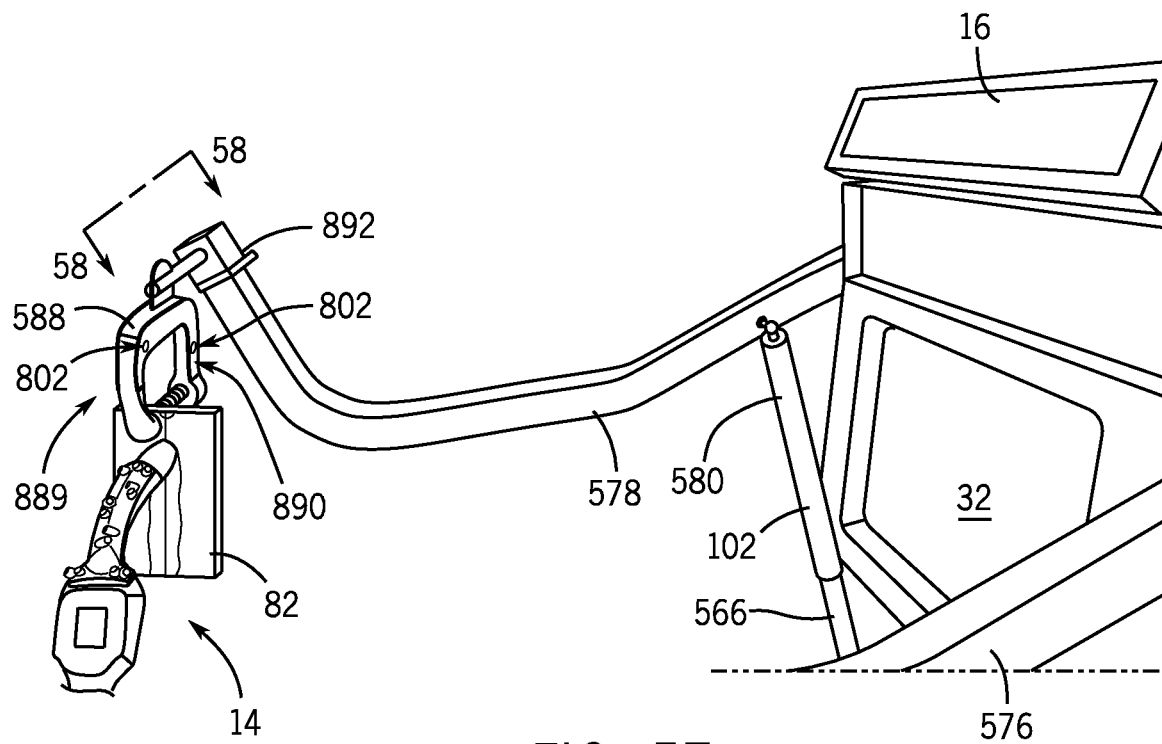
FIG. 57 is a perspective view of an embodiment of the arms and clamp assembly of the welding stand, in accordance with aspects of the present disclosure.

FIG. 57 is a perspective view of an embodiment of the welding stand 12, the arms 576, 578, and the clamp assembly 588. As discussed above, the first and second arms 576, 578 are rotatable about the support structure 566 to enable the first and second arms 576, 578 to be positioned at a selected height for vertical and/or overhead welding. As illustrated, the second arm 578 includes a clamp assembly 588 for coupling the workpiece 82 to the second arm 578. The second arm 578 and the clamp assembly 588 may be positioned at various heights relative the training stand 12. Additionally, or in the alternative, the clamp assembly 588 may be coupled to each arm 576, 578, and the clamp assembly 588 may be oriented in various directions relative to the sensing device 16. As may be appreciated, the clamp assembly 588 may include multiple visual markers 802 markers (e.g., reflective and/or light emitting) to facilitate tracking by the sensing device 16. For example, in certain embodiments, the clamp assembly 588 may include three markers on one surface (e.g., in one plane) of a clamp body 889, and a fourth marker on another surface (e.g., in a different plane) to facilitate tracking by the sensing device 16. A clamp face 890 of the clamp body 889 may be substantially parallel to the sensing device 16, or oriented at an offset angle from the sensing device 16. A mount 892 couples the clamp assembly 588 to the second arm 578.

Figure 58:
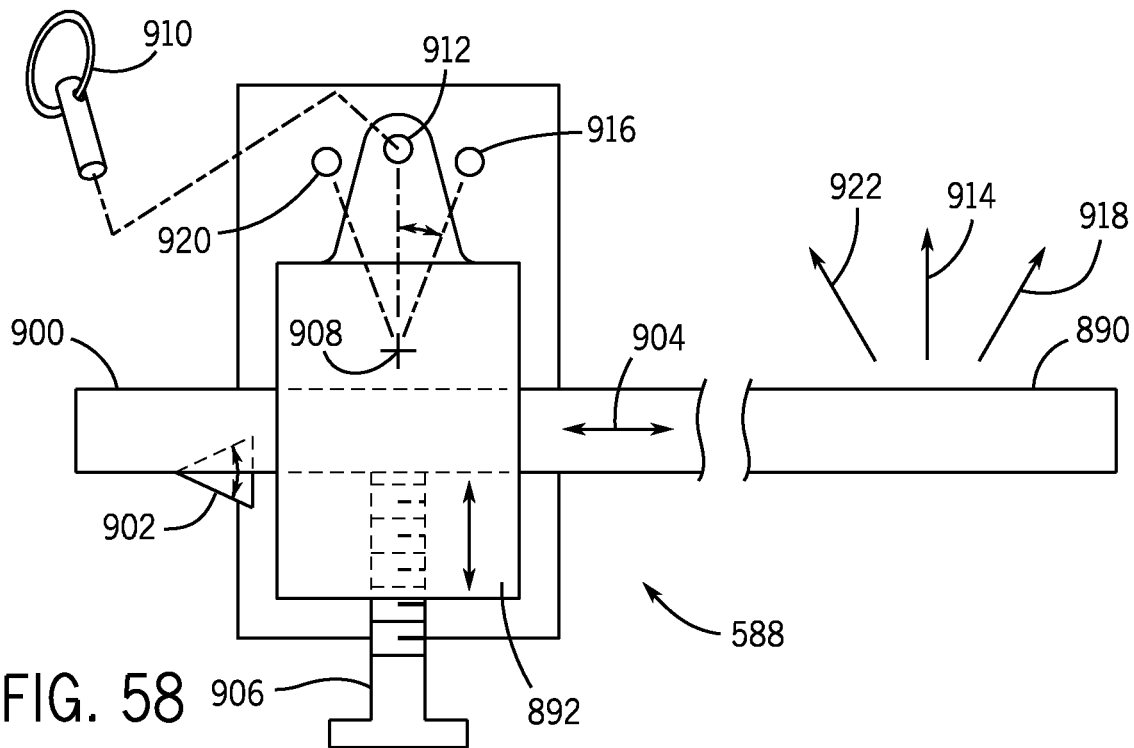
FIG. 58 is a top view of an embodiment of a mount of the clamp assembly of FIG. 57, taken along line 58-58, in accordance with aspects of the present disclosure.

FIG. 58 is a top view of an embodiment of the mount 892 of the clamp assembly 588 of FIG. 57, taken along line 58-58. A clamp axle 900 couples the mount 892 to the clamp body 889. In some embodiments, a retaining feature 902 of the clamp axle 900 may limit the movement of the clamp axle 900 along a clamp axis 904 in at least one direction. Furthermore, a clamp fastener 906 may interface with the retaining feature 902 and the mount 892 to retain the clamp axle 900 in a desired position along the clamp axis 904. The mount 892 may rotate about an axis 908, thereby adjusting the orientation of the clamp body 889 and the clamp face 890 relative to the sensing device 16. In some embodiments, a fastener 910 (e.g., pin) may couple the mount 892 to the second arm 578 at a desired orientation. The fastener 910 may be fixedly coupled to the mount 892, thereby preventing removal of the fastener 910 from the welding system 10. In some embodiments, the retaining feature 902 and/or the fastener 910 may be biased (e.g., spring loaded) with respect to the clamp assembly 588, thereby enabling automatic engagement with the clamp assembly 588 in one or more predetermined positions. For example, inserting the fastener 910 into a first recess 912 orients the clamp face 890 in a first direction 914 substantially parallel to sensing device 16, inserting the fastener 910 into a second recess 916 orients the clamp face 890 in a second direction 918, and inserting the fastener 910 into a third recess 920 orients the clamp face 890 in a third direction 922. The second and third directions 918 and 922 may be oriented within approximately 10, 20, 30, 40, or 50 degrees of direction 914 (e.g., towards the sensing device 16). The second and third directions 918 and 922 of FIG. 58 are approximately 30° offset from the first direction 914. When the clamp assembly 588 is mounted on the second arm 578 and the clamp face is oriented in the second direction 918, the clamp assembly 588 may be configured for welding in positions in which a portion of the workpiece 82 may obscure part of the joint from view of the sensing device 16. For example, welds performed in the 3F position (e.g., vertical fillet welds of T and lap joints) may be readily observed by the sensing device 16 when the workpiece 82 is coupled to the clamp assembly 588 on the second arm 578 such that the clamp face 890 is oriented in the second direction 918.

Figure 59:
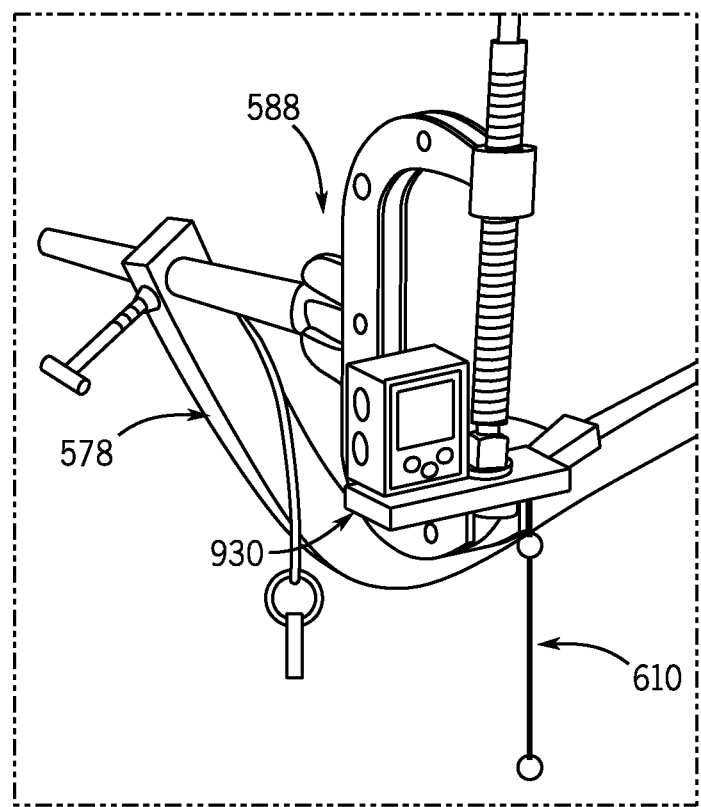
FIG. 59 is perspective view of an embodiment of a calibration block coupled to the clamp assembly of FIG. 57, in accordance with aspects of the present disclosure.

The position and the orientation of the arms and respective clamp assemblies are calibrated to enable the sensing device 16 to track the movement of the welding torch 14 relative to a joint of the workpiece 82 coupled to the clamp assembly 588. As illustrated in FIG. 59, a calibration block 930 may be coupled to the clamp assembly 588 to facilitate the calibration of the clamp assembly 588. In some embodiments, the calibration tool 610 of FIGS. 44 and 45 is coupled to the calibration block 930 such that the calibration tool 610 extends from the calibration block 930 at a predefined angle (e.g., perpendicular). The calibration block 930 and the calibration tool 610 may enable the sensing device 16 to calibrate the normal vector of the clamp assembly 588, to calibrate the normal vector of workpieces 82 secured to the clamp assembly 588, and/or to calibrate the true vertical (i.e., zenith) vector relative to the floor. The sensing device 16, via the computer 18, may determine a rigid body model and/or a centroid of clamp markers for the clamp assembly 588 when mounted to each arm 576, 578, during which different sides of the clamp assembly 588 are in view of the sensing device 16 where each side of the clamp assembly 588 has a unique configuration of markers. The sensing device 16 may be coupled to the arms 576, 578 so that as each arm is raised and lowered, a y-value of a centroid of the clamp markers of the respective side changes. As discussed above, movement of each arm 576, 578 may adjust the orientation of the sensing device 16. Accordingly the sensing device 16 may determine the y-value of the centroid of clamp markers for the clamp assembly 588 at multiple heights of the respective arms 576, 578. The computer 18 may determine the zenith vector for each of the centroids at the respective heights, thereby enabling the computer 18 to determine (e.g., interpolate) the zenith vector for any height using the y-value of the centroid of clamp markers when the clamp assembly 588 is coupled to each arm 576, 578. A level may be utilized with the clamp calibration block 930 during calibration at each height to ensure the orientation of calibration tool 610 accurately represents the zenith vector. The y-value of the centroid of clamp markers can also be used to determine the height of the clamp and to provide the operator with feedback on correct height positioning for welding session. The height of the clamp assembly 588 during a welding session may be stored with the welding data 327 for each welding session. In some embodiments, the welding system 10 may determine the orientation of the clamp assembly 588 relative to the sensing device 16, thereby enabling the welding system 10 to notify the operator if the workpiece 82 is in an improper orientation for the welding session. For example, the welding system 10 may notify the operator when the clamp assembly 588 and workpiece 82 are oriented such that the visual markers 802 of the welding torch 14 would be at least partially obscured from view of the sensing device 16 during the welding session, thereby enabling the operator to adjust the clamp assembly 588 so that all of the visual markers 802 may be observed.

Figure 60:
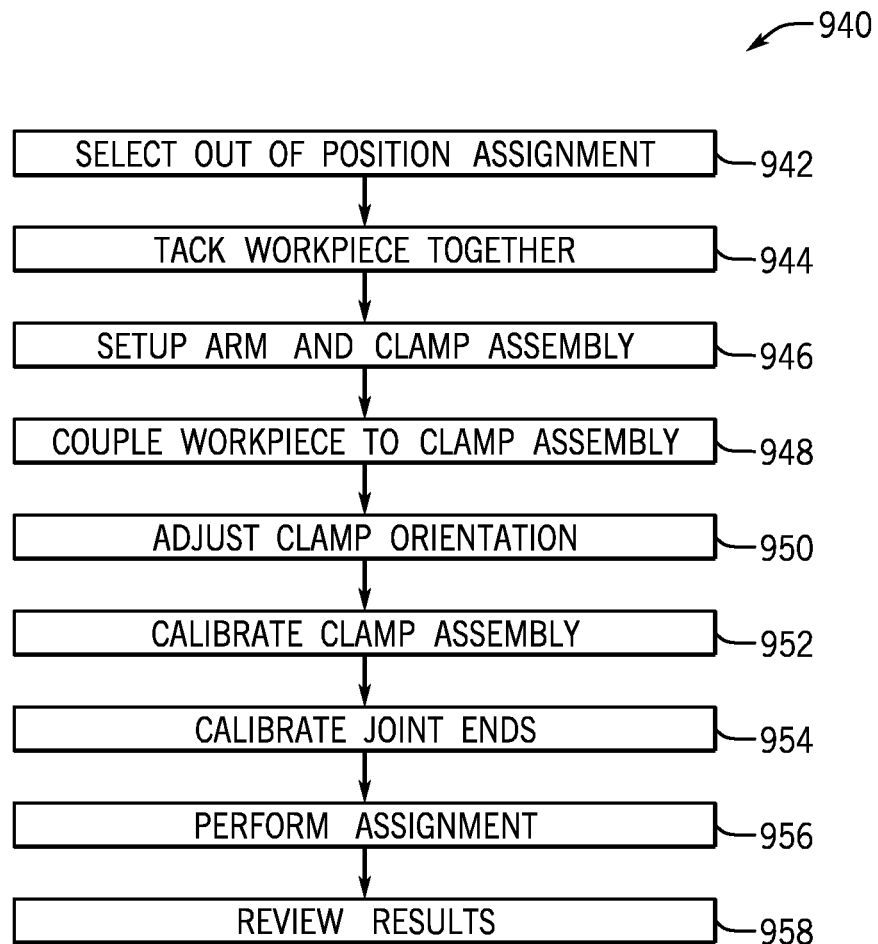
FIG. 60 is an embodiment of a method for the set up of the arms of the training stand for an out of position welding assignment, in accordance with aspects of the present disclosure.

FIG. 60 is a flowchart 940 that illustrates the set up and execution of assignment welding session utilizing one of the arms for a vertical or overhead (e.g., out of position) session. The operator selects (block 942) an out of position session (e.g., 2G, 3G, 3F, 4G, 4F) and tacks (block 944) the workpiece together. The operator then sets up (block 946) the desired arm to the height corresponding to the session and adjusts the clamp assembly for calibration with the sensing device. Upon setup of the arm and clamp assembly, the operator couples (block 948) the workpiece to the clamp assembly. Then the operator may adjust (block 950) the clamp orientation, such as if the workpiece at least partially obscures the joint from the sensing device, if markers of the workpiece or clamp assembly are obscured from the sensing device, or if the clamp assembly is not substantially perpendicular to the ground, or any combination thereof. After adjusting the clamp orientation, the operator, an instructor, or an administrator may calibrate (block 952) the clamp assembly. In some embodiments, the calibration may be performed once for each occasion that the arm is moved or for each occasion that the clamp assembly is attached to the arm, such that the clamp assembly may not calibrated prior to each session. The calibration of the clamp assembly may validate that the clamp assembly is detected in the configuration and/or orientation specified for the session. The operator calibrates (block 954) the joint ends, thereby establishing the 2 points in a line representing the joint. In some embodiments, such as for welding sessions in the 3F position, the operator calibrates (block 954) the joint ends utilizing the calibration tool 610 described above with FIGS. 44 and 45, where an axis of the calibration tool is held within approximately 5° of parallel to the sensing device. As may be appreciated, welding sessions in other positions may be calibrated with the calibration tool having other orientations relative to the sensing device. Additionally, or in the alternative, the computer may compensate for orientations of the calibration tool during calibrations where the markers of the calibration tool are observed at a skewed angle. For example, the computer may determine the angle of the calibration tool relative to the clamp assembly, then utilize the determined angle to adjust calibration values of the joint ends. After the calibration of the joint ends, then the operator performs (block 956) the welding session and reviews (block 958) the results. In some embodiments, the display of the training stand and/or the display of the welding torch may provide instructions to the operator to guide the setup for the welding session.

The sensing device 16 may track the position and orientation of the clamp assembly 588, the workpiece 82, and the welding torch 14 prior to performing assignment welding session, during the welding session, and after performing the welding session. As discussed above, the sensing device 16 may include a camera that detects visual markers 802, such as visual markers of the clamp assembly 588, the workpiece 82, and the welding torch 14. In some embodiments, the computer 18 may utilize data corresponding to the visual markers 802 of fixed surfaces (e.g., the clamp assembly 588, the workpiece 82) for reference with respect to other tracked objects in the welding environment whenever the visual markers 802 of the fixed surfaces are detectable. That is, the visual markers 802 of the fixed surfaces facilitate real-time tracking of other objects (e.g., welding torch 14, calibration tool 610) within the welding environment. The visual markers 802 detected by the camera of the sensing device 16 may include passive markers (e.g., stickers, reflectors, patterns) and/or active markers (e.g., lights, LEDs). The passive markers may be best observed with a first exposure setting of the camera of the sensing device 16, and the active markers may be best observed with a second exposure setting of the camera, which may be different than the first exposure setting. In some embodiments, the visual markers 802 of the clamp assembly 588 and the workpiece 82 may be passive markers, and the visual markers 802 of the welding torch 14 may be active markers (e.g., LEDs 64). Moreover, the passive markers may be illuminated by lights (e.g., LEDs 64) of the sensing device 16, where light (e.g., infrared light) from the lights reflects off the passive markers and is observed by cameras of the sensing device 16. Accordingly, the exposure setting of the camera may be adjusted based at least in part on the type of visual marker to be observed. As may be appreciated, the second exposure setting for sampling the active markers that emit light may be less than the first exposure setting for sampling the passive markers that reflect light.

The computer 18 may alternately track the visual markers 802 of the welding torch 14 and the fixed surfaces of the welding environment prior to performing and during performance of a welding session (e.g., simulated welding assignment, live welding assignment). Accordingly, the computer 18 may track in real-time the position and the orientation of the welding torch 14, the clamp assembly 588, and the workpiece 82 relative to each other and to the training stand 12. Prior to live welding, the computer 18 may primarily track the visual markers 802 of welding torch 14 when detecting the position and orientation of objects in the welding environment about the training stand 12, and the computer 18 may secondarily track the visual markers 802 of the fixed surfaces (e.g., main welding surface 88, clamp assembly 588, clamped workpiece 82). The active markers of the welding torch 14 may be turned on substantially continuously before, during, and after a simulated or live welding session (e.g., welding assignment). The computer 18 may control the exposure setting of the camera of the sensing device 16 to control the respective sampling rates of the fixed surfaces and the welding torch 14. For example, the visual markers 802 of the welding torch 14 may be sampled 1.5, 2, 3, 4, 5, or more times than the visual markers 802 of the fixed surfaces are sampled. That is, the computer 18 cycles the exposure setting of the camera between the second exposure setting (e.g., low exposure value to track the active markers of the welding torch 14) and the first exposure setting (e.g., high exposure value to track the passive markers of the fixed surfaces).

Prior to initiating a simulated welding session (e.g., welding assignment), the computer 18 may control the lights of the sensing device 16 (e.g., LEDs 64) to be turned on, thereby enabling the computer 18 to track the passive markers of the fixed surface and the active markers of the welding torch 14 prior to initiating the simulated welding session, during the simulated welding session, and after the simulated welding session. As described above, the computer 18 may cycle the exposure setting of the camera to sample the passive markers with the first exposure setting and to sample the active markers with the second exposure setting. During live welding (e.g., while the trigger of the welding torch 14 is actuated), the computer 18 may control the lights of the sensing device 16 to pulse at an increased brightness level, thereby cyclically increasing the reflected light from the passive markers. Pulsing the lights may enable the camera of the sensing device to readily track the passive markers with a reduced exposure setting during live welding with the bright arc and spatter. The computer 18 may control the exposure setting of the camera to be synchronized with the pulsing of the lights of the sensing device, such that the lights pulse more brightly when the exposure setting is at the first (e.g., high) exposure setting, and the lights dim when the exposure setting is at the second (e.g., low) exposure setting. Additionally, or in the alternative, the computer 18 may control the lights of the sensing device 16 to turn off during calibration of the clamp assembly 588, thereby distinguishing the active markers of the welding torch 14 from the passive markers of the clamp assembly 588. In some embodiments, a pulsed brightness level of the lights of the sensing device 16 may be greater than when the lights turned on substantially continuously. The sensing device 16 may more readily detect the passive markers at the greater brightness level of the lights than at the lower brightness level. However, pulsing the lights of the sensing device 16 during a simulated weld may unintentionally activate an auto-darkening circuit of a welding helmet. Accordingly, the lights of the sensing device 16 may be pulsed during live welding when the welding helmet is darkened due to the arc, yet the lights of the sensing device are turned continuously on during simulated welding when the welding helmet is not darkened.

In some embodiments, the welding system 10 may track a multi-pass (e.g., multi-run) session, thereby recording welding data 327 for each pass (e.g., run) of the multi-pass session. As discussed above with FIG. 40, the control circuitry 52 of the welding system 10 may record the welding data 327 for each run of the multi-run session as a single welding operation for determining a quality of the multi-run session or for otherwise reviewing the multi-run session. In some embodiments, the control circuitry 52 of the welding system 10 may record welding data 327 for a multi-run session as a group of runs that correspond to a serial number or other identifier for the multi-run session. That is, the welding data 327 for a multi-run session may be reviewed and evaluated as a group, or each run of the multi-run session may be reviewed and evaluated separately. Multi-run sessions may include, but are not limited to a live process, a simulated process, a virtual reality process, or any combination thereof.

Figure 61:
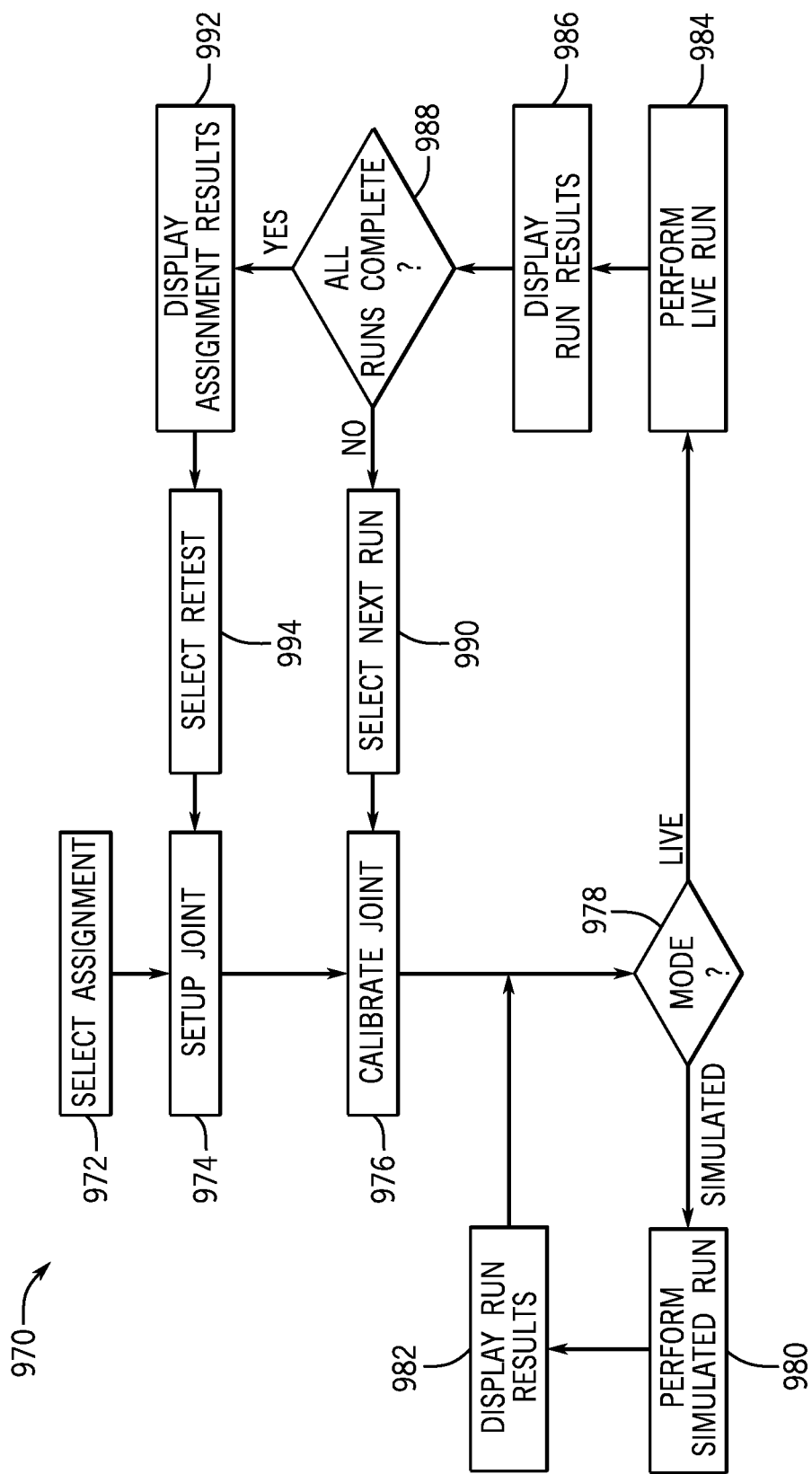
FIG. 61 is an embodiment of a method for the selection and execution of a multi-pass welding assignment with the welding system, in accordance with aspects of the present disclosure.

FIG. 61 is a flowchart 970 that illustrates the selection and execution of a multi-pass (e.g., multi-run) welding session (e.g., welding assignment). The operator selects (block 972) a multi-run session and sets up (block 974) the workpiece 82 together on the training stand 12. Set up of the workpiece 82 may include clamping the workpiece 82 to the training stand 12. The operator calibrates (block 976) the joint, such as by utilizing the joint calibration tool 610 to calibrate the position of a first end of the joint and the second end of the joint. As may be appreciated, the joint calibration tool 610 may directly interface with the workpiece 82 for the calibration (block 976) prior to the first run of the multi-run session. The operator selects (node 978) whether to perform the next (i.e., first) run of the multi-run session in a simulated welding mode or a live welding mode. In some embodiments, the selected welding session (e.g., welding assignment) may prohibit or limit the quantity of simulated welds that may be performed prior to live welds. In some embodiments, the selected session may prohibit the live welding mode until completion (e.g., satisfactory completion) of a simulated weld. When the simulated weld mode is selected, the operator performs (block 980) the simulated run. The control circuitry 52 may display (block 982) the results of the simulated run via the display 32 of the training stand 12 and/or the display 62 of the welding torch 14. For example, the control circuitry 52 may display the weld data 327 from the simulated run and the target specifications for the simulated run. Additionally, or in the alternative, the control circuitry may display the weld score for the simulated run. After completing the simulated run, the operator again selects (nodes 978) whether to perform the next run in the simulated welding mode or in the live welding mode.

When the live welding mode is selected, the operator performs (block 984) the live weld run on the calibrated joint. The control circuitry 52 may display (block 986) the results of the live run via the display 32 of the training stand 12 and/or the display 62 of the welding torch 14. For example, the control circuitry 52 may display the weld data 327 from the live run and the target specifications for the live run. Additionally, or in the alternative, the control circuitry 52 may display the weld score for the live run. The displayed results for the live run may be displayed with results of any previous simulated runs for the same joint.

Each run (e.g., simulated or live) of the multi-run welding session (e.g., welding assignment) may be evaluated separately based at least in part on target specifications (e.g., minimum, goal, maximum) for torch position parameters (e.g., work angle, travel angle, CTWD, travel speed, aim) and/or electrical parameters (e.g., weld voltage, weld current, wire feed speed). For example, a rootpass run may have different specification parameters than subsequent runs. After a run of the multi-run session is completed, the control circuitry 52 may determine whether the completed run of the session satisfies the target parameter values for the respective run. For example, the welding data 327 for a run of the multi-run session may be compared with the target parameter values to generate a score for each parameter and/or a total score for the respective run. The control circuitry 52 may determine whether the run passes the target specifications for the respective run.

The control circuitry 52 determines (node 988) whether all of the runs of the selected welding session (e.g., welding assignment) have been completed. If all of the runs of the selected multi-run session have not been completed, then the operator selects (block 990) the next run. In some embodiments, the operator may proceed to the next run of the multi-run session regardless of whether the previous run passes the target specifications. Additionally, or in the alternative, the operator may proceed to the next run of the multi-run session regardless of whether the weld data 327 for the previous run is complete. For example, if the sensing device 16 cannot track the position and the orientation of the welding torch 14 for at least a portion of a run of the multi-run session, the operator may continue performing each run of the multi-run session. The operator calibrates (block 976) the joint for each run of a multi-run session, such as by utilizing the joint calibration tool 610 to calibrate the position of a first end of the joint and the second end of the joint. As may be appreciated, joint calibration tool 610 may have directly interfaced with the workpiece 82 for the initial calibration of the joint prior to the first run. Subsequent calibrations may directly interface the joint calibration tool 610 with the previously formed weld bead of one or more previous runs. Accordingly, the calibrated ends of the joint for each run may have a different position relative to the sensing device 16 of the welding system 10. When the subsequent calibration for the next run is completed, the operator again selects (nodes 978) whether to perform the next run in the simulated welding mode or in the live welding mode.

If all of the runs of the selected multi-run session have been completed, then the control circuitry 52 may display (block 992) the results of each of the live runs via the display 32 of the training stand 12 and/or the display of the welding torch 14. For example, the control circuitry 52 may display the weld data 327 from each of the live runs and the target specifications for each of the live runs. Additionally, or in the alternative, the control circuitry 52 may determine whether the group of runs passes the target specifications for the multi-run session based on one or more evaluations of the runs. For example, the control circuitry 52 may evaluate the group of runs based on a geometric mean of the scores for each run, an arithmetic mean of the scores for each run, whether each run was completed with a passing score, or any combination thereof. In some embodiments, a threshold quantity (e.g., 1, 2, or 3) of runs with untracked welding torch position and orientation may not affect the evaluation of the multi-run session. That is, the one or more runs with untracked welding torch position and orientation may not be counted in the geometric and/or arithmetic mean. Upon display of the session results (block 992), the operator may select (block 994) to retest with selected session. The operator removes the previously tested joint, and sets up (block 974) a new joint for the retest. The control circuitry 52 may assign a different serial number to the new joint for the retest than the serial number of the previously tested joint, thereby enabling the operator and an instructor to review and evaluate the weld data 327 from each joint.

As described herein, various parameters may be tracked (e.g., detected, displayed, and stored) during operation of the welding system 10 (e.g., in real-time while the welding system 10 is being used) including, but not limited to, torch position parameters (e.g., work angle, travel angle, CTWD, travel speed, aim) and arc parameters (e.g., weld voltage, weld current, wire feed speed). The arc parameters, for example, may be detected in the welding torch 14 (e.g., using the voltage sensor 425, the current sensor 427, or other sensors, as illustrated in FIG. 25), converted using analog-to-digital conversion (ADC) circuitry, and communicated to the computer 18 via a communication interface 68 (e.g., RS-232 communication channel), as discussed herein with respect to FIG. 1. Alternatively to, or in addition to, being detected in the welding torch 14 (e.g., in the handle of the welding torch 14 illustrated in FIG. 5), the arc parameters may be detected in the weld cable 80, the welding power supply 28, the wire feeder 30, or some combination thereof, each of which are illustrated in FIG. 2.

Figure 62:
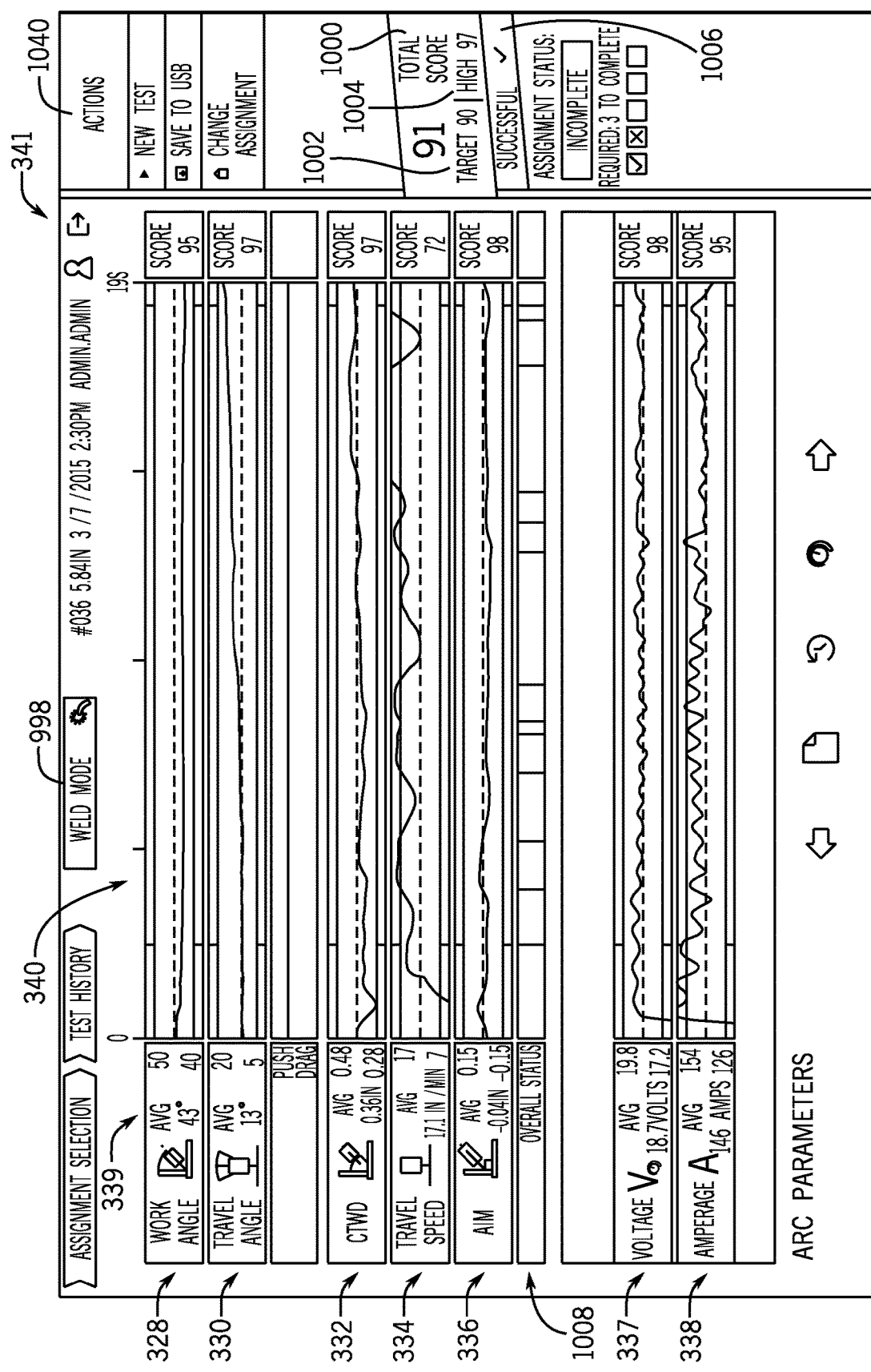
FIG. 62 is an embodiment of a screen illustrating data, including arc parameters, corresponding to a weld in accordance with aspects of the present disclosure.

The welding system 10 may detect and display (e.g., numerically, graphically, and so forth) the arc parameters via a screen viewable on the display 32 of the welding system 10 similar to the screens illustrated in FIGS. 20 and 21, for example. An exemplary screen 996 having a weld mode indicator 998 that indicates that the welding system 10 is in a live-arc weld mode may be displayed on the display 32 is illustrated in FIG. 62. As illustrated in FIG. 62, the arc parameters may be displayed on the screen 996. For example, in the illustrated screen 996, a voltage graph 340 may display a time series of voltage 337 of the arc produced by the welding torch 14, and an amperage graph 340 may display a time series of the current 338 produced by the welding torch 14. In certain embodiments, filters may be applied to at least some of the arc parameters and the torch position parameters to smooth out noise in the time series graphs 340 of the values detected by the welding torch 14.

It will be appreciated that the arc parameters may be time synchronized by the welding software 244 in real-time with the torch position parameters that is captured through the motion tracking system (e.g., the sensing device 16). In other words, the arc parameters and the torch position parameters may all be graphed on their respective graphs 340 such that data points for each of the time series are vertically aligned with data points from each of the other time series that are captured at approximately the same time (e.g., within 100 milliseconds, within 10 milliseconds, or even closer in time, in certain embodiments). This enables the user to correlate the arc parameters with the torch position parameters. Although not illustrated in FIG. 62, in certain embodiments, wire feed speed may also be detected in real-time in the same manner as voltage and current.

As illustrated in FIG. 62, in certain embodiments, each arc parameter (as well as each torch position parameter) may be individually scored in relation to a pre-defined upper limit, lower limit, and/or target value, and the scores 341 may be depicted on the screen 996. In addition, in certain embodiments, a total score 1000 may be determined by the welding software 244 and depicted on the screen 996. In addition, in certain embodiments, the total score 1000, indications of target total scores 1002 and high total scores 1004 (for example, of an entire class) may be determined by the welding software 244 and depicted on the screen 996. In addition, in certain embodiments, an indication 1006 of whether the test was successful or not successful may also be determined by the welding software 244 and depicted on the screen 996. In certain embodiments, the total score 1000 may be based on the individual scores 341 for the torch position parameters, but not based on the individual scores 341 for the arc parameters.

In addition, as illustrated in FIG. 62, in certain embodiments, an overall status bar 1008 may be depicted on the screen 996. The overall status bar 1008 may include indications of whether all of the torch position parameters are within their respective upper and lower limits or not. For example, if one of the torch position parameters are not within their respective upper and lower limits, the overall status bar 1008 may indicate, at the same vertical position on the screen 996 as the corresponding torch position parameter values, a red status. Conversely, if all of the torch position parameters are within their respective upper and lower limits, the overall status bar 1008 may indicate, at the same vertical position on the screen 996 as the corresponding torch position parameter values, a green status. It will be appreciated that other status colors may be used in other embodiments.

Figure 63:
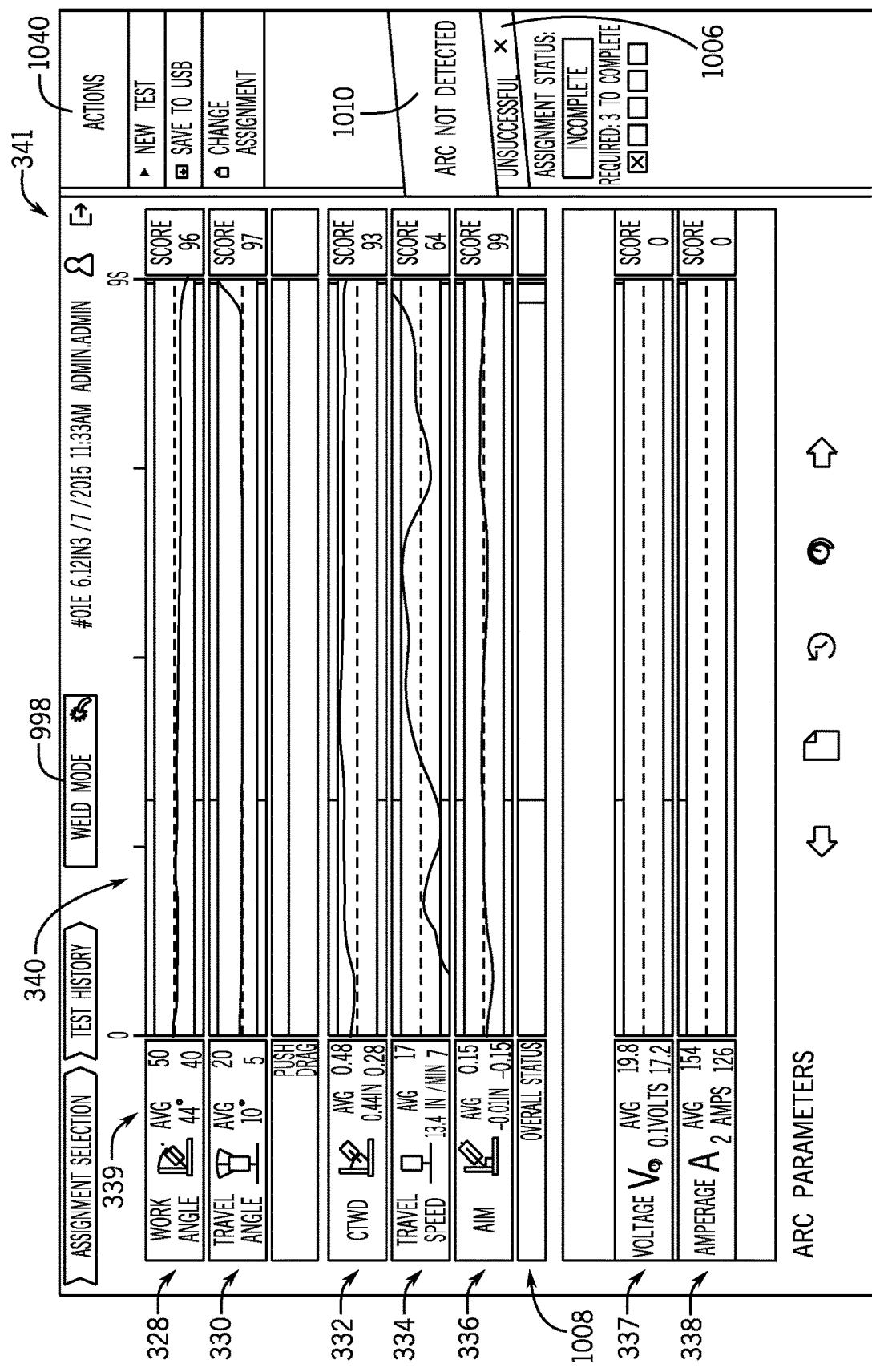
FIG. 63 is an embodiment of a screen illustrating data corresponding to a weld test for which an arc has not been detected in accordance with aspects of the present disclosure.

As illustrated, in certain embodiments, the value 339 for each of the parameters (e.g., the torch position parameters and the arc parameters) may be displayed as an average value over the course of a test period. For example, as illustrated in FIG. 62, the average voltage and amperage over the test period depicted are 18.7 volts and 146 amps, respectively. FIG. 63 is another illustration of the screen 996 depicted in FIG. 62. In this instance, the average voltage and amperage is depicted as being 0.1 volts and 2 amps, respectively, which are on the order of noise, indicating that an actual welding arc is not being detected. In such a situation, the amperage and voltage can be used by the welding software 244 to determine whether or not welding took place during a given "weld mode" test period. If the value of either voltage or amperage is below a certain predetermined threshold (e.g., the average voltage is less than 10 volts) or between a certain predetermined minimum and maximum threshold (e.g., the average voltage is between −8 volts and +10 volts), the welding software 244 may determine that a weld actually did not take place during the time period. In such a scenario, the welding software 244 may automatically mark a test as failed (or "unsuccessful") and/or the test may be flagged by the welding software 244 as having no welding detected. For example, as illustrated, in certain embodiments, if the average voltage and/or the average amperage for a given test period do not meet certain predetermined threshold(s) or fall within certain predetermined range(s), the indication 1006 of whether the test was successful or not successful may depict that the test was "Unsuccessful" (which may also be displayed for other reasons, such as the total score does not meet a specific requirement, for example). In addition, as also illustrated, in certain embodiments, when the average voltage and/or the average amperage for a given test period do not meet certain predetermined threshold(s) or fall within certain predetermined range(s), instead of depicting the total score 1000 on the screen 996, an "Arc Not Detected" message 1010 may be depicted instead.

Figure 64:
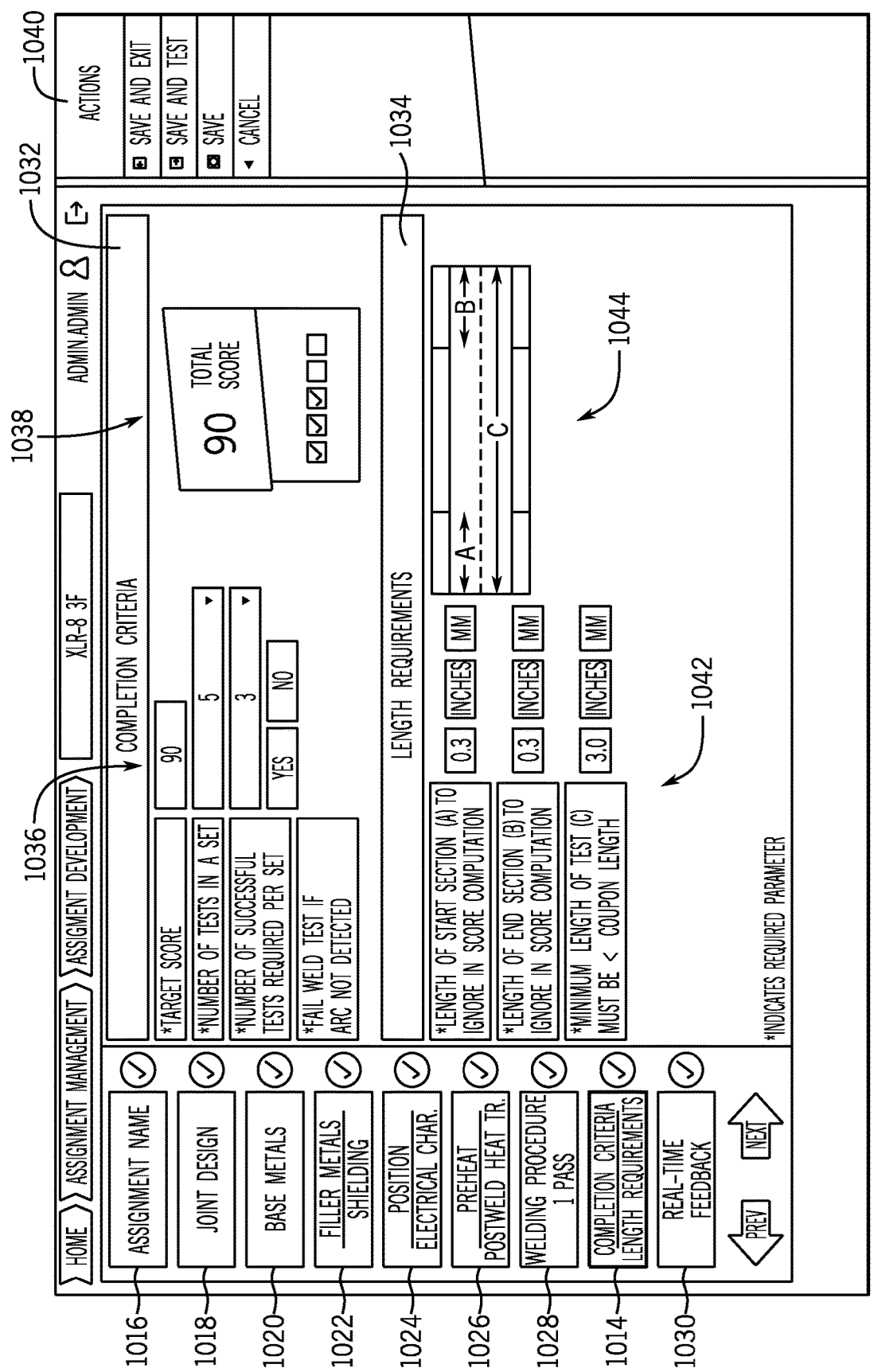
FIG. 64 is an embodiment of a screen illustrating assignment development routines in accordance with aspects of the present disclosure.

FIG. 64 illustrates an exemplary screen 1012 that may be displayed as part of the assignment development routines of the welding software 244. In particular, FIG. 64 illustrates a screen 1012 that enables input of completion criteria for a series of weld tests and length requirements associated with the testing. As illustrated, the screen 1012 is displayed when the Completion Criteria/Length Requirements tab 1014 of the assignment development routines is selected (and, therefore, highlighted on screen 1012). As illustrated, other tabs associated with configuration settings of the assignment development routines of the welding software 244 may include, but are not limited to, an Assignment Name tab 1016 that causes a screen to be displayed where the assignment name and other general information relating to the assignment may be entered; a Joint Design tab 1018 that causes a screen to be displayed where properties of the joint to be welded upon (e.g., type of joint, length, etc.) may be entered; a Base Metals tab 1020 that causes a screen to be displayed where properties related to the base metals to be welded upon may be entered; a Filler Metals/Shielding tab 1022 that causes a screen to be displayed where properties relating to the filler metals (e.g., of the welding electrode) and shielding gas(es) may be entered; a Position/Electrical Char. tab 1024 that causes a screen to be displayed where properties (e.g., upper limits, lower limits, target values, etc.) of the torch position parameters and the arc parameters, respectively, may be entered; a Preheat/Postweld Heat Tr. tab 1026 that causes a screen to be displayed where properties relating to preheating and postweld heating, respectively, may be entered; a Welding Procedure/1 Pass tab 1028 that causes a screen to be displayed where properties relating to the welding procedure (e.g., process type, etc.) and the number of passes in the test (e.g., one pass or more than one pass); and a Real-Time Feedback tab 1030 that causes a screen to be displayed where properties relating to real-time feedback may be entered. It will be appreciated that, in certain embodiments, all of the properties relating to an assignment may be entered on the described screens, may be automatically detected by the welding software 244 (e.g., based on specific equipment of the welding system 10, based on other properties that are set, and so forth), or some combination thereof.

As illustrated in FIG. 64, the screen 1012 relating to the Completion Criteria/Length Requirements tab 1014 includes a first section 1032 specifically dedicated to the completion criteria properties and a second section 1034 specifically dedicated to length requirements associated with the testing. In certain embodiments, in the completion criteria section 1032 of the screen 1012, a series of inputs 1036 enables a target score (e.g., 90 as illustrated), a number of weld tasks in a set of weld tasks (e.g., 5 as illustrated), a number of successful weld test required per weld set (e.g., 3 as illustrated), and whether a weld test will be failed if an arc is not detected (e.g., as shown in FIG. 63) to be entered. In addition, as illustrated, in certain embodiments, a depiction 1038 of what these selections of completion criteria will look like to the user (e.g., as illustrated in FIG. 62 in the Actions section 1040 of the screen 996). In addition, in certain embodiments, in the length requirements section 1034 of the screen 1012, a series of inputs 1042 enables a length of a start section (A) of a weld that will be ignored in the score compilations, an end section (B) of a weld that will be ignored in the score compilations, and a maximum length (C) of the test, which may be less than the coupon length (which may, for example, be entered via the screen relating to the Joint Design tab 1018) to be entered. In addition, in certain embodiments, respective illustrations 1044 of relative dimensions of the entered properties relating to the length requirements may also be depicted to aid the user in setting the length requirements.

Figure 65:
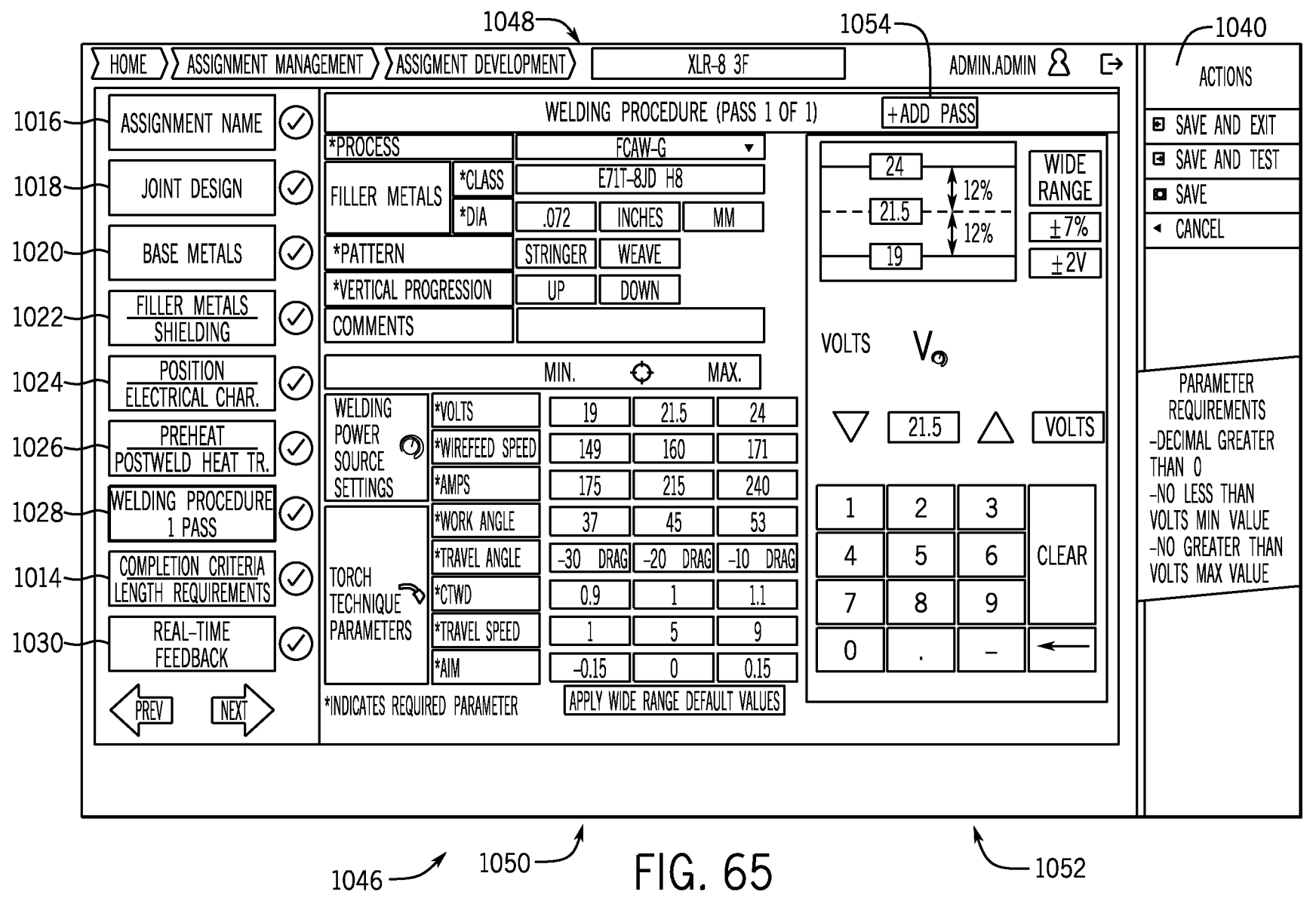

FIG. 65 illustrates an exemplary screen 1046 that may be displayed when the Welding Procedure/1 Pass tab 1028 is selected. As described above, this screen 1046 enables properties relating to the welding procedure and the number of passes in the test (e.g., one pass or more than one pass) to be entered. As illustrated, in certain embodiments, a first series of inputs 1048 enables a process type (e.g., FCAW-G as illustrated), a class and diameter of the filler metals (e.g., the welding electrode) (e.g., E71T-8JD H8 and 0.072 inches, respectively, as illustrated), a weld pattern (e.g., stringer vs. weave; stringer as illustrated), a vertical progression (e.g., up vs. down; up as illustrated), and any comments related to the welding procedure to be entered. In addition, as illustrated, in certain embodiments, a second series of inputs 1050 enables minimum, target, and maximum values for the arc parameters (e.g., volts, wirefeed speed, and amps), labeled as Welding Power Source Settings, and the torch position parameters (e.g., work angle, travel angle, CTWD, travel speed, and aim), labeled as Torch Technique Parameters, to be entered. Also as illustrated, in certain embodiments, a third series of inputs 1052 enable more detailed input relating to minimum, target, and maximum values (e.g., relating to how much deviation from target values are allowed for the upper and lower limits, and so forth) for a highlighted arc parameter or torch position parameter (e.g., volts as illustrated). In certain embodiments, when more than one pass is selected for a given assignment, the minimum, target, and maximum values for the arc parameters and/or the torch position parameters may be individually set for each pass within the assignment. In certain embodiments, entry of properties for multiple passes for a given assignment may be enabled via an Add Pass button 1054, as illustrated.

Figure 66:
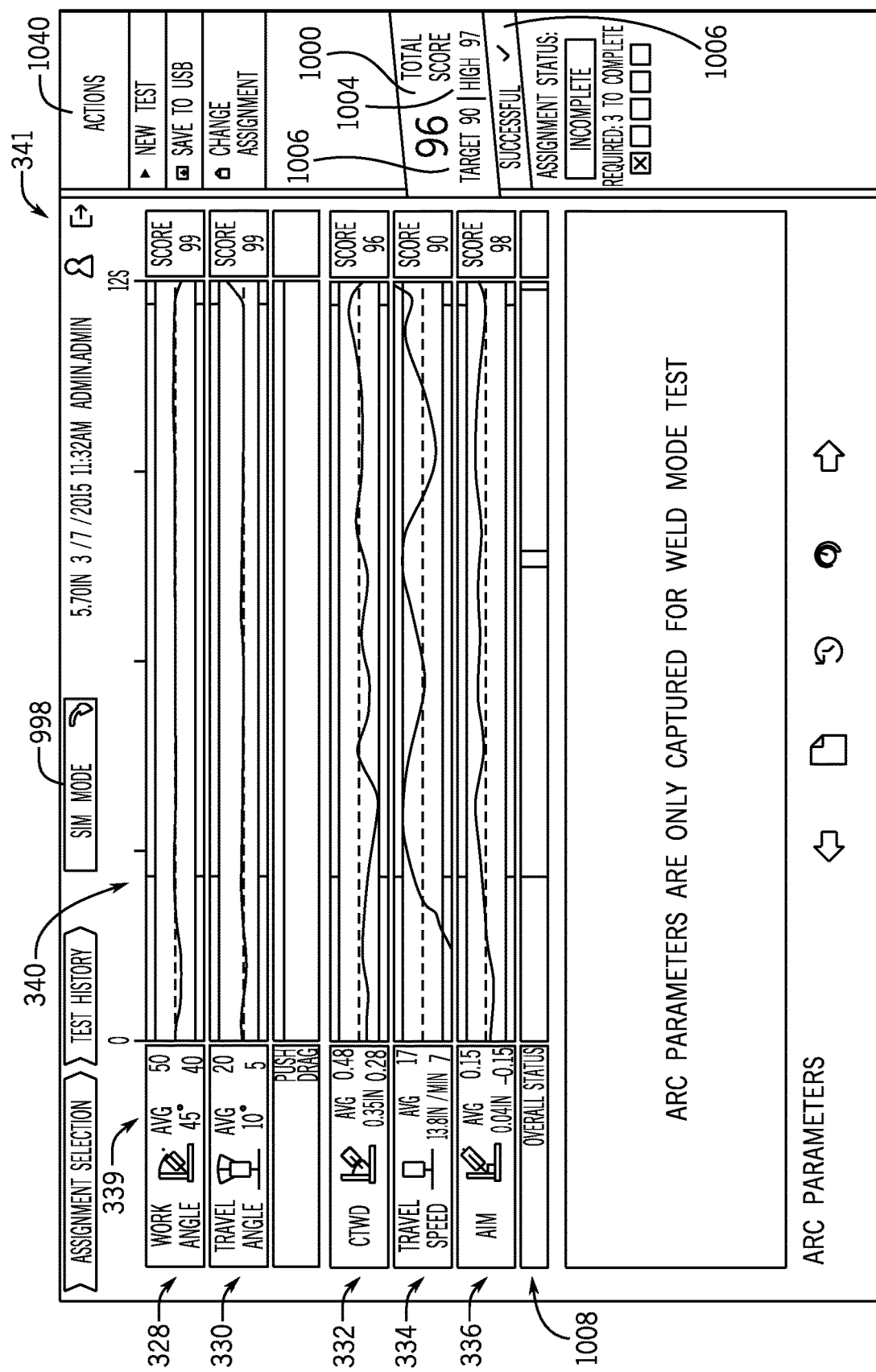
FIG. 66 is an embodiment of a screen illustrating data corresponding to a simulated weld in accordance with aspects of the present disclosure.

As discussed above with respect to FIGS. 62 and 63, the arc parameters may be displayed when the welding software 244 is in a live-arc weld mode. Conversely, FIG. 66 illustrates an exemplary screen 1056 that depicts the welding software 244 when in a simulated weld mode, as indicated by the weld mode indicator 998. As illustrated, when the welding software 244 is in a simulated weld mode, the arc parameters are not displayed since actual welding is disabled in this mode, and a message indicating as much may be displayed instead.

Figure 67:
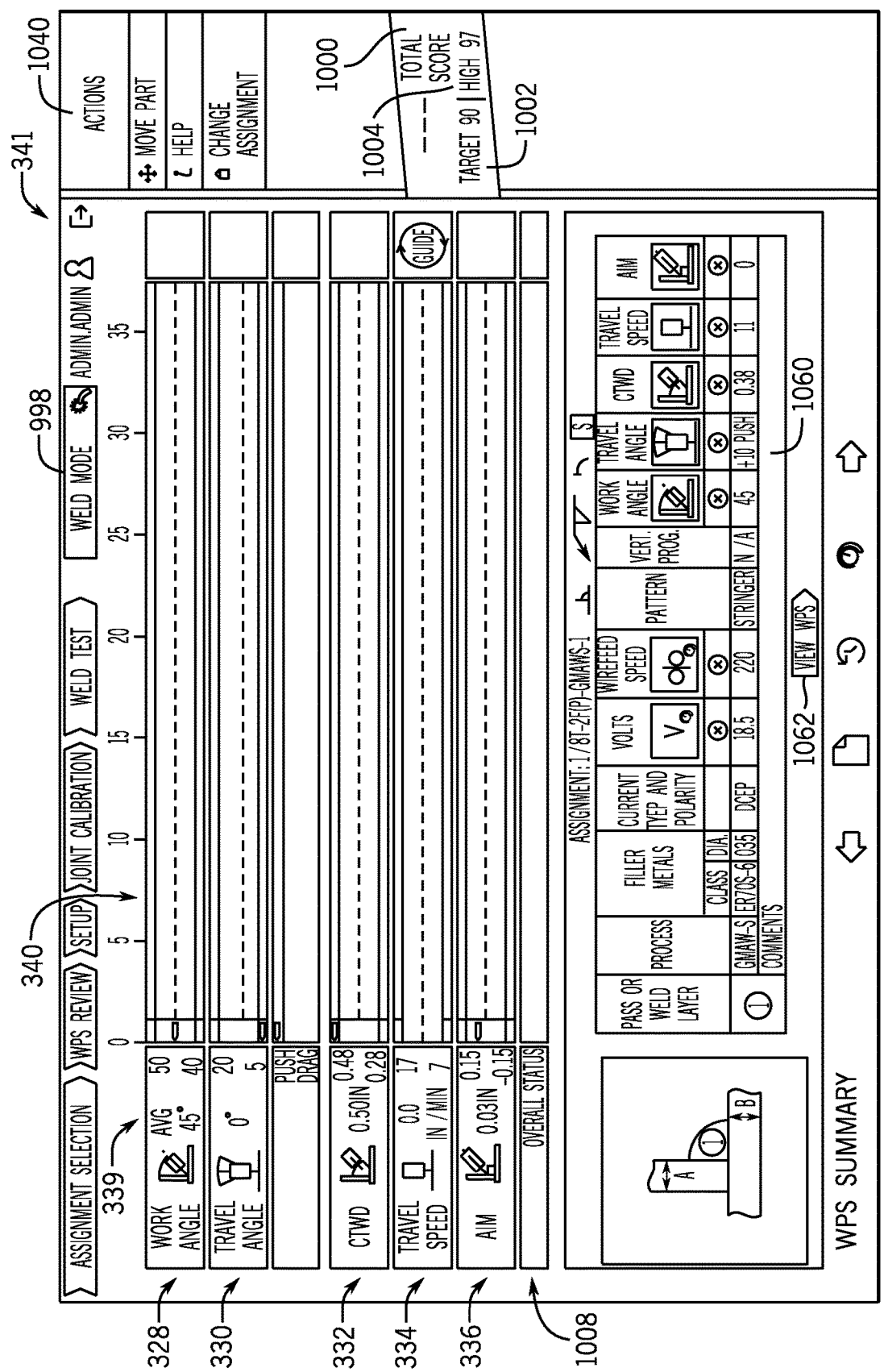
FIG. 67 is an embodiment of a screen illustrating data corresponding to a weld prior to initiation of the weld in accordance with aspects of the present disclosure.
Figure 68:
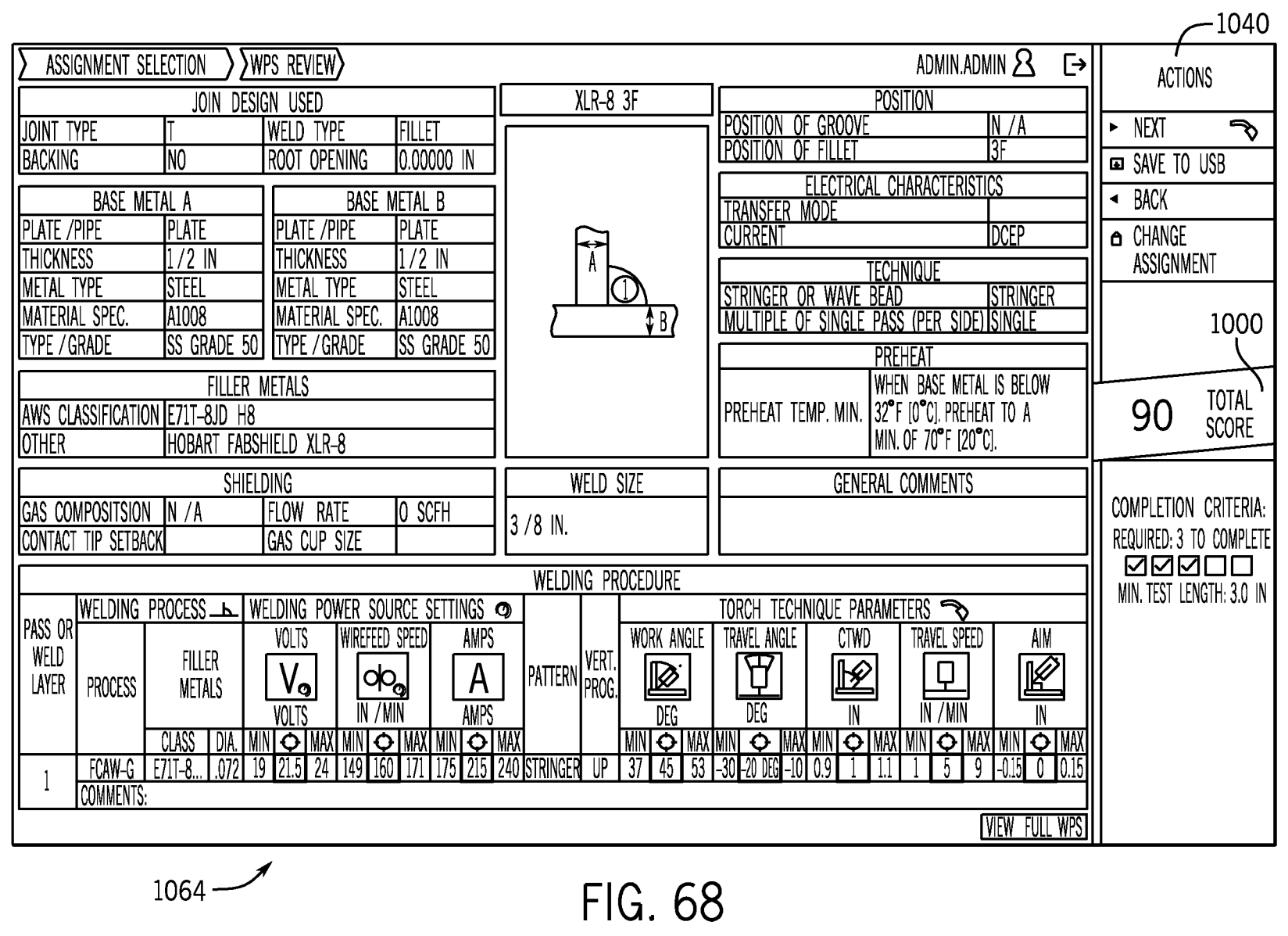

In certain embodiments, the arc parameters are not displayed by default below the torch position parameters, such as illustrated in FIGS. 62 and 63. Rather, FIG. 67 illustrates an exemplary screen 1058 that is depicted by default (i.e., before a weld test has been initiated). As illustrated, instead of the arc parameters, a welding procedure summary pane 1060 is illustrated to summarize for the user what the overall properties (e.g., target properties) for a given test weld are. In certain embodiments, from the welding procedure summary pane 1060, a user may select a View WPS button 1062, which will cause the screen 1064 illustrated in FIG. 68 to be displayed. As illustrated, FIG. 68 is a summary of all of the information relating to all of the parameters of a weld test session or a weld test assignment (e.g., which may be entered via selection of the various assignment development tabs 1014-1030 illustrated in FIGS. 64 and 65).

Figure 69:
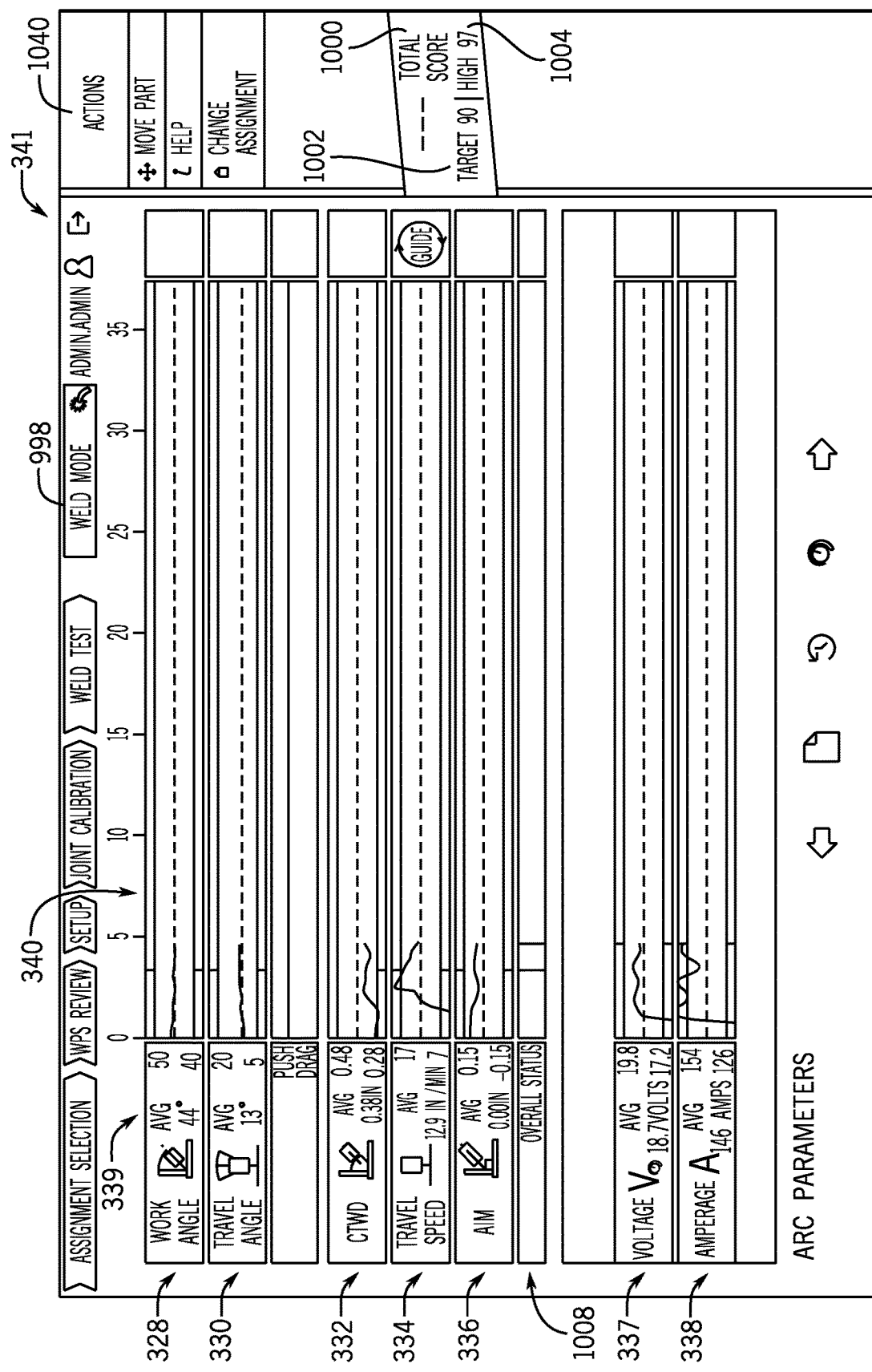
FIG. 69 is an embodiment of a screen illustrating data, including arc parameters, corresponding to a weld during a weld test in accordance with aspects of the present disclosure.

Returning now to FIG. 67, once the user has completed pre-test procedures and is prepared to begin a weld test, upon activation of the trigger 70 of the welding torch 14 to start a weld test, the welding procedure summary pane 1060 is replaced by the information relating to the arc parameters to display the real-time graphing of the arc parameters during performance of the weld test (see, e.g., FIG. 69), allowing the user to view all graphs relating to the torch position parameters and the arc parameters in real-time during the weld test. Indeed, in certain embodiments, upon activation of the trigger 70 of the welding torch 14 to start a weld test, whatever screen is currently being displayed may be replaced with, for example, the screen 996 illustrated in FIG. 69 such that all of the torch position parameters and arc parameters may be graphically displayed in real-time.

Figure 70:
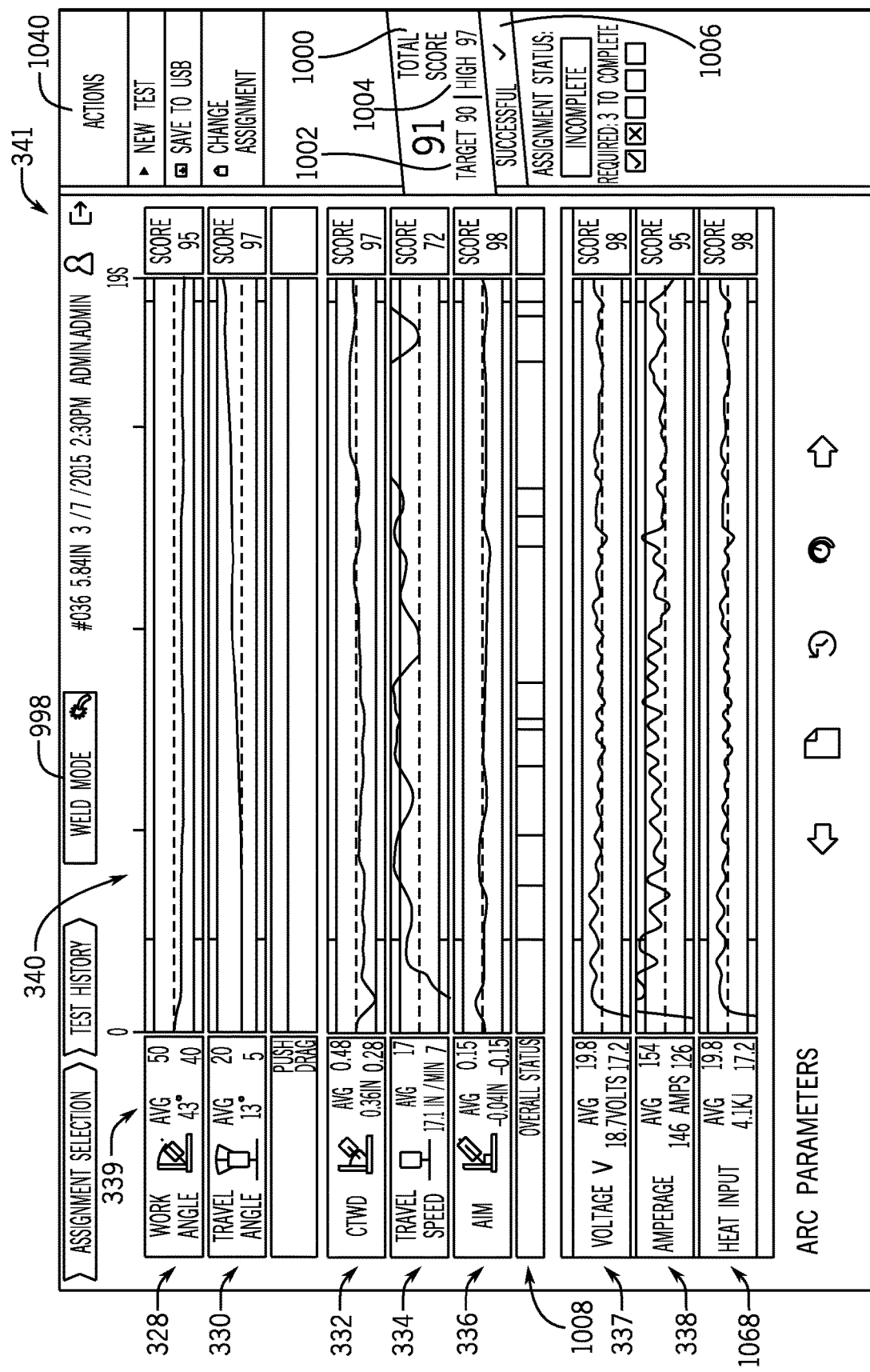
FIG. 70 is an embodiment of a screen illustrating data, including heat input, corresponding to a weld in accordance with aspects of the present disclosure.

FIG. 70 illustrates an alternative screen 1066 that may be displayed following the performance of a test weld. As illustrated, in certain embodiments, in addition to the arc parameters (e.g., voltage, amperage, wire feed speed), heat input 1068 may be displayed and, as with all of the other torch position parameters and the arc parameters, is time synchronized along their respective time series. In general, the detected voltage and amperage data and the detected travel speed data may be used to compute the heat input in real-time for each point in time along the time series (e.g., time-based) or at each location along the weld joint (e.g., distance-based). In particular, in certain embodiments, the heat input (in kilojoules) may be calculated as a function of the voltage, the amperage, and the travel speed (in inched per minute) as:

$$HeatInput = \frac{Amps \times Volts \times 60}{1000 \times TravelSpeed}$$

In addition, although not illustrated in FIG. 70, in certain embodiments, the weld size (fillet size; in millimeters) can be computed in real-time using the wire feed speed (WFS; in inches per minute), which may either be detected or specified by a user, travel speed (in meters per minute), and a predetermined value for efficiency (%), and wire diameter (in millimeters) as:

$$FilletSize = \sqrt{\frac{(\frac{\pi}{4} \times WireDiameter^2) \times (25.4 \times WFS) \times Efficiency}{\left(\frac{1000 \times TravelSpeed}{2}\right)}}$$

In certain embodiments, the predetermined value for efficiency may take into account any detected spatter, which may be determined using the techniques disclosed in "Devices and Methods for Analyzing Spatter Generating Events", U.S. Patent Application No. 2013/0262000, filed on Mar. 30, 2012 in the name of Richard Martin Hutchison et al., which is hereby incorporated into its entirety. For example, the predetermined value of efficiency may be adjusted to, for example, lower the predetermined value of efficiency when more spatter generating events are determined to occur, increase the predetermined value of efficiency when fewer spatter generating events are determined to occur, and so forth.

As used herein, the term "predetermined range" may mean any of the following: a group of numbers bounded by a predetermined upper limit and a predetermined lower limit, a group of number greater than a predetermined limit, and a group of numbers less than a predetermined limit. Moreover, the range may include numbers equal to the one or more predetermined limits.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A system comprising:
   a manual marking tool comprising a handle for manipulating the manual marking tool;
   a marking wheel with a plurality of applicators having predetermined geometric properties disposed circumferentially in a predetermined repeating pattern about the marking wheel and spaced apart from one another about the circumference of the marking wheel, wherein the manual marking tool is configured to apply one or more markers from a respective applicators of the plurality of applicators in the predetermined repeating pattern on a first surface of a workpiece for a live welding session, wherein the one or more markers comprise the predetermined geometric properties;
   a camera configured to detect a first set of the one or more markers on the first surface of the workpiece and to detect a second set of the one or more markers on a second surface of the workpiece that is different than the first surface;
   a welding torch configured to perform welding for the live welding session; and
   a controller coupled to the camera, wherein the controller is configured to determine at least one of the first surface, the second surface, and a weld joint based at least in part on the detected first and second sets of the one or more markers,
   wherein the controller is configured to determine a position and an orientation of the welding torch relative to the workpiece based at least in part on the detected first and second sets of the one or more markers.

2. The system of claim 1, wherein the one or more markers comprise a paint, an ink, or any combination thereof.

3. The system of claim 1, wherein the predetermined geometric properties of the one or more markers comprise an asymmetric shape.

4. The system of claim 1, wherein the manual marking tool is configured to apply the one or more markers on the first surface of the workpiece when the marking wheel is rolled along the workpiece.

5. The system of claim 1, wherein the one or more markers comprise a continuous marking.

6. The system of claim 1, wherein the first set of the one or more markers comprises first predetermined geometric properties, the second set of the one or more markers comprises second predetermined geometric properties, and the second set of the one or more markers is different than the first set of the one or more markers.

7. The system of claim 1, wherein the camera is configured to detect the welding torch.

8. The system of claim 7, wherein the welding torch comprises one or more torch markers, wherein the camera is configured to detect the welding torch via detection of the one or more torch markers.

9. The system of claim 7, wherein the controller is configured to determine a position and an orientation of the welding torch relative to the workpiece based at least in part on the detected welding torch and the detected first set of the one or more markers.

10. The system of claim 1, wherein the camera is coupled to a welding helmet.

11. The system of claim 1, wherein the camera is coupled to the welding torch.

12. A system comprising:
a manual marking tool having a handle and a marking wheel with a plurality of applicators, wherein:
the plurality of applicators comprising a continuous asymmetric shape disposed circumferentially in a predetermined repeating pattern about the marking wheel,
the marking wheel is configured to roll along a workpiece for a live welding session and to apply one or more markers to the workpiece in the predetermined repeating pattern when the one or more applicators on the marking wheel interface with the workpiece to form a first set of one or more markers on a first surface of the workpiece and a second set of one or more markers on a second surface of the workpiece,
the second surface is different than the first surface, and
at least one of the first set of the one or more markers and the second set of the one or more markers comprise the continuous asymmetric shape;
a camera configured to detect the first set of the one or more markers on the first surface of the workpiece and to detect the second set of the one or more markers on the second surface of the workpiece that is different than the first surface; and
a controller coupled to the camera, wherein the controller is configured to:
determine the first and the second surfaces of the workpiece based on the detection of the first set and the second set of the one or more markers, and
determine a weld joint based at least in part on one or both of the determined first set of the one or more markers and the determined second set of the one or more markers.

13. The system of claim 12, wherein the one or more markers comprise a paint, an ink, or any combination thereof.

14. The system of claim 12, wherein each applicator is configured to apply a respective marker of the one or more markers to the workpiece when the respective applicator interfaces with the workpiece.

15. The system of claim 6, wherein each marker of the one or more markers comprises a picture, text, or any combination thereof.

16. A method comprising:
applying a first set of one or more markers to a first surface of a workpiece by rolling a marking wheel comprising a plurality of applicators comprising predetermined geometric properties disposed circumferentially in a predetermined repeating pattern about the marking wheel and spaced apart from one another about the circumference of the marking wheel, wherein the plurality of applicators apply a plurality of markers in the predetermined repeating pattern and comprising the predetermined geometric properties along the workpiece by use of a handle to be manipulated by a user;
detecting the applied first set of one or more markers with a camera;
applying, via the marking wheel, a second set of one or more markers comprising second geometric properties to a second surface of the workpiece that is different from the first surface;
detecting the applied second set of one or more markers with the camera;
determining, via processing circuitry coupled to the camera, at least one of the first surface, the second surface, and a weld joint based at least in part on the detected first and second sets of one or more markers; and
determining a position and an orientation of a welding torch relative to the workpiece based at least in part on the detected first and second sets of the one or more markers.

17. The method of claim 16, wherein applying the first set of one or more markers comprising first predetermined geometric properties comprises rolling the marking wheel along the first surface of the workpiece to transfer the one or more markers of the first set from the marking wheel tool to the first surface.

18. The method of claim 16, comprising:
detecting the welding torch with the camera during a live welding session; and
determining, via the processing circuitry coupled to the camera, the position and the orientation of the welding torch relative to the workpiece based at least in part on the detected first set of one or more markers and the detected welding torch.

19. The method of claim 16, wherein the camera is coupled to the welding torch.

20. The method of claim 16, wherein the camera is coupled to a welding helmet.

21. The method of claim 16, wherein the marking tool wheel comprises a plurality of discrete applicators, each discrete applicator is configured to apply a respective marker of the one or more markers when the respective discrete applicator interfaces with the first workpiece.

22. The method of claim 17, wherein applying the second set of one or more markers comprises rolling the marking wheel along the second surface of the workpiece to transfer the one or more markers of the second set from the manual marking tool to the first surface.

* * * * *